US009388417B2

(12) United States Patent
Lee et al.

(10) Patent No.: US 9,388,417 B2
(45) Date of Patent: Jul. 12, 2016

(54) SYNTHESIS-REGULATING SRNA AND METHOD FOR PREPARING SAME

(71) Applicant: Korea Advanced Institute of Science and Technology, Daejeon (KR)

(72) Inventors: Sang Yup Lee, Daejeon (KR); Dokyun Na, Gyeongsangnam-do (KR); Seung Min Yoo, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 14/371,557

(22) PCT Filed: Jan. 11, 2013

(86) PCT No.: PCT/KR2013/000235
§ 371 (c)(1),
(2) Date: Jul. 10, 2014

(87) PCT Pub. No.: WO2013/105807
PCT Pub. Date: Jul. 18, 2013

(65) Prior Publication Data
US 2014/0377752 A1  Dec. 25, 2014

(30) Foreign Application Priority Data

Jan. 11, 2012 (KR) ........................ 10-2012-0003609

(51) Int. Cl.
| | |
|---|---|
| *C12N 15/63* | (2006.01) |
| *C12N 1/21* | (2006.01) |
| *C12N 15/113* | (2010.01) |
| *C12P 7/22* | (2006.01) |
| *C12P 13/22* | (2006.01) |
| *C12N 15/70* | (2006.01) |
| *C12P 13/00* | (2006.01) |

(52) U.S. Cl.
CPC ............ *C12N 15/1138* (2013.01); *C12N 15/63* (2013.01); *C12N 15/70* (2013.01); *C12P 7/22* (2013.01); *C12P 13/001* (2013.01); *C12P 13/225* (2013.01); *C12N 2310/11* (2013.01); *C12N 2310/531* (2013.01)

(58) Field of Classification Search
USPC ........ 435/6.1, 91.1, 91.31, 375, 6.11, 252.33, 435/320.1; 536/23.1, 24.5
See application file for complete search history.

(56) References Cited

FOREIGN PATENT DOCUMENTS

WO        2007119574 A2    10/2007

OTHER PUBLICATIONS

Chen et al. J. Bacteriol., vol. 186, No. 20, pp. 6689-6697 (2004).*
Kawamoto et al (Molecular Microbiol., vol. 61, No. 4, pp. 1013-1022 (2006).*
Zhang et al, Biochem. Biophys. Res. Comm., vol. 343, pp. 950-955 (2006).*
Chen, S., et al., "MicC, a Second Small-RNA Regulator of Omp Protein Expression in *Escherichia coli*", "Journal of Bacteriology", Oct. 2004, pp. 6689-6697, vol. 186, No. 20.
Datsenko, K., et al., "One-step inactivation of chromosomal genes in *Escherichia coli* K-12 using PCR products", "Proc. Natl. Acad. Sci. USA (PNAS)", Jun. 6, 2000, pp. 6640-6645, vol. 97, No. 12.
Kawamoto, H., et al., "Base-pairing requirement for RNA silencing by a bacterial small RNA and acceleration of duplex formation by Hfq", "Molecular Microbiology", Jul. 12, 2006, pp. 1013-1022, vol. 61, No. 4.
Luetke-Eversloh, T., et al., "L-Tyrosine production by deregulated strains of *Escherichia coli*", "Appl Microbiol Biotechnol", Jan. 13, 2007, pp. 103-110, vol. 75.
Na, D., et al., "Mathematical modeling of translation initiation for the estimation of its efficiency to computationally design mRNA sequences with desired expression levels in prokaryotes", "BMC Systems Biology", 2010, pp. 1-16, vol. 4, No. 71.
Neumann, E., et al., "Gene transfer into mouse lyoma cells by electroporation in high electric fields", "The EMBO Journal", 1982, pp. 841-845, vol. 1, No. 7.

(Continued)

*Primary Examiner* — Jane Zara
(74) *Attorney, Agent, or Firm* — Hultquist, PLLC; Steven J. Hultquist

(57) ABSTRACT

The present invention relates to a novel customized sRNA that reduces gene expression in prokaryotic cells, a preparation method thereof, and the use thereof, and more particularly to a synthetic sRNA comprising an Hfq binding site, derived from the sRNA of any one of MicC, SgrS and MicF, and a region that base-pairs with the target gene mRNA, and to a preparation method thereof and the use thereof. The synthetic sRNA according to the invention has an advantage in that the degree of inhibition of the target gene can be controlled by regulating the ability of the synthetic sRNA to bind to the mRNA of the target gene. The use of the synthetic sRNA that regulates the expression of the target gene makes it possible to effectively construct a recombinant microorganism without using a conventional gene deletion method and to reduce the expression of the target gene, and thus the synthetic sRNA is useful for the production of recombinant microorganisms. Also, the synthetic sRNA can be quickly applied to various strains, and thus is very suitable for the measurement of metabolic capabilities of strains and the selection of the most suitable strain. In addition, recombinant microorganisms, which are obtained by metabolic flux manipulation using the synthetic sRNA and produce tyrosine or cadaverine with high efficiency, are useful in the drug and industrial fields. In other words, the use of the sRNA according to the present invention can make it easy to select target genes whose expression is to be inhibited for the highly efficient production of metabolites. Accordingly, the synthetic sRNA can be used to construct recombinant strains for efficient production of various metabolites and to establish efficient methods for production of various metabolites, and thus is highly useful.

11 Claims, 30 Drawing Sheets

(56) References Cited

OTHER PUBLICATIONS

Qian, Z., et al., "Metabolic Engineering of *Escherichia coli* for the Production of Cadaverine: A Five Carbon Diamine", "Biotechnol. Bioeng.", Sep. 1, 2010, pp. 93-103, vol. 108.

Wadler, C., et al., "A dual function for a bacterial small RNA: SgrS performs base pairing-dependent regulation and encodes a functional polypeptide", "PNAS", Dec. 18, 2007, pp. 20454-20459, vol. 104, No. 51.

Zhang, Y., et al., "Identifying Hfq-binding small RNA targets in *Escherichia coli*", "Biochemical and Biophysical Research Communications", Mar. 20, 2006, pp. 950-955, vol. 343.

Coleman, J., et al, "The use of RNAs complementary to specific mRNAs to regulate the expression of individual bacterial genes", Cell, Jun. 1984, pp. 429-436, vol. 37.

Kang, Z., et al., "Small RNA regulators in bacteria: powerful tools for metabolic engineering and synthetic biology", Applied Microbiology and Biotechnology, Feb. 12, 2014, pp. 3413-3424, vol. 98.

Kim, B., et al., "Metabolic engineering of *Escherichia coli* for the production of phenol from glucose", Biotechnology Journal, Oct. 11, 2013, pp. 621-629, vol. 9.

Kim, B., et al., "Supplemental Information for Metabolic engineering of *Escherichia coli* for the production of phenol from glucose", Biotechnology Journal, Oct. 11, 2013, pp. 1-2, vol. 9.

Maki, K., et al., "A minimal base-pairing region of a bacterial small RNA SgrS required for translational repression of ptsG mRNA", Moleculary Microbiology, Apr. 8, 2010, pp. 782-792, vol. 76, No. 3.

Man, S., et al., "Artificial trans-encoded small non-coding RNAs specifically silence the selected gene expression in bacteria", Nucleic Acids Research, Feb. 3, 2011, pp. e50 (1-16), vol. 39, No. 8.

Man, S., et al., "Supplementary Data: Artificial trans-encoded small non-coding RNAs specifically silence the selected gene expression in bacteria", Nucleic Acids Research, Feb. 3, 2011, pp. 1-40, vol. 39, No. 8.

Na, D., et al., "Metabolic engineering of *Escherichia coli* using synthetic small regulatory RNAs", Nature Biotechnology, Jan. 20, 2013, pp. 170-174, vol. 31, No. 2.

Na, D., et al., "Supplementary Information: Metabolic engineering of *Escherichia coli* using synthetic small regulatory RNAs", Nature Biotechnology, Jan. 20, 2013, pp. 1-57, vol. 31, No. 2.

Sharma, V., et al., "Engineering Artificial Small RNAs for Conditional Gene Silencing in *Escherichia coli*", ACS Synthetic Biology, Aug. 29, 2011, pp. 6-13, vol. 1.

Sharma V., et al., "Supporting Information: Engineering Artificial Small RNAs for Conditional Gene Silencing in *Escherichia coli*", ACS Synthetic Biology, Aug. 29, 2011, pp. 1-4, vol. 1.

\* cited by examiner

FIG. 2

SgrS
GATGAAGCAA GGGGGTGCCC CATGCGTCAG TTTATCAGC ACTATTTAC CGCGACAGCG
AAGTTGTGCT GGTTGCGTTG GTTAAGCGTC CCACAACGAT TAACCATGCT TGAAGCACTG
ATGCAGTGGG ATGACCGCAA TTCTGAAAGT TGA*cttgcct gggaatgtaa tcggccacta*
*tcgtgtaag* ATCACCCGCC AGCAGATTAT ACCTGCTGGT TTTTTTT (SEQ ID NO: 139)

MicC
*cttgtctcc tccgctgccc caggtttttt* TTCTGTTGG GCCATTGCAT TGCCACTGAT
TTCCAACAT ATAAAAAGAC AAGCCCGAAC AGTCGTCCGG GCTTTTTTTC TCGAG
(SEQ ID NO: 140)

MicF
*gtttggaaa ttcgcttgat tttacgaacc cca*GCATTTC TGAATGTCTG TTTACCCCTA
TTTCAACCGG ATGCCTCCCA TTCGGTTTTT TTT (SEQ ID NO: 141)

DsReda mRNA                           Estimated RBS    (SEQ ID NO: 142)
TTATTAATTA *aggaggaca aatatatggt gagcagtgag aacgtcatca* CCGAGTTCAT
                 :::::::::: :::::::::: :::::::::: :::::::
            3' TTCCTCCTGT TTATATACCG CTCGTCACTC TTGCAGTA 5' Anti-DsReda
                                     (SEQ ID NO: 143)

FIG. 6

AraC mRNA
ttaattaa AAGGAGAAAAACGGATGGCTGAAGCGCAAAATGATC ccctgctgccg (SEQ ID NO: 159)
         TTCCTCTTTTGCCTACCGACTTCGCGTTTTACTAG     (SEQ ID NO: 160)
                          Anti-AraC

LuxR mRNA
ttaattaa AAGGAGCAATCAAAATGAACATCAAGAACATCAACG cgaacgagaag (SEQ ID NO: 161)
         TTCCTCGTTAGTTTTACTTGTAGTTCTTGTAGTTGC    (SEQ ID NO: 162)
                          Anti-LuxR

Kan<sup>R</sup> mRNA ttttaatt AAGGAGTCGTTTACATGATTGAACAAGATGGATTGC acgcaggttct (SEQ ID NO: 163)
         TTCCTCAGCAAATGTACTAACTTGTTCTACCTAACG    (SEQ ID NO: 164)
                          Anti-Kan<sup>R</sup>

FIG. 7
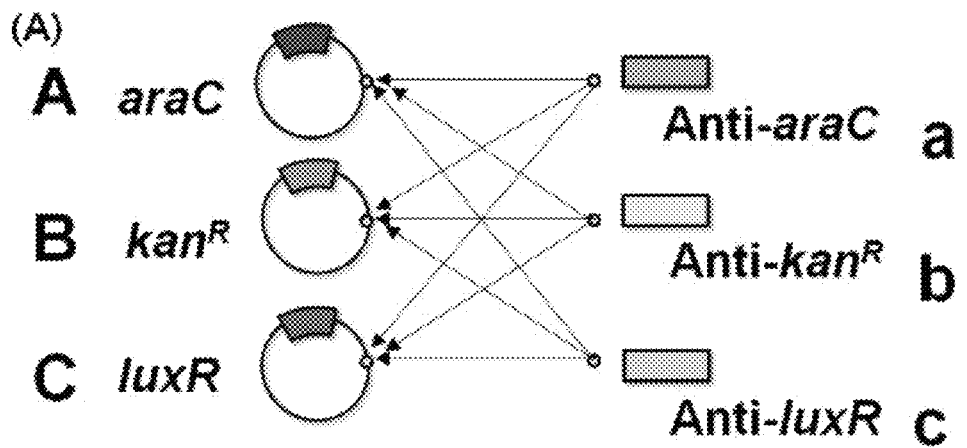
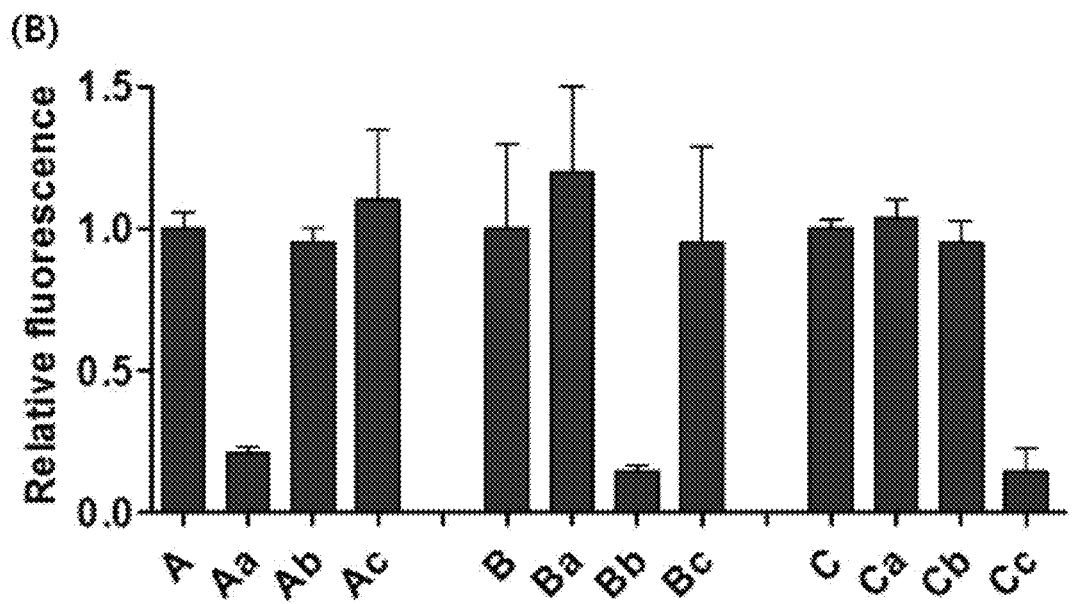

FIG. 8

| sRNAs | Target mRNAs | | |
|---|---|---|---|
| | LuxR | Kan$^R$ | AraC |
| Anti-LuxR | -53.7 | -17.5 | -14.1 |
| Anti-Kan$^R$ | -12.2 | -56.2 | -13.1 |
| Anti-AraC | -13.5 | -15.4 | -59.5 |

FIG. 10
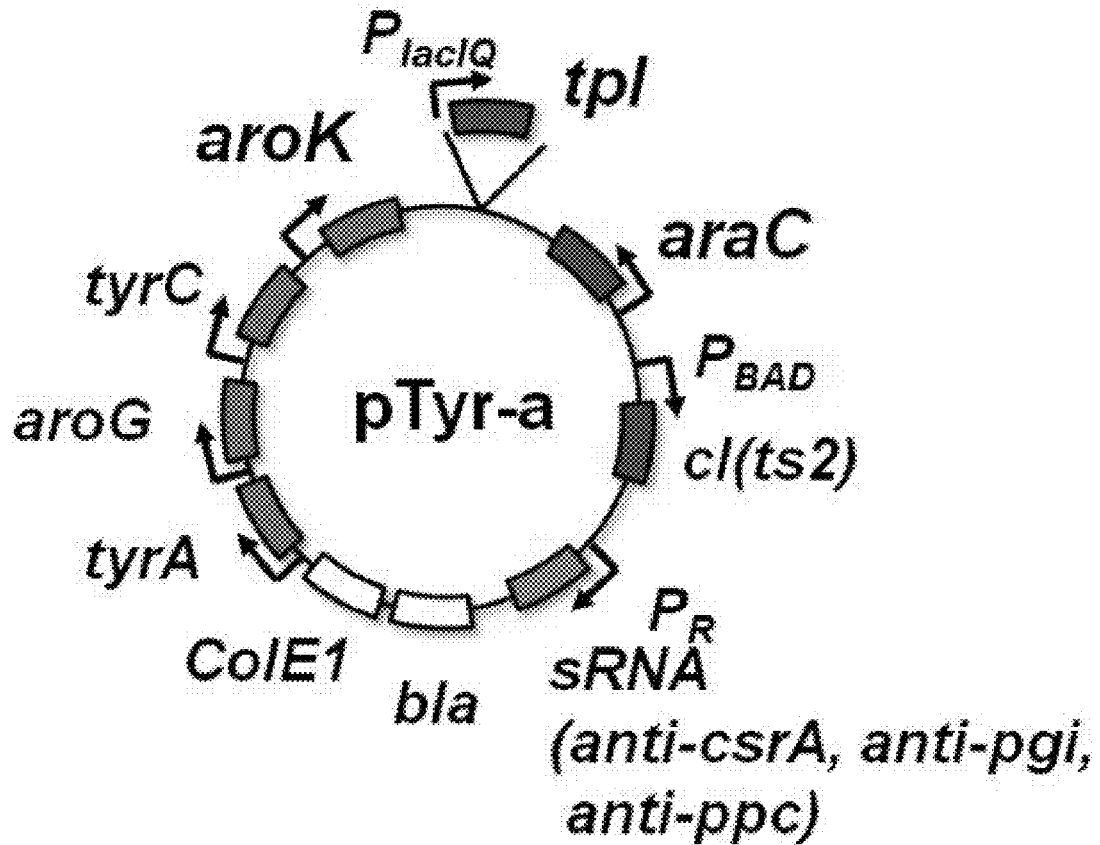
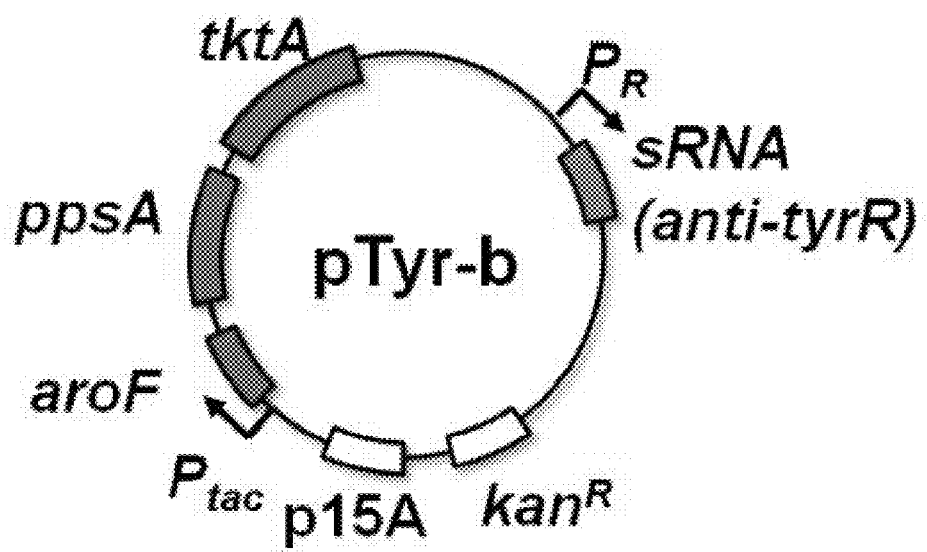

FIG. 13

```
pgi mRNA              ATGAAAAACA TCAATCCAAC GCAG  (SEQ ID NO: 165)
                      :::::::::: :::::::::: ::::
sRNA(anti-pgi)        TACTTTTTGT AGTTAGGTTG CGTC  (SEQ ID NO: 166)
sRNA(anti-pgi-D1)     TACTTTTTGT AGT-AGGTTG CGTC  (SEQ ID NO: 167)
sRNA(anti-pgi-D2)     TACTTTTTGT AG--AGGTTG CGTC  (SEQ ID NO: 168)
```

FIG. 23
A. DsRed2
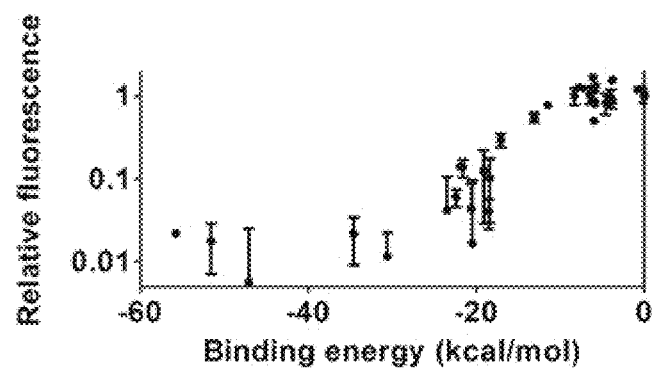
B. LacZ
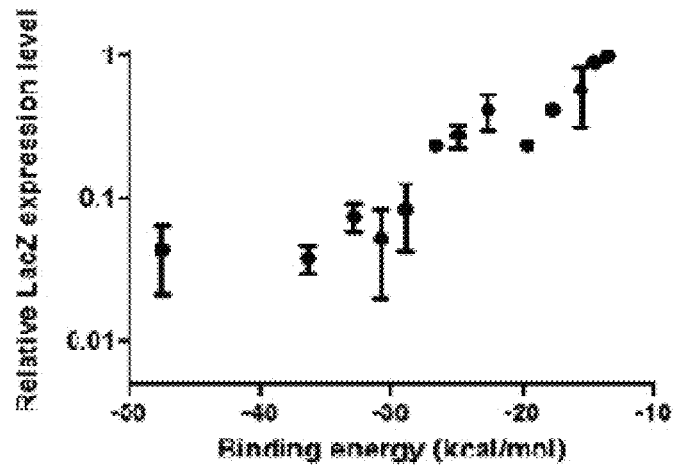

FIG. 29
A
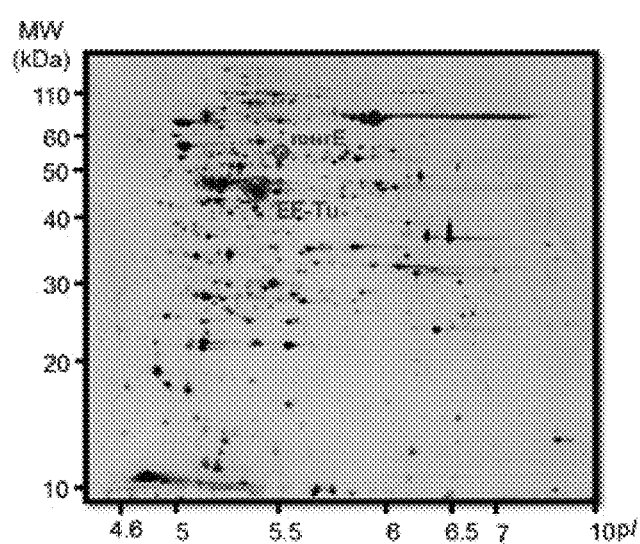
B
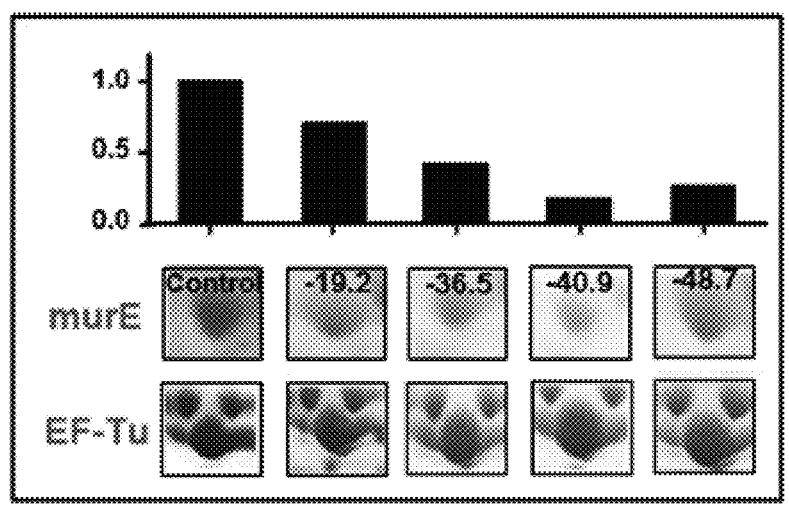

SEQUENCE LISTING

```
<160> NUMBER OF SEQ ID NOS: 492

<210> SEQ ID NO 1
<211> LENGTH: 2561
<212> TYPE: DNA
<213> ORGANISM: Artificial
<220> FEATURE:
<223> OTHER INFORMATION: pWA plasmid

<400> SEQUENCE: 1
```

```
catatgagat ggtaagccct cccgtatcgt agttatctac acgacgggga gtcaggcaac    60
tatggatgaa cgaaatagac agatcgctga gataggtgcc tcactgatta agcattggta   120
actgtcagac caagtttact catatatact ttagattgat ttaaaacttc attttttaatt   180 taaaaggatc taggtgaaga tccttttttga taatctcatg accaaaatcc cttaacgtga   240
gttttcgttc cactgagcgt cagaccccgt agaaaagatc aaaggatctt cttgagatcc   300 ttttttttctg cgcgtaatct gctgcttgca acaaaaaaaa ccaccgctac cagcggtggt   360
ttgtttgccg gatcaagagc taccaactct ttttccgaag gtaactggct tcagcagagc   420
gcagatacca aatactgtcc ttctagtgta gccgtagtta ggccaccact tcaagaactc   480
tgtagcaccg cctacatacc tcgctctgct aatcctgtta ccagtggctg ctgccagtgg   540
cgataagtcg tgtcttaccg ggttggactc aagacgatag ttaccggata aggcgcagcg   600
gtcgggctga acggggggtt cgtgcacaca gcccagcttg gagcgaacga cctacaccga   660
actgagatac ctacagcgtg agctatgaga aagcgccacg cttcccgaag ggagaaaggc   720
ggacaggtat ccggtaagcg gcagggtcgg aacaggagag cgcacgaggg agcttccagg   780
gggaaacgcc tggtatcttt atagtcctgt cgggtttcgc cacctctgac ttgagcgtcg   840 attttttgtga tgctcgtcag gggggcggag cctatggaaa aacgccagca acgcggcctt   900
tttacggttc ctggcctttt gctggccttt tgctcacatg ttctttcctg cgttatcccc   960
tgattctgtg gataaccgta ttaccgcctt tgagtgagct gataccgctc gccgcagccg  1020
aacgaccgag cgcagcgagt cagtgagcga ggaacatatg tgacagctta tcgcatgcct  1080
aggtaaaccc aggaggtata gggcgaattg ggtaccgggc cccccctcga ggtcgacggt  1140
atcgataagc ttgatatcga attcctgcag cccgggggat ccactagttc tagagcggcc  1200
gccaccgcgg tggagctcca gcttttgttc cctttagtga gttagtgtct aggttcccac  1260
tagatctcaa atgtgctggg cacatgtttg atttataagg gattttgccg atttcggcct  1320
attggttaaa aaatgagctg atttaacaaa aatttaacgc gaattttaac aaaatattaa  1380
cgcttacaat ttaggtggca cttttcgggg aaatgtgcgc ggaaccccta tttgtttatt  1440
tttctaaata cattcaaata tgtatccgct catgagacaa taaccctgat aaatgcttca  1500
ataatattga aaaggaaga gtatgagtat tcaacatttc cgtgtcgccc ttattccctt  1560
ttttgcggca ttttgccttc ctgttttttgc tcacccagaa acgctggtga agtaaaaga  1620 tgctgaagat cagttgggtg cacgagtggg ttacatcgaa ctggatctca acagcggtaa  1680
gatccttgag agttttcgcc ccgaagaacg ttttccaatg atgagcactt ttaaagttct  1740
gctatgtggc gcggtattat cccgtattga cgccgggcaa gagcaactcg gtcgccgcat  1800
acactattct cagaatgact tggttgagta ctcaccagtc acagaaaagc atcttacgga  1860
tggcatgaca gtaagagaat tatgcagtgc tgccataacc atgagtgata acactgcggc  1920
caacttactt ctgacaacga tcggaggacc gaaggagcta accgcttttt tgcacaacat  1980
gggggatcat gtaactcgcc ttgatcgttg ggaaccggag ctgaatgaag ccataccaaa  2040
cgacgagcgt gacaccacga tgcctgtagc aatggcaaca acgttgcgca aactattaac  2100
tggcgaacta cttactctag cttcccggca acaattaata gactggatgg aggcggataa  2160
agttgcagga ccacttctgc gctcggccct tccggctggc tggtttattg ctgataaatc  2220
tggagccggt gagcgtgggt ctcgcggtat cattgcagca ctggggccag atggtaagcc  2280
ctcccgtatc gtagttatct acacgacggg gagtcaggca actatggatg aacgaaatag  2340
```

-continued

```
acagatcgct gagataggtg cctcactgat taagcattgg taactgtcag accaagttta      2400
ctcatatata ctttagattg atttaaaact tcatttttaa tttaaaagga tctaggtgaa      2460
gatccttttt gataatctca acatgttgcc aacttactga tttagtgtat gatggtgttt      2520
ttgaggtgct ccagtggctt ctgtttctat cagctgtccc t                         2561
```

```
<210> SEQ ID NO 2
<211> LENGTH: 52
<212> TYPE: DNA
<213> ORGANISM: Artificial
<220> FEATURE:
<223> OTHER INFORMATION: primer

<400> SEQUENCE: 2
aagctggagc tcaatactag tcgatttatt atgacaactt gacggctaca tc             52
```

```
<210> SEQ ID NO 3
<211> LENGTH: 47
<212> TYPE: DNA
<213> ORGANISM: Artificial
<220> FEATURE:
<223> OTHER INFORMATION: primer

<400> SEQUENCE: 3
gaattcaatt aattaattaa aattcccaaa aaaacgggta tggagaa                   47
```

```
<210> SEQ ID NO 4
<211> LENGTH: 57
<212> TYPE: DNA
<213> ORGANISM: Artificial
<220> FEATURE:
<223> OTHER INFORMATION: primer

<400> SEQUENCE: 4
gggaatttta attaaaagga gacccgggat atgagcacaa aaagaaacc attaaca         57
```

```
<210> SEQ ID NO 5
<211> LENGTH: 33
<212> TYPE: DNA
<213> ORGANISM: Artificial
<220> FEATURE:
<223> OTHER INFORMATION: primer

<400> SEQUENCE: 5
aattatgaat tcttagccaa acgtctcttc agg                                  33
```

```
<210> SEQ ID NO 6
<211> LENGTH: 101
<212> TYPE: DNA
<213> ORGANISM: Artificial
<220> FEATURE:
<223> OTHER INFORMATION: primer

<400> SEQUENCE: 6
aatatgaatt cccaggcatc aaataaaacg aaaggctcag tcgaaagact gggcctttcg     60
ttttatctgt tgtttgtcgg tgaacgctct ctactagagt c                        101
```

```
<210> SEQ ID NO 7
<211> LENGTH: 97
<212> TYPE: DNA
<213> ORGANISM: Artificial
<220> FEATURE:
<223> OTHER INFORMATION: primer

<400> SEQUENCE: 7
```
aatattctag atataaacgc agaaaggccc acccgaaggt gagccagtgt gactctagta      60
gagagcgttc accgacaaac aacagataaa acgaaag                               97

<210> SEQ ID NO 8
<211> LENGTH: 33
<212> TYPE: DNA
<213> ORGANISM: Artificial
<220> FEATURE:
<223> OTHER INFORMATION: primer

<400> SEQUENCE: 8 tttttctcg agccaggcat caaataaaac gaa                                    33

<210> SEQ ID NO 9
<211> LENGTH: 34
<212> TYPE: DNA
<213> ORGANISM: Artificial
<220> FEATURE:
<223> OTHER INFORMATION: primer

<400> SEQUENCE: 9
gaattgggta cctataaacg cagaaaggcc cacc                                  34

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
gaagttatcg ctagtcagtg gcc                                              23

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
ccccacaacg gaacaactct                                                  20

<210> SEQ ID NO 12
<211> LENGTH: 84
<212> TYPE: DNA
<213> ORGANISM: Artificial
<220> FEATURE:
<223> OTHER INFORMATION: primer

<400> SEQUENCE: 12
ctgcaggaat ctaacaccg tgcgtgttga ctattttacc tctggcggtg ataatggttg        60
ctttctgttg ggccattgca ttgc                                             84

<210> SEQ ID NO 13
<211> LENGTH: 29
<212> TYPE: DNA
<213> ORGANISM: Artificial
<220> FEATURE:
<223> OTHER INFORMATION: primer

<400> SEQUENCE: 13
ctcgagaaaa aaagcccgga cgactgttc                                        29

```
<210> SEQ ID NO 14
<211> LENGTH: 79
<212> TYPE: DNA
<213> ORGANISM: Artificial
<220> FEATURE:
<223> OTHER INFORMATION: primer

<400> SEQUENCE: 14
ctgcaggaat tctaacaccg tgcgtgttga ctattttacc tctggcggtg ataatggttg    60
cgatgaagca aggggggtgc                                                79

<210> SEQ ID NO 15
<211> LENGTH: 34
<212> TYPE: DNA
<213> ORGANISM: Artificial
<220> FEATURE:
<223> OTHER INFORMATION: primer

<400> SEQUENCE: 15
ctcgagaaaa aaaaccagca ggtataatct gctg                                34

<210> SEQ ID NO 16
<211> LENGTH: 74
<212> TYPE: DNA
<213> ORGANISM: Artificial
<220> FEATURE:
<223> OTHER INFORMATION: primer

<400> SEQUENCE: 16
ctgcaggaat tctaacaccg tgcgtgttga ctattttacc tctggcggtg ataatggttg    60
ctcatttctg aatg                                                      74

<210> SEQ ID NO 17
<211> LENGTH: 79
<212> TYPE: DNA
<213> ORGANISM: Artificial
<220> FEATURE:
<223> OTHER INFORMATION: primer

<400> SEQUENCE: 17
tcgagaaaaa aaaccgaatg cgaggcatcc ggttgaaata ggggtaaaca gacattcaga    60
aatgagcaac cattatcac                                                 79

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
agtgggaacc tagacactaa                                                20

<210> SEQ ID NO 19
<211> LENGTH: 18
<212> TYPE: DNA
<213> ORGANISM: Artificial
<220> FEATURE:
<223> OTHER INFORMATION: primer

<400> SEQUENCE: 19
ctaggtaaac ccaggagg                                                  18
```

| <210> SEQ ID NO 20 |
| <211> LENGTH: 2179 |
| <212> TYPE: DNA |
| <213> ORGANISM: Artificial |
| <220> FEATURE: |
| <223> OTHER INFORMATION: pR15CA |

<400> SEQUENCE: 20

```
agatctcaaa tgtgctgggc cctggtgcaa aacctttcgc ggtatggcat gatagcgcca      60
tcgagatttt caggagctaa ggaagctaaa atggagaaaa aaatcactgg atataccacc     120
gttgatatat cccaatggca tcgtaaagaa cattttgagg catttcagtc agttgctcaa     180
tgtacctata accagaccgt tcagctggat attacggcct ttttaaagac cgtaaagaaa     240
aataagcaca gttttatcc ggcctttatt cacattcttg cccgcctgat gaatgctcat     300
ccggaatttc gtatggcaat gaaagacggt gagctggtga tatgggatag tgttcaccct     360
tgttcaccg ttttccatga gcaaactgaa acgttttcat cgctctggag tgaataccac     420
gacgatttcc ggcagtttct cacatatatt cgcaagatgt ggcgtgttac ggtgaaaacc     480
tggcctattt ccctaaaggg tttattgaga atatgttttt cgtctcagcc aatccctggg     540
tgagtttcac cagttttgat ttaaacgtgg ccaatatgga caacttcttc gcccccgttt     600
tcaccatggg caaatattat acgcaaggcg acaaggtgct gatgccgctg gcgattcagg     660
ttcatcatgc cgtctgtgat ggcttccatg tcggcagaat gcttaatgaa ttacaacagt     720
actgcgatga gtggcagggc ggggcgtaat tttttaagg cagttattgg tgcccttaaa     780
cgcactagtc caggcatcaa ataaaacgaa aggctcagtc gaaagactgg cctttcgtt     840
ttatctgttt ttgtcggtga acgctctcta ctagagtcac actggctcac cttcgggtgg     900
gcctttctgc gtttatagca tgctgccaac ttactgattt agtgtatgat ggtgtttttg     960
aggtgctcca gtggcttctg tttctatcag ctgtccctcc tgttcagcta ctgacggggt    1020
ggtgcgtaac ggcaaaagca ccgccggaca tcagcgctag cggagtgtat actggcttac    1080
tatgttggca ctgatgaggg tgtcagtgaa gtgcttcatg tggcaggaga aaaaaggctg    1140
caccggtgcg tcagcagaat atgtgataca ggatatattc cgcttcctcg ctcactgact    1200
cgctacgctc ggtcgttcga ctgcggcgag cggaaatggc ttacgaacgg ggcggagatt    1260
tcctggaaga tgccaggaag atacttaaca gggaagtgag agggccgcgg caaagccgtt    1320
tttccatagg ctccgccccc ctgacaagca tcacgaaatc tgacgctcaa atcagtggtg    1380
gcgaaacccg acaggactat aaagatacca ggcgtttccc cctggcggct ccctcgtgcg    1440
ctctcctgtt cctgcctttc ggtttaccgg tgtcattccg ctgttatggc cgcgtttgtc    1500
tcattccacg cctgacactc agttccgggt aggcagttcg ctccaagctg gactgtatgc    1560
acgaaccccc cgttcagtcc gaccgctgcg ccttatccgg taactatcgt cttgagtcca    1620
acccggaaag acatgcaaaa gcaccactgg cagcagccac tggtaattga tttagaggag    1680
ttagtcttga agtcatgcgc cggttaaggc taaactgaaa ggacaagttt tggtgactgc    1740
gctcctccaa gccagttacc tcggttcaaa gagttggtag ctcagagaac cttcgaaaaa    1800
ccgccctgca aggcggtttt ttcgttttca gagcaagaga ttacgcgcag accaaaacga    1860
tctcaagaag atcatcttat taatcagata aaatatttct agatttcagt gcaatttatc    1920
tcttcaaatg tagcacctga agtcagcccc atacgatata agttgtaatt ctcatgtttg    1980
acagcttatc gcatgcctag gtaaaccag gaggtatagg gcgaattggg taccgggccc    2040
cccctcgagg tcgacggtat cgataagctt gatatcgaat tcctgcagcc cggggatcc    2100
```

```
actagttcta gagcggccgc caccgcggtg gagctccagc ttttgttccc tttagtgagt    2160
tagtgtctag gttcccact                                                 2179
```

<210> SEQ ID NO 21
<211> LENGTH: 38
<212> TYPE: DNA
<213> ORGANISM: Artificial
<220> FEATURE:
<223> OTHER INFORMATION: primer

<400> SEQUENCE: 21

```
ataattctcg agccaggcat caaataaaac gaaaggct                            38
```

<210> SEQ ID NO 22
<211> LENGTH: 33
<212> TYPE: DNA
<213> ORGANISM: Artificial
<220> FEATURE:
<223> OTHER INFORMATION: primer

<400> SEQUENCE: 22

```
aattaggtac ctataaacgc agaaaggccc acc                                 33
```

<210> SEQ ID NO 23
<211> LENGTH: 36
<212> TYPE: DNA
<213> ORGANISM: Artificial
<220> FEATURE:
<223> OTHER INFORMATION: primer

<400> SEQUENCE: 23

```
aattagaatt cgtggataac cgtattaccg cctttg                              36
```

<210> SEQ ID NO 24
<211> LENGTH: 67
<212> TYPE: DNA
<213> ORGANISM: Artificial
<220> FEATURE:
<223> OTHER INFORMATION: primer

<400> SEQUENCE: 24

```
aattactcga gaattattta attaataaag ttaattttt tttttgtgt gaaattgtta      60 tccgctc                                                              67
```

<210> SEQ ID NO 25
<211> LENGTH: 37
<212> TYPE: DNA
<213> ORGANISM: Artificial
<220> FEATURE:
<223> OTHER INFORMATION: primer

<400> SEQUENCE: 25

```
aattattaat taaaggagg acaaatatat ggcgagc                              37
```

<210> SEQ ID NO 26
<211> LENGTH: 74
<212> TYPE: DNA
<213> ORGANISM: Artificial
<220> FEATURE:
<223> OTHER INFORMATION: primer

<400> SEQUENCE: 26

```
aattactcga gttacgccac cagggcatag ttttcatcat tgccgccag gaacaggtgg     60 tggcggccct cggt                                                      74
```

<210> SEQ ID NO 27
<211> LENGTH: 50
<212> TYPE: DNA
<213> ORGANISM: Artificial
<220> FEATURE:
<223> OTHER INFORMATION: primer

<400> SEQUENCE: 27
gcgagcagtg agaacgtcat aagtcaactt tcagaattgc ggtcatccca           50

<210> SEQ ID NO 28
<211> LENGTH: 45
<212> TYPE: DNA
<213> ORGANISM: Artificial
<220> FEATURE:
<223> OTHER INFORMATION: primer

<400> SEQUENCE: 28
catatatttg tcctccttaa atcacccgcc agcagattat acctg                45

<210> SEQ ID NO 29
<211> LENGTH: 48
<212> TYPE: DNA
<213> ORGANISM: Artificial
<220> FEATURE:
<223> OTHER INFORMATION: primer

<400> SEQUENCE: 29
gcgagcagtg agaacgtcat gcaaccatta tcaccgccag aggtaaaa             48

<210> SEQ ID NO 30
<211> LENGTH: 45
<212> TYPE: DNA
<213> ORGANISM: Artificial
<220> FEATURE:
<223> OTHER INFORMATION: primer

<400> SEQUENCE: 30
catatatttg tcctcctttc atttctgaat gtctgtttac cccta                45

<210> SEQ ID NO 31
<211> LENGTH: 48
<212> TYPE: DNA
<213> ORGANISM: Artificial
<220> FEATURE:
<223> OTHER INFORMATION: primer

<400> SEQUENCE: 31
gcgagcagtg agaacgtcat gcaaccatta tcaccgccag aggtaaaa             48

<210> SEQ ID NO 32
<211> LENGTH: 43
<212> TYPE: DNA
<213> ORGANISM: Artificial
<220> FEATURE:
<223> OTHER INFORMATION: primer

<400> SEQUENCE: 32
catatatttg tcctcctttc atttctgaat gtctgtttac ccc                  43

<210> SEQ ID NO 33
<211> LENGTH: 26
<212> TYPE: DNA
<213> ORGANISM: Artificial
<220> FEATURE:

-continued

<223> OTHER INFORMATION: primer

<400> SEQUENCE: 33
gacaaatata tggcgagcag tgagaa                                              26

<210> SEQ ID NO 34
<211> LENGTH: 23
<212> TYPE: DNA
<213> ORGANISM: Artificial
<220> FEATURE:
<223> OTHER INFORMATION: primer

<400> SEQUENCE: 34
tttctgttgg gccattgcat tgc                                                 23

<210> SEQ ID NO 35
<211> LENGTH: 27
<212> TYPE: DNA
<213> ORGANISM: Artificial
<220> FEATURE:
<223> OTHER INFORMATION: primer

<400> SEQUENCE: 35
caccgagcaa ccattatcac cgccaga                                             27

<210> SEQ ID NO 36
<211> LENGTH: 22
<212> TYPE: DNA
<213> ORGANISM: Artificial
<220> FEATURE:
<223> OTHER INFORMATION: primer

<400> SEQUENCE: 36
atgacgttct cactgctcgc ca                                                  22

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
gcgagcagtg agaacgtcat                                                     20

<210> SEQ ID NO 38
<211> LENGTH: 23
<212> TYPE: DNA
<213> ORGANISM: Artificial
<220> FEATURE:
<223> OTHER INFORMATION: primer

<400> SEQUENCE: 38
tttctgttgg gccattgcat tgc                                                 23

<210> SEQ ID NO 39
<211> LENGTH: 39
<212> TYPE: DNA
<213> ORGANISM: Artificial
<220> FEATURE:
<223> OTHER INFORMATION: primer

<400> SEQUENCE: 39
caccgagttc atgcgcttgc aaccattatc accgccaga                                39

```
<210> SEQ ID NO 40
<211> LENGTH: 22
<212> TYPE: DNA
<213> ORGANISM: Artificial
<220> FEATURE:
<223> OTHER INFORMATION: primer

<400> SEQUENCE: 40
atgacgttct cactgctcgc ca                                              22

<210> SEQ ID NO 41
<211> LENGTH: 38
<212> TYPE: DNA
<213> ORGANISM: Artificial
<220> FEATURE:
<223> OTHER INFORMATION: primer

<400> SEQUENCE: 41
tgttcaccgg gcaaccatta tcaccgccag aggtaaaa                             38

<210> SEQ ID NO 42
<211> LENGTH: 35
<212> TYPE: DNA
<213> ORGANISM: Artificial
<220> FEATURE:
<223> OTHER INFORMATION: primer

<400> SEQUENCE: 42
gctcctcgct ttctgttggg ccattgcatt gccac                                35

<210> SEQ ID NO 43
<211> LENGTH: 37
<212> TYPE: DNA
<213> ORGANISM: Artificial
<220> FEATURE:
<223> OTHER INFORMATION: primer

<400> SEQUENCE: 43
catcctggtg caaccattat caccgccaga ggtaaaa                              37

<210> SEQ ID NO 44
<211> LENGTH: 33
<212> TYPE: DNA
<213> ORGANISM: Artificial
<220> FEATURE:
<223> OTHER INFORMATION: primer

<400> SEQUENCE: 44
ggcaccaccc cggtgaacag ctcctcgctt tct                                  33

<210> SEQ ID NO 45
<211> LENGTH: 38
<212> TYPE: DNA
<213> ORGANISM: Artificial
<220> FEATURE:
<223> OTHER INFORMATION: primer

<400> SEQUENCE: 45
gggtggtgcc gcaaccatta tcaccgccag aggtaaaa                             38

<210> SEQ ID NO 46
<211> LENGTH: 35
<212> TYPE: DNA
<213> ORGANISM: Artificial
<220> FEATURE:
<223> OTHER INFORMATION: primer
```

<400> SEQUENCE: 46
cggtgaacat tctgttggg ccattgcatt gccac                                35

<210> SEQ ID NO 47
<211> LENGTH: 37
<212> TYPE: DNA
<213> ORGANISM: Artificial
<220> FEATURE:
<223> OTHER INFORMATION: primer

<400> SEQUENCE: 47
cgagctggag caaccattat caccgccaga ggtaaaa                              37

<210> SEQ ID NO 48
<211> LENGTH: 33
<212> TYPE: DNA
<213> ORGANISM: Artificial
<220> FEATURE:
<223> OTHER INFORMATION: primer

<400> SEQUENCE: 48
accaggatgg gcaccacccc ggtgaacatt tct                                  33

<210> SEQ ID NO 49
<211> LENGTH: 38
<212> TYPE: DNA
<213> ORGANISM: Artificial
<220> FEATURE:
<223> OTHER INFORMATION: primer

<400> SEQUENCE: 49
catcctggtc gcaaccatta tcaccgccag aggtaaaa                             38

<210> SEQ ID NO 50
<211> LENGTH: 35
<212> TYPE: DNA
<213> ORGANISM: Artificial
<220> FEATURE:
<223> OTHER INFORMATION: primer

<400> SEQUENCE: 50
ggcaccacct ttctgttggg ccattgcatt gccac                                35

<210> SEQ ID NO 51
<211> LENGTH: 37
<212> TYPE: DNA
<213> ORGANISM: Artificial
<220> FEATURE:
<223> OTHER INFORMATION: primer

<400> SEQUENCE: 51
ggcgacgtag caaccattat caccgccaga ggtaaaa                              37

<210> SEQ ID NO 52
<211> LENGTH: 31
<212> TYPE: DNA
<213> ORGANISM: Artificial
<220> FEATURE:
<223> OTHER INFORMATION: primer

<400> SEQUENCE: 52
gtccagctcg accaggatgg gcaccacctt t                                    31

<210> SEQ ID NO 53
<211> LENGTH: 33

```
<212> TYPE: DNA
<213> ORGANISM: Artificial
<220> FEATURE:
<223> OTHER INFORMATION: primer

<400> SEQUENCE: 53
actacaagaa gcgcaaccat tatcaccgcc aga                           33

<210> SEQ ID NO 54
<211> LENGTH: 35
<212> TYPE: DNA
<213> ORGANISM: Artificial
<220> FEATURE:
<223> OTHER INFORMATION: primer

<400> SEQUENCE: 54
cggggatgtc ggtttctgtt gggccattgc attgc                        35

<210> SEQ ID NO 55
<211> LENGTH: 33
<212> TYPE: DNA
<213> ORGANISM: Artificial
<220> FEATURE:
<223> OTHER INFORMATION: primer

<400> SEQUENCE: 55
caagaagctg tcgcaaccat tatcaccgcc aga                           33

<210> SEQ ID NO 56
<211> LENGTH: 34
<212> TYPE: DNA
<213> ORGANISM: Artificial
<220> FEATURE:
<223> OTHER INFORMATION: primer

<400> SEQUENCE: 56
tagtcgggga ttttctgttg gccattgca ttgc                           34

<210> SEQ ID NO 57
<211> LENGTH: 74
<212> TYPE: DNA
<213> ORGANISM: Artificial
<220> FEATURE:
<223> OTHER INFORMATION: primer

<400> SEQUENCE: 57
ttaattaaaa tctactctag aggtgcaggg gcaggcgctg gtgcgggtgc catggcgagc   60
agtgagaacg tcat                                                    74

<210> SEQ ID NO 58
<211> LENGTH: 34
<212> TYPE: DNA
<213> ORGANISM: Artificial
<220> FEATURE:
<223> OTHER INFORMATION: primer

<400> SEQUENCE: 58
aatactccgc ggtataaacg cagaaaggcc cacc                          34

<210> SEQ ID NO 59
<211> LENGTH: 41
<212> TYPE: DNA
<213> ORGANISM: Artificial
<220> FEATURE:
<223> OTHER INFORMATION: primer
```

<400> SEQUENCE: 59
tcattttgat tgctcctttt tctgttgggc cattgcattg c    41

<210> SEQ ID NO 60
<211> LENGTH: 39
<212> TYPE: DNA
<213> ORGANISM: Artificial
<220> FEATURE:
<223> OTHER INFORMATION: primer

<400> SEQUENCE: 60
ctgaagcgca aaatgatcgc aaccattatc accgccaga    39

<210> SEQ ID NO 61
<211> LENGTH: 41
<212> TYPE: DNA
<213> ORGANISM: Artificial
<220> FEATURE:
<223> OTHER INFORMATION: primer

<400> SEQUENCE: 61
ccatccgttt ttctcctttt tctgttgggc cattgcattg c    41

<210> SEQ ID NO 62
<211> LENGTH: 37
<212> TYPE: DNA
<213> ORGANISM: Artificial
<220> FEATURE:
<223> OTHER INFORMATION: primer

<400> SEQUENCE: 62
gaacaagatg gattgcgcaa ccattatcac cgccaga    37

<210> SEQ ID NO 63
<211> LENGTH: 43
<212> TYPE: DNA
<213> ORGANISM: Artificial
<220> FEATURE:
<223> OTHER INFORMATION: primer

<400> SEQUENCE: 63
aatcatgtaa acgactcctt tttctgttgg gccattgcat tgc    43

<210> SEQ ID NO 64
<211> LENGTH: 79
<212> TYPE: DNA
<213> ORGANISM: Artificial
<220> FEATURE:
<223> OTHER INFORMATION: primer

<400> SEQUENCE: 64
aattattaat taaaatctac atcgatggtg caggggcagg cgctggtgcg ggtgccatgg    60
cgagcagtga gaacgtcat    79

<210> SEQ ID NO 65
<211> LENGTH: 49
<212> TYPE: DNA
<213> ORGANISM: Artificial
<220> FEATURE:
<223> OTHER INFORMATION: primer

<400> SEQUENCE: 65
aattattaat taaggagcaa tcaaaatgaa catcaagaac atcaacgcg    49

```
<210> SEQ ID NO 66
<211> LENGTH: 40
<212> TYPE: DNA
<213> ORGANISM: Artificial
<220> FEATURE:
<223> OTHER INFORMATION: primer

<400> SEQUENCE: 66
aattaatcga tatttttaag gtatggacaa ttaatggcgc                          40

<210> SEQ ID NO 67
<211> LENGTH: 34
<212> TYPE: DNA
<213> ORGANISM: Artificial
<220> FEATURE:
<223> OTHER INFORMATION: primer

<400> SEQUENCE: 67
aattattaat taaaaggaga aaaacggatg gctg                                34

<210> SEQ ID NO 68
<211> LENGTH: 37
<212> TYPE: DNA
<213> ORGANISM: Artificial
<220> FEATURE:
<223> OTHER INFORMATION: primer

<400> SEQUENCE: 68
aattaatcga ttgacaactt gacggctaca tcattca                             37

<210> SEQ ID NO 69
<211> LENGTH: 50
<212> TYPE: DNA
<213> ORGANISM: Artificial
<220> FEATURE:
<223> OTHER INFORMATION: primer

<400> SEQUENCE: 69
aattattaat taaggagtcg tttacatgat tgaacaagat ggattgcacg               50

<210> SEQ ID NO 70
<211> LENGTH: 35
<212> TYPE: DNA
<213> ORGANISM: Artificial
<220> FEATURE:
<223> OTHER INFORMATION: primer

<400> SEQUENCE: 70
aattaatcga tgaagaactc gtcaagaagg cgata                               35

<210> SEQ ID NO 71
<211> LENGTH: 36
<212> TYPE: DNA
<213> ORGANISM: Artificial
<220> FEATURE:
<223> OTHER INFORMATION: primer

<400> SEQUENCE: 71
aattatgaat tcatgcaaaa agacgcgctg aataac                              36

<210> SEQ ID NO 72
<211> LENGTH: 31
<212> TYPE: DNA
<213> ORGANISM: Artificial
<220> FEATURE:
<223> OTHER INFORMATION: primer
```

<400> SEQUENCE: 72
taattgagct cttaagccac gcgagccgtc a                              31

<210> SEQ ID NO 73
<211> LENGTH: 41
<212> TYPE: DNA
<213> ORGANISM: Artificial
<220> FEATURE:
<223> OTHER INFORMATION: primer

<400> SEQUENCE: 73
atcatatcta gaaggaggtt attcatgtcc tcacgtaaag a                   41

<210> SEQ ID NO 74
<211> LENGTH: 29
<212> TYPE: DNA
<213> ORGANISM: Artificial
<220> FEATURE:
<223> OTHER INFORMATION: primer

<400> SEQUENCE: 74
ttcgttgcat gcttacagca gttcttttg                                 29

<210> SEQ ID NO 75
<211> LENGTH: 46
<212> TYPE: DNA
<213> ORGANISM: Artificial
<220> FEATURE:
<223> OTHER INFORMATION: primer

<400> SEQUENCE: 75
aattaagagc tcttaattaa cggttaaata tgcaaagata aatgcg              46

<210> SEQ ID NO 76
<211> LENGTH: 34
<212> TYPE: DNA
<213> ORGANISM: Artificial
<220> FEATURE:
<223> OTHER INFORMATION: primer

<400> SEQUENCE: 76
aattaaacta gattatttct tcagttcagc cagg                           34

<210> SEQ ID NO 77
<211> LENGTH: 90
<212> TYPE: DNA
<213> ORGANISM: Artificial
<220> FEATURE:
<223> OTHER INFORMATION: primer

<400> SEQUENCE: 77
gagctcctga tggctagctc agtcctaggg attatgctag ccatatcgaa aggatagtct    60
tgataaccat aagtttaatt aagcggccgc                                    90

<210> SEQ ID NO 78
<211> LENGTH: 90
<212> TYPE: DNA
<213> ORGANISM: Artificial
<220> FEATURE:
<223> OTHER INFORMATION: primer

<400> SEQUENCE: 78
gcggccgctt aattaaactt atggttatca agactatcct ttcgatatgg ctagcataat    60
ccctaggact gagctagcca tcaggagctc                                    90

```
<210> SEQ ID NO 79
<211> LENGTH: 37
<212> TYPE: DNA
<213> ORGANISM: Artificial
<220> FEATURE:
<223> OTHER INFORMATION: primer

<400> SEQUENCE: 79
ataattgaat tcccaggcat caaataaaac gaaaggc                              37

<210> SEQ ID NO 80
<211> LENGTH: 37
<212> TYPE: DNA
<213> ORGANISM: Artificial
<220> FEATURE:
<223> OTHER INFORMATION: primer

<400> SEQUENCE: 80
cgaattgggt acctataaac gcagaaaggc ccacccg                              37

<210> SEQ ID NO 81
<211> LENGTH: 33
<212> TYPE: DNA
<213> ORGANISM: Artificial
<220> FEATURE:
<223> OTHER INFORMATION: primer

<400> SEQUENCE: 81
aatcatttaa ttaaacggct cgcgtggctt aag                                  33

<210> SEQ ID NO 82
<211> LENGTH: 34
<212> TYPE: DNA
<213> ORGANISM: Artificial
<220> FEATURE:
<223> OTHER INFORMATION: primer

<400> SEQUENCE: 82
aattaagaat tcttactggc gattgtcatt cgcc                                 34

<210> SEQ ID NO 83
<211> LENGTH: 19
<212> TYPE: DNA
<213> ORGANISM: Artificial
<220> FEATURE:
<223> OTHER INFORMATION: primer

<400> SEQUENCE: 83
tttggcctcg cgtcgtgca                                                  19

<210> SEQ ID NO 84
<211> LENGTH: 19
<212> TYPE: DNA
<213> ORGANISM: Artificial
<220> FEATURE:
<223> OTHER INFORMATION: primer

<400> SEQUENCE: 84
atagatgcct cgcgctccg                                                  19

<210> SEQ ID NO 85
<211> LENGTH: 24
<212> TYPE: DNA
<213> ORGANISM: Artificial
<220> FEATURE:
```

<223> OTHER INFORMATION: primer

<400> SEQUENCE: 85
tgcagcgttt tcagagtgaa agcc 24

<210> SEQ ID NO 86
<211> LENGTH: 22
<212> TYPE: DNA
<213> ORGANISM: Artificial
<220> FEATURE:
<223> OTHER INFORMATION: primer

<400> SEQUENCE: 86
cgtaatcgcc gaaccagtgc tc 22

<210> SEQ ID NO 87
<211> LENGTH: 43
<212> TYPE: DNA
<213> ORGANISM: Artificial
<220> FEATURE:
<223> OTHER INFORMATION: primer

<400> SEQUENCE: 87
ttaattaaag gagaaaaaat gaattatcag aacgacgatt tac 43

<210> SEQ ID NO 88
<211> LENGTH: 25
<212> TYPE: DNA
<213> ORGANISM: Artificial
<220> FEATURE:
<223> OTHER INFORMATION: primer

<400> SEQUENCE: 88
gaattcttac ccgcgacgcg ctttt 25

<210> SEQ ID NO 89
<211> LENGTH: 34
<212> TYPE: DNA
<213> ORGANISM: Artificial
<220> FEATURE:
<223> OTHER INFORMATION: primer

<400> SEQUENCE: 89
aattaattaa ttaagactct cgcaatatct tatg 34

<210> SEQ ID NO 90
<211> LENGTH: 33
<212> TYPE: DNA
<213> ORGANISM: Artificial
<220> FEATURE:
<223> OTHER INFORMATION: primer

<400> SEQUENCE: 90
aattaagaat tcttagttgc tttccagcat gtg 33

<210> SEQ ID NO 91
<211> LENGTH: 43
<212> TYPE: DNA
<213> ORGANISM: Artificial
<220> FEATURE:
<223> OTHER INFORMATION: primer

<400> SEQUENCE: 91
ttaattaagg agaaaaaaat gaccgtcttt aagcatattg cca 43

-continued

<210> SEQ ID NO 92
<211> LENGTH: 34
<212> TYPE: DNA
<213> ORGANISM: Artificial
<220> FEATURE:
<223> OTHER INFORMATION: primer

<400> SEQUENCE: 92
gaattcttaa gggtgaatat cgtggtctgt tttt         34

<210> SEQ ID NO 93
<211> LENGTH: 25
<212> TYPE: DNA
<213> ORGANISM: Artificial
<220> FEATURE:
<223> OTHER INFORMATION: primer

<400> SEQUENCE: 93
aatatgatca ccccacaata tctcg                   25

<210> SEQ ID NO 94
<211> LENGTH: 19
<212> TYPE: DNA
<213> ORGANISM: Artificial
<220> FEATURE:
<223> OTHER INFORMATION: primer

<400> SEQUENCE: 94
gagaaactca cctgccgct                          19

<210> SEQ ID NO 95
<211> LENGTH: 29
<212> TYPE: DNA
<213> ORGANISM: Artificial
<220> FEATURE:
<223> OTHER INFORMATION: primer

<400> SEQUENCE: 95
aattaaacta gtctgatggc tagctcagt               29

<210> SEQ ID NO 96
<211> LENGTH: 42
<212> TYPE: DNA
<213> ORGANISM: Artificial
<220> FEATURE:
<223> OTHER INFORMATION: primer

<400> SEQUENCE: 96
attaatgagc tcataatttc tagatataaa cgcagaaagg cc    42

<210> SEQ ID NO 97
<211> LENGTH: 28
<212> TYPE: DNA
<213> ORGANISM: Artificial
<220> FEATURE:
<223> OTHER INFORMATION: primer

<400> SEQUENCE: 97
agtcttttgt gcaaccatta tcaccgcc                28

<210> SEQ ID NO 98
<211> LENGTH: 32
<212> TYPE: DNA
<213> ORGANISM: Artificial
<220> FEATURE:
<223> OTHER INFORMATION: primer -continued

<400> SEQUENCE: 98
tccagacgca ttttctgttg ggccattgca tt                32

<210> SEQ ID NO 99
<211> LENGTH: 30
<212> TYPE: DNA
<213> ORGANISM: Artificial
<220> FEATURE:
<223> OTHER INFORMATION: primer

<400> SEQUENCE: 99
tattccgcat tggcaaccat tatcaccgcc                30

<210> SEQ ID NO 100
<211> LENGTH: 30
<212> TYPE: DNA
<213> ORGANISM: Artificial
<220> FEATURE:
<223> OTHER INFORMATION: primer

<400> SEQUENCE: 100
ttgttcgttc attttctgtt gggccattgc                30

<210> SEQ ID NO 101
<211> LENGTH: 30
<212> TYPE: DNA
<213> ORGANISM: Artificial
<220> FEATURE:
<223> OTHER INFORMATION: primer

<400> SEQUENCE: 101
actcgtcgag ttgcaaccat tatcaccgcc                30

<210> SEQ ID NO 102
<211> LENGTH: 30
<212> TYPE: DNA
<213> ORGANISM: Artificial
<220> FEATURE:
<223> OTHER INFORMATION: primer

<400> SEQUENCE: 102
cagaatcagc attttctgtt gggccattgc                30

<210> SEQ ID NO 103
<211> LENGTH: 30
<212> TYPE: DNA
<213> ORGANISM: Artificial
<220> FEATURE:
<223> OTHER INFORMATION: primer

<400> SEQUENCE: 103
aatccaacgc aggcaaccat tatcaccgcc                30

<210> SEQ ID NO 104
<211> LENGTH: 30
<212> TYPE: DNA
<213> ORGANISM: Artificial
<220> FEATURE:
<223> OTHER INFORMATION: primer

<400> SEQUENCE: 104 gatgttttc attttctgtt gggccattgc                 30

<210> SEQ ID NO 105
<211> LENGTH: 35

```
<212> TYPE: DNA
<213> ORGANISM: Artificial
<220> FEATURE:
<223> OTHER INFORMATION: primer

<400> SEQUENCE: 105
taatttacta gtatggctga agcgcaaaat gatcc                                    35

<210> SEQ ID NO 106
<211> LENGTH: 30
<212> TYPE: DNA
<213> ORGANISM: Artificial
<220> FEATURE:
<223> OTHER INFORMATION: primer

<400> SEQUENCE: 106
aattaaacta gttaacaccg tgcgtgttga                                          30

<210> SEQ ID NO 107
<211> LENGTH: 32
<212> TYPE: DNA
<213> ORGANISM: Artificial
<220> FEATURE:
<223> OTHER INFORMATION: primer

<400> SEQUENCE: 107
aattaagcta gctataaacg cagaaaggcc ca                                       32

<210> SEQ ID NO 108
<211> LENGTH: 29
<212> TYPE: DNA
<213> ORGANISM: Artificial
<220> FEATURE:
<223> OTHER INFORMATION: primer

<400> SEQUENCE: 108
atccaacgca ggcaaccatt atcaccgcc                                           29

<210> SEQ ID NO 109
<211> LENGTH: 28
<212> TYPE: DNA
<213> ORGANISM: Artificial
<220> FEATURE:
<223> OTHER INFORMATION: primer

<400> SEQUENCE: 109
tccaacgcag gcaaccatta tcaccgcc                                            28

<210> SEQ ID NO 110
<211> LENGTH: 43
<212> TYPE: DNA
<213> ORGANISM: Artificial
<220> FEATURE:
<223> OTHER INFORMATION: primer

<400> SEQUENCE: 110
aattattaat taaacaattc tcaaaatcag aagagtattg cta                           43

<210> SEQ ID NO 111
<211> LENGTH: 31
<212> TYPE: DNA
<213> ORGANISM: Artificial
<220> FEATURE:
<223> OTHER INFORMATION: primer

<400> SEQUENCE: 111
```
aattactcga gcagcatctg atcgtcgaag g            31

<210> SEQ ID NO 112
<211> LENGTH: 43
<212> TYPE: DNA
<213> ORGANISM: Artificial
<220> FEATURE:
<223> OTHER INFORMATION: primer

<400> SEQUENCE: 112
aattattaat taataattgt tcttttttca ggtgaaggtt ccc            43

<210> SEQ ID NO 113
<211> LENGTH: 34
<212> TYPE: DNA
<213> ORGANISM: Artificial
<220> FEATURE:
<223> OTHER INFORMATION: primer

<400> SEQUENCE: 113
aattactcga gaccgcgtaa atcaatgcct ctta            34

<210> SEQ ID NO 114
<211> LENGTH: 40
<212> TYPE: DNA
<213> ORGANISM: Artificial
<220> FEATURE:
<223> OTHER INFORMATION: primer

<400> SEQUENCE: 114
aattattaat taactctttt aatctttcaa ggagcaaaga            40

<210> SEQ ID NO 115
<211> LENGTH: 32
<212> TYPE: DNA
<213> ORGANISM: Artificial
<220> FEATURE:
<223> OTHER INFORMATION: primer

<400> SEQUENCE: 115
aattactcga gacgctggta gatctcttca cg            32

<210> SEQ ID NO 116
<211> LENGTH: 37
<212> TYPE: DNA
<213> ORGANISM: Artificial
<220> FEATURE:
<223> OTHER INFORMATION: primer

<400> SEQUENCE: 116
aattattaat taaataagat ggggtgtctg gggtaat            37

<210> SEQ ID NO 117
<211> LENGTH: 31
<212> TYPE: DNA
<213> ORGANISM: Artificial
<220> FEATURE:
<223> OTHER INFORMATION: primer

<400> SEQUENCE: 117
aattactcga gatcattgcc agcgcgtgaa g            31

<210> SEQ ID NO 118
<211> LENGTH: 90
<212> TYPE: DNA
<213> ORGANISM: Artificial

```
<220> FEATURE:
<223> OTHER INFORMATION: primer

<400> SEQUENCE: 118
gagctcttgg tgcaaaacct ttcgcggtat ggcatgatag cgccaagcac atatcgaaag    60
gatagtcttg ataaccataa gtttaattaa                                     90

<210> SEQ ID NO 119
<211> LENGTH: 89
<212> TYPE: DNA
<213> ORGANISM: Artificial
<220> FEATURE:
<223> OTHER INFORMATION: primer

<400> SEQUENCE: 119
ttaattaaac tttatggttat caagactatc ctttcgatat gtgcttggcg ctatcatgcc    60
ataccgcgaa aggttttgca ccagagctc                                      89

<210> SEQ ID NO 120
<211> LENGTH: 48
<212> TYPE: DNA
<213> ORGANISM: Artificial
<220> FEATURE:
<223> OTHER INFORMATION: primer

<400> SEQUENCE: 120
ttaattaaag gagaaagatt atgagaaact atcctgcaga accttata                 48

<210> SEQ ID NO 121
<211> LENGTH: 53
<212> TYPE: DNA
<213> ORGANISM: Artificial
<220> FEATURE:
<223> OTHER INFORMATION: primer

<400> SEQUENCE: 121
gaattcttaa tggtgatgat ggtgatgcgc ttacgctttc ggttcaaaac gcg           53

<210> SEQ ID NO 122
<211> LENGTH: 30
<212> TYPE: DNA
<213> ORGANISM: Artificial
<220> FEATURE:
<223> OTHER INFORMATION: primer

<400> SEQUENCE: 122
cattaactag ttggtgcaaa acctttcgcg                                     30

<210> SEQ ID NO 123
<211> LENGTH: 30
<212> TYPE: DNA
<213> ORGANISM: Artificial
<220> FEATURE:
<223> OTHER INFORMATION: primer

<400> SEQUENCE: 123
aaagcaaaac tcgcaaccat tatcaccgcc                                     30

<210> SEQ ID NO 124
<211> LENGTH: 34
<212> TYPE: DNA
<213> ORGANISM: Artificial
<220> FEATURE:
<223> OTHER INFORMATION: primer
```

```
<400> SEQUENCE: 124
tgtatcagcc attttctgtt gggccattgc attg                                34

<210> SEQ ID NO 125
<211> LENGTH: 30
<212> TYPE: DNA
<213> ORGANISM: Artificial
<220> FEATURE:
<223> OTHER INFORMATION: primer

<400> SEQUENCE: 125
acaggccacc atgcaaccat tatcaccgcc                                     30

<210> SEQ ID NO 126
<211> LENGTH: 33
<212> TYPE: DNA
<213> ORGANISM: Artificial
<220> FEATURE:
<223> OTHER INFORMATION: primer

<400> SEQUENCE: 126
ttacgcgtca ttttctgttg ggccattgca ttg                                 33

<210> SEQ ID NO 127
<211> LENGTH: 30
<212> TYPE: DNA
<213> ORGANISM: Artificial
<220> FEATURE:
<223> OTHER INFORMATION: primer

<400> SEQUENCE: 127
aatttgcgcg acgcaaccat tatcaccgcc                                     30

<210> SEQ ID NO 128
<211> LENGTH: 34
<212> TYPE: DNA
<213> ORGANISM: Artificial
<220> FEATURE:
<223> OTHER INFORMATION: primer

<400> SEQUENCE: 128
acgatctgcc actttctgtt gggccattgc attg                                34

<210> SEQ ID NO 129
<211> LENGTH: 30
<212> TYPE: DNA
<213> ORGANISM: Artificial
<220> FEATURE:
<223> OTHER INFORMATION: primer

<400> SEQUENCE: 129
aacccttagc cagcaaccat tatcaccgcc                                     30

<210> SEQ ID NO 130
<211> LENGTH: 33
<212> TYPE: DNA
<213> ORGANISM: Artificial
<220> FEATURE:
<223> OTHER INFORMATION: primer

<400> SEQUENCE: 130
acgctaatca ttttctgttg ggccattgca ttg                                 33

<210> SEQ ID NO 131
<211> LENGTH: 30
```

<212> TYPE: DNA
<213> ORGANISM: Artificial
<220> FEATURE:
<223> OTHER INFORMATION: primer

<400> SEQUENCE: 131
aagttcggcg gtgcaaccat tatcaccgcc                                      30

<210> SEQ ID NO 132
<211> LENGTH: 34
<212> TYPE: DNA
<213> ORGANISM: Artificial
<220> FEATURE:
<223> OTHER INFORMATION: primer

<400> SEQUENCE: 132
caacactcgc attttctgtt gggccattgc attg                                 34

<210> SEQ ID NO 133
<211> LENGTH: 30
<212> TYPE: DNA
<213> ORGANISM: Artificial
<220> FEATURE:
<223> OTHER INFORMATION: primer

<400> SEQUENCE: 133
tatgccccgg ctgcaaccat tatcaccgcc                                      30

<210> SEQ ID NO 134
<211> LENGTH: 34
<212> TYPE: DNA
<213> ORGANISM: Artificial
<220> FEATURE:
<223> OTHER INFORMATION: primer

<400> SEQUENCE: 134
aactttaacc attttctgtt gggccattgc attg                                 34

<210> SEQ ID NO 135
<211> LENGTH: 30
<212> TYPE: DNA
<213> ORGANISM: Artificial
<220> FEATURE:
<223> OTHER INFORMATION: primer

<400> SEQUENCE: 135
aatctgaaag atgcaaccat tatcaccgcc                                      30

<210> SEQ ID NO 136
<211> LENGTH: 34
<212> TYPE: DNA
<213> ORGANISM: Artificial
<220> FEATURE:
<223> OTHER INFORMATION: primer

<400> SEQUENCE: 136
gtagagtttc attttctgtt gggccattgc attg                                 34

<210> SEQ ID NO 137
<211> LENGTH: 30
<212> TYPE: DNA
<213> ORGANISM: Artificial
<220> FEATURE:
<223> OTHER INFORMATION: primer

<400> SEQUENCE: 137
agcaccacca ttgcaaccat tatcaccgcc        30

<210> SEQ ID NO 138
<211> LENGTH: 34
<212> TYPE: DNA
<213> ORGANISM: Artificial
<220> FEATURE:
<223> OTHER INFORMATION: primer

<400> SEQUENCE: 138
aatgcgtttc attttctgtt gggccattgc attg        34

<210> SEQ ID NO 139
<211> LENGTH: 227
<212> TYPE: DNA
<213> ORGANISM: Artificial
<220> FEATURE:
<223> OTHER INFORMATION: SgrS

<400> SEQUENCE: 139
gatgaagcaa gggggtgccc catgcgtcag ttttatcagc actattttac cgcgacagcg        60
aagttgtgct ggttgcgttg gttaagcgtc ccacaacgat taaccatgct tgaaggactg        120
atgcagtggg atgaccgcaa ttctgaaagt tgacttgcct gcatcatgtg tgactgagta        180
ttggtgtaaa atcacccgcc agcagattat acctgctggt tttttttt        227

<210> SEQ ID NO 140
<211> LENGTH: 115
<212> TYPE: DNA
<213> ORGANISM: Artificial
<220> FEATURE:
<223> OTHER INFORMATION: MicC

<400> SEQUENCE: 140
gttatatgcc tttattgtca cagattttat tttctgttgg gccattgcat tgccactgat        60
tttccaacat ataaaaagac aagcccgaac agtcgtccgg gctttttttc tcgag        115

<210> SEQ ID NO 141
<211> LENGTH: 93
<212> TYPE: DNA
<213> ORGANISM: Artificial
<220> FEATURE:
<223> OTHER INFORMATION: MicF

<400> SEQUENCE: 141
gctatcatca ttaactttat ttattaccgt cattcatttc tgaatgtctg tttaccccta        60
tttcaaccgg atgcctcgca ttcggttttt ttt        93

<210> SEQ ID NO 142
<211> LENGTH: 60
<212> TYPE: DNA
<213> ORGANISM: Artificial
<220> FEATURE:
<223> OTHER INFORMATION: DsRed2 mRNA fragment

<400> SEQUENCE: 142
ttattaatta aaggaggaca aatatatggc gagcagtgag aacgtcatca ccgagttcat        60

<210> SEQ ID NO 143
<211> LENGTH: 38
<212> TYPE: DNA
<213> ORGANISM: Artificial
<220> FEATURE:
<223> OTHER INFORMATION: Anti-DsRed2

<400> SEQUENCE: 143
atgacgttct cactgctcgc catatatttg tcctcctt                    38

<210> SEQ ID NO 144
<211> LENGTH: 86
<212> TYPE: DNA
<213> ORGANISM: Artificial
<220> FEATURE:
<223> OTHER INFORMATION: DsRed2 mRNA fragment

<400> SEQUENCE: 144
aaggaggaca aatatatggc gagcagtgag aacgtcatca ccgagttcat gcgcttcaag    60
gtgcgcatgg agggcaccgt gaacgg                                  86

<210> SEQ ID NO 145
<211> LENGTH: 28
<212> TYPE: DNA
<213> ORGANISM: Artificial
<220> FEATURE:
<223> OTHER INFORMATION: DsRed2 mRNA fragment

<400> SEQUENCE: 145
ccgacatccc cgactacaag aagctgtc                               28

<210> SEQ ID NO 146
<211> LENGTH: 38
<212> TYPE: DNA
<213> ORGANISM: Artificial
<220> FEATURE:
<223> OTHER INFORMATION: basepairing region A

<400> SEQUENCE: 146
atgacgttct cactgctcgc catatatttg tcctcctt                    38

<210> SEQ ID NO 147
<211> LENGTH: 32
<212> TYPE: DNA
<213> ORGANISM: Artificial
<220> FEATURE:
<223> OTHER INFORMATION: basepairing region B1

<400> SEQUENCE: 147
atgacgttct cactgctcgc catatatttg tc                          32

<210> SEQ ID NO 148
<211> LENGTH: 38
<212> TYPE: DNA
<213> ORGANISM: Artificial
<220> FEATURE:
<223> OTHER INFORMATION: basepairing region B2

<400> SEQUENCE: 148
tcggtgatga cgttctcact gctcgccata tatttgtc                    38

<210> SEQ ID NO 149
<211> LENGTH: 20
<212> TYPE: DNA
<213> ORGANISM: Artificial
<220> FEATURE:
<223> OTHER INFORMATION: basepairing region C1

<400> SEQUENCE: 149
atgacgttct cactgctcgc                                        20

<210> SEQ ID NO 150
<211> LENGTH: 38
<212> TYPE: DNA
<213> ORGANISM: Artificial
<220> FEATURE:
<223> OTHER INFORMATION: basepairing region C2

<400> SEQUENCE: 150
aagcgcatga actcggtgat gacgttctca ctgctcgc        38

<210> SEQ ID NO 151
<211> LENGTH: 19
<212> TYPE: DNA
<213> ORGANISM: Artificial
<220> FEATURE:
<223> OTHER INFORMATION: basepairing region D1

<400> SEQUENCE: 151
aactcggtga tgacgttct        19

<210> SEQ ID NO 152
<211> LENGTH: 37
<212> TYPE: DNA
<213> ORGANISM: Artificial
<220> FEATURE:
<223> OTHER INFORMATION: basepairing region D2

<400> SEQUENCE: 152
cgcaccttga agcgcatgaa ctcggtgatg acgttct        37

<210> SEQ ID NO 153
<211> LENGTH: 19
<212> TYPE: DNA
<213> ORGANISM: Artificial
<220> FEATURE:
<223> OTHER INFORMATION: basepairing region E1

<400> SEQUENCE: 153
aagcgcatga actcggtga        19

<210> SEQ ID NO 154
<211> LENGTH: 37
<212> TYPE: DNA
<213> ORGANISM: Artificial
<220> FEATURE:
<223> OTHER INFORMATION: basepairing region E2

<400> SEQUENCE: 154
ccctccatgc gcaccttgaa gcgcatgaac tcggtga        37

<210> SEQ ID NO 155
<211> LENGTH: 19
<212> TYPE: DNA
<213> ORGANISM: Artificial
<220> FEATURE:
<223> OTHER INFORMATION: GCGCACCTTGAAGCGCATG

<400> SEQUENCE: 155
gcgcaccttg aagcgcatg        19

<210> SEQ ID NO 156
<211> LENGTH: 37
<212> TYPE: DNA
<213> ORGANISM: Artificial
<220> FEATURE:
<223> OTHER INFORMATION: basepairing region F2

```
<400> SEQUENCE: 156
gttcacggtg ccctccatgc gcaccttgaa gcgcatg                              37

<210> SEQ ID NO 157
<211> LENGTH: 24
<212> TYPE: DNA
<213> ORGANISM: Artificial
<220> FEATURE:
<223> OTHER INFORMATION: basepairing region G1

<400> SEQUENCE: 157
gcttcttgta gtcggggatg tcgg                                           24

<210> SEQ ID NO 158
<211> LENGTH: 23
<212> TYPE: DNA
<213> ORGANISM: Artificial
<220> FEATURE:
<223> OTHER INFORMATION: basepairing region G2

<400> SEQUENCE: 158
gacagcttct tgtagtcggg gat                                            23

<210> SEQ ID NO 159
<211> LENGTH: 55
<212> TYPE: DNA
<213> ORGANISM: Artificial
<220> FEATURE:
<223> OTHER INFORMATION: AraC mRNA

<400> SEQUENCE: 159
ttaattaaaa ggagaaaaac ggatggctga agcgcaaaat gatcccctgc tgccg         55

<210> SEQ ID NO 160
<211> LENGTH: 36
<212> TYPE: DNA
<213> ORGANISM: Artificial
<220> FEATURE:
<223> OTHER INFORMATION: Anti-AraC

<400> SEQUENCE: 160
gatcattttg cgcttcagcc atccgttttt ctcctt                              36

<210> SEQ ID NO 161
<211> LENGTH: 55
<212> TYPE: DNA
<213> ORGANISM: Artificial
<220> FEATURE:
<223> OTHER INFORMATION: LuxR mRNA

<400> SEQUENCE: 161
ttaattaaaa ggagcaatca aaatgaacat caagaacatc aacgcgaacg agaag         55

<210> SEQ ID NO 162
<211> LENGTH: 36
<212> TYPE: DNA
<213> ORGANISM: Artificial
<220> FEATURE:
<223> OTHER INFORMATION: Anti-LuxR

<400> SEQUENCE: 162
cgttgatgtt cttgatgttc attttgattg ctcctt                              36

<210> SEQ ID NO 163
```

```
<211> LENGTH: 55
<212> TYPE: DNA
<213> ORGANISM: Artificial
<220> FEATURE:
<223> OTHER INFORMATION: KanR mRNA

<400> SEQUENCE: 163
ttttaattaa ggagtcgttt acatgattga acaagatgga ttgcacgcag gttct            55

<210> SEQ ID NO 164
<211> LENGTH: 36
<212> TYPE: DNA
<213> ORGANISM: Artificial
<220> FEATURE:
<223> OTHER INFORMATION: Anti-KanR

<400> SEQUENCE: 164
gcaatccatc ttgttcaatc atgtaaacga ctcctt                                 36

<210> SEQ ID NO 165
<211> LENGTH: 24
<212> TYPE: DNA
<213> ORGANISM: Artificial
<220> FEATURE:
<223> OTHER INFORMATION: pgi mRNA

<400> SEQUENCE: 165
atgaaaaaca tcaatccaac gcag                                              24

<210> SEQ ID NO 166
<211> LENGTH: 24
<212> TYPE: DNA
<213> ORGANISM: Artificial
<220> FEATURE:
<223> OTHER INFORMATION: sRNA(anti-pgi)

<400> SEQUENCE: 166
ctgcgttgga ttgatgtttt tcat                                              24

<210> SEQ ID NO 167
<211> LENGTH: 23
<212> TYPE: DNA
<213> ORGANISM: Artificial
<220> FEATURE:
<223> OTHER INFORMATION: sRNA(anti-pgi-D1)

<400> SEQUENCE: 167
ctgcgttgga tgatgttttt cat                                               23

<210> SEQ ID NO 168
<211> LENGTH: 22
<212> TYPE: DNA
<213> ORGANISM: Artificial
<220> FEATURE:
<223> OTHER INFORMATION: sRNA(anti-pgi-D2)

<400> SEQUENCE: 168
ctgcgttgga gatgttttc at                                                 22

<210> SEQ ID NO 169
<211> LENGTH: 35
<212> TYPE: DNA
<213> ORGANISM: Artificial
<220> FEATURE:
<223> OTHER INFORMATION: Anti-dsRed2 variants
<220> FEATURE:
<221> NAME/KEY: misc_feature
```

```
<222> LOCATION: (1)..(16)
<223> OTHER INFORMATION: n is a, c, g, or t

<400> SEQUENCE: 169
nnnnnnnnnn nnnnnngcaa ccattatcac cgcca                              35

<210> SEQ ID NO 170
<211> LENGTH: 35
<212> TYPE: DNA
<213> ORGANISM: Artificial
<220> FEATURE:
<223> OTHER INFORMATION: Anti-dsRed2 variants
<220> FEATURE:
<221> NAME/KEY: misc_feature
<222> LOCATION: (1)..(16)
<223> OTHER INFORMATION: n is a, c, g, or t

<400> SEQUENCE: 170
nnnnnnnnnn nnnnnngcaa ccattatcac cgcca                              35

<210> SEQ ID NO 171
<211> LENGTH: 33
<212> TYPE: DNA
<213> ORGANISM: Artificial
<220> FEATURE:
<223> OTHER INFORMATION: Anti-LacZ forward primer

<400> SEQUENCE: 171
atgatgcaac cattatcacc gccagaggta aaa                                33

<210> SEQ ID NO 172
<211> LENGTH: 32
<212> TYPE: DNA
<213> ORGANISM: Artificial
<220> FEATURE:
<223> OTHER INFORMATION: Anti-LacZ reverse primer

<400> SEQUENCE: 172
ggtcattttc tgttgggcca ttgcattgcc ac                                 32

<210> SEQ ID NO 173
<211> LENGTH: 34
<212> TYPE: DNA
<213> ORGANISM: Artificial
<220> FEATURE:
<223> OTHER INFORMATION: Anti-LacZ forward primer

<400> SEQUENCE: 173
atgattgcaa ccattatcac cgccagaggt aaaa                               34

<210> SEQ ID NO 174
<211> LENGTH: 32
<212> TYPE: DNA
<213> ORGANISM: Artificial
<220> FEATURE:
<223> OTHER INFORMATION: Anti-LacZ reverse primer

<400> SEQUENCE: 174
ggtcattttc tgttgggcca ttgcattgcc ac                                 32

<210> SEQ ID NO 175
<211> LENGTH: 34
<212> TYPE: DNA
<213> ORGANISM: Artificial
<220> FEATURE:
<223> OTHER INFORMATION: Anti-LacZ forward primer
```

<400> SEQUENCE: 175
tgattagcaa ccattatcac cgccagaggt aaaa                                34

<210> SEQ ID NO 176
<211> LENGTH: 33
<212> TYPE: DNA
<213> ORGANISM: Artificial
<220> FEATURE:
<223> OTHER INFORMATION: Anti-LacZ reverse primer

<400> SEQUENCE: 176
tggtcatttt ctgttgggcc attgcattgc cac                                 33

<210> SEQ ID NO 177
<211> LENGTH: 35
<212> TYPE: DNA
<213> ORGANISM: Artificial
<220> FEATURE:
<223> OTHER INFORMATION: Anti-LacZ forward primer

<400> SEQUENCE: 177
tgattacgca accattatca ccgccagagg taaaa                               35

<210> SEQ ID NO 178
<211> LENGTH: 33
<212> TYPE: DNA
<213> ORGANISM: Artificial
<220> FEATURE:
<223> OTHER INFORMATION: Anti-LacZ reverse primer

<400> SEQUENCE: 178
tggtcatttt ctgttgggcc attgcattgc cac                                 33

<210> SEQ ID NO 179
<211> LENGTH: 35
<212> TYPE: DNA
<213> ORGANISM: Artificial
<220> FEATURE:
<223> OTHER INFORMATION: Anti-LacZ forward primer

<400> SEQUENCE: 179
gattacggca accattatca ccgccagagg taaaa                               35

<210> SEQ ID NO 180
<211> LENGTH: 34
<212> TYPE: DNA
<213> ORGANISM: Artificial
<220> FEATURE:
<223> OTHER INFORMATION: Anti-LacZ reverse primer

<400> SEQUENCE: 180
atggtcattt tctgttgggc cattgcattg ccac                                34

<210> SEQ ID NO 181
<211> LENGTH: 36
<212> TYPE: DNA
<213> ORGANISM: Artificial
<220> FEATURE:
<223> OTHER INFORMATION: Anti-LacZ forward primer

<400> SEQUENCE: 181
gattacgggc aaccattatc accgccagag gtaaaa                              36

<210> SEQ ID NO 182
<211> LENGTH: 34

```
<212> TYPE: DNA
<213> ORGANISM: Artificial
<220> FEATURE:
<223> OTHER INFORMATION: Anti-LacZ reverse primer

<400> SEQUENCE: 182
atggtcattt tctgttgggc cattgcattg ccac                                   34

<210> SEQ ID NO 183
<211> LENGTH: 36
<212> TYPE: DNA
<213> ORGANISM: Artificial
<220> FEATURE:
<223> OTHER INFORMATION: Anti-LacZ forward primer

<400> SEQUENCE: 183
attacggagc aaccattatc accgccagag gtaaaa                                 36

<210> SEQ ID NO 184
<211> LENGTH: 35
<212> TYPE: DNA
<213> ORGANISM: Artificial
<220> FEATURE:
<223> OTHER INFORMATION: Anti-LacZ reverse primer

<400> SEQUENCE: 184
catggtcatt ttctgttggg ccattgcatt gccac                                  35

<210> SEQ ID NO 185
<211> LENGTH: 37
<212> TYPE: DNA
<213> ORGANISM: Artificial
<220> FEATURE:
<223> OTHER INFORMATION: Anti-LacZ forward primer

<400> SEQUENCE: 185
ttacggattg caaccattat caccgccaga ggtaaaa                                37

<210> SEQ ID NO 186
<211> LENGTH: 36
<212> TYPE: DNA
<213> ORGANISM: Artificial
<220> FEATURE:
<223> OTHER INFORMATION: Anti-LacZ reverse primer

<400> SEQUENCE: 186
tcatggtcat tttctgttgg gccattgcat tgccac                                 36

<210> SEQ ID NO 187
<211> LENGTH: 38
<212> TYPE: DNA
<213> ORGANISM: Artificial
<220> FEATURE:
<223> OTHER INFORMATION: Anti-LacZ forward primer

<400> SEQUENCE: 187
ttacggattc gcaaccatta tcaccgccag aggtaaaa                               38

<210> SEQ ID NO 188
<211> LENGTH: 36
<212> TYPE: DNA
<213> ORGANISM: Artificial
<220> FEATURE:
<223> OTHER INFORMATION: Anti-LacZ reverse primer

<400> SEQUENCE: 188
```
tcatggtcat tttctgttgg gccattgcat tgccac                      36

<210> SEQ ID NO 189
<211> LENGTH: 38
<212> TYPE: DNA
<213> ORGANISM: Artificial
<220> FEATURE:
<223> OTHER INFORMATION: Anti-LacZ forward primer

<400> SEQUENCE: 189
tacggattca gcaaccatta tcaccgccag aggtaaaa                    38

<210> SEQ ID NO 190
<211> LENGTH: 37
<212> TYPE: DNA
<213> ORGANISM: Artificial
<220> FEATURE:
<223> OTHER INFORMATION: Anti-LacZ reverse primer

<400> SEQUENCE: 190
atcatggtca ttttctgttg ggccattgca ttgccac                     37

<210> SEQ ID NO 191
<211> LENGTH: 39
<212> TYPE: DNA
<213> ORGANISM: Artificial
<220> FEATURE:
<223> OTHER INFORMATION: Anti-LacZ forward primer

<400> SEQUENCE: 191
tacggattca cgcaaccatt atcaccgcca gaggtaaaa                   39

<210> SEQ ID NO 192
<211> LENGTH: 37
<212> TYPE: DNA
<213> ORGANISM: Artificial
<220> FEATURE:
<223> OTHER INFORMATION: Anti-LacZ reverse primer

<400> SEQUENCE: 192
atcatggtca ttttctgttg ggccattgca ttgccac                     37

<210> SEQ ID NO 193
<211> LENGTH: 40
<212> TYPE: DNA
<213> ORGANISM: Artificial
<220> FEATURE:
<223> OTHER INFORMATION: Anti-LacZ forward primer

<400> SEQUENCE: 193
acggattcac tggcaaccat tatcaccgcc agaggtaaaa                  40

<210> SEQ ID NO 194
<211> LENGTH: 38
<212> TYPE: DNA
<213> ORGANISM: Artificial
<220> FEATURE:
<223> OTHER INFORMATION: Anti-LacZ reverse primer

<400> SEQUENCE: 194
aatcatggtc attttctgtt gggccattgc attgccac                    38

<210> SEQ ID NO 195
<211> LENGTH: 42
<212> TYPE: DNA
<213> ORGANISM: Artificial

```
<220> FEATURE:
<223> OTHER INFORMATION: Anti-LacZ forward primer

<400> SEQUENCE: 195
ggattcactg gccggcaacc attatcaccg ccagaggtaa aa                              42

<210> SEQ ID NO 196
<211> LENGTH: 40
<212> TYPE: DNA
<213> ORGANISM: Artificial
<220> FEATURE:
<223> OTHER INFORMATION: Anti-LacZ reverse primer

<400> SEQUENCE: 196
gtaatcatgg tcattttctg ttgggccatt gcattgccac                                40

<210> SEQ ID NO 197
<211> LENGTH: 30
<212> TYPE: DNA
<213> ORGANISM: Artificial
<220> FEATURE:
<223> OTHER INFORMATION: Rmo primer

<400> SEQUENCE: 197
aattaaagat cttaacaccg tgcgtgttga                                            30

<210> SEQ ID NO 198
<211> LENGTH: 26
<212> TYPE: DNA
<213> ORGANISM: Artificial
<220> FEATURE:
<223> OTHER INFORMATION: Rmo primer

<400> SEQUENCE: 198
gagctctata aacgcagaaa ggccca                                               26

<210> SEQ ID NO 199
<211> LENGTH: 24
<212> TYPE: DNA
<213> ORGANISM: Artificial
<220> FEATURE:
<223> OTHER INFORMATION: Rmo primer

<400> SEQUENCE: 199
actagttaac accgtgcgtg ttga                                                 24

<210> SEQ ID NO 200
<211> LENGTH: 26
<212> TYPE: DNA
<213> ORGANISM: Artificial
<220> FEATURE:
<223> OTHER INFORMATION: Rmo primer

<400> SEQUENCE: 200
ggatcctata aacgcagaaa ggccca                                               26

<210> SEQ ID NO 201
<211> LENGTH: 24
<212> TYPE: DNA
<213> ORGANISM: Artificial
<220> FEATURE:
<223> OTHER INFORMATION: Rmo primer

<400> SEQUENCE: 201
gcatgctaac accgtgcgtg ttga                                                 24
```

```
<210> SEQ ID NO 202
<211> LENGTH: 26
<212> TYPE: DNA
<213> ORGANISM: Artificial
<220> FEATURE:
<223> OTHER INFORMATION: Rmo primer

<400> SEQUENCE: 202
gtcgactata aacgcagaaa ggccca                                          26

<210> SEQ ID NO 203
<211> LENGTH: 28
<212> TYPE: DNA
<213> ORGANISM: Artificial
<220> FEATURE:
<223> OTHER INFORMATION: pWAS-anti-csrA primer

<400> SEQUENCE: 203
ttcctcgtcg gcaaccatta tcaccgcc                                        28

<210> SEQ ID NO 204
<211> LENGTH: 28
<212> TYPE: DNA
<213> ORGANISM: Artificial
<220> FEATURE:
<223> OTHER INFORMATION: pWAS-anti-csrA primer

<400> SEQUENCE: 204
gaatcagcat tttctgttgg gccattgc                                        28

<210> SEQ ID NO 205
<211> LENGTH: 29
<212> TYPE: DNA
<213> ORGANISM: Artificial
<220> FEATURE:
<223> OTHER INFORMATION: pWAS-anti-csrA primer

<400> SEQUENCE: 205
gactcgtcga ggcaaccatt atcaccgcc                                       29

<210> SEQ ID NO 206
<211> LENGTH: 29
<212> TYPE: DNA
<213> ORGANISM: Artificial
<220> FEATURE:
<223> OTHER INFORMATION: pWAS-anti-csrA primer

<400> SEQUENCE: 206
agaatcagca ttttctgttg gccattgc                                        29

<210> SEQ ID NO 207
<211> LENGTH: 27
<212> TYPE: DNA
<213> ORGANISM: Artificial
<220> FEATURE:
<223> OTHER INFORMATION: pWAS-anti-csrA primer

<400> SEQUENCE: 207
taactcgtcg gcaaccatta tcaccgc                                         27

<210> SEQ ID NO 208
<211> LENGTH: 28
<212> TYPE: DNA
<213> ORGANISM: Artificial
<220> FEATURE:
<223> OTHER INFORMATION: pWAS-anti-csrA primer
```

<400> SEQUENCE: 208
gaatcagcat tttctgttgg gccattgc                                      28

<210> SEQ ID NO 209
<211> LENGTH: 33
<212> TYPE: DNA
<213> ORGANISM: Artificial
<220> FEATURE:
<223> OTHER INFORMATION: pWAS-anti-csrA primer

<400> SEQUENCE: 209
tcgtcgagtt ggtgggcaac cattatcacc gcc                                33

<210> SEQ ID NO 210
<211> LENGTH: 31
<212> TYPE: DNA
<213> ORGANISM: Artificial
<220> FEATURE:
<223> OTHER INFORMATION: pWAS-anti-csrA primer

<400> SEQUENCE: 210
tcagaatcag cattttctgt tgggccattg c                                  31

<210> SEQ ID NO 211
<211> LENGTH: 33
<212> TYPE: DNA
<213> ORGANISM: Artificial
<220> FEATURE:
<223> OTHER INFORMATION: pWAS-anti-csrA primer

<400> SEQUENCE: 211
ccgtcgagtt ggtgggcaac cattatcacc gcc                                33

<210> SEQ ID NO 212
<211> LENGTH: 31
<212> TYPE: DNA
<213> ORGANISM: Artificial
<220> FEATURE:
<223> OTHER INFORMATION: pWAS-anti-csrA primer

<400> SEQUENCE: 212
tcagaatcag cattttctgt tgggccattg c                                  31

<210> SEQ ID NO 213
<211> LENGTH: 33
<212> TYPE: DNA
<213> ORGANISM: Artificial
<220> FEATURE:
<223> OTHER INFORMATION: pWAS-anti-csrA primer

<400> SEQUENCE: 213
agtcgagttg gtgaggcaac cattatcacc gcc                                33

<210> SEQ ID NO 214
<211> LENGTH: 33
<212> TYPE: DNA
<213> ORGANISM: Artificial
<220> FEATURE:
<223> OTHER INFORMATION: pWAS-anti-csrA primer

<400> SEQUENCE: 214
cgtcagaatc agcattttct gttgggccat tgc                                33

<210> SEQ ID NO 215

```
<210> SEQ ID NO 215
<211> LENGTH: 33
<212> TYPE: DNA
<213> ORGANISM: Artificial
<220> FEATURE:
<223> OTHER INFORMATION: pWAS-anti-csrA primer

<400> SEQUENCE: 215
gtcgagttgg tgagggcaac cattatcacc gcc                                33

<210> SEQ ID NO 216
<211> LENGTH: 33
<212> TYPE: DNA
<213> ORGANISM: Artificial
<220> FEATURE:
<223> OTHER INFORMATION: pWAS-anti-csrA primer

<400> SEQUENCE: 216
agtcagaatc agcattttct gttgggccat tgc                                33

<210> SEQ ID NO 217
<211> LENGTH: 32
<212> TYPE: DNA
<213> ORGANISM: Artificial
<220> FEATURE:
<223> OTHER INFORMATION: pWAS-anti-csrA primer

<400> SEQUENCE: 217
tcgagttggt gagggcaacc attatcaccg cc                                 32

<210> SEQ ID NO 218
<211> LENGTH: 34
<212> TYPE: DNA
<213> ORGANISM: Artificial
<220> FEATURE:
<223> OTHER INFORMATION: pWAS-anti-csrA primer

<400> SEQUENCE: 218
cggtcagaat cagcattttc tgttgggcca ttgc                               34

<210> SEQ ID NO 219
<211> LENGTH: 30
<212> TYPE: DNA
<213> ORGANISM: Artificial
<220> FEATURE:
<223> OTHER INFORMATION: anti-accA forward primer

<400> SEQUENCE: 219
ttccttgatt ttgcaaccat tatcaccgcc                                    30

<210> SEQ ID NO 220
<211> LENGTH: 34
<212> TYPE: DNA
<213> ORGANISM: Artificial
<220> FEATURE:
<223> OTHER INFORMATION: anti-accA reverse primer

<400> SEQUENCE: 220
attcagactc attttctgtt gggccattgc attg                               34

<210> SEQ ID NO 221
<211> LENGTH: 30
<212> TYPE: DNA
<213> ORGANISM: Artificial
<220> FEATURE:
<223> OTHER INFORMATION: anti-accB forward primer

<400> SEQUENCE: 221
```
aagattaaaa aagcaaccat tatcaccgcc                                              30

<210> SEQ ID NO 222
<211> LENGTH: 34
<212> TYPE: DNA
<213> ORGANISM: Artificial
<220> FEATURE:
<223> OTHER INFORMATION: anti-accB reverse primer

<400> SEQUENCE: 222
acgaatatcc attttctgtt gggccattgc attg                                         34

<210> SEQ ID NO 223
<211> LENGTH: 30
<212> TYPE: DNA
<213> ORGANISM: Artificial
<220> FEATURE:
<223> OTHER INFORMATION: anti-accC forward primer

<400> SEQUENCE: 223
attgttattg ccgcaaccat tatcaccgcc                                              30

<210> SEQ ID NO 224
<211> LENGTH: 34
<212> TYPE: DNA
<213> ORGANISM: Artificial
<220> FEATURE:
<223> OTHER INFORMATION: anti-accC reverse primer

<400> SEQUENCE: 224
tttatccagc attttctgtt gggccattgc attg                                         34

<210> SEQ ID NO 225
<211> LENGTH: 30
<212> TYPE: DNA
<213> ORGANISM: Artificial
<220> FEATURE:
<223> OTHER INFORMATION: anti-accD forward primer

<400> SEQUENCE: 225
gaacgaatta aagcaaccat tatcaccgcc                                              30

<210> SEQ ID NO 226
<211> LENGTH: 34
<212> TYPE: DNA
<213> ORGANISM: Artificial
<220> FEATURE:
<223> OTHER INFORMATION: anti-accD reverse primer

<400> SEQUENCE: 226
aatccagctc attttctgtt gggccattgc attg                                         34

<210> SEQ ID NO 227
<211> LENGTH: 30
<212> TYPE: DNA
<213> ORGANISM: Artificial
<220> FEATURE:
<223> OTHER INFORMATION: anti-accE forward primer

<400> SEQUENCE: 227
ttcccaaatg acgcaaccat tatcaccgcc                                              30

<210> SEQ ID NO 228
<211> LENGTH: 34
<212> TYPE: DNA

```
<213> ORGANISM: Artificial
<220> FEATURE:
<223> OTHER INFORMATION: anti-accE reverse primer

<400> SEQUENCE: 228
acgttctgac attttctgtt gggccattgc attg                                    34

<210> SEQ ID NO 229
<211> LENGTH: 30
<212> TYPE: DNA
<213> ORGANISM: Artificial
<220> FEATURE:
<223> OTHER INFORMATION: anti-accF forward primer

<400> SEQUENCE: 229
atcaaagtac cggcaaccat tatcaccgcc                                         30

<210> SEQ ID NO 230
<211> LENGTH: 34
<212> TYPE: DNA
<213> ORGANISM: Artificial
<220> FEATURE:
<223> OTHER INFORMATION: anti-accF reverse primer

<400> SEQUENCE: 230
ttcgatagcc attttctgtt gggccattgc attg                                    34

<210> SEQ ID NO 231
<211> LENGTH: 30
<212> TYPE: DNA
<213> ORGANISM: Artificial
<220> FEATURE:
<223> OTHER INFORMATION: anti-ackA forward primer

<400> SEQUENCE: 231
gcaacgttag tcgcaaccat tatcaccgcc                                         30

<210> SEQ ID NO 232
<211> LENGTH: 38
<212> TYPE: DNA
<213> ORGANISM: Artificial
<220> FEATURE:
<223> OTHER INFORMATION: anti-ackA reverse primer

<400> SEQUENCE: 232
tccccggaac attcattttc tgttgggcca ttgcattg                                38

<210> SEQ ID NO 233
<211> LENGTH: 30
<212> TYPE: DNA
<213> ORGANISM: Artificial
<220> FEATURE:
<223> OTHER INFORMATION: anti-adiY forward primer

<400> SEQUENCE: 233
agcgaccaac ctgcaaccat tatcaccgcc                                         30

<210> SEQ ID NO 234
<211> LENGTH: 34
<212> TYPE: DNA
<213> ORGANISM: Artificial
<220> FEATURE:
<223> OTHER INFORMATION: anti-adiY reverse primer

<400> SEQUENCE: 234
gcaaatcctc attttctgtt gggccattgc attg                                    34
```

<210> SEQ ID NO 235
<211> LENGTH: 30
<212> TYPE: DNA
<213> ORGANISM: Artificial
<220> FEATURE:
<223> OTHER INFORMATION: anti-argB forward primer

<400> SEQUENCE: 235
attatcaaac tggcaaccat tatcaccgcc                                      30

<210> SEQ ID NO 236
<211> LENGTH: 34
<212> TYPE: DNA
<213> ORGANISM: Artificial
<220> FEATURE:
<223> OTHER INFORMATION: anti-argB reverse primer

<400> SEQUENCE: 236
taatggattc attttctgtt gggccattgc attg                                 34

<210> SEQ ID NO 237
<211> LENGTH: 30
<212> TYPE: DNA
<213> ORGANISM: Artificial
<220> FEATURE:
<223> OTHER INFORMATION: anti-argC forward primer

<400> SEQUENCE: 237
ctgattgtgg gtgcaaccat tatcaccgcc                                      30

<210> SEQ ID NO 238
<211> LENGTH: 34
<212> TYPE: DNA
<213> ORGANISM: Artificial
<220> FEATURE:
<223> OTHER INFORMATION: anti-argC reverse primer

<400> SEQUENCE: 238
cgtattcaac attttctgtt gggccattgc attg                                 34

<210> SEQ ID NO 239
<211> LENGTH: 30
<212> TYPE: DNA
<213> ORGANISM: Artificial
<220> FEATURE:
<223> OTHER INFORMATION: anti-argG forward primer

<400> SEQUENCE: 239
ctcaagcatc tcgcaaccat tatcaccgcc                                      30

<210> SEQ ID NO 240
<211> LENGTH: 34
<212> TYPE: DNA
<213> ORGANISM: Artificial
<220> FEATURE:
<223> OTHER INFORMATION: anti-argG reverse primer

<400> SEQUENCE: 240
aatcgtcgtc attttctgtt gggccattgc attg                                 34

<210> SEQ ID NO 241
<211> LENGTH: 30
<212> TYPE: DNA
<213> ORGANISM: Artificial
<220> FEATURE:

<223> OTHER INFORMATION: anti-argH forward primer

<400> SEQUENCE: 241
ggcgggcgtt ttgcaaccat tatcaccgcc					30

<210> SEQ ID NO 242
<211> LENGTH: 34
<212> TYPE: DNA
<213> ORGANISM: Artificial
<220> FEATURE:
<223> OTHER INFORMATION: anti-argH reverse primer

<400> SEQUENCE: 242
ccaaagtgcc attttctgtt gggccattgc attg				34

<210> SEQ ID NO 243
<211> LENGTH: 30
<212> TYPE: DNA
<213> ORGANISM: Artificial
<220> FEATURE:
<223> OTHER INFORMATION: anti-asnC forward primer

<400> SEQUENCE: 243
ctgatcgaca atgcaaccat tatcaccgcc					30

<210> SEQ ID NO 244
<211> LENGTH: 34
<212> TYPE: DNA
<213> ORGANISM: Artificial
<220> FEATURE:
<223> OTHER INFORMATION: anti-asnC reverse primer

<400> SEQUENCE: 244
ataattttcc attttctgtt gggccattgc attg				34

<210> SEQ ID NO 245
<211> LENGTH: 30
<212> TYPE: DNA
<213> ORGANISM: Artificial
<220> FEATURE:
<223> OTHER INFORMATION: anti-aspA forward primer

<400> SEQUENCE: 245
attcgtatcg aagcaaccat tatcaccgcc					30

<210> SEQ ID NO 246
<211> LENGTH: 34
<212> TYPE: DNA
<213> ORGANISM: Artificial
<220> FEATURE:
<223> OTHER INFORMATION: anti-aspA reverse primer

<400> SEQUENCE: 246
gttgtttgac attttctgtt gggccattgc attg				34

<210> SEQ ID NO 247
<211> LENGTH: 30
<212> TYPE: DNA
<213> ORGANISM: Artificial
<220> FEATURE:
<223> OTHER INFORMATION: anti-crp forward primer

<400> SEQUENCE: 247
aaaccgcaaa cagcaaccat tatcaccgcc					30

```
<210> SEQ ID NO 248
<211> LENGTH: 34
<212> TYPE: DNA
<213> ORGANISM: Artificial
<220> FEATURE:
<223> OTHER INFORMATION: anti-crp reverse primer

<400> SEQUENCE: 248
gccaagcacc attttctgtt gggccattgc attg                              34

<210> SEQ ID NO 249
<211> LENGTH: 30
<212> TYPE: DNA
<213> ORGANISM: Artificial
<220> FEATURE:
<223> OTHER INFORMATION: anti-csiD forward primer

<400> SEQUENCE: 249
accgccgtac aagcaaccat tatcaccgcc                                   30

<210> SEQ ID NO 250
<211> LENGTH: 34
<212> TYPE: DNA
<213> ORGANISM: Artificial
<220> FEATURE:
<223> OTHER INFORMATION: anti-csiD reverse primer

<400> SEQUENCE: 250
cagtgcattc attttctgtt gggccattgc attg                              34

<210> SEQ ID NO 251
<211> LENGTH: 30
<212> TYPE: DNA
<213> ORGANISM: Artificial
<220> FEATURE:
<223> OTHER INFORMATION: anti-csiR forward primer

<400> SEQUENCE: 251
tctctggatg gcgcaaccat tatcaccgcc                                   30

<210> SEQ ID NO 252
<211> LENGTH: 34
<212> TYPE: DNA
<213> ORGANISM: Artificial
<220> FEATURE:
<223> OTHER INFORMATION: anti-csiR reverse primer

<400> SEQUENCE: 252
cgtaatggtc attttctgtt gggccattgc attg                              34

<210> SEQ ID NO 253
<211> LENGTH: 30
<212> TYPE: DNA
<213> ORGANISM: Artificial
<220> FEATURE:
<223> OTHER INFORMATION: anti-cytR forward primer

<400> SEQUENCE: 253
aagcaggaaa ctgcaaccat tatcaccgcc                                   30

<210> SEQ ID NO 254
<211> LENGTH: 34
<212> TYPE: DNA
<213> ORGANISM: Artificial
<220> FEATURE:
<223> OTHER INFORMATION: anti-cytR reverse primer
```

<400> SEQUENCE: 254
cttcgctttc actttctgtt gggccattgc attg    34

<210> SEQ ID NO 255
<211> LENGTH: 30
<212> TYPE: DNA
<213> ORGANISM: Artificial
<220> FEATURE:
<223> OTHER INFORMATION: anti-dcuA forward primer

<400> SEQUENCE: 255
gaactcatca tagcaaccat tatcaccgcc    30

<210> SEQ ID NO 256
<211> LENGTH: 34
<212> TYPE: DNA
<213> ORGANISM: Artificial
<220> FEATURE:
<223> OTHER INFORMATION: anti-dcuA reverse primer

<400> SEQUENCE: 256
tacaactagc attttctgtt gggccattgc attg    34

<210> SEQ ID NO 257
<211> LENGTH: 30
<212> TYPE: DNA
<213> ORGANISM: Artificial
<220> FEATURE:
<223> OTHER INFORMATION: anti-deoB forward primer

<400> SEQUENCE: 257
tttattatgg tggcaaccat tatcaccgcc    30

<210> SEQ ID NO 258
<211> LENGTH: 34
<212> TYPE: DNA
<213> ORGANISM: Artificial
<220> FEATURE:
<223> OTHER INFORMATION: anti-deoB reverse primer

<400> SEQUENCE: 258
tgcacgtttc attttctgtt gggccattgc attg    34

<210> SEQ ID NO 259
<211> LENGTH: 30
<212> TYPE: DNA
<213> ORGANISM: Artificial
<220> FEATURE:
<223> OTHER INFORMATION: anti-deoC forward primer

<400> SEQUENCE: 259
aaagcaagca gcgcaaccat tatcaccgcc    30

<210> SEQ ID NO 260
<211> LENGTH: 34
<212> TYPE: DNA
<213> ORGANISM: Artificial
<220> FEATURE:
<223> OTHER INFORMATION: anti-deoC reverse primer

<400> SEQUENCE: 260
cagatcagtc attttctgtt gggccattgc attg    34

<210> SEQ ID NO 261
<211> LENGTH: 30

```
<212> TYPE: DNA
<213> ORGANISM: Artificial
<220> FEATURE:
<223> OTHER INFORMATION: anti-deoR forward primer

<400> SEQUENCE: 261
cgcgaagagc gtgcaaccat tatcaccgcc                                    30

<210> SEQ ID NO 262
<211> LENGTH: 34
<212> TYPE: DNA
<213> ORGANISM: Artificial
<220> FEATURE:
<223> OTHER INFORMATION: anti-deoR reverse primer

<400> SEQUENCE: 262
acgtgtttcc attttctgtt gggccattgc attg                               34

<210> SEQ ID NO 263
<211> LENGTH: 37
<212> TYPE: DNA
<213> ORGANISM: Artificial
<220> FEATURE:
<223> OTHER INFORMATION: anti-fabH forward primer

<400> SEQUENCE: 263
taatggagct gtcattttct gttgggccat tgcattg                            37

<210> SEQ ID NO 264
<211> LENGTH: 36
<212> TYPE: DNA
<213> ORGANISM: Artificial
<220> FEATURE:
<223> OTHER INFORMATION: anti-fabH reverse primer

<400> SEQUENCE: 264
accctattga tcgttgcaac cattatcacc gccaga                             36

<210> SEQ ID NO 265
<211> LENGTH: 30
<212> TYPE: DNA
<213> ORGANISM: Artificial
<220> FEATURE:
<223> OTHER INFORMATION: anti-fadD forward primer

<400> SEQUENCE: 265
tggcttaacc gtgcaaccat tatcaccgcc                                    30

<210> SEQ ID NO 266
<211> LENGTH: 34
<212> TYPE: DNA
<213> ORGANISM: Artificial
<220> FEATURE:
<223> OTHER INFORMATION: anti-fadD reverse primer

<400> SEQUENCE: 266
aaccttcttc aatttctgtt gggccattgc attg                               34

<210> SEQ ID NO 267
<211> LENGTH: 30
<212> TYPE: DNA
<213> ORGANISM: Artificial
<220> FEATURE:
<223> OTHER INFORMATION: anti-fadR forward primer

<400> SEQUENCE: 267
```
gcgcaaagcc cggcaaccat tatcaccgcc      30

<210> SEQ ID NO 268
<211> LENGTH: 34
<212> TYPE: DNA
<213> ORGANISM: Artificial
<220> FEATURE:
<223> OTHER INFORMATION: anti-fadR reverse primer

<400> SEQUENCE: 268
cttaatgacc attttctgtt gggccattgc attg      34

<210> SEQ ID NO 269
<211> LENGTH: 30
<212> TYPE: DNA
<213> ORGANISM: Artificial
<220> FEATURE:
<223> OTHER INFORMATION: anti-fbp forward primer

<400> SEQUENCE: 269
ggtgaattta ttgcaaccat tatcaccgcc      30

<210> SEQ ID NO 270
<211> LENGTH: 34
<212> TYPE: DNA
<213> ORGANISM: Artificial
<220> FEATURE:
<223> OTHER INFORMATION: anti-fbp reverse primer

<400> SEQUENCE: 270
taacgttttc attttctgtt gggccattgc attg      34

<210> SEQ ID NO 271
<211> LENGTH: 30
<212> TYPE: DNA
<213> ORGANISM: Artificial
<220> FEATURE:
<223> OTHER INFORMATION: anti-fnr forward primer

<400> SEQUENCE: 271
aagcgaatta tagcaaccat tatcaccgcc      30

<210> SEQ ID NO 272
<211> LENGTH: 34
<212> TYPE: DNA
<213> ORGANISM: Artificial
<220> FEATURE:
<223> OTHER INFORMATION: anti-fnr reverse primer

<400> SEQUENCE: 272
ttccgggatc attttctgtt gggccattgc attg      34

<210> SEQ ID NO 273
<211> LENGTH: 30
<212> TYPE: DNA
<213> ORGANISM: Artificial
<220> FEATURE:
<223> OTHER INFORMATION: anti-fruR forward primer

<400> SEQUENCE: 273
gaaatcgctc gggcaaccat tatcaccgcc      30

<210> SEQ ID NO 274
<211> LENGTH: 34
<212> TYPE: DNA
<213> ORGANISM: Artificial

<220> FEATURE:
<223> OTHER INFORMATION: anti-fruR reverse primer

<400> SEQUENCE: 274
atccagtttc actttctgtt gggccattgc attg                            34

<210> SEQ ID NO 275
<211> LENGTH: 30
<212> TYPE: DNA
<213> ORGANISM: Artificial
<220> FEATURE:
<223> OTHER INFORMATION: anti-ftsL forward primer

<400> SEQUENCE: 275
gtgacagaag ctgcaaccat tatcaccgcc                                 30

<210> SEQ ID NO 276
<211> LENGTH: 34
<212> TYPE: DNA
<213> ORGANISM: Artificial
<220> FEATURE:
<223> OTHER INFORMATION: anti-ftsL reverse primer

<400> SEQUENCE: 276
tctgctgatc attttctgtt gggccattgc attg                            34

<210> SEQ ID NO 277
<211> LENGTH: 30
<212> TYPE: DNA
<213> ORGANISM: Artificial
<220> FEATURE:
<223> OTHER INFORMATION: anti-ftsQ forward primer

<400> SEQUENCE: 277
gctctgaaca cggcaaccat tatcaccgcc                                 30

<210> SEQ ID NO 278
<211> LENGTH: 34
<212> TYPE: DNA
<213> ORGANISM: Artificial
<220> FEATURE:
<223> OTHER INFORMATION: anti-ftsQ reverse primer

<400> SEQUENCE: 278
agcctgcgac attttctgtt gggccattgc attg                            34

<210> SEQ ID NO 279
<211> LENGTH: 30
<212> TYPE: DNA
<213> ORGANISM: Artificial
<220> FEATURE:
<223> OTHER INFORMATION: anti-ftsW forward primer

<400> SEQUENCE: 279
ctccctcgcc tggcaaccat tatcaccgcc                                 30

<210> SEQ ID NO 280
<211> LENGTH: 34
<212> TYPE: DNA
<213> ORGANISM: Artificial
<220> FEATURE:
<223> OTHER INFORMATION: anti-ftsW reverse primer

<400> SEQUENCE: 280
agataaacgc attttctgtt gggccattgc attg                            34

```
<210> SEQ ID NO 281
<211> LENGTH: 30
<212> TYPE: DNA
<213> ORGANISM: Artificial
<220> FEATURE:
<223> OTHER INFORMATION: anti-ftsZ forward primer

<400> SEQUENCE: 281
atggaactta ccgcaaccat tatcaccgcc                                     30

<210> SEQ ID NO 282
<211> LENGTH: 34
<212> TYPE: DNA
<213> ORGANISM: Artificial
<220> FEATURE:
<223> OTHER INFORMATION: anti-ftsZ reverse primer

<400> SEQUENCE: 282
tggttcaaac attttctgtt gggccattgc attg                                34

<210> SEQ ID NO 283
<211> LENGTH: 30
<212> TYPE: DNA
<213> ORGANISM: Artificial
<220> FEATURE:
<223> OTHER INFORMATION: anti-fur forward primer

<400> SEQUENCE: 283
aataccgccc tagcaaccat tatcaccgcc                                     30

<210> SEQ ID NO 284
<211> LENGTH: 34
<212> TYPE: DNA
<213> ORGANISM: Artificial
<220> FEATURE:
<223> OTHER INFORMATION: anti-fur reverse primer

<400> SEQUENCE: 284
gttatcagtc attttctgtt gggccattgc attg                                34

<210> SEQ ID NO 285
<211> LENGTH: 30
<212> TYPE: DNA
<213> ORGANISM: Artificial
<220> FEATURE:
<223> OTHER INFORMATION: anti-gabD forward primer

<400> SEQUENCE: 285
gacagtaact tagcaaccat tatcaccgcc                                     30

<210> SEQ ID NO 286
<211> LENGTH: 34
<212> TYPE: DNA
<213> ORGANISM: Artificial
<220> FEATURE:
<223> OTHER INFORMATION: anti-gabD reverse primer

<400> SEQUENCE: 286
gttaagtttc attttctgtt gggccattgc attg                                34

<210> SEQ ID NO 287
<211> LENGTH: 30
<212> TYPE: DNA
<213> ORGANISM: Artificial
<220> FEATURE:
<223> OTHER INFORMATION: anti-gabP forward primer
```

```
<400> SEQUENCE: 287
tcgcaaccac atgcaaccat tatcaccgcc                                           30

<210> SEQ ID NO 288
<211> LENGTH: 34
<212> TYPE: DNA
<213> ORGANISM: Artificial
<220> FEATURE:
<223> OTHER INFORMATION: anti-gabP reverse primer

<400> SEQUENCE: 288
tgattgcccc attttctgtt gggccattgc attg                                      34

<210> SEQ ID NO 289
<211> LENGTH: 30
<212> TYPE: DNA
<213> ORGANISM: Artificial
<220> FEATURE:
<223> OTHER INFORMATION: anti-gabT forward primer

<400> SEQUENCE: 289
aaagagttaa tggcaaccat tatcaccgcc                                           30

<210> SEQ ID NO 290
<211> LENGTH: 34
<212> TYPE: DNA
<213> ORGANISM: Artificial
<220> FEATURE:
<223> OTHER INFORMATION: anti-gabT reverse primer

<400> SEQUENCE: 290
attgctgttc attttctgtt gggccattgc attg                                      34

<210> SEQ ID NO 291
<211> LENGTH: 30
<212> TYPE: DNA
<213> ORGANISM: Artificial
<220> FEATURE:
<223> OTHER INFORMATION: anti-gadA forward primer

<400> SEQUENCE: 291
ctgttaacgg atgcaaccat tatcaccgcc                                           30

<210> SEQ ID NO 292
<211> LENGTH: 34
<212> TYPE: DNA
<213> ORGANISM: Artificial
<220> FEATURE:
<223> OTHER INFORMATION: anti-gadA reverse primer

<400> SEQUENCE: 292
cttctggtcc attttctgtt gggccattgc attg                                      34

<210> SEQ ID NO 293
<211> LENGTH: 30
<212> TYPE: DNA
<213> ORGANISM: Artificial
<220> FEATURE:
<223> OTHER INFORMATION: anti-gadB forward primer

<400> SEQUENCE: 293
caagtaacgg atgcaaccat tatcaccgcc                                           30

<210> SEQ ID NO 294
```

```
<211> LENGTH: 34
<212> TYPE: DNA
<213> ORGANISM: Artificial
<220> FEATURE:
<223> OTHER INFORMATION: anti-gadB reverse primer

<400> SEQUENCE: 294
cttcttatcc attttctgtt gggccattgc attg                              34

<210> SEQ ID NO 295
<211> LENGTH: 30
<212> TYPE: DNA
<213> ORGANISM: Artificial
<220> FEATURE:
<223> OTHER INFORMATION: anti-gadC forward primer

<400> SEQUENCE: 295
gtacagacag gtgcaaccat tatcaccgcc                                   30

<210> SEQ ID NO 296
<211> LENGTH: 34
<212> TYPE: DNA
<213> ORGANISM: Artificial
<220> FEATURE:
<223> OTHER INFORMATION: anti-gadC reverse primer

<400> SEQUENCE: 296
tgatgtagcc attttctgtt gggccattgc attg                              34

<210> SEQ ID NO 297
<211> LENGTH: 37
<212> TYPE: DNA
<213> ORGANISM: Artificial
<220> FEATURE:
<223> OTHER INFORMATION: anti-glcC forward primer

<400> SEQUENCE: 297
acgttcatct ttcattttct gttgggccat tgcattg                           37

<210> SEQ ID NO 298
<211> LENGTH: 36
<212> TYPE: DNA
<213> ORGANISM: Artificial
<220> FEATURE:
<223> OTHER INFORMATION: anti-glcC reverse primer

<400> SEQUENCE: 298
cgccctattt gcgaagcaac cattatcacc gccaga                            36

<210> SEQ ID NO 299
<211> LENGTH: 30
<212> TYPE: DNA
<213> ORGANISM: Artificial
<220> FEATURE:
<223> OTHER INFORMATION: anti-glpK forward primer

<400> SEQUENCE: 299
aaatatatcg ttgcaaccat tatcaccgcc                                   30

<210> SEQ ID NO 300
<211> LENGTH: 34
<212> TYPE: DNA
<213> ORGANISM: Artificial
<220> FEATURE:
<223> OTHER INFORMATION: anti-glpK reverse primer

<400> SEQUENCE: 300
```
tttttcagtc attttctgtt gggccattgc attg                        34

<210> SEQ ID NO 301
<211> LENGTH: 30
<212> TYPE: DNA
<213> ORGANISM: Artificial
<220> FEATURE:
<223> OTHER INFORMATION: anti-glpR forward primer

<400> SEQUENCE: 301
caacgtcaca acgcaaccat tatcaccgcc                             30

<210> SEQ ID NO 302
<211> LENGTH: 34
<212> TYPE: DNA
<213> ORGANISM: Artificial
<220> FEATURE:
<223> OTHER INFORMATION: anti-glpR reverse primer

<400> SEQUENCE: 302
tgtttgtttc attttctgtt gggccattgc attg                        34

<210> SEQ ID NO 303
<211> LENGTH: 30
<212> TYPE: DNA
<213> ORGANISM: Artificial
<220> FEATURE:
<223> OTHER INFORMATION: anti-glpX forward primer

<400> SEQUENCE: 303
cttgccatcg aagcaaccat tatcaccgcc                             30

<210> SEQ ID NO 304
<211> LENGTH: 34
<212> TYPE: DNA
<213> ORGANISM: Artificial
<220> FEATURE:
<223> OTHER INFORMATION: anti-glpX reverse primer

<400> SEQUENCE: 304
ttctcgtctc attttctgtt gggccattgc attg                        34

<210> SEQ ID NO 305
<211> LENGTH: 30
<212> TYPE: DNA
<213> ORGANISM: Artificial
<220> FEATURE:
<223> OTHER INFORMATION: anti-gltA forward primer

<400> SEQUENCE: 305
aaagcaaaac tcgcaaccat tatcaccgcc                             30

<210> SEQ ID NO 306
<211> LENGTH: 34
<212> TYPE: DNA
<213> ORGANISM: Artificial
<220> FEATURE:
<223> OTHER INFORMATION: anti-gltA reverse primer

<400> SEQUENCE: 306
tgtatcagcc attttctgtt gggccattgc attg                        34

<210> SEQ ID NO 307
<211> LENGTH: 30
<212> TYPE: DNA

<210> SEQ ID NO 307
<211> LENGTH: 30
<212> TYPE: DNA
<213> ORGANISM: Artificial
<220> FEATURE:
<223> OTHER INFORMATION: anti-hfld forward primer

<400> SEQUENCE: 307
tactatgaca tcgcaaccat tatcaccgcc                                    30

<210> SEQ ID NO 308
<211> LENGTH: 34
<212> TYPE: DNA
<213> ORGANISM: Artificial
<220> FEATURE:
<223> OTHER INFORMATION: anti-hfld reverse primer

<400> SEQUENCE: 308
attctttgcc actttctgtt gggccattgc attg                               34

<210> SEQ ID NO 309
<211> LENGTH: 37
<212> TYPE: DNA
<213> ORGANISM: Artificial
<220> FEATURE:
<223> OTHER INFORMATION: anti-ihfa forward primer

<400> SEQUENCE: 309
ttttgtaagc gccattttct gttgggccat tgcattg                            37

<210> SEQ ID NO 310
<211> LENGTH: 36
<212> TYPE: DNA
<213> ORGANISM: Artificial
<220> FEATURE:
<223> OTHER INFORMATION: anti-ihfa reverse primer

<400> SEQUENCE: 310
gctgaaatgt cagaagcaac cattatcacc gccaga                             36

<210> SEQ ID NO 311
<211> LENGTH: 37
<212> TYPE: DNA
<213> ORGANISM: Artificial
<220> FEATURE:
<223> OTHER INFORMATION: anti-ihfb forward primer

<400> SEQUENCE: 311
ttctgacttg gtcattttct gttgggccat tgcattg                            37

<210> SEQ ID NO 312
<211> LENGTH: 36
<212> TYPE: DNA
<213> ORGANISM: Artificial
<220> FEATURE:
<223> OTHER INFORMATION: anti-ihfb reverse primer

<400> SEQUENCE: 312
ttgatagaaa gacttgcaac cattatcacc gccaga                             36

<210> SEQ ID NO 313
<211> LENGTH: 30
<212> TYPE: DNA
<213> ORGANISM: Artificial
<220> FEATURE:
<223> OTHER INFORMATION: anti-ilvB forward primer

<400> SEQUENCE: 313
ggcacaacat cggcaaccat tatcaccgcc                                    30

<210> SEQ ID NO 314
<211> LENGTH: 34
<212> TYPE: DNA
<213> ORGANISM: Artificial
<220> FEATURE:
<223> OTHER INFORMATION: anti-ilvB reverse primer

<400> SEQUENCE: 314
cgaacttgcc attttctgtt gggccattgc attg                               34

<210> SEQ ID NO 315
<211> LENGTH: 30
<212> TYPE: DNA
<213> ORGANISM: Artificial
<220> FEATURE:
<223> OTHER INFORMATION: anti-ilvC forward primer

<400> SEQUENCE: 315
ttcaatacac tggcaaccat tatcaccgcc                                    30

<210> SEQ ID NO 316
<211> LENGTH: 34
<212> TYPE: DNA
<213> ORGANISM: Artificial
<220> FEATURE:
<223> OTHER INFORMATION: anti-ilvC reverse primer

<400> SEQUENCE: 316
gtagttagcc attttctgtt gggccattgc attg                               34

<210> SEQ ID NO 317
<211> LENGTH: 30
<212> TYPE: DNA
<213> ORGANISM: Artificial
<220> FEATURE:
<223> OTHER INFORMATION: anti-ilvD forward primer

<400> SEQUENCE: 317
cgttccgcca ccgcaaccat tatcaccgcc                                    30

<210> SEQ ID NO 318
<211> LENGTH: 34
<212> TYPE: DNA
<213> ORGANISM: Artificial
<220> FEATURE:
<223> OTHER INFORMATION: anti-ilvD reverse primer

<400> SEQUENCE: 318
gtacttaggc attttctgtt gggccattgc attg                               34

<210> SEQ ID NO 319
<211> LENGTH: 30
<212> TYPE: DNA
<213> ORGANISM: Artificial
<220> FEATURE:
<223> OTHER INFORMATION: anti-ilvG_1 forward primer

<400> SEQUENCE: 319
cacagtgggt gggcaaccat tatcaccgcc                                    30

<210> SEQ ID NO 320
<211> LENGTH: 32
<212> TYPE: DNA
<213> ORGANISM: Artificial
<220> FEATURE:

<223> OTHER INFORMATION: anti-ilvG_1 reverse primer

<400> SEQUENCE: 320
cgccattcat tttctgttgg gccattgcat tg                32

<210> SEQ ID NO 321
<211> LENGTH: 30
<212> TYPE: DNA
<213> ORGANISM: Artificial
<220> FEATURE:
<223> OTHER INFORMATION: anti-ilvG_2 forward primer

<400> SEQUENCE: 321
aacaactgtc gggcaaccat tatcaccgcc                30

<210> SEQ ID NO 322
<211> LENGTH: 32
<212> TYPE: DNA
<213> ORGANISM: Artificial
<220> FEATURE:
<223> OTHER INFORMATION: anti-ilvG_2 reverse primer

<400> SEQUENCE: 322
ttaacaacaa tttctgttgg gccattgcat tg                32

<210> SEQ ID NO 323
<211> LENGTH: 30
<212> TYPE: DNA
<213> ORGANISM: Artificial
<220> FEATURE:
<223> OTHER INFORMATION: anti-ilvH forward primer

<400> SEQUENCE: 323
ttatcagtct tagcaaccat tatcaccgcc                30

<210> SEQ ID NO 324
<211> LENGTH: 34
<212> TYPE: DNA
<213> ORGANISM: Artificial
<220> FEATURE:
<223> OTHER INFORMATION: anti-ilvH reverse primer

<400> SEQUENCE: 324
tatccggcgc attttctgtt gggccattgc attg                34

<210> SEQ ID NO 325
<211> LENGTH: 30
<212> TYPE: DNA
<213> ORGANISM: Artificial
<220> FEATURE:
<223> OTHER INFORMATION: anti-ilvL forward primer

<400> SEQUENCE: 325
ctacgagtga ttgcaaccat tatcaccgcc                30

<210> SEQ ID NO 326
<211> LENGTH: 34
<212> TYPE: DNA
<213> ORGANISM: Artificial
<220> FEATURE:
<223> OTHER INFORMATION: anti-ilvL reverse primer

<400> SEQUENCE: 326
aagggctgtc attttctgtt gggccattgc attg                34

```
<210> SEQ ID NO 327
<211> LENGTH: 30
<212> TYPE: DNA
<213> ORGANISM: Artificial
<220> FEATURE:
<223> OTHER INFORMATION: anti-ilvM forward primer

<400> SEQUENCE: 327
caggtcaatg tagcaaccat tatcaccgcc                                  30

<210> SEQ ID NO 328
<211> LENGTH: 34
<212> TYPE: DNA
<213> ORGANISM: Artificial
<220> FEATURE:
<223> OTHER INFORMATION: anti-ilvM reverse primer

<400> SEQUENCE: 328
atgttgcatc attttctgtt gggccattgc attg                             34

<210> SEQ ID NO 329
<211> LENGTH: 30
<212> TYPE: DNA
<213> ORGANISM: Artificial
<220> FEATURE:
<223> OTHER INFORMATION: anti-ilvN forward primer

<400> SEQUENCE: 329
actcatgaca acgcaaccat tatcaccgcc                                  30

<210> SEQ ID NO 330
<211> LENGTH: 34
<212> TYPE: DNA
<213> ORGANISM: Artificial
<220> FEATURE:
<223> OTHER INFORMATION: anti-ilvN reverse primer

<400> SEQUENCE: 330
tgtgttttgc attttctgtt gggccattgc attg                             34

<210> SEQ ID NO 331
<211> LENGTH: 30
<212> TYPE: DNA
<213> ORGANISM: Artificial
<220> FEATURE:
<223> OTHER INFORMATION: anti-ilvX forward primer

<400> SEQUENCE: 331
acaaaattct gtgcaaccat tatcaccgcc                                  30

<210> SEQ ID NO 332
<211> LENGTH: 34
<212> TYPE: DNA
<213> ORGANISM: Artificial
<220> FEATURE:
<223> OTHER INFORMATION: anti-ilvX reverse primer

<400> SEQUENCE: 332
gctgttattc attttctgtt gggccattgc attg                             34

<210> SEQ ID NO 333
<211> LENGTH: 30
<212> TYPE: DNA
<213> ORGANISM: Artificial
<220> FEATURE:
<223> OTHER INFORMATION: anti-lexA forward primer
```

<400> SEQUENCE: 333
acggccaggc aagcaaccat tatcaccgcc            30

<210> SEQ ID NO 334
<211> LENGTH: 34
<212> TYPE: DNA
<213> ORGANISM: Artificial
<220> FEATURE:
<223> OTHER INFORMATION: anti-lexA reverse primer

<400> SEQUENCE: 334
taacgctttc attttctgtt gggccattgc attg            34

<210> SEQ ID NO 335
<211> LENGTH: 30
<212> TYPE: DNA
<213> ORGANISM: Artificial
<220> FEATURE:
<223> OTHER INFORMATION: anti-lpxC forward primer

<400> SEQUENCE: 335
aggacactta aagcaaccat tatcaccgcc            30

<210> SEQ ID NO 336
<211> LENGTH: 34
<212> TYPE: DNA
<213> ORGANISM: Artificial
<220> FEATURE:
<223> OTHER INFORMATION: anti-lpxC reverse primer

<400> SEQUENCE: 336
ttgtttgatc attttctgtt gggccattgc attg            34

<210> SEQ ID NO 337
<211> LENGTH: 30
<212> TYPE: DNA
<213> ORGANISM: Artificial
<220> FEATURE:
<223> OTHER INFORMATION: anti-marA forward primer

<400> SEQUENCE: 337
gcaacgttag tcgcaaccat tatcaccgcc            30

<210> SEQ ID NO 338
<211> LENGTH: 34
<212> TYPE: DNA
<213> ORGANISM: Artificial
<220> FEATURE:
<223> OTHER INFORMATION: anti-marA reverse primer

<400> SEQUENCE: 338
tccccggaac attttctgtt gggccattgc attg            34

<210> SEQ ID NO 339
<211> LENGTH: 30
<212> TYPE: DNA
<213> ORGANISM: Artificial
<220> FEATURE:
<223> OTHER INFORMATION: anti-metJ forward primer

<400> SEQUENCE: 339
agcggcgaat atgcaaccat tatcaccgcc            30

<210> SEQ ID NO 340
<211> LENGTH: 34

```
<212> TYPE: DNA
<213> ORGANISM: Artificial
<220> FEATURE:
<223> OTHER INFORMATION: anti-metJ reverse primer

<400> SEQUENCE: 340
ccattcagcc attttctgtt gggccattgc attg                              34

<210> SEQ ID NO 341
<211> LENGTH: 30
<212> TYPE: DNA
<213> ORGANISM: Artificial
<220> FEATURE:
<223> OTHER INFORMATION: anti-modE forward primer

<400> SEQUENCE: 341
atccttctca ccgcaaccat tatcaccgcc                                   30

<210> SEQ ID NO 342
<211> LENGTH: 34
<212> TYPE: DNA
<213> ORGANISM: Artificial
<220> FEATURE:
<223> OTHER INFORMATION: anti-modE reverse primer

<400> SEQUENCE: 342
ttcggcctgc attttctgtt gggccattgc attg                              34

<210> SEQ ID NO 343
<211> LENGTH: 30
<212> TYPE: DNA
<213> ORGANISM: Artificial
<220> FEATURE:
<223> OTHER INFORMATION: anti-nadB forward primer

<400> SEQUENCE: 343
cctgaacatt cagcaaccat tatcaccgcc                                   30

<210> SEQ ID NO 344
<211> LENGTH: 34
<212> TYPE: DNA
<213> ORGANISM: Artificial
<220> FEATURE:
<223> OTHER INFORMATION: anti-nadB reverse primer

<400> SEQUENCE: 344
gagagtattc attttctgtt gggccattgc attg                              34

<210> SEQ ID NO 345
<211> LENGTH: 36
<212> TYPE: DNA
<213> ORGANISM: Artificial
<220> FEATURE:
<223> OTHER INFORMATION: anti-nagC forward primer

<400> SEQUENCE: 345
ccgcctggtg tcattttctg ttgggccatt gcattg                            36

<210> SEQ ID NO 346
<211> LENGTH: 36
<212> TYPE: DNA
<213> ORGANISM: Artificial
<220> FEATURE:
<223> OTHER INFORMATION: anti-nagC reverse primer

<400> SEQUENCE: 346
```
acaagctcag atagggcaac cattatcacc gccaga                                36

<210> SEQ ID NO 347
<211> LENGTH: 30
<212> TYPE: DNA
<213> ORGANISM: Artificial
<220> FEATURE:
<223> OTHER INFORMATION: anti-narL forward primer

<400> SEQUENCE: 347
gaaccggcta ctgcaaccat tatcaccgcc                                       30

<210> SEQ ID NO 348
<211> LENGTH: 34
<212> TYPE: DNA
<213> ORGANISM: Artificial
<220> FEATURE:
<223> OTHER INFORMATION: anti-narL reverse primer

<400> SEQUENCE: 348
ctgattactc attttctgtt gggccattgc attg                                  34

<210> SEQ ID NO 349
<211> LENGTH: 30
<212> TYPE: DNA
<213> ORGANISM: Artificial
<220> FEATURE:
<223> OTHER INFORMATION: anti-pck forward primer

<400> SEQUENCE: 349
aatggtttga ccgcaaccat tatcaccgcc                                       30

<210> SEQ ID NO 350
<211> LENGTH: 34
<212> TYPE: DNA
<213> ORGANISM: Artificial
<220> FEATURE:
<223> OTHER INFORMATION: anti-pck reverse primer

<400> SEQUENCE: 350
gttaacgcgc attttctgtt gggccattgc attg                                  34

<210> SEQ ID NO 351
<211> LENGTH: 30
<212> TYPE: DNA
<213> ORGANISM: Artificial
<220> FEATURE:
<223> OTHER INFORMATION: anti-PdhR forward primer

<400> SEQUENCE: 351
aaaatccgcc aagcaaccat tatcaccgcc                                       30

<210> SEQ ID NO 352
<211> LENGTH: 34
<212> TYPE: DNA
<213> ORGANISM: Artificial
<220> FEATURE:
<223> OTHER INFORMATION: anti-PdhR reverse primer

<400> SEQUENCE: 352
gctgtaggcc attttctgtt gggccattgc attg                                  34

<210> SEQ ID NO 353
<211> LENGTH: 30
<212> TYPE: DNA
<213> ORGANISM: Artificial

```
<220> FEATURE:
<223> OTHER INFORMATION: anti-phoP forward primer

<400> SEQUENCE: 353
gttgttgaag acgcaaccat tatcaccgcc                                    30

<210> SEQ ID NO 354
<211> LENGTH: 34
<212> TYPE: DNA
<213> ORGANISM: Artificial
<220> FEATURE:
<223> OTHER INFORMATION: anti-phoP reverse primer

<400> SEQUENCE: 354
cagtacgcgc attttctgtt gggccattgc attg                               34

<210> SEQ ID NO 355
<211> LENGTH: 30
<212> TYPE: DNA
<213> ORGANISM: Artificial
<220> FEATURE:
<223> OTHER INFORMATION: anti-pnuC forward primer

<400> SEQUENCE: 355
agtgtgcaga atgcaaccat tatcaccgcc                                    30

<210> SEQ ID NO 356
<211> LENGTH: 34
<212> TYPE: DNA
<213> ORGANISM: Artificial
<220> FEATURE:
<223> OTHER INFORMATION: anti-pnuC reverse primer

<400> SEQUENCE: 356
aaaaaaatcc attttctgtt gggccattgc attg                               34

<210> SEQ ID NO 357
<211> LENGTH: 30
<212> TYPE: DNA
<213> ORGANISM: Artificial
<220> FEATURE:
<223> OTHER INFORMATION: anti-ppsA forward primer

<400> SEQUENCE: 357
ggctcgtcac cggcaaccat tatcaccgcc                                    30

<210> SEQ ID NO 358
<211> LENGTH: 34
<212> TYPE: DNA
<213> ORGANISM: Artificial
<220> FEATURE:
<223> OTHER INFORMATION: anti-ppsA reverse primer

<400> SEQUENCE: 358
attgttggac attttctgtt gggccattgc attg                               34

<210> SEQ ID NO 359
<211> LENGTH: 30
<212> TYPE: DNA
<213> ORGANISM: Artificial
<220> FEATURE:
<223> OTHER INFORMATION: anti-purA forward primer

<400> SEQUENCE: 359
gtcgtcgtac tggcaaccat tatcaccgcc                                    30
```

```
<210> SEQ ID NO 360
<211> LENGTH: 34
<212> TYPE: DNA
<213> ORGANISM: Artificial
<220> FEATURE:
<223> OTHER INFORMATION: anti-purA reverse primer

<400> SEQUENCE: 360
gttgttaccc attttctgtt gggccattgc attg                              34

<210> SEQ ID NO 361
<211> LENGTH: 30
<212> TYPE: DNA
<213> ORGANISM: Artificial
<220> FEATURE:
<223> OTHER INFORMATION: anti-purB forward primer

<400> SEQUENCE: 361
tcactgaccg ccgcaaccat tatcaccgcc                                   30

<210> SEQ ID NO 362
<211> LENGTH: 34
<212> TYPE: DNA
<213> ORGANISM: Artificial
<220> FEATURE:
<223> OTHER INFORMATION: anti-purB reverse primer

<400> SEQUENCE: 362
ggataattcc attttctgtt gggccattgc attg                              34

<210> SEQ ID NO 363
<211> LENGTH: 30
<212> TYPE: DNA
<213> ORGANISM: Artificial
<220> FEATURE:
<223> OTHER INFORMATION: anti-purR forward primer

<400> SEQUENCE: 363
aaagatgtag cggcaaccat tatcaccgcc                                   30

<210> SEQ ID NO 364
<211> LENGTH: 34
<212> TYPE: DNA
<213> ORGANISM: Artificial
<220> FEATURE:
<223> OTHER INFORMATION: anti-purR reverse primer

<400> SEQUENCE: 364
tattgttgcc attttctgtt gggccattgc attg                              34

<210> SEQ ID NO 365
<211> LENGTH: 30
<212> TYPE: DNA
<213> ORGANISM: Artificial
<220> FEATURE:
<223> OTHER INFORMATION: anti-puuE forward primer

<400> SEQUENCE: 365
gaattccatc aggcaaccat tatcaccgcc                                   30

<210> SEQ ID NO 366
<211> LENGTH: 34
<212> TYPE: DNA
<213> ORGANISM: Artificial
<220> FEATURE:
<223> OTHER INFORMATION: anti-puuE reverse primer
```

```
<400> SEQUENCE: 366
attgttgctc attttctgtt gggccattgc attg                              34

<210> SEQ ID NO 367
<211> LENGTH: 30
<212> TYPE: DNA
<213> ORGANISM: Artificial
<220> FEATURE:
<223> OTHER INFORMATION: anti-rbsA forward primer

<400> SEQUENCE: 367
cttcagctta aagcaaccat tatcaccgcc                                   30

<210> SEQ ID NO 368
<211> LENGTH: 34
<212> TYPE: DNA
<213> ORGANISM: Artificial
<220> FEATURE:
<223> OTHER INFORMATION: anti-rbsA reverse primer

<400> SEQUENCE: 368
taatgcttcc attttctgtt gggccattgc attg                              34

<210> SEQ ID NO 369
<211> LENGTH: 30
<212> TYPE: DNA
<213> ORGANISM: Artificial
<220> FEATURE:
<223> OTHER INFORMATION: anti-rbsB forward primer

<400> SEQUENCE: 369
aaactggcta ccgcaaccat tatcaccgcc                                   30

<210> SEQ ID NO 370
<211> LENGTH: 34
<212> TYPE: DNA
<213> ORGANISM: Artificial
<220> FEATURE:
<223> OTHER INFORMATION: anti-rbsB reverse primer

<400> SEQUENCE: 370
tttcatgttc attttctgtt gggccattgc attg                              34

<210> SEQ ID NO 371
<211> LENGTH: 30
<212> TYPE: DNA
<213> ORGANISM: Artificial
<220> FEATURE:
<223> OTHER INFORMATION: anti-rbsD forward primer

<400> SEQUENCE: 371
accgttctta atgcaaccat tatcaccgcc                                   30

<210> SEQ ID NO 372
<211> LENGTH: 34
<212> TYPE: DNA
<213> ORGANISM: Artificial
<220> FEATURE:
<223> OTHER INFORMATION: anti-rbsD reverse primer

<400> SEQUENCE: 372
gccttttttc attttctgtt gggccattgc attg                              34

<210> SEQ ID NO 373
```

```
<210> SEQ ID NO 373
<211> LENGTH: 30
<212> TYPE: DNA
<213> ORGANISM: Artificial
<220> FEATURE:
<223> OTHER INFORMATION: anti-rbsK forward primer

<400> SEQUENCE: 373
ggcagcctcg ttgcaaccat tatcaccgcc                                    30

<210> SEQ ID NO 374
<211> LENGTH: 34
<212> TYPE: DNA
<213> ORGANISM: Artificial
<220> FEATURE:
<223> OTHER INFORMATION: anti-rbsK reverse primer

<400> SEQUENCE: 374
tgcgttttgc attttctgtt gggccattgc attg                               34

<210> SEQ ID NO 375
<211> LENGTH: 30
<212> TYPE: DNA
<213> ORGANISM: Artificial
<220> FEATURE:
<223> OTHER INFORMATION: anti-rbsR forward primer

<400> SEQUENCE: 375
aaagatgttg ccgcaaccat tatcaccgcc                                    30

<210> SEQ ID NO 376
<211> LENGTH: 34
<212> TYPE: DNA
<213> ORGANISM: Artificial
<220> FEATURE:
<223> OTHER INFORMATION: anti-rbsR reverse primer

<400> SEQUENCE: 376
cattgtagcc aatttctgtt gggccattgc attg                               34

<210> SEQ ID NO 377
<211> LENGTH: 30
<212> TYPE: DNA
<213> ORGANISM: Artificial
<220> FEATURE:
<223> OTHER INFORMATION: anti-rcsB forward primer

<400> SEQUENCE: 377
aacgtaatta ttgcaaccat tatcaccgcc                                    30

<210> SEQ ID NO 378
<211> LENGTH: 34
<212> TYPE: DNA
<213> ORGANISM: Artificial
<220> FEATURE:
<223> OTHER INFORMATION: anti-rcsB reverse primer

<400> SEQUENCE: 378
catattgttc attttctgtt gggccattgc attg                               34

<210> SEQ ID NO 379
<211> LENGTH: 30
<212> TYPE: DNA
<213> ORGANISM: Artificial
<220> FEATURE:
<223> OTHER INFORMATION: anti-rutR forward primer

<400> SEQUENCE: 379
```
gcagtgaaaa cagcaaccat tatcaccgcc        30

<210> SEQ ID NO 380
<211> LENGTH: 34
<212> TYPE: DNA
<213> ORGANISM: Artificial
<220> FEATURE:
<223> OTHER INFORMATION: anti-rutR reverse primer

<400> SEQUENCE: 380
gccttgcgtc attttctgtt gggccattgc attg        34

<210> SEQ ID NO 381
<211> LENGTH: 29
<212> TYPE: DNA
<213> ORGANISM: Artificial
<220> FEATURE:
<223> OTHER INFORMATION: anti-serA forward primer

<400> SEQUENCE: 381
tcgctggaga aagcaaccat tatcaccgc        29

<210> SEQ ID NO 382
<211> LENGTH: 34
<212> TYPE: DNA
<213> ORGANISM: Artificial
<220> FEATURE:
<223> OTHER INFORMATION: anti-serA reverse primer

<400> SEQUENCE: 382
tacctttgcc attttctgtt gggccattgc attg        34

<210> SEQ ID NO 383
<211> LENGTH: 30
<212> TYPE: DNA
<213> ORGANISM: Artificial
<220> FEATURE:
<223> OTHER INFORMATION: anti-serC forward primer

<400> SEQUENCE: 383
ttcaatttta gtgcaaccat tatcaccgcc        30

<210> SEQ ID NO 384
<211> LENGTH: 34
<212> TYPE: DNA
<213> ORGANISM: Artificial
<220> FEATURE:
<223> OTHER INFORMATION: anti-serC reverse primer

<400> SEQUENCE: 384
gatttgagcc attttctgtt gggccattgc attg        34

<210> SEQ ID NO 385
<211> LENGTH: 30
<212> TYPE: DNA
<213> ORGANISM: Artificial
<220> FEATURE:
<223> OTHER INFORMATION: anti-soxS forward primer

<400> SEQUENCE: 385
aaaattattc aggcaaccat tatcaccgcc        30

<210> SEQ ID NO 386
<211> LENGTH: 34
<212> TYPE: DNA

```
<213> ORGANISM: Artificial
<220> FEATURE:
<223> OTHER INFORMATION: anti-soxS reverse primer

<400> SEQUENCE: 386
ctgatgggac attttctgtt gggccattgc attg                                    34

<210> SEQ ID NO 387
<211> LENGTH: 30
<212> TYPE: DNA
<213> ORGANISM: Artificial
<220> FEATURE:
<223> OTHER INFORMATION: anti-sroD forward primer

<400> SEQUENCE: 387
gcgcgcggca aagcaaccat tatcaccgcc                                         30

<210> SEQ ID NO 388
<211> LENGTH: 34
<212> TYPE: DNA
<213> ORGANISM: Artificial
<220> FEATURE:
<223> OTHER INFORMATION: anti-sroD reverse primer

<400> SEQUENCE: 388
ttcgtcacgt aatttctgtt gggccattgc attg                                    34

<210> SEQ ID NO 389
<211> LENGTH: 30
<212> TYPE: DNA
<213> ORGANISM: Artificial
<220> FEATURE:
<223> OTHER INFORMATION: anti-zwf forward primer

<400> SEQUENCE: 389
caaacagccc aggcaaccat tatcaccgcc                                         30

<210> SEQ ID NO 390
<211> LENGTH: 34
<212> TYPE: DNA
<213> ORGANISM: Artificial
<220> FEATURE:
<223> OTHER INFORMATION: anti-zwf reverse primer

<400> SEQUENCE: 390
cgttaccgcc attttctgtt gggccattgc attg                                    34

<210> SEQ ID NO 391
<211> LENGTH: 30
<212> TYPE: DNA
<213> ORGANISM: Artificial
<220> FEATURE:
<223> OTHER INFORMATION: anti-asnA forward primer

<400> SEQUENCE: 391
tacattgcca aagcaaccat tatcaccgcc                                         30

<210> SEQ ID NO 392
<211> LENGTH: 34
<212> TYPE: DNA
<213> ORGANISM: Artificial
<220> FEATURE:
<223> OTHER INFORMATION: anti-asnA reverse primer

<400> SEQUENCE: 392
agcggttttc attttctgtt gggccattgc attg                                    34
```

<210> SEQ ID NO 393
<211> LENGTH: 30
<212> TYPE: DNA
<213> ORGANISM: Artificial
<220> FEATURE:
<223> OTHER INFORMATION: anti-asnB forward primer

<400> SEQUENCE: 393
tttggcgtat tcgcaaccat tatcaccgcc                                    30

<210> SEQ ID NO 394
<211> LENGTH: 34
<212> TYPE: DNA
<213> ORGANISM: Artificial
<220> FEATURE:
<223> OTHER INFORMATION: anti-asnB reverse primer

<400> SEQUENCE: 394
aattgaacac attttctgtt gggccattgc attg                               34

<210> SEQ ID NO 395
<211> LENGTH: 30
<212> TYPE: DNA
<213> ORGANISM: Artificial
<220> FEATURE:
<223> OTHER INFORMATION: anti-carA forward primer

<400> SEQUENCE: 395
gcgctattgg ttgcaaccat tatcaccgcc                                    30

<210> SEQ ID NO 396
<211> LENGTH: 34
<212> TYPE: DNA
<213> ORGANISM: Artificial
<220> FEATURE:
<223> OTHER INFORMATION: anti-carA reverse primer

<400> SEQUENCE: 396
tgacttaatc aatttctgtt gggccattgc attg                               34

<210> SEQ ID NO 397
<211> LENGTH: 30
<212> TYPE: DNA
<213> ORGANISM: Artificial
<220> FEATURE:
<223> OTHER INFORMATION: anti-carB forward primer

<400> SEQUENCE: 397
acagatataa aagcaaccat tatcaccgcc                                    30

<210> SEQ ID NO 398
<211> LENGTH: 34
<212> TYPE: DNA
<213> ORGANISM: Artificial
<220> FEATURE:
<223> OTHER INFORMATION: anti-carB reverse primer

<400> SEQUENCE: 398
acgttttggc attttctgtt gggccattgc attg                               34

<210> SEQ ID NO 399
<211> LENGTH: 30
<212> TYPE: DNA
<213> ORGANISM: Artificial
<220> FEATURE:

<223> OTHER INFORMATION: anti-ddlB forward primer

<400> SEQUENCE: 399
atcgcggtcc tggcaaccat tatcaccgcc                                        30

<210> SEQ ID NO 400
<211> LENGTH: 34
<212> TYPE: DNA
<213> ORGANISM: Artificial
<220> FEATURE:
<223> OTHER INFORMATION: anti-ddlB reverse primer

<400> SEQUENCE: 400
tttatcagtc attttctgtt gggccattgc attg                                   34

<210> SEQ ID NO 401
<211> LENGTH: 30
<212> TYPE: DNA
<213> ORGANISM: Artificial
<220> FEATURE:
<223> OTHER INFORMATION: anti-deoA forward primer

<400> SEQUENCE: 401
caagaaatta ttgcaaccat tatcaccgcc                                        30

<210> SEQ ID NO 402
<211> LENGTH: 34
<212> TYPE: DNA
<213> ORGANISM: Artificial
<220> FEATURE:
<223> OTHER INFORMATION: anti-deoA reverse primer

<400> SEQUENCE: 402
tgcgagaaac aatttctgtt gggccattgc attg                                   34

<210> SEQ ID NO 403
<211> LENGTH: 34
<212> TYPE: DNA
<213> ORGANISM: Artificial
<220> FEATURE:
<223> OTHER INFORMATION: anti-deoD forward primer

<400> SEQUENCE: 403
tgcgagaaac aatttctgtt gggccattgc attg                                   34

<210> SEQ ID NO 404
<211> LENGTH: 34
<212> TYPE: DNA
<213> ORGANISM: Artificial
<220> FEATURE:
<223> OTHER INFORMATION: anti-deoD reverse primer

<400> SEQUENCE: 404
tggggtagcc attttctgtt gggccattgc attg                                   34

<210> SEQ ID NO 405
<211> LENGTH: 37
<212> TYPE: DNA
<213> ORGANISM: Artificial
<220> FEATURE:
<223> OTHER INFORMATION: anti-dpiA forward primer

<400> SEQUENCE: 405
taatggagct gtcattttct gttgggccat tgcattg                                37

```
<210> SEQ ID NO 406
<211> LENGTH: 36
<212> TYPE: DNA
<213> ORGANISM: Artificial
<220> FEATURE:
<223> OTHER INFORMATION: anti-dpiA reverse primer

<400> SEQUENCE: 406
accctattga tcgttgcaac cattatcacc gccaga                    36

<210> SEQ ID NO 407
<211> LENGTH: 30
<212> TYPE: DNA
<213> ORGANISM: Artificial
<220> FEATURE:
<223> OTHER INFORMATION: anti-fis forward primer

<400> SEQUENCE: 407
cgcgtaaatt ctgcaaccat tatcaccgcc                           30

<210> SEQ ID NO 408
<211> LENGTH: 34
<212> TYPE: DNA
<213> ORGANISM: Artificial
<220> FEATURE:
<223> OTHER INFORMATION: anti-fis reverse primer

<400> SEQUENCE: 408
ttgttcgaac attttctgtt gggccattgc attg                      34

<210> SEQ ID NO 409
<211> LENGTH: 30
<212> TYPE: DNA
<213> ORGANISM: Artificial
<220> FEATURE:
<223> OTHER INFORMATION: anti-gadE forward primer

<400> SEQUENCE: 409
atgacgaaag atgcaaccat tatcaccgcc                           30

<210> SEQ ID NO 410
<211> LENGTH: 34
<212> TYPE: DNA
<213> ORGANISM: Artificial
<220> FEATURE:
<223> OTHER INFORMATION: anti-gadE reverse primer

<400> SEQUENCE: 410
gagaaaaatc attttctgtt gggccattgc attg                      34

<210> SEQ ID NO 411
<211> LENGTH: 30
<212> TYPE: DNA
<213> ORGANISM: Artificial
<220> FEATURE:
<223> OTHER INFORMATION: anti-gadW forward primer

<400> SEQUENCE: 411
tgctcggtga tcgcaaccat tatcaccgcc                           30

<210> SEQ ID NO 412
<211> LENGTH: 34
<212> TYPE: DNA
<213> ORGANISM: Artificial
<220> FEATURE:
<223> OTHER INFORMATION: anti-gadW reverse primer
```

```
<400> SEQUENCE: 412
gacatgagtc attttctgtt gggccattgc attg                              34

<210> SEQ ID NO 413
<211> LENGTH: 30
<212> TYPE: DNA
<213> ORGANISM: Artificial
<220> FEATURE:
<223> OTHER INFORMATION: anti-gadX forward primer

<400> SEQUENCE: 413
catgggaatt gtgcaaccat tatcaccgcc                                   30

<210> SEQ ID NO 414
<211> LENGTH: 34
<212> TYPE: DNA
<213> ORGANISM: Artificial
<220> FEATURE:
<223> OTHER INFORMATION: anti-gadX reverse primer

<400> SEQUENCE: 414
tagtgattgc attttctgtt gggccattgc attg                              34

<210> SEQ ID NO 415
<211> LENGTH: 30
<212> TYPE: DNA
<213> ORGANISM: Artificial
<220> FEATURE:
<223> OTHER INFORMATION: anti-glpF forward primer

<400> SEQUENCE: 415
tcaaccttga aagcaaccat tatcaccgcc                                   30

<210> SEQ ID NO 416
<211> LENGTH: 34
<212> TYPE: DNA
<213> ORGANISM: Artificial
<220> FEATURE:
<223> OTHER INFORMATION: anti-glpF reverse primer

<400> SEQUENCE: 416
tgtttgactc attttctgtt gggccattgc attg                              34

<210> SEQ ID NO 417
<211> LENGTH: 30
<212> TYPE: DNA
<213> ORGANISM: Artificial
<220> FEATURE:
<223> OTHER INFORMATION: anti-ilvY forward primer

<400> SEQUENCE: 417
gatctgaaaa ccgcaaccat tatcaccgcc                                   30

<210> SEQ ID NO 418
<211> LENGTH: 34
<212> TYPE: DNA
<213> ORGANISM: Artificial
<220> FEATURE:
<223> OTHER INFORMATION: anti-ilvY reverse primer

<400> SEQUENCE: 418
gcgtaaatcc actttctgtt gggccattgc attg                              34

<210> SEQ ID NO 419
<211> LENGTH: 30
```

```
<212> TYPE: DNA
<213> ORGANISM: Artificial
<220> FEATURE:
<223> OTHER INFORMATION: anti-ivbL forward primer

<400> SEQUENCE: 419
atgctcaacg cagcaaccat tatcaccgcc                                      30

<210> SEQ ID NO 420
<211> LENGTH: 34
<212> TYPE: DNA
<213> ORGANISM: Artificial
<220> FEATURE:
<223> OTHER INFORMATION: anti-ivbL reverse primer

<400> SEQUENCE: 420
ggaagtagtc attttctgtt gggccattgc attg                                 34

<210> SEQ ID NO 421
<211> LENGTH: 30
<212> TYPE: DNA
<213> ORGANISM: Artificial
<220> FEATURE:
<223> OTHER INFORMATION: anti-lhgO forward primer

<400> SEQUENCE: 421
gtgattattg gcgcaaccat tatcaccgcc                                      30

<210> SEQ ID NO 422
<211> LENGTH: 34
<212> TYPE: DNA
<213> ORGANISM: Artificial
<220> FEATURE:
<223> OTHER INFORMATION: anti-lhgO reverse primer

<400> SEQUENCE: 422
aaaatcatac attttctgtt gggccattgc attg                                 34

<210> SEQ ID NO 423
<211> LENGTH: 30
<212> TYPE: DNA
<213> ORGANISM: Artificial
<220> FEATURE:
<223> OTHER INFORMATION: anti-lpd forward primer

<400> SEQUENCE: 423
atcaaaactc aggcaaccat tatcaccgcc                                      30

<210> SEQ ID NO 424
<211> LENGTH: 34
<212> TYPE: DNA
<213> ORGANISM: Artificial
<220> FEATURE:
<223> OTHER INFORMATION: anti-lpd reverse primer

<400> SEQUENCE: 424
ttcagtactc attttctgtt gggccattgc attg                                 34

<210> SEQ ID NO 425
<211> LENGTH: 30
<212> TYPE: DNA
<213> ORGANISM: Artificial
<220> FEATURE:
<223> OTHER INFORMATION: anti-lrp forward primer

<400> SEQUENCE: 425
```

```
aagaagcgcc ctgcaaccat tatcaccgcc                                    30

<210> SEQ ID NO 426
<211> LENGTH: 34
<212> TYPE: DNA
<213> ORGANISM: Artificial
<220> FEATURE:
<223> OTHER INFORMATION: anti-lrp reverse primer

<400> SEQUENCE: 426
gctatctacc attttctgtt gggccattgc attg                               34

<210> SEQ ID NO 427
<211> LENGTH: 30
<212> TYPE: DNA
<213> ORGANISM: Artificial
<220> FEATURE:
<223> OTHER INFORMATION: anti-metB forward primer

<400> SEQUENCE: 427
acaggccacc atgcaaccat tatcaccgcc                                    30

<210> SEQ ID NO 428
<211> LENGTH: 33
<212> TYPE: DNA
<213> ORGANISM: Artificial
<220> FEATURE:
<223> OTHER INFORMATION: anti-metB reverse primer

<400> SEQUENCE: 428
ttacgcgtca ttttctgttg ggccattgca ttg                                33

<210> SEQ ID NO 429
<211> LENGTH: 30
<212> TYPE: DNA
<213> ORGANISM: Artificial
<220> FEATURE:
<223> OTHER INFORMATION: anti-metL forward primer

<400> SEQUENCE: 429
gcgcaggcag gggcaaccat tatcaccgcc                                    30

<210> SEQ ID NO 430
<211> LENGTH: 34
<212> TYPE: DNA
<213> ORGANISM: Artificial
<220> FEATURE:
<223> OTHER INFORMATION: anti-metL reverse primer

<400> SEQUENCE: 430
aatcacactc attttctgtt gggccattgc attg                               34

<210> SEQ ID NO 431
<211> LENGTH: 30
<212> TYPE: DNA
<213> ORGANISM: Artificial
<220> FEATURE:
<223> OTHER INFORMATION: anti-mraY forward primer

<400> SEQUENCE: 431
ctggccgaac atgcaaccat tatcaccgcc                                    30

<210> SEQ ID NO 432
<211> LENGTH: 34
<212> TYPE: DNA
<213> ORGANISM: Artificial
```

```
<220> FEATURE:
<223> OTHER INFORMATION: anti-mraY reverse primer

<400> SEQUENCE: 432
ccaaactaac attttctgtt gggccattgc attg                              34

<210> SEQ ID NO 433
<211> LENGTH: 30
<212> TYPE: DNA
<213> ORGANISM: Artificial
<220> FEATURE:
<223> OTHER INFORMATION: anti-mraZ forward primer

<400> SEQUENCE: 433
gcaacgttag tcgcaaccat tatcaccgcc                                   30

<210> SEQ ID NO 434
<211> LENGTH: 34
<212> TYPE: DNA
<213> ORGANISM: Artificial
<220> FEATURE:
<223> OTHER INFORMATION: anti-mraZ reverse primer

<400> SEQUENCE: 434
tccccggaac attttctgtt gggccattgc attg                              34

<210> SEQ ID NO 435
<211> LENGTH: 30
<212> TYPE: DNA
<213> ORGANISM: Artificial
<220> FEATURE:
<223> OTHER INFORMATION: anti-murE forward primer

<400> SEQUENCE: 435
aatttgcgcg acgcaaccat tatcaccgcc                                   30

<210> SEQ ID NO 436
<211> LENGTH: 34
<212> TYPE: DNA
<213> ORGANISM: Artificial
<220> FEATURE:
<223> OTHER INFORMATION: anti-murE reverse primer

<400> SEQUENCE: 436
acgatctgcc actttctgtt gggccattgc attg                              34

<210> SEQ ID NO 437
<211> LENGTH: 30
<212> TYPE: DNA
<213> ORGANISM: Artificial
<220> FEATURE:
<223> OTHER INFORMATION: anti-murF forward primer

<400> SEQUENCE: 437
aacccttagc cagcaaccat tatcaccgcc                                   30

<210> SEQ ID NO 438
<211> LENGTH: 33
<212> TYPE: DNA
<213> ORGANISM: Artificial
<220> FEATURE:
<223> OTHER INFORMATION: anti-murF reverse primer

<400> SEQUENCE: 438
acgctaatca ttttctgttg ggccattgca ttg                               33
```

<210> SEQ ID NO 439
<211> LENGTH: 30
<212> TYPE: DNA
<213> ORGANISM: Artificial
<220> FEATURE:
<223> OTHER INFORMATION: anti-murG forward primer

<400> SEQUENCE: 439
ggaaagcgat tagcaaccat tatcaccgcc 30

<210> SEQ ID NO 440
<211> LENGTH: 34
<212> TYPE: DNA
<213> ORGANISM: Artificial
<220> FEATURE:
<223> OTHER INFORMATION: anti-murG reverse primer

<400> SEQUENCE: 440
ttgaccactc attttctgtt gggccattgc attg 34

<210> SEQ ID NO 441
<211> LENGTH: 30
<212> TYPE: DNA
<213> ORGANISM: Artificial
<220> FEATURE:
<223> OTHER INFORMATION: anti-nac forward primer

<400> SEQUENCE: 441
cgcctgaaat acgcaaccat tatcaccgcc 30

<210> SEQ ID NO 442
<211> LENGTH: 34
<212> TYPE: DNA
<213> ORGANISM: Artificial
<220> FEATURE:
<223> OTHER INFORMATION: anti-nac reverse primer

<400> SEQUENCE: 442
tctgaagttc attttctgtt gggccattgc attg 34

<210> SEQ ID NO 443
<211> LENGTH: 30
<212> TYPE: DNA
<213> ORGANISM: Artificial
<220> FEATURE:
<223> OTHER INFORMATION: anti-nadA forward primer

<400> SEQUENCE: 443
tttgatccag acgcaaccat tatcaccgcc 30

<210> SEQ ID NO 444
<211> LENGTH: 34
<212> TYPE: DNA
<213> ORGANISM: Artificial
<220> FEATURE:
<223> OTHER INFORMATION: anti-nadA reverse primer

<400> SEQUENCE: 444
cattacgctc attttctgtt gggccattgc attg 34

<210> SEQ ID NO 445
<211> LENGTH: 37
<212> TYPE: DNA
<213> ORGANISM: Artificial
<220> FEATURE:
<223> OTHER INFORMATION: anti-nsrR forward primer

<400> SEQUENCE: 445
actcgttaac tgcactttct gttgggccat tgcattg                37

<210> SEQ ID NO 446
<211> LENGTH: 36
<212> TYPE: DNA
<213> ORGANISM: Artificial
<220> FEATURE:
<223> OTHER INFORMATION: anti-nsrR reverse primer

<400> SEQUENCE: 446
ttcactgatt acggagcaac cattatcacc gccaga                36

<210> SEQ ID NO 447
<211> LENGTH: 30
<212> TYPE: DNA
<213> ORGANISM: Artificial
<220> FEATURE:
<223> OTHER INFORMATION: anti-panC forward primer

<400> SEQUENCE: 447
gaaaccctgc cggcaaccat tatcaccgcc                30

<210> SEQ ID NO 448
<211> LENGTH: 34
<212> TYPE: DNA
<213> ORGANISM: Artificial
<220> FEATURE:
<223> OTHER INFORMATION: anti-panC reverse primer

<400> SEQUENCE: 448
gataattaac actttctgtt gggccattgc attg                34

<210> SEQ ID NO 449
<211> LENGTH: 30
<212> TYPE: DNA
<213> ORGANISM: Artificial
<220> FEATURE:
<223> OTHER INFORMATION: anti-panD forward primer

<400> SEQUENCE: 449
atgctgcagg gcgcaaccat tatcaccgcc                30

<210> SEQ ID NO 450
<211> LENGTH: 34
<212> TYPE: DNA
<213> ORGANISM: Artificial
<220> FEATURE:
<223> OTHER INFORMATION: anti-panD reverse primer

<400> SEQUENCE: 450
cgtgcgaatc attttctgtt gggccattgc attg                34

<210> SEQ ID NO 451
<211> LENGTH: 30
<212> TYPE: DNA
<213> ORGANISM: Artificial
<220> FEATURE:
<223> OTHER INFORMATION: anti-pgl forward primer

<400> SEQUENCE: 451
gtttatatcg ccgcaaccat tatcaccgcc                30

<210> SEQ ID NO 452

```
<211> LENGTH: 34
<212> TYPE: DNA
<213> ORGANISM: Artificial
<220> FEATURE:
<223> OTHER INFORMATION: anti-pgl reverse primer

<400> SEQUENCE: 452
tgtttgcttc attttctgtt gggccattgc attg                              34

<210> SEQ ID NO 453
<211> LENGTH: 30
<212> TYPE: DNA
<213> ORGANISM: Artificial
<220> FEATURE:
<223> OTHER INFORMATION: anti-pyrB forward primer

<400> SEQUENCE: 453
ctatatcaga aagcaaccat tatcaccgcc                                   30

<210> SEQ ID NO 454
<211> LENGTH: 34
<212> TYPE: DNA
<213> ORGANISM: Artificial
<220> FEATURE:
<223> OTHER INFORMATION: anti-pyrB reverse primer

<400> SEQUENCE: 454
cggattagcc attttctgtt gggccattgc attg                              34

<210> SEQ ID NO 455
<211> LENGTH: 30
<212> TYPE: DNA
<213> ORGANISM: Artificial
<220> FEATURE:
<223> OTHER INFORMATION: anti-pyrC forward primer

<400> SEQUENCE: 455
tcccaggtat tagcaaccat tatcaccgcc                                   30

<210> SEQ ID NO 456
<211> LENGTH: 34
<212> TYPE: DNA
<213> ORGANISM: Artificial
<220> FEATURE:
<223> OTHER INFORMATION: anti-pyrC reverse primer

<400> SEQUENCE: 456
tggtgcagtc attttctgtt gggccattgc attg                              34

<210> SEQ ID NO 457
<211> LENGTH: 30
<212> TYPE: DNA
<213> ORGANISM: Artificial
<220> FEATURE:
<223> OTHER INFORMATION: anti-pyrI forward primer

<400> SEQUENCE: 457
aataaattgc aggcaaccat tatcaccgcc                                   30

<210> SEQ ID NO 458
<211> LENGTH: 34
<212> TYPE: DNA
<213> ORGANISM: Artificial
<220> FEATURE:
<223> OTHER INFORMATION: anti-pyrI reverse primer

<400> SEQUENCE: 458
```

```
atcgtgtgtc attttctgtt gggccattgc attg                              34
```

<210> SEQ ID NO 459
<211> LENGTH: 30
<212> TYPE: DNA
<213> ORGANISM: Artificial
<220> FEATURE:
<223> OTHER INFORMATION: anti-rob forward primer

<400> SEQUENCE: 459

```
ggcattattc gcgcaaccat tatcaccgcc                                   30
```

<210> SEQ ID NO 460
<211> LENGTH: 34
<212> TYPE: DNA
<213> ORGANISM: Artificial
<220> FEATURE:
<223> OTHER INFORMATION: anti-rob reverse primer

<400> SEQUENCE: 460

```
ggcctgatcc attttctgtt gggccattgc attg                              34
```

<210> SEQ ID NO 461
<211> LENGTH: 30
<212> TYPE: DNA
<213> ORGANISM: Artificial
<220> FEATURE:
<223> OTHER INFORMATION: anti-rpe forward primer

<400> SEQUENCE: 461

```
ttgattgccc ccgcaaccat tatcaccgcc                                   30
```

<210> SEQ ID NO 462
<211> LENGTH: 34
<212> TYPE: DNA
<213> ORGANISM: Artificial
<220> FEATURE:
<223> OTHER INFORMATION: anti-rpe reverse primer

<400> SEQUENCE: 462

```
atactgtttc attttctgtt gggccattgc attg                              34
```

<210> SEQ ID NO 463
<211> LENGTH: 30
<212> TYPE: DNA
<213> ORGANISM: Artificial
<220> FEATURE:
<223> OTHER INFORMATION: anti-talA forward primer

<400> SEQUENCE: 463

```
gacggcatca aagcaaccat tatcaccgcc                                   30
```

<210> SEQ ID NO 464
<211> LENGTH: 34
<212> TYPE: DNA
<213> ORGANISM: Artificial
<220> FEATURE:
<223> OTHER INFORMATION: anti-talA reverse primer

<400> SEQUENCE: 464

```
taactcgttc attttctgtt gggccattgc attg                              34
```

<210> SEQ ID NO 465
<211> LENGTH: 30
<212> TYPE: DNA

```
<213> ORGANISM: Artificial
<220> FEATURE:
<223> OTHER INFORMATION: anti-talB forward primer

<400> SEQUENCE: 465
ttgacctccc ttgcaaccat tatcaccgcc                                    30

<210> SEQ ID NO 466
<211> LENGTH: 34
<212> TYPE: DNA
<213> ORGANISM: Artificial
<220> FEATURE:
<223> OTHER INFORMATION: anti-talB reverse primer

<400> SEQUENCE: 466
tttgtccgtc attttctgtt gggccattgc attg                               34

<210> SEQ ID NO 467
<211> LENGTH: 30
<212> TYPE: DNA
<213> ORGANISM: Artificial
<220> FEATURE:
<223> OTHER INFORMATION: anti-thrA forward primer

<400> SEQUENCE: 467
aagttcggcg gtgcaaccat tatcaccgcc                                    30

<210> SEQ ID NO 468
<211> LENGTH: 34
<212> TYPE: DNA
<213> ORGANISM: Artificial
<220> FEATURE:
<223> OTHER INFORMATION: anti-thrA reverse primer

<400> SEQUENCE: 468
caacactcgc attttctgtt gggccattgc attg                               34

<210> SEQ ID NO 469
<211> LENGTH: 30
<212> TYPE: DNA
<213> ORGANISM: Artificial
<220> FEATURE:
<223> OTHER INFORMATION: anti-thrC forward primer

<400> SEQUENCE: 469
aatctgaaag atgcaaccat tatcaccgcc                                    30

<210> SEQ ID NO 470
<211> LENGTH: 34
<212> TYPE: DNA
<213> ORGANISM: Artificial
<220> FEATURE:
<223> OTHER INFORMATION: anti-thrC reverse primer

<400> SEQUENCE: 470
gtagagtttc attttctgtt gggccattgc attg                               34

<210> SEQ ID NO 471
<211> LENGTH: 30
<212> TYPE: DNA
<213> ORGANISM: Artificial
<220> FEATURE:
<223> OTHER INFORMATION: anti-thrL forward primer

<400> SEQUENCE: 471
agcaccacca ttgcaaccat tatcaccgcc                                    30
```

<210> SEQ ID NO 472
<211> LENGTH: 34
<212> TYPE: DNA
<213> ORGANISM: Artificial
<220> FEATURE:
<223> OTHER INFORMATION: anti-thrL reverse primer

<400> SEQUENCE: 472
aatgcgtttc attttctgtt gggccattgc attg                              34

<210> SEQ ID NO 473
<211> LENGTH: 30
<212> TYPE: DNA
<213> ORGANISM: Artificial
<220> FEATURE:
<223> OTHER INFORMATION: anti-tktA forward primer

<400> SEQUENCE: 473
aaagagcttg ccgcaaccat tatcaccgcc                                   30

<210> SEQ ID NO 474
<211> LENGTH: 34
<212> TYPE: DNA
<213> ORGANISM: Artificial
<220> FEATURE:
<223> OTHER INFORMATION: anti-tktA reverse primer

<400> SEQUENCE: 474
acgtgaggac attttctgtt gggccattgc attg                              34

<210> SEQ ID NO 475
<211> LENGTH: 30
<212> TYPE: DNA
<213> ORGANISM: Artificial
<220> FEATURE:
<223> OTHER INFORMATION: anti-tktB forward primer

<400> SEQUENCE: 475
gaccttgcca atgcaaccat tatcaccgcc                                   30

<210> SEQ ID NO 476
<211> LENGTH: 34
<212> TYPE: DNA
<213> ORGANISM: Artificial
<220> FEATURE:
<223> OTHER INFORMATION: anti-tktB reverse primer

<400> SEQUENCE: 476
ttttcgggac attttctgtt gggccattgc attg                              34

<210> SEQ ID NO 477
<211> LENGTH: 30
<212> TYPE: DNA
<213> ORGANISM: Artificial
<220> FEATURE:
<223> OTHER INFORMATION: anti-torR forward primer

<400> SEQUENCE: 477
attgttattg ttgcaaccat tatcaccgcc                                   30

<210> SEQ ID NO 478
<211> LENGTH: 34
<212> TYPE: DNA
<213> ORGANISM: Artificial
<220> FEATURE:

<223> OTHER INFORMATION: anti-torR reverse primer

<400> SEQUENCE: 478
gtgatgtggc attttctgtt gggccattgc attg                                34

<210> SEQ ID NO 479
<211> LENGTH: 24
<212> TYPE: DNA
<213> ORGANISM: Artificial
<220> FEATURE:
<223> OTHER INFORMATION: anti-murE forward primer

<400> SEQUENCE: 479
gatcgtgcaa ccattatcac cgcc                                           24

<210> SEQ ID NO 480
<211> LENGTH: 28
<212> TYPE: DNA
<213> ORGANISM: Artificial
<220> FEATURE:
<223> OTHER INFORMATION: anti-murE reverse primer

<400> SEQUENCE: 480
tgccactttc tgttgggcca ttgcattg                                       28

<210> SEQ ID NO 481
<211> LENGTH: 25
<212> TYPE: DNA
<213> ORGANISM: Artificial
<220> FEATURE:
<223> OTHER INFORMATION: anti-murE forward primer

<400> SEQUENCE: 481
gtcgtaagca accattatca ccgcc                                          25

<210> SEQ ID NO 482
<211> LENGTH: 29
<212> TYPE: DNA
<213> ORGANISM: Artificial
<220> FEATURE:
<223> OTHER INFORMATION: anti-murE reverse primer

<400> SEQUENCE: 482
ctgccacttt ctgttgggcc attgcattg                                      29

<210> SEQ ID NO 483
<211> LENGTH: 26
<212> TYPE: DNA
<213> ORGANISM: Artificial
<220> FEATURE:
<223> OTHER INFORMATION: anti-murE forward primer

<400> SEQUENCE: 483
tcgtaattgc aaccattatc accgcc                                         26

<210> SEQ ID NO 484
<211> LENGTH: 30
<212> TYPE: DNA
<213> ORGANISM: Artificial
<220> FEATURE:
<223> OTHER INFORMATION: anti-murE reverse primer

<400> SEQUENCE: 484
tctgccactt tctgtgggc cattgcattg                                      30

```
<210> SEQ ID NO 485
<211> LENGTH: 29
<212> TYPE: DNA
<213> ORGANISM: Artificial
<220> FEATURE:
<223> OTHER INFORMATION: anti-murE forward primer

<400> SEQUENCE: 485
taatttgcgc ggcaaccatt atcaccgcc                                   29

<210> SEQ ID NO 486
<211> LENGTH: 33
<212> TYPE: DNA
<213> ORGANISM: Artificial
<220> FEATURE:
<223> OTHER INFORMATION: anti-murE reverse primer

<400> SEQUENCE: 486
cgatctgcca ctttctgttg ggccattgca ttg                              33

<210> SEQ ID NO 487
<211> LENGTH: 31
<212> TYPE: DNA
<213> ORGANISM: Artificial
<220> FEATURE:
<223> OTHER INFORMATION: anti-murE forward primer

<400> SEQUENCE: 487
atttgcgcga cctgcaacca ttatcaccgc c                                31

<210> SEQ ID NO 488
<211> LENGTH: 35
<212> TYPE: DNA
<213> ORGANISM: Artificial
<220> FEATURE:
<223> OTHER INFORMATION: anti-murE reverse primer

<400> SEQUENCE: 488
tacgatctgc cactttctgt tgggccattg cattg                            35

<210> SEQ ID NO 489
<211> LENGTH: 32
<212> TYPE: DNA
<213> ORGANISM: Artificial
<220> FEATURE:
<223> OTHER INFORMATION: anti-murE forward primer

<400> SEQUENCE: 489
tttgcgcgac cttcgcaacc attatcaccg cc                               32

<210> SEQ ID NO 490
<211> LENGTH: 36
<212> TYPE: DNA
<213> ORGANISM: Artificial
<220> FEATURE:
<223> OTHER INFORMATION: anti-murE reverse primer

<400> SEQUENCE: 490
ttacgatctg ccactttctg ttgggccatt gcattg                           36

<210> SEQ ID NO 491
<211> LENGTH: 33
<212> TYPE: DNA
<213> ORGANISM: Artificial
<220> FEATURE:
<223> OTHER INFORMATION: anti-murE forward primer
```

-continued

```
<400> SEQUENCE: 491
ttgcgcgacc ttcttgcaac cattatcacc gcc                                    33

<210> SEQ ID NO 492
<211> LENGTH: 37
<212> TYPE: DNA
<213> ORGANISM: Artificial
<220> FEATURE:
<223> OTHER INFORMATION: anti-murE reverse primer

<400> SEQUENCE: 492
attacgatct gccactttct gttgggccat tgcattg                                37
```

SYNTHESIS-REGULATING SRNA AND METHOD FOR PREPARING SAME

CROSS-REFERENCE TO RELATED APPLICATIONS

This application is a U.S. national phase under the provisions of 35 U.S.C. §371 of International Patent Application No. PCT/KR13/00235 filed Jan. 11, 2013, which in turn claims priority of Korean Patent Application No. 10-2012-0003609 filed Jan. 11, 2012. The disclosures of such international patent application and Korean priority patent application are hereby incorporated herein by reference in their respective entireties, for all purposes.

TECHNICAL FIELD

The present invention relates to a novel customized sRNA that reduces gene expression in prokaryotic cells, a preparation method thereof, and the use thereof, and more particularly to a synthetic sRNA comprising an Hfq binding site, derived from the sRNA of any one of MicC, SgrS and MicF, and a region that base-pairs with the target gene mRNA, and to a preparation method thereof and the use thereof.

BACKGROUND ART

In recent years, worldwide concerns about environmental issues and the depletion of limited resources have increased rapidly. As an alternative to solve such problems, the construction of production systems based on environmentally friendly and renewable organisms has been of increasing interest. Such systems can be constructed by regulating metabolic pathways in organisms to optimize metabolic fluxes for desired metabolites, and various molecular biological techniques are required in this process for regulating metabolic pathways.

Methods for regulating metabolic pathways include a method of increasing the expression of enzymes required for biosynthetic processes to enhance metabolic fluxes, and a method of preventing metabolic fluxes that are used for cell growth and the production of other metabolites and deleting genes in order to produce desired metabolites. A gene deletion method that is currently widely used is a method in which the gene to be deleted is replaced by any sequence homologous thereto using recombinase so that the function of the gene is lost (Datsenko et al, *PNAS*, 97(12): 6640-6645, 2000). However, this gene deletion method has the following problems.

First, the time required that is for gene deletion is relatively long. Considering the time required that is replace the chromosomal gene with the homologous sequence and the time that is required to remove an antibiotic resistance gene, used to select cells from which gene deletion was normally removed, from the chromosome, a time of one week or longer is require to remove one gene. This long gene deletion time interferes with the development of metabolic engineering focused on efficiently producing metabolites by metabolic pathway regulation, compared to molecular biology technology that has developed rapidly in recent years.

Second, gene deletion causes complete loss of function of the gene. This suggests that the expression level of the gene cannot be regulated to a desired level. In order to efficiently produce a desired metabolite in an intracellular metabolic pathway, gene deletion is attempted to block a metabolic flux that goes to the metabolic pathway. However, if the blocked metabolic flux produces a substance essential for cell growth, the growth of the cells from which the gene was deleted will be significantly inhibited or will not occur. In order to maximize the efficiency of production of a desired metabolite, cells that produce the desired metabolite should be easily grown while a metabolic flux to the desired metabolite should also be optimized. Thus, there is a need for a method capable of producing a desired substance while maintaining cell growth by regulating the level of gene expression, rather than simply deleting the gene for the purpose of regulating the metabolic flux.

Third, the gene deleted from the chromosome by a conventional gene deletion method is difficult to restore. In addition, if the deletion of the same gene is attempted in other strains, all the processes should be attempted again, and thus large amounts of time and effort are required.

Thus, in order to overcome the limitations of the conventional gene deletion method, it should be possible to reduce the expression level of the gene of interest without modifying the chromosomal sequence of the strain. Also, it should be possible to regulate the expression level of the gene and to easily apply the regulation of expression of the same gene to other strains. Further, it is required to construct and apply the gene regulatory system in a fast and convenient manner.

Accordingly, the present inventors attempted to construct a short-length customized synthetic sRNA using a method satisfying the above-described requirements.

A total of 101 *E. coli* sRNAs are currently known (Pichon et al., *Nucleic Acids Research*, DOI:10.1093/nar/gkr1141, 2011), and the mechanisms thereof are currently being studied. It has been reported to date that a large number of sRNAs form a specific secondary structure, even though they have different sequences, and that the Hfq protein recognizes and binds to the sRNAs. The functions of Hfq are to increase the half life of sRNA so that the sRNA effectively functions even in a small amount, and to assist the binding of the sRNA to the target mRNA so that the target mRNA functions quickly, and to bind RNase to the target mRNA to promote the degradation of the target mRNA to thereby more effectively reduce the expression of the gene.

The fundamental functions of *E. coli* sRNA have been continuously studied, but there are little or no reports on the use of the above-described mechanisms to construct synthetic sRNAs. According to recent reports on the construction of *E. coli* sRNAs, effective sRNAs have been constructed by random mutagenesis and screening (Sharma et al, ACS Synthetic Biology, DOI: 10.1021/sb200001q, 2011).

Accordingly, the present inventors have made extensive efforts to construct a novel, short-length customized synthetic sRNA in order to overcome the limitations of the conventional gene deletion method, and as a result, have construct a synthetic sRNA comprising an Hfq binding site, derived from MicC, SgrS and/or MicF, and a region homologous to the target mRNA such as DsRed2 mRNA, AraC mRNA, KanR mRNA or LuxR mRNA, and have found that test results for the expression of the target mRNA indicate that an efficient sRNA can be constructed without relying on conventional random methods. In addition, the present inventors have constructed synthetic sRNAs that inhibit the expression of tyrR (tyrosine regulator), csrA (carbon storage regulator), pgi (glucose-6-phosphate isomerase), ppc (phosphoenolpyruvate carboxylase) and the like, and have found that these synthetic sRNAs show effects similar to those of actual gene deletion and can be used to regulate the production of a desired metabolite, thereby completing the present invention.

The information disclosed in the Background Art section is only for the enhancement of understanding of the background of the present invention, and therefore may not contain infor-

DISCLOSURE OF INVENTION

Technical Problem

It is an object of the present invention to provide a novel, short-length customized synthetic sRNA, which overcomes the limitations of the conventional gene deletion method and can be used to regulate the mRNA expression of various target genes with high efficiency, a preparation method thereof and the use thereof.

Technical Solution

To achieve the above object, the present invention provides an sRNA (small regulatory RNA) for inhibiting gene expression in prokaryotes, the sRNA comprising: an Hfq binding site derived from the sRNA of any one of MicC, SgrS and MicF; and a region that base-pairs with the target gene mRNA.

The present invention also provides an isolated nucleic acid encoding the sRNA.

The present invention also provides an expression vector comprising the isolated nucleic acid encoding the sRNA.

The present invention also provides a recombinant microorganism having the sRNA introduced therein.

The present invention also provides a recombinant microorganism transformed with the expression vector.

The present invention also provides a method for preparing an sRNA, the method comprising linking a nucleic acid, which encodes a region that base-pairs with the target gene mRNA, to a nucleic acid that encodes an Hfq binding site derived from the sRNA of any one of MicC, SgrS and MicF.

The present invention also provides a method for inhibiting the expression of a target gene, the method comprising the steps of: introducing or expressing the sRNA in a prokaryote; and inhibiting the expression of the mRNA of the target gene.

The present invention also provides a composition for inhibiting gene expression in prokaryotes, the composition comprising the sRNA.

The present invention also provides a method for screening a gene that needs to be deleted to produce a useful substance, the method comprising the steps of:

(a) inhibiting the expression of at least one gene among genes, which are present in a strain for producing the useful substance and participate in the pathway of biosynthesis of the useful substance, using the sRNA that targets the gene; and (b) selecting the gene whose expression was inhibited, as the gene that needs to be deleted to produce the useful substance, if the production yield of the useful substance is increased by inhibition of the expression of the gene.

The present invention also provides a method for improving a strain for producing a useful substance, the method comprising the steps of:

(a) inhibiting the expression of at least one gene among genes, which are present in a strain for producing the useful substance and participate in the pathway of biosynthesis of the useful substance, using the sRNA that targets the gene;

(b) selecting the gene whose expression was inhibited, as the gene that needs to be deleted to produce the useful substance, if the production yield of the useful substance is increased by inhibition of the expression of the gene; and (c) constructing a recombinant strain having a deletion of the selected gene or a combination of the selected genes.

The present invention also provides a recombinant microorganism having an enhanced ability to produce tyrosine, the recombinant microorganism being obtained by inactivating the functions of tyrR and csrA genes in a host cell having the tyrosine biosynthesis pathway.

The present invention also provides a recombinant microorganism having an ability to produce phenol, the recombinant microorganism being obtained by introducing or amplifying a tpl gene in the above-described recombinant microorganism.

The present invention also provides a method for producing a recombinant microorganism having an enhanced ability to produce tyrosine, the method comprising inactivating the functions of tyrR and csrA genes in a host cell having the tyrosine biosynthesis pathway.

The present invention also provides a recombinant microorganism having an enhanced ability to produce cadaverine, the recombinant microorganism being obtained by inactivating the function of at least one gene, selected from the group consisting of murE (UDP-N-acetylmuramoylalanyl-D-glutamate-2,6-diaminopimelate ligase), metB (cystathionine gamma-synthase), thrL (thr operon leader peptide), ackA (propionate kinase/acetate kinase activity), pdhR (pyruvate dehydrogenase complex regulator), ilvG_1 (acetolactate synthase II, large subunit, N-ter fragment (pseudogene)), carB (carbamoyl phosphate synthetase), serC (phosphohydroxythreonine aminotransferase/3-phosphoserine aminotransferase), ilvN (acetohydroxybutanoate synthase/acetolactate synthase), Crp (CRP transcriptional dual regulator), ilvD (dihydroxy acid dehydratase), ilvY (IlvY DNA-binding transcriptional dual regulator), glpK (glycerol kinase), glpF (glycerol MIP channel), pta (Phosphate acetyltransferase), tktA (transketolase I), hflD (lysogenization regulator), deoA (thymidine phosphorylase/uracil phosphorylase), gadE (GadE controls the transcription of genes involved in glutamate dependent system), rbsK (ribokinase), ilvL (ilvGEDA operon leader peptide), ilvC (acetohydroxy acid isomeroreductase), accA (acetyl-CoA carboxyltransferase, alpha-subunit), ilvM (acetohydroxybutanoate synthase/acetolactate synthase), argB (acetylglutamate kinase), thrA (aspartate kinase/homoserine dehydrogenase), carA (carbamoyl phosphate synthetase), fbp (fructose-1,6-bisphosphatase), rbsD (ribose pyranase), panD (Aspartate 1-decarboxylase), aspA (aspartate ammonia-lyase), rcsB (RcsB-BglJ DNA-binding transcriptional activator), ivbL (The ilvB operon leader peptide), lexA (LexA represses the transcription of several genes involved in the cellular response to DNA damage), rbsA (ribose ABC transporter), murF (D-alanyl-D-alanine-adding enzyme), and thrC (threonine synthase), in a host cell having the cadaverine biosynthesis pathway.

The present invention also provides a method for producing a recombinant microorganism having an enhanced ability to produce cadaverine, the method comprising inactivating the function of at least one gene, selected from the group consisting of murE (UDP-N-acetylmuramoylalanyl-D-glutamate-2,6-diaminopimelate ligase), metB (cystathionine gamma-synthase), thrL (thr operon leader peptide), ackA (propionate kinase/acetate kinase activity), pdhR (pyruvate dehydrogenase complex regulator), ilvG_1 (acetolactate synthase II, large subunit, N-ter fragment (pseudogene)), carB (carbamoyl phosphate synthetase), serC (phosphohydroxythreonine aminotransferase/3-phosphoserine aminotransferase), ilvN (acetohydroxybutanoate synthase/acetolactate synthase), Crp (CRP transcriptional dual regulator), ilvD (dihydroxy acid dehydratase), ilvY (IlvY DNA-binding transcriptional dual regulator), glpK (glycerol kinase), glpF (glycerol MIP channel), pta (Phosphate acetyltransferase), tktA (transketolase I), hflD (lysogenization regulator), deoA (thymidine phosphorylase/uracil phosphorylase), gadE (GadE controls the transcription of genes involved in glutamate dependent system), rbsK (ribokinase), ilvL (ilvGEDA operon leader peptide), ilvC (acetohydroxy acid isomeroreductase), accA (acetyl-CoA carboxyltransferase, alpha-subunit), ilvM (acetohydroxybutanoate synthase/acetolactate synthase), argB (acetylglutamate kinase), thrA (aspartate kinase/homoserine dehydrogenase), carA (carbamoyl phosphate synthetase), fbp (fructose-1,6-bisphosphatase), rbsD (ribose pyranase), panD (Aspartate 1-decarboxylase), aspA (aspartate ammonia-lyase), rcsB (RcsB-BglJ DNA-binding transcriptional activator), ivbL (The ilvB operon leader peptide), lexA (LexA represses the transcription of several genes involved in the cellular response to DNA damage), rbsA (ribose ABC transporter), murF (D-alanyl-D-alanine-adding enzyme), and thrC (threonine synthase), in a host cell having the cadaverine biosynthesis pathway.

Other features and embodiments of the present invention will be more apparent from the following detailed descriptions and the appended claims.

BRIEF DESCRIPTION OF THE DRAWINGS

FIG. 2 shows the sequences of SgrS, MicF and MicF, the sequence of the reporter DsRed2 mRNA, and a complementary sequence binding to the RBS thereof.

FIG. 6 shows the AraC, LuxR and KanR mRNA sequences and the sequences complementary to RBS that is attached to synthetic sRNAs so as to bind thereto.

FIG. 7 is a graphic diagram showing the cross-reactivity between AraC, LuxR or KanR and a synthetic sRNA that inhibits AraC, LuxR or KanR.

FIG. 8 shows the results of calculating the energy of binding between AraC, LuxR or KanR and a synthetic sRNA, constructed so as to bind to AraC, LuxR or KanR, using the mfold software.

In FIG. 9, the green box indicates the gene to be overexpressed, the red box indicates the gene to be silenced by a synthetic sRNA, and ⊖ indicates the removal of feedback inhibition.

FIG. 10 is a schematic view of a plasmid constructed for tyrosine production.

FIG. 13 shows anti-pgi, anti-pgi-D1 and anti-pgi-D2 binding sequences.

FIG. 23 shows the experimental results obtained by preparing synthetic sRNAs, which inhibit the expression of DsRed2 and LacZ genes with various binding energies, and examining whether the use of the synthetic sRNAs regulates the expression of the genes to various levels.

FIG. 29 shows the results of an experiment performed to examine whether various anti-murE synthetic sRNAs influence the actual production of MurE protein.

BEST MODE FOR CARRYING OUT THE INVENTION

Unless otherwise defined, all technical and scientific terms used herein have the same meaning as commonly understood by one of ordinary skill in the art to which the invention pertains. Generally, the nomenclature used herein are well known and commonly used in the art.

The definition of main terms used in the detailed description of the invention is as follows.

As used herein, the term "sRNA (small RNA)" refers to a short-length RNA, which is usually 200 or less nucleotides in length, is not translated into protein and effectively inhibits the translation of a specific mRNA by complementary binding.

As used herein, the term "ribosome binding site (RBS)" refers to a site where ribosome binds to mRNA for the transcription of the mRNA.

As used herein, the term "gene" is intended to have the broadest meaning, and the gene can encode a structural protein or a regulatory protein. Herein, the regulatory protein includes a transcriptional factor, a heat shock protein, or a protein that is involved in DNA/RNA replication, transcription and/or translation. Also, the target gene whose expression is to be inhibited may be present as an extrachromosomal element.

In one aspect, the present invention is directed to a novel, short-length synthesis regulatory sRNA. That is, the present invention is directed to an sRNA (small regulatory RNA) for inhibiting gene expression in prokaryotes, the sRNA comprising: an Hfq binding site derived from the sRNA of any one of MicC, SgrS and MicF; and a region that base-pairs with the target gene mRNA.

In the present invention, structures that guarantee the stable function of synthetic sRNAs were selected, and then a binding site for the more effective inhibition of expression of target mRNA was selected. Also, whether it is possible to prepare synthetic sRNAs for inhibiting target mRNAs other than DsRed2 mRNA was examined. Further, a cross-reactivity test was performed to examine whether the constructed sRNA can inhibit the expression of mRNAs other than the target mRNA. As a result, novel synthetic sRNA structures according to the present invention and a preparation method thereof were developed.

Figure 1:
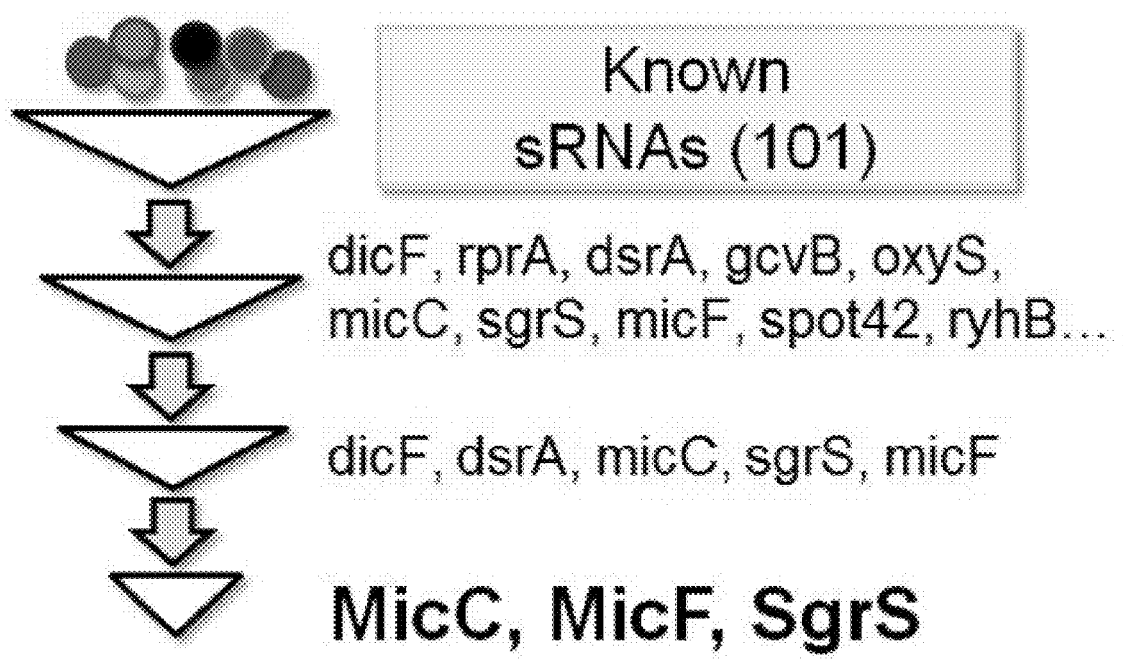
FIG. 1 shows a process for selecting basic structures for the effective function of synthetic sRNAs.

First, in order to establish structural sequences that bind to Hfq for the stable function of synthetic sRNAs and effectively inhibit the expression of target genes, a group of sRNA structure candidates suitable for the purpose was selected from 101 sRNAs present in *E. coli*, and continuous screening operations were performed, thereby finally selecting three sRNAs (FIG. 1).

The selected three sRNAs are MicC, SgrS and MicF. MicC binds to the mRNA of OmpC that assists in the passage of ions or hydrophilic substances through the *E. coli* cell membrane. SgrS binds to the mRNA of PtsG protein that is present in the cell membrane and functions to transfer glucose, and MicF binds to and inhibits the expression of the mRNA of the membrane protein OmpF that passes amino acids, ions, sugar and the like, which have a molecular weight of 600 Da or less (Wadler et al, *PNAS*, 104(51):20254-20459, 2007; Chen et al, *J. Bacteriology*, 186(20): 6689, 2004).

Figure 3:
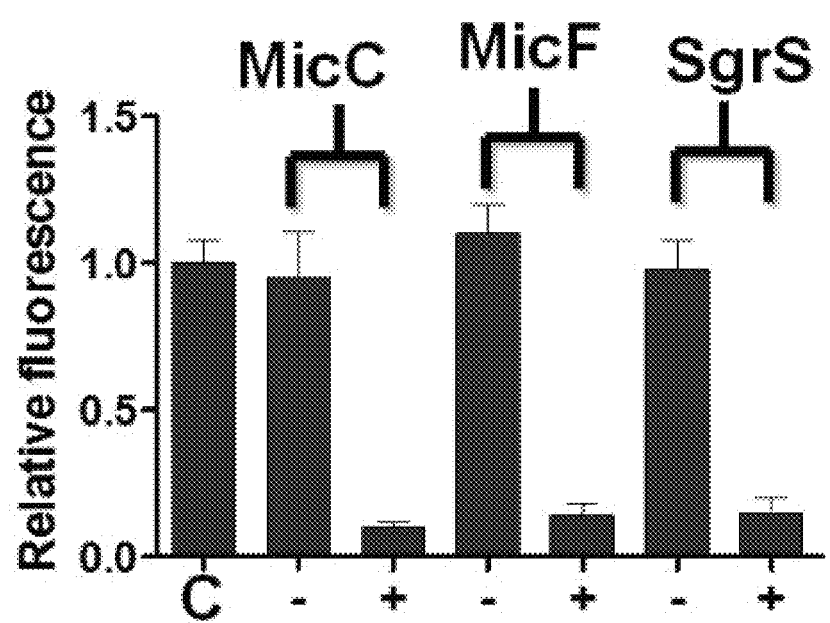
FIG. 3 is a graphic diagram showing the inhibition of expression of DsRed2 after complementary binding between MicC, MicF or SgrS and DsRed2 RBS.

In an example of the present invention, the sites of the three sRNAs, which bind to the target mRNA, were removed, and the sRNAs were constructed so as to bind to the RBS of DsRed2 mRNA in order to measure the ability of the sRNAs to inhibit expression (FIG. 2). In FIG. 2, the target mRNA-binding sequence of each of the candidate sRNAs was underlined and indicated by a red color, and it was replaced with the sequence indicated by Anti-DsRed2. As used herein, the term "RBS of DsRed2" means an actual binding site that physiologically covered by ribosome, which is bound to the mRNA so that the site cannot be recognized by other proteins. The RBS is defined as a region of 36 by from the start point of the Shine-Dalgarno sequence in the 3' end direction. It can be predicted using the results of previously reported studies (Na et al., *BMC Systems Biology*, 4(1):71, 2010). The constructed synthetic sRNAs inhibited the expression of DsRed2 by 86% when the Hfq binding site of SgrS was used, 85% when the Hfq binding site of MicF was used, and 90% when the Hfq binding site of MicC was used (FIG. 3). Thus, in the present invention, the Hfq binding site of MicC is preferably used.

Figure 4:
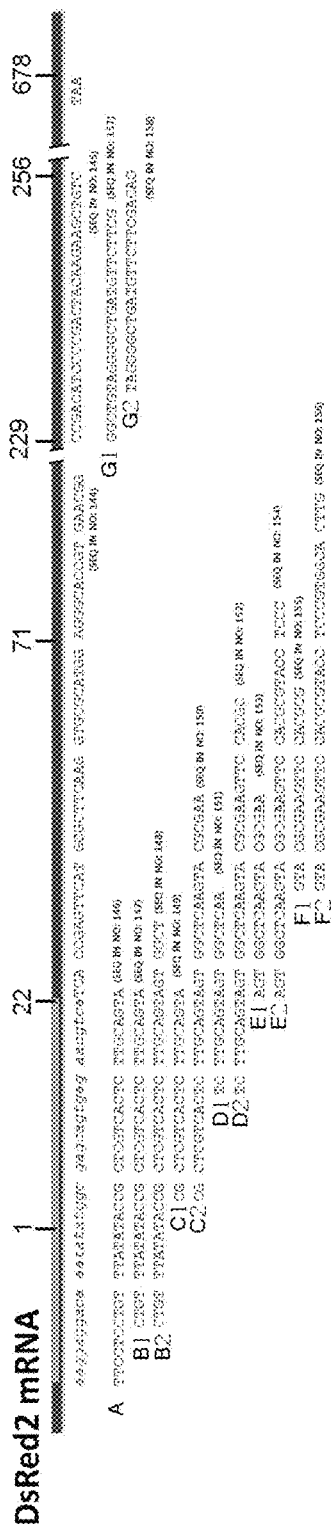
FIG. 4 shows various complementary sequences binding to DsRed2.
Figure 5:
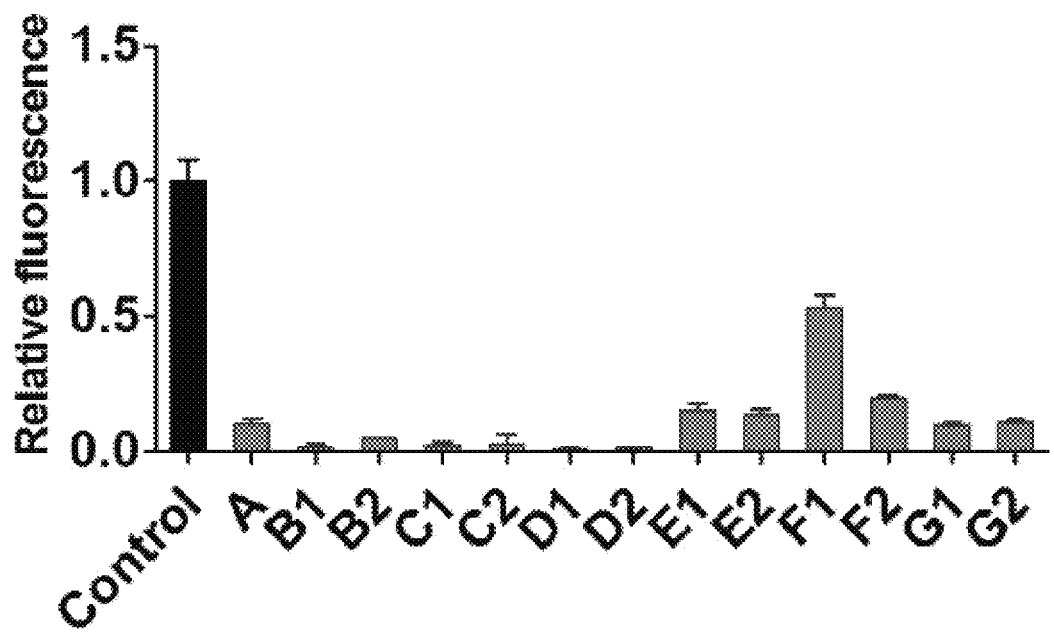
FIG. 5 is a graphic diagram showing the degree of inhibition of DsRed2 after binding of the Hfq binding site of MicC to various complementary sequences binding to DsRed2.

In another example of the present invention, whether various sequences located around the RBS of the mRNA sequence of the target gene are suitable as binding sites was experimentally examined. Specifically, from synthetic sRNAs that bind to the RBS of the target mRNA, synthetic sRNAs that bind to the RBS, a portion thereof, or regions other than the RBS, were constructed, and these binding sites had various lengths of 19 to 37 nucleotides (FIG. 4). As a result, it was shown that synthetic sRNAs that bind to at least a portion of the RBS showed an inhibitory effect of at least 90% and that synthetic sRNAs that do not bind to the RBS also had an inhibitory efficiency of 47-90% (FIG. 5). In other words, sRNAs that bind to at least a portion of the RBS show excellent expression inhibitory effects. Thus, in the present invention, the region that base-pairs with the target gene mRNA may base-pair with all or part of the RBS of the target gene mRNA. As used herein, the expression "base-pairs with part" means that base-pairing with the RBS of the target gene mRNA with a binding energy of −30 kcal/mol or higher (about 20 nucleotides or more) and also means base-pairing with part of the RBS of the target gene mRNA or a region located around thereof, as shown in FIG. 4. Herein, the region that base-pairs with the RBS consists of one or more nucleotides, and preferably 9 or more nucleotides. In the present invention, when a synthetic sRNA binds to regions other than the RBS, the effect thereof can be relatively low, but this synthetic sRNA can also be used to regulate the expression level. Meanwhile, even when the region that base-pairs with the target gene mRNA had various lengths of 19-37 nucleotides, the sRNA according to the present invention showed expression inhibitory effects. Thus, the region that base-pairs with the target gene mRNA may have a minimum size that can base-pair with the target gene. For example, the region may have a length of 20-50 nucleotides, and preferably 19-37 nucleotides.

In another example of the present invention, it was found that, when a site that does not bind to the mRNA of the target gene was formed by deleting one or two nucleotides from the region that base-pairs with the mRNA of the target gene, the degree of inhibition of expression could be regulated. Thus, in the present invention, a site that does not bind to the mRNA of the target gene can be formed by deleting or substituting one or more nucleotides in the region that base-pairs with the mRNA of the target gene. In addition, a site that does not bind to the mRNA of the target can also be formed by inserting or deleting one or more nucleotides in the region that base-pairs with the mRNA of the target gene. Herein, in order to base-pair with the mRNA of the target gene, 1-10 nucleotides, preferably 1-5 nucleotides should be deleted, substituted or inserted so that the binding energy is between −30 kcal/mol and −13 kcal/mol.

In another example of the present invention, an experiment was performed to examine whether the synthetic sRNA not only simply inhibits the expression of the target mRNA, but also regulates the expression to various levels to regulate the production of protein to various levels, thereby more precisely regulating cell metabolic pathways. Specifically, a synthetic sRNA that inhibits the expression of DsRed2 gene, and a synthetic sRNA that inhibits the expression of lacZ gene, were constructed. Also, synthetic sRNAs were constructed to bind to each mRNA with a binding energy ranging from 0 to −60 kcal/mol, and the degree of the inhibition of expression of the target mRNA by each of the synthetic sRNAs was measured (FIG. 23). As a result, it could be seen that, in the range from about −10 kcal/mol to −40 kcal/mol, the expression of the target mRNA decreased linearly, and at −40 kcal/mol or lower, an additional decrease in the expression did not occur. This indicates that, when the synthetic sRNA according to the present invention is constructed to bind to the target mRNA with a binding energy ranging from −10 kcal/mol to −40 kcal/mol, it can inhibit the expression of the target mRNA to a desired level. Thus, in the present invention, the region that base-pairs with the target gene mRNA is preferably constructed so that the energy of binding to the target gene mRNA is in the range from −10 kcal/mol to −40 kcal/mol. More preferably, the region that base-pairs with the target gene mRNA is preferably constructed so that the energy of binding to the target gene mRNA is in the range from −20 kcal/mol to −40 kcal/mol.

Figure 24:
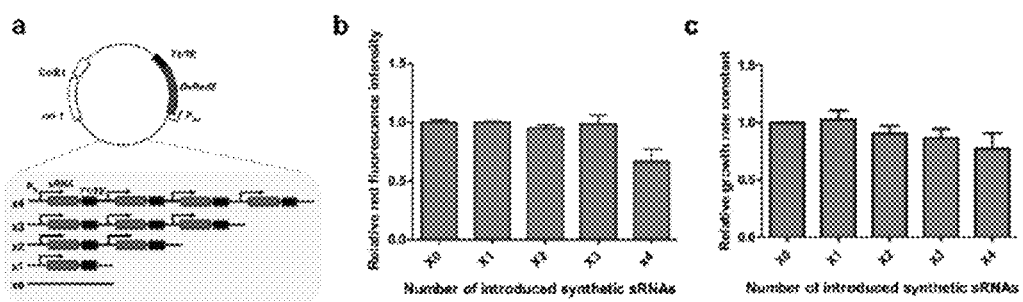
FIG. 24 shows the results of an experiment performed to examine whether the introduction of synthetic sRNAs inhibits protein expression and cell growth in microorganisms.

Meanwhile, when the synthetic sRNA is additionally introduced into a plasmid in order to regulate the expression of the target gene and is produced in cells, the sRNA can interfere with the growth of the cells by using the energy source of the cells. Thus, in another example of the present invention, whether the additionally introduced synthetic sRNA has any influence on cell growth and intracellular protein expression was examined (FIG. 24). 0, 1, 2, 3 and 4 synthetic sRNAs were introduced into a plasmid having a ColE1 replication origin, and the change in the expression level of DsRed2 gene in the plasmid was measured. As a result, it could be seen that the introduction of up to three synthetic sRNAs did not influence the expression of DsRed2 (FIG. 24b). Also, whether the introduction of 0, 1, 2, 3 and 4 synthetic sRNAs has any influence on the growth rate of cells was measured. In this case, the optical density (600 nm) at the log growth phase of cells was measured and fitted into the following cell growth curve equation to calculate cell growth constant (k) per time:

$$y = y_0 \exp(k \cdot t)$$

wherein $y_0$ is the initial O.D.600 value, and t is time. As a result, it could be seen that, when up to three synthetic sRNAs were introduced, the k value slightly decreased, but the decrease was not significant. This indicates that the introduction of up to three synthetic sRNAs into cells does not significantly influence the growth of the cells (FIG. 24c).

In another example of the present invention, an experiment was performed to examine whether other synthetic sRNAs for inhibiting other target mRNAs can be constructed based on the above-described method for constructing synthetic sRNAs and whether the inhibitory effects of the other synthetic sRNAs are sufficient. For example, synthetic sRNAs for inhibiting AraC, KanR and LuxR mRNA other than DsRed2 were constructed (FIG. 6). Combinations of the three constructed sRNAs and three genes were made, and the inhibition of expression by each of the combinations was examined. For this examination, DsRed2 protein was fused to each of the genes to emit red fluorescence. The results of the experiment indicated that the inhibition rates of expression of the target mRNAs by the sRNAs were uniform (80-860) and that the expression of other mRNAs did not differ from the case in which no synthetic sRNA was used.

The energy of binding between the three synthetic sRNAs and the respective target mRNAs was estimated. As a result, the energy of binding to the intended target was in the range from −53.7 to −59.5 kcal/mol, whereas the energy of binding to other mRNAs was in the range from −12.2 to −13.5 kcal/mol. The results of the analysis indicate that, when the energy of binding to the target mRNA is about −50 kcal/mol or lower and the energy of binding to other mRNAs is −13 kcal/mol or higher, the sRNA can sufficiently inhibit only the desired target without cross reactivity. In other words, the synthetic sRNA constructed according to the method of the present invention has characteristics in that it sufficiently inhibits the expression of the target mRNA and does not inhibit the expression of other mRNAs.

It is to be understood that the RBS of the transcribed mRNA can be sufficiently predicted from the results of previously reported studies and that the synthetic sRNA constructed from MicC, or if necessary, SgrS or MicF, can be made so as to bind to any mRNA.

Also, it will be obvious to those skilled in the art that the method for preparing synthetic sRNAs according to the present invention can be applied to genes other than the DsRed2, AraC, kanR and LuxR included in the examples of the present invention in the same manner, and thus the scope of the present invention is not limited to these genes. In addition, from the above-mentioned study results indicating that RBS sites can be predicted in prokaryotes in the same manner and that sRNA is evolutionally conserved in prokaryotes, it can be seen that the method for preparing the synthetic sRNA can also be applied to other prokaryotes, including *Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus, Clostridium, Corynebacterium, Streptomyces, Bifidobacterium,* and *Cyclobacterium,* in addition to *E. coli.*

In the present invention, the Hfq binding site derived from the sRNA of any one of MicC, SgrS and MicF may be located successively from the region that base-pairs with the target gene mRNA or may be linked to the region by a linker such as a nucleic acid fragment. As used herein, "base-pairing" means base-pairing between nucleic acid sequences. The region that base-pairs with the target gene mRNA may have a sequence complementarity of about 70-80% or more, preferably about 80-90% or more, and even more preferably 95-990 or more, to the target gene mRNA.

In addition, the sRNA of the present invention may be synthesized according to a general method, but is not limited thereto. In other words, the sRNA may be chemically or enzymatically synthesized.

The sRNA according to the present invention may comprise a chemical modification. The chemical modification may be the substitution of the hydroxyl group at position 2' of the ribose of at least one nucleotide included in the sRNA by any one of a hydrogen atom, a fluorine atom, an —O-alkyl group, an —O-acyl group and an amino group. In addition, the chemical modification may also be the substitution of the hydroxyl group by any one of —Br, —Cl, —R, —R'OR, —SH, —SR, —N3 and —CN (R=alkyl, aryl, or alkylene) in order to increase the ability to deliver the sRNA. Furthermore, the chemical modification may be the substitution of the phosphate backbone of at least one nucleotide by any one of a phosphorothioate form, a phosphorodithioate form, an alkylphosphonate form, a phosphoroamidate form and a boranophosphate form. Moreover, the chemical modification may be the substitution of at least one nucleotide included in the siRNA by any one of LNA (locked nucleic acid), UNA (unlocked nucleic acid), morpholino, and PNA (peptide nucleic acid).

In another aspect, the present invention is directed to an isolated nucleic acid encoding the sRNA, and an expression vector comprising the isolated nucleic acid encoding the sRNA.

In the present invention, "nucleic acid" may be RNA, DNA, stabilized RNA or stabilized DNA. As used herein, the term "encoding" refers to a nucleic acid sequence encoding the sRNA and complementary to the sRNA.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector. For the purpose of the present invention, the plasmid vector is preferably used. A typical plasmid vector which can be used for this purpose contains: (a) a replication origin by which replication occurs efficiently such that several hundred plasmid vectors per host cell are created; (b) an antibiotic-resistant gene by which host cells transformed with the plasmid vector can be selected; and (c) restriction enzyme cutting sites into which foreign DNA fragments can be inserted. Even if suitable restriction enzyme cutting sites are not present in the vector, the use of a conventional synthetic oligonucleotide adaptor or linker enables the easy ligation between the vector and the foreign DNA fragments. After ligation, the vector should be transformed into suitable host cells. The transformation can be easily achieved by the calcium chloride method or electroporation (Neumann, et al., *EMBO J.*, 1:841, 1982). As the vector which is used for the expression of the sRNA according to the present invention, an expression vector known in the art may be used.

A nucleotide sequence is operably linked when it is arranged in a functional relationship with another nucleic acid sequence. The nucleotide sequence may be a gene and a control sequence(s) linked to be capable of expressing the gene when it binds to a control sequence(s) (e.g., transcription-activating protein). For example, DNA for a pre-sequence or a secretory leader is operably linked to DNA encoding polypeptide when expressed as pre-protein participating in secretion of polypeptide; a promoter or an enhancer is operably linked to a coding sequence when affecting the transcription of the sequence; and a RBS is operably linked to a coding sequence when affecting the transcription of the sequence, or to a coding sequence when arranged to facilitate translation. Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when the site does not exist, a synthetic oligonucleotide adaptor or a linker is used according to a conventional method.

In still another aspect, the present invention is directed to a recombinant microorganism transformed with the expression vector comprising an isolated nucleic acid encoding the sRNA.

As used herein, the term "transformation" means that DNA can be replicated as a factor outside of chromosome or by means of completion of the entire chromosome by introducing DNA into a host.

Of course, it should be understood that all vectors do not equally function to express DNA sequences according to the present invention. Similarly, all hosts do not equally function with respect to the same expression system. However, one skilled in the art may appropriately select from among various vectors, expression control sequences, and hosts without either departing from the scope of the present invention or bearing excessive experimental burden. For example, a vector must be selected considering a host, because the vector must be replicated in the host. Specifically, the copy number of the vector, the ability of regulating the copy number and the expression of other protein encoded by the corresponding vector (e.g., the expression of an antibiotic marker) should also be considered.

In still another aspect, the present invention relates to effectively inhibiting the expression of an intracellular gene without deletion of the gene to change the flux of metabolic pathways to thereby increase the production of a desired metabolite. In one example of the present invention, it was found that the flux of metabolic pathways can be artificially regulated by inhibiting the expression of an intracellular target gene using the synthetic sRNA, whereby tyrosine and phenol can be produced with high efficiency in *E. coli*. In another example of the present invention, it was found that cadaverine can be produced with high efficiency in *E. coli* using the same principle. Accordingly, the present invention is directed to a method for inhibiting the expression of a target gene, the method comprising the steps of: introducing or expression the sRNA in a prokaryote; and inhibiting the mRNA expression of the target gene.

In yet another aspect, the present invention is directed to a method for inhibiting the expression of a target gene, the method comprising the steps of: introducing or expressing the sRNA in a prokaryote; and inhibiting the expression of the mRNA of the target gene.

Preferably, the expression of the sRNA can be induced by a promoter that operates according to binding of an inducer such as arabinose or can be inhibited by a temperature-sensitive transcription factor such as cI.

Specifically, for right expression of the synthetic sRNA, the expression of the sRNA can be doubly regulated using an exogenous inducer and a temperature-sensitive transcription factor. Specifically, the synthetic sRNA can be expressed by the phage lambda promoter PR, and the expression thereof can be surely controlled using arabinose concentration and temperature by expressing the temperature-sensitive protein cI(ts2) from a pBAD promoter.

The sRNA according to the present invention can be used to screen a gene that needs to be deleted to produce a useful substance. The method for screening the gene that needs to be deleted to produce a useful substance comprises the step of: (a) inhibiting the expression of at least one gene among genes, which are present in a strain for producing the useful substance and participate in the pathway of biosynthesis of the useful substance, using the sRNA that targets the gene; and (b) selecting the gene whose expression was inhibited, as the gene that needs to be deleted to produce the useful substance, if the production yield of the useful substance is increased by inhibition of the expression of the gene. As used herein, the term "deleted" is meant to include mutating, replacing or deleting part of the gene of interest, or introducing one or more nucleotides into the gene, or introducing a gene, an enzyme or a chemical substance, which inhibits the expression or activity of the enzyme of interest, thereby inhibiting the activity of the enzyme. In addition, the selected gene to be deleted may also be used to improve the strain for producing the useful substance.

In a further aspect, the present invention is directed to a method for improving a strain for producing a useful substance, the method comprising the steps of:

(a) inhibiting the expression of at least one gene among genes, which are present in a strain for producing the useful substance and participate in the pathway of biosynthesis of the useful substance, using the sRNA that targets the gene;

(b) selecting the gene whose expression was inhibited, as the gene that needs to be deleted to produce the useful substance, if the production yield of the useful substance is increased by inhibition of the expression of the gene; and (c) constructing a recombinant strain having a deletion of the selected gene or a combination of the selected genes.

In an example of the present invention, it was found that, when the expression of tyrR and csrA in a host cell having the tyrosine biosynthesis pathway was inhibited using the sRNA according to the present invention, the production of tyrosine in the cell was increased.

In a still further aspect, the present invention is directed to a recombinant microorganism having an enhanced ability to produce tyrosine, the recombinant microorganism being obtained by inactivating the functions of tyrR and csrA genes in a host cell having the tyrosine biosynthesis pathway.

As used herein, the term "inactivation of function" is meant to include mutating, replacing or deleting part of the gene of interest, or introducing one or more nucleotides into the gene, or introducing a gene, an enzyme or a chemical substance, which inhibits the expression or activity of the enzyme of interest, thereby inhibiting the activity of the enzyme. Thus, a method of inactivating the function of a specific gene is not limited to any particular method, so long as the activity of the specific gene of interest and the activity of the enzyme that is encoded by the gene is inhibited by conventional methods, including inhibition of expression by antisense RNA, homologous recombination, homologous recombination by expression of various recombinant enzymes (lambda recombinase, etc.), and insertion of a specific sequence using reverse transcriptase and RNA.

In addition, in one example of the present invention, a recombinant plasmid was constructed, which overexpresses the following genes involved in the tyrosine biosynthesis pathway (FIG. 10): ppsA that encodes phenolpthiocerol synthesis type-I polyketide synthase A; tktA that encodes transketolase; aroG and aroF that encode 3-deoxy-7-phosphoheptulonate synthase; aroK that encodes shikimate kinase I; tyrA that encodes chorismate mutase; and tyrC that encodes *Zymomonas mobilis*-derived prephenate dehydrogenase. Particularly, the present invention provides a recombinant plasmid constructed by performing site-directed mutagenesis of one or more amino acid residues in feedback-resistant aroG and tyrA to increase the activation of the tyrosine metabolic pathway (aroG A146N and tyrA A354V/M531, LutkeEversloh et al, Applied Microbiology and Biotechnology, 75:103, 1999).

The recombinant plasmid constructed as described above was transformed into 14 different *E. coli* strains (K-12 strains (C600, DH5α, ER2925, JM110, MG1655, S17-1, T1R (One shot(R) ccdB SurvivalTM2 T1R, Invitrogen), TG1, TOP10, W3110, XL1-Blue), B strain (BL21(DE3), W strain, and a hybrid (HB101) of K-12 and B strains)), and then the production of tyrosine in each of the transformed strains was measured (FIG.

Although 14 microbial strains belonging to the genus *Escherichia* are illustrated in the present invention, the scope of the present invention is not limited to these 14 microbial strains, because it is evident that the synthetic sRNA and recombinant plasmid of the present invention likewise operate in *Escherichia, Bacillus, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus, Clostridium, Corynebacterium, Streptomyces, Bifidobacterium* and *Cyclobacterium*.

It can be seen that the strains showed different abilities to produce tyrosine, even though the tyrosine biosynthesis pathway was activated by the same biosynthesis pathway. This suggests that even strains belonging to *E. coli* species have different intracellular activities. Thus, this indicates that, for metabolic engineering, the production of a desired compound in all different strains should be examined in order to reach the maximum yield of the desired compound. Accordingly, it can be seen that it is difficult to perform this examination by modifying the chromosomal sequence according to the conventional time-consuming deletion method. Therefore, it can be seen that technology of reducing the expression of a target gene in a manner similar to the gene deletion method without modifying the chromosomal sequence, that is, the synthetic sRNA technology according to the present invention, is highly useful.

Figure 11:
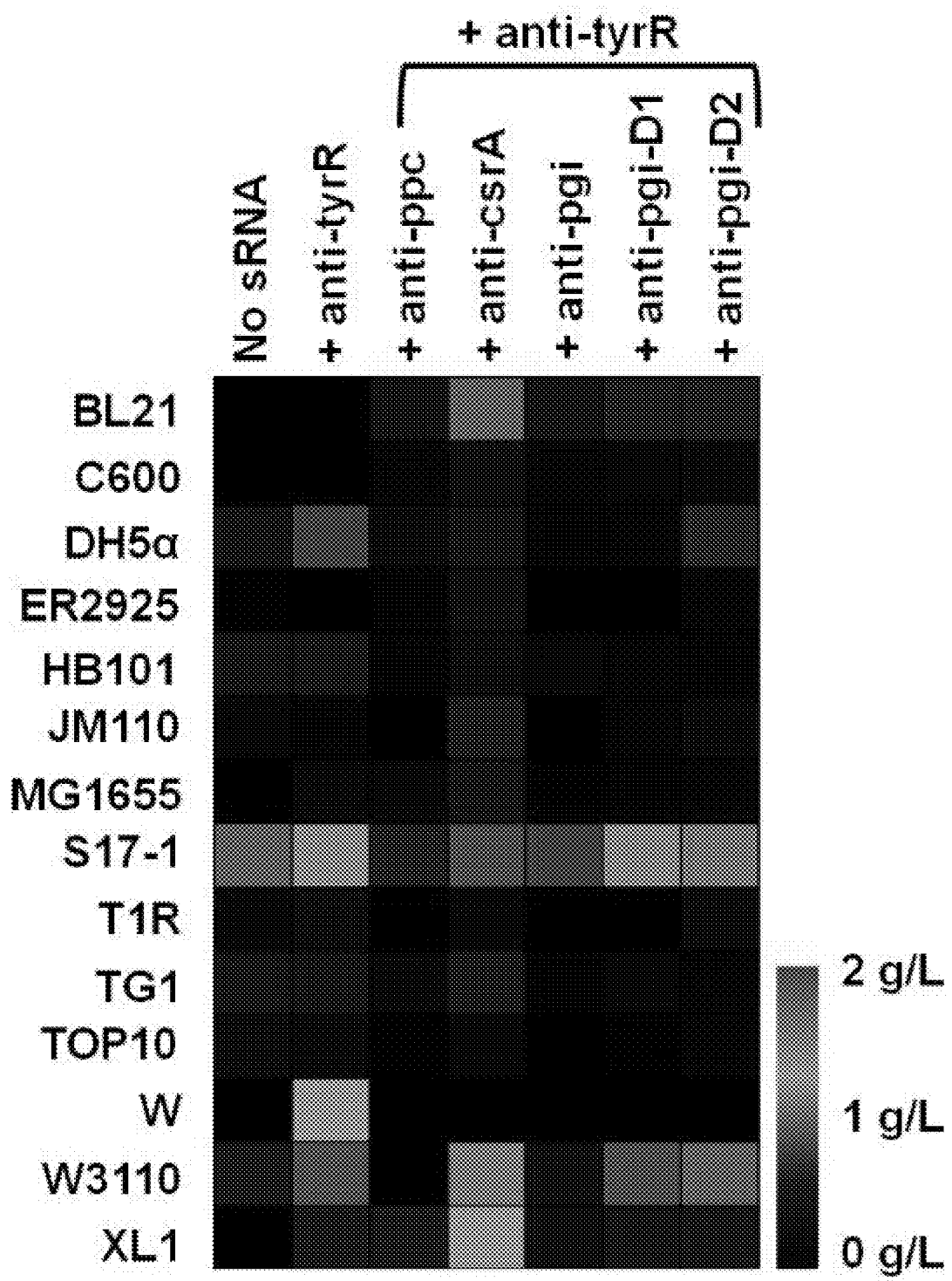
FIG. 11 is a graphic diagram showing the results obtained by amplifying the expression of tyrosine biosynthesis pathway-related genes for tyrosine production, inhibiting the expression of tyrR, ppc, csrA and pgi with synthetic sRNAs, and then comparing the production of tyrosine in various *E. coli* strains (pgi also includes an additional synthetic sRNA (anti-pgi-D1, -D2) whose expression was regulated).

In the present invention, anti-tyrR synthetic sRNA that targets tyrR mRNA was cloned into the recombinant plasmid constructed as described above, and the effects thereof in the 14 different strains were examined in the same manner. Each of the remaining three synthetic sRNAs that regulate other metabolic fluxes was cloned into the same recombinant plasmid, and the effects thereof were examined in combination (FIG. 11). As a result, it could be seen that, when tyrR was inhibited, the production of tyrosine in most of the strains increased. However, when a synthetic sRNA that inhibits the expression of ppc or pgi was additionally introduced, the production of tyrosine decreased rather than increased. Particularly, it could be seen that, when the expression of pgi was inhibited, the growth rate of the *E. coli* strain significantly decreased, and for this reason, the overall production of tyrosine in the strain decreased.

Figure 12:
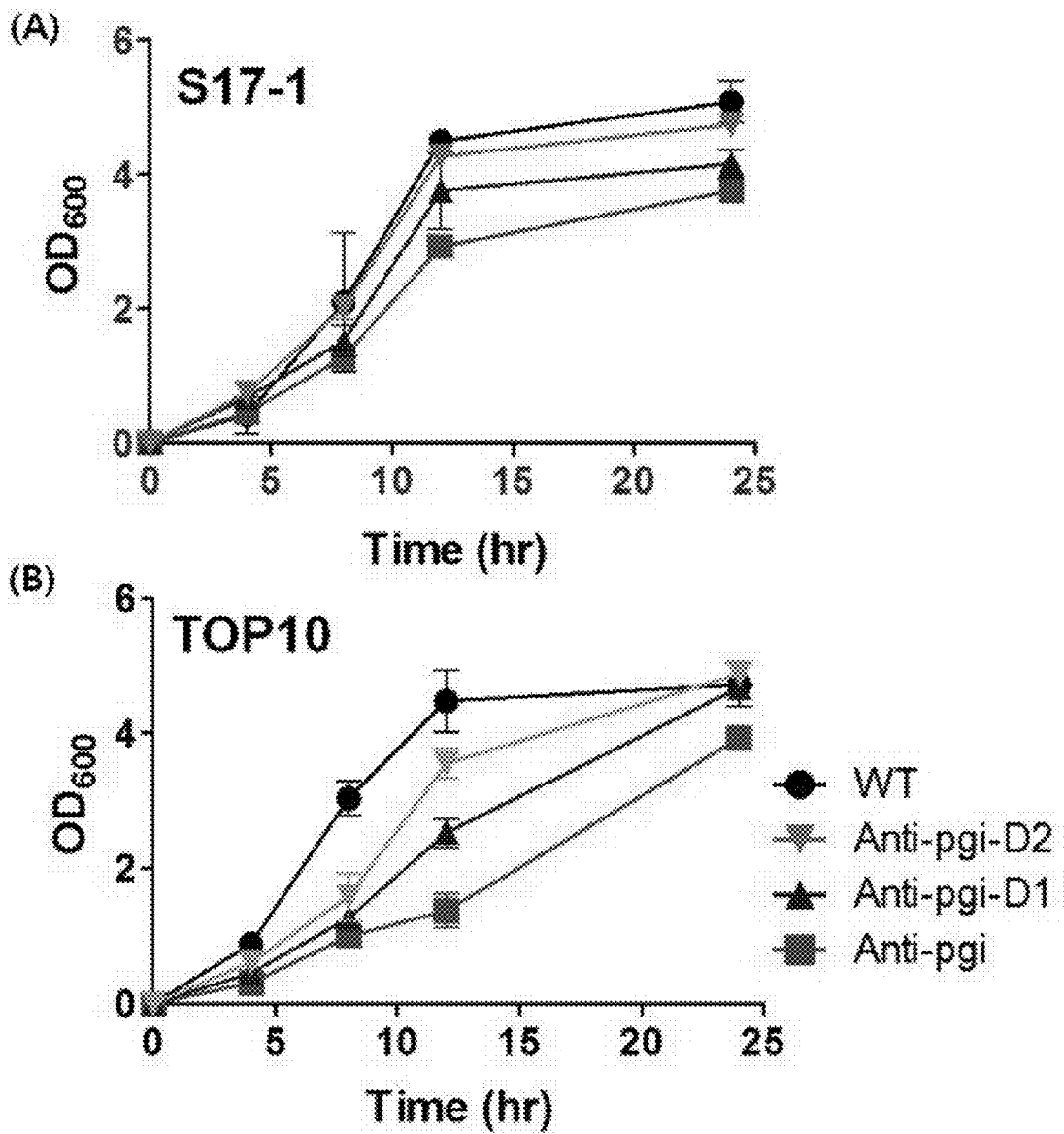
FIG. 12 shows growth curves of S17-1 and TOP10 strains according to anti-pgi, anti-pgi-D1 and anti-pgi-D2 synthetic sRNAs.

In the present invention, the degree of inhibition of expression of the gene pgi was more diversified in order to balance between the growth of the host cell and the metabolic flux to tyrosine, thereby increasing the overall production of tyrosine. For this purpose, part of the binding sequence of the synthesis regulatory gene anti-pgi was deleted in order to reduce the binding ability. Specifically, as shown in FIG. 13, one or two nucleotides of the bonding sequence were deleted, and then changes in cell growth and tyrosine production were observed. As a result, as can be seen in FIG. 11, as the degree of inhibition of the gene decreased, the production of tyrosine increased while the growth rate of the host cell also increased. With respect to this, FIG. 12 shows an S17-1 strain having the highest ability to produce tyrosine and a TOP10 strain having the lowest ability to produce tyrosine.

Through the above-described procedures performed in the present invention, it was found that the *E. coli* strain S17-1 in which the expression of the genes tyrR and csrA were inhibited showed the highest ability to produce tyrosine (2 g/L).

Figure 15:
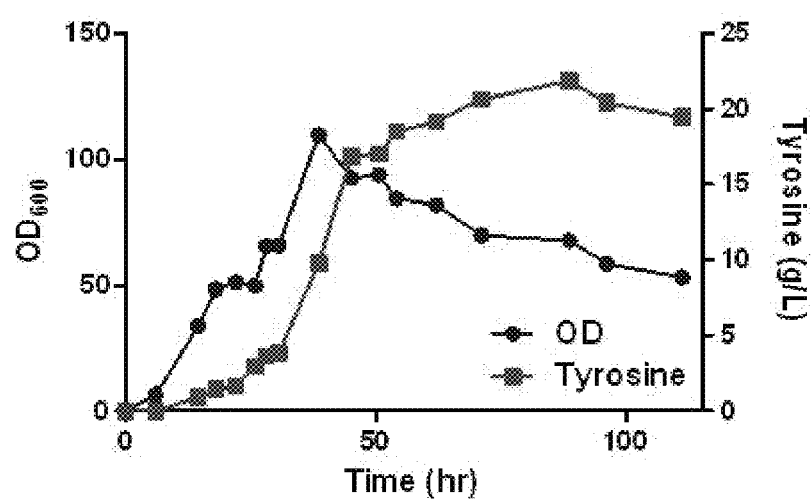
FIG. 15 is a graphic diagram showing the results of fermentation of S17-1 (pTyr-a(anti-csrA), pTyr-b(anti-tyrR)) recombinant microorganisms.

Fermentation was performed using the recombinant S17-1 strain constructed in the present invention, and as a result, it was shown that the production of tyrosine could reach up to 21.9 g/L (FIG. 15).

Figure 14:
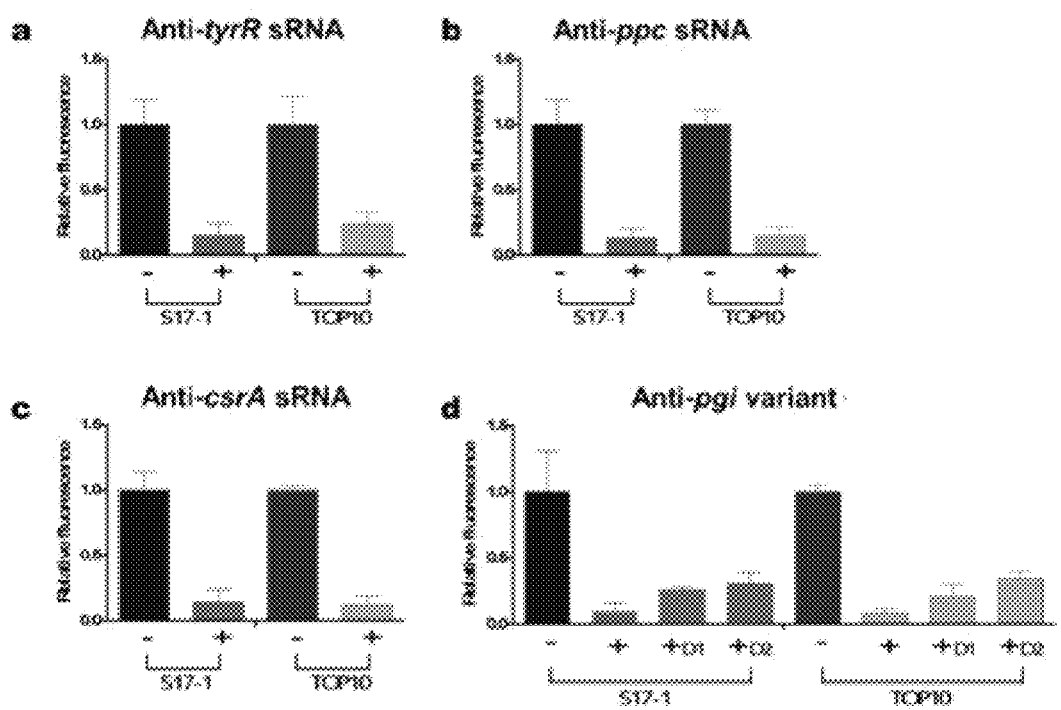
FIG. 14 is a graphic diagram showing the inhibition of expression of a target gene in S17-1 and TOP10 by anti-tyrR, anti-csrA, anti-ppc, anti-pgi, anti-pgi-D1 and anti-pgi-D2.

In order to verify that the production of the desired compound tyrosine varies depending on the metabolic ability of cells even for the same metabolic engineering and to demonstrate that the constructed synthetic sRNA effectively the expression of its target RNA, the degrees of inhibition of expression of the target RNA in the S17-1 and TOP10 strains were measured (FIG. 14). As a result, it was shown that the expression of the target mRNA in the two strains was effectively inhibited by about 80-90%. This indicates that the synthetic sRNA shows similar inhibitory effects regardless of strains.

In the present invention, it was found that the synthetic sRNA can be used to regulate metabolic fluxes and that, due to its advantage in that it eliminates the need to modify the chromosomal sequence, the amounts of production of tyrosine caused by the inhibition of expression of the target gene in various *E. coli* strains can be effectively determined at the same time.

In the present invention, tyrosine phenol lyase (TPL) was additionally cloned into the constructed plasmid in order to change tyrosine to phenol and produce phenol. Also, the constructed plasmid was introduced into the 14 different *E. coli* strains tested as described above, and then the production of phenol in the *E. coli* strains was measured. As a result, it was shown in the production of phenol in the W3110 strain was 357.6 mg/L, and the production of phenol in the S17-1 strain that showed the highest ability to produce tyrosine was 68.8 mg/L. This is the first successful production of phenol in *E. coli*.

In a yet further aspect, the present invention is directed to a recombinant microorganism having an ability to produce phenol, the recombinant microorganism being obtained by introducing or amplifying a tpl gene in the above-described recombinant microorganism.

Figure 17:
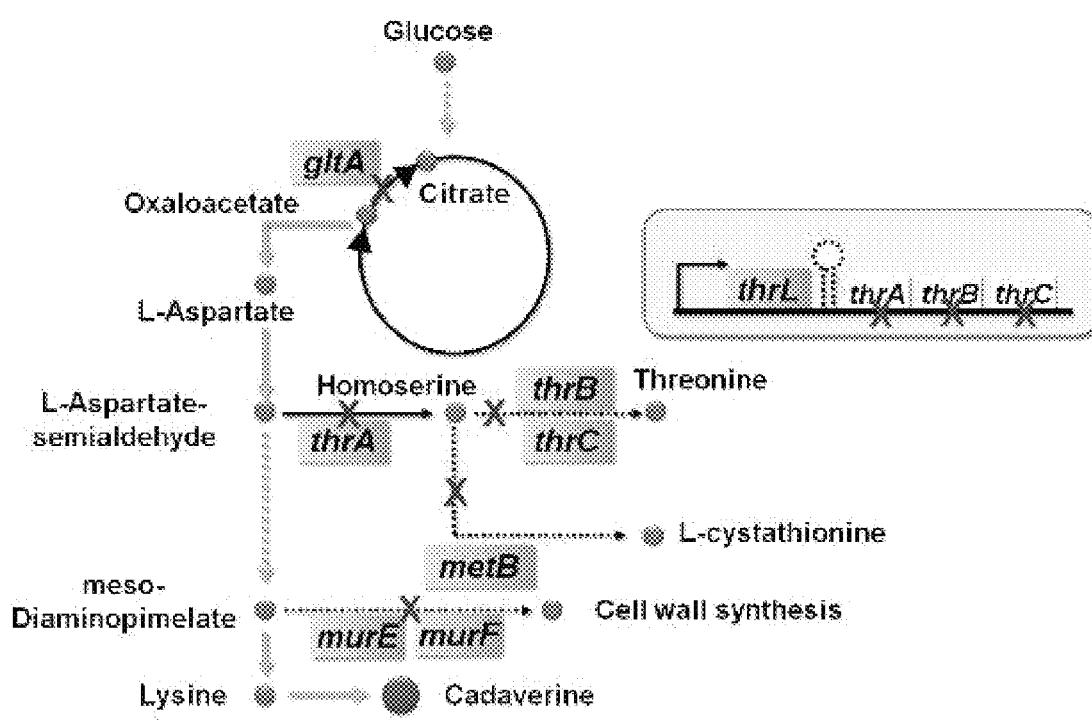
FIG. 17 shows the cadaverine biosynthesis pathway in *E. coli*. The red box indicates the target genes to be silenced by synthetic sRNA.
Figure 18:
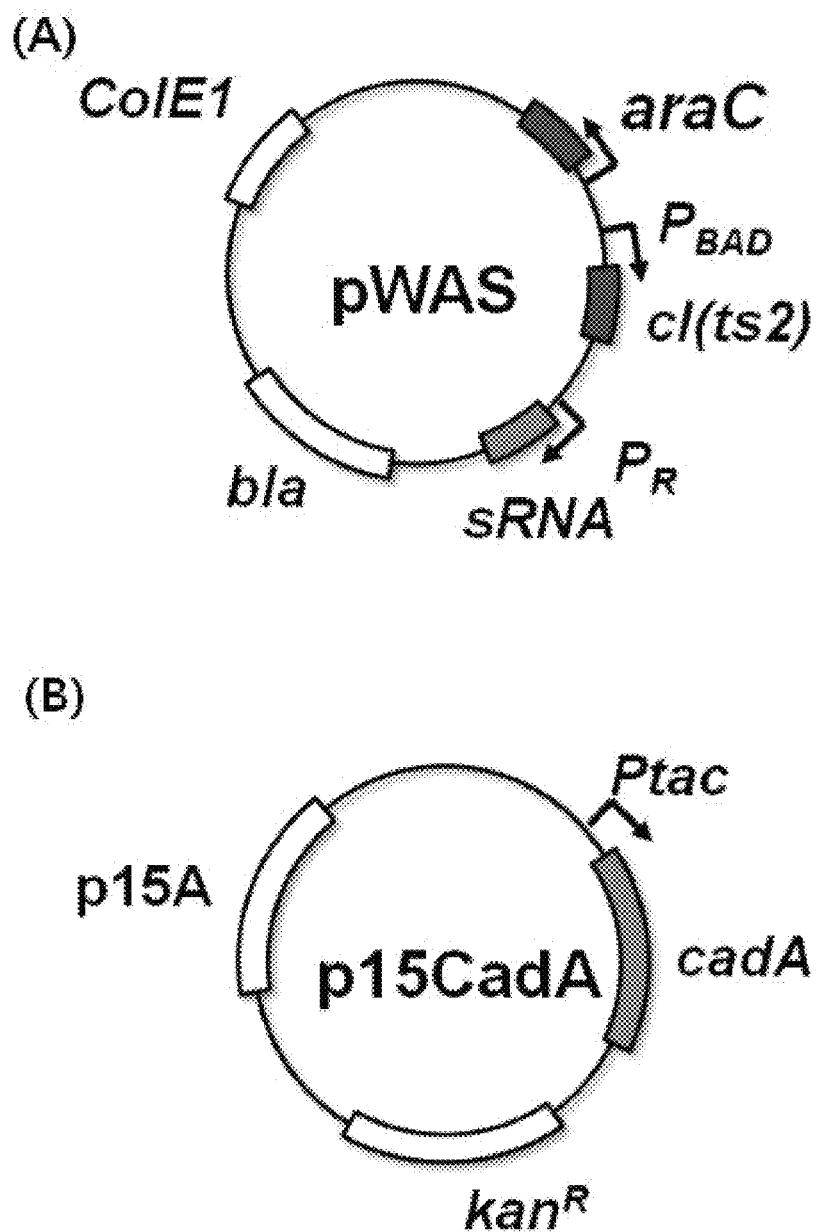
FIG. 18 is a schematic view showing a plasmid to be transformed to increase the production of cadaverine.

In another example of the present invention, whether a metabolic flux can be regulated by the synthetic sRNA to increase the production of cadaverine was examined. For this purpose, the W3110 recombinant strain (XQ56) reported to produce cadaverine through the lysine biosynthesis pathway was used as a basic strain (FIG. 17) (Qian et al, Biotechnology and Bioengineering, 108(1): 93-103, 2011). The basic strain already included a p15CadA recombinant plasmid, and the synthetic sRNA was cloned into the separate plasmid pWAS and transformed into the strain (FIG. 18).

In order to increase the amount of metabolites required for the production of Cadaverine, the following eight candidate genes to be inhibited were selected: gltA (citrate synthase), thrA (aspartate kinase I), thrB (homoserine kinase), thrC (threonine synthase), thrL (throperonleaderpeptide), metB (cystathionine gamma-synthase), murE (UDP-N-acetylmuramoyl-L-alanyl-D-glutamate-L-lysine ligase), and murF (UDP-N-acetylmuramoylalanyl-D-glutamyl-2,6-diaminopimelate-D-alanyl-D-alanine ligase).

Figure 19:
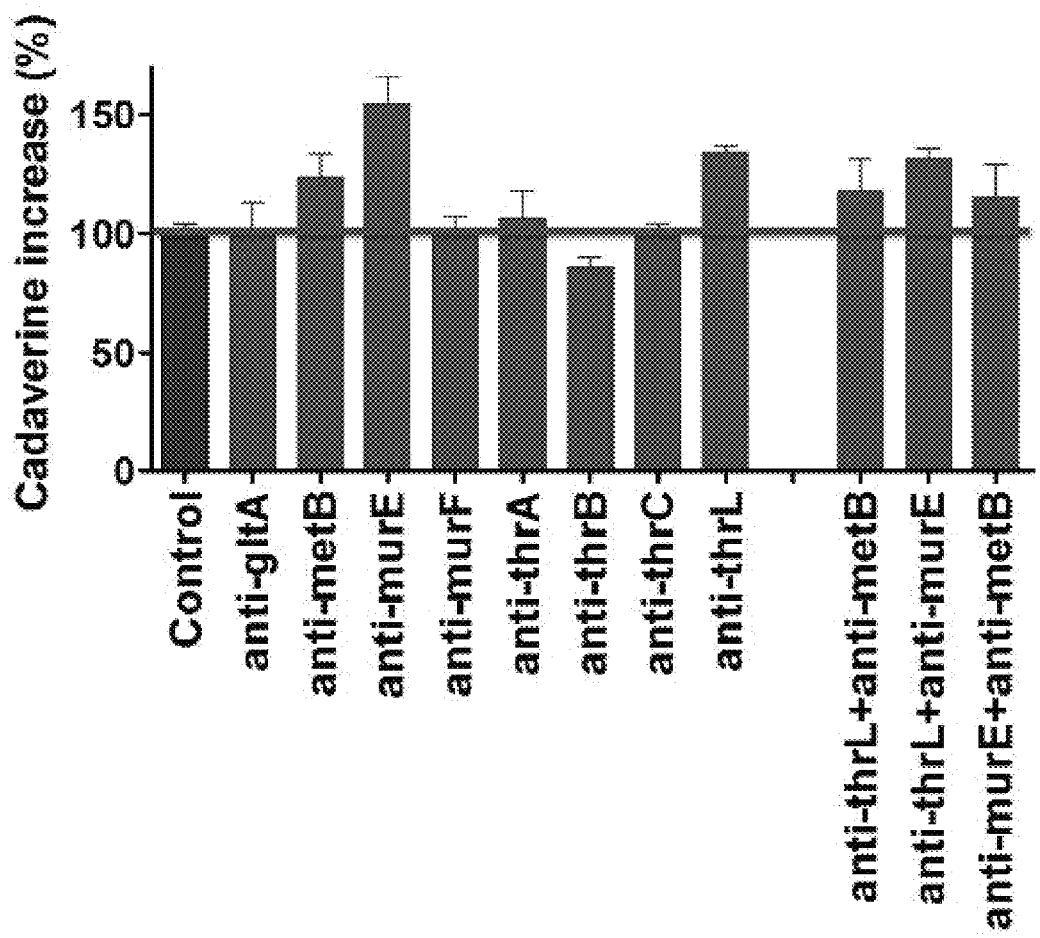
FIG. 19 is a graphic diagram showing the changes in the production of cadaverine after introduction of synthetic sRNAs (Control contains a p15CadA plasmid in an XQ56 strain and contains no synthetic sRNA. The concentration of cadaverine in the control is 1.3 g/L).

After transformation with the recombinant plasmid containing the constructed synthetic sRNA, the production of cadaverine was measured. The production of cadaverine in the basic strain was 1.4±0.05 g/L, and when it was taken as 100%, the strains in which the expressions of each of murE, metB and thrL among the eight candidate genes were inhibited showed increases in cadaverine production of 55% (2.15 g/L) for murE, 24% (1.73 g/L) for metB and 34% (1.87 g/L) for thrL (FIG. 19).

Figure 27:
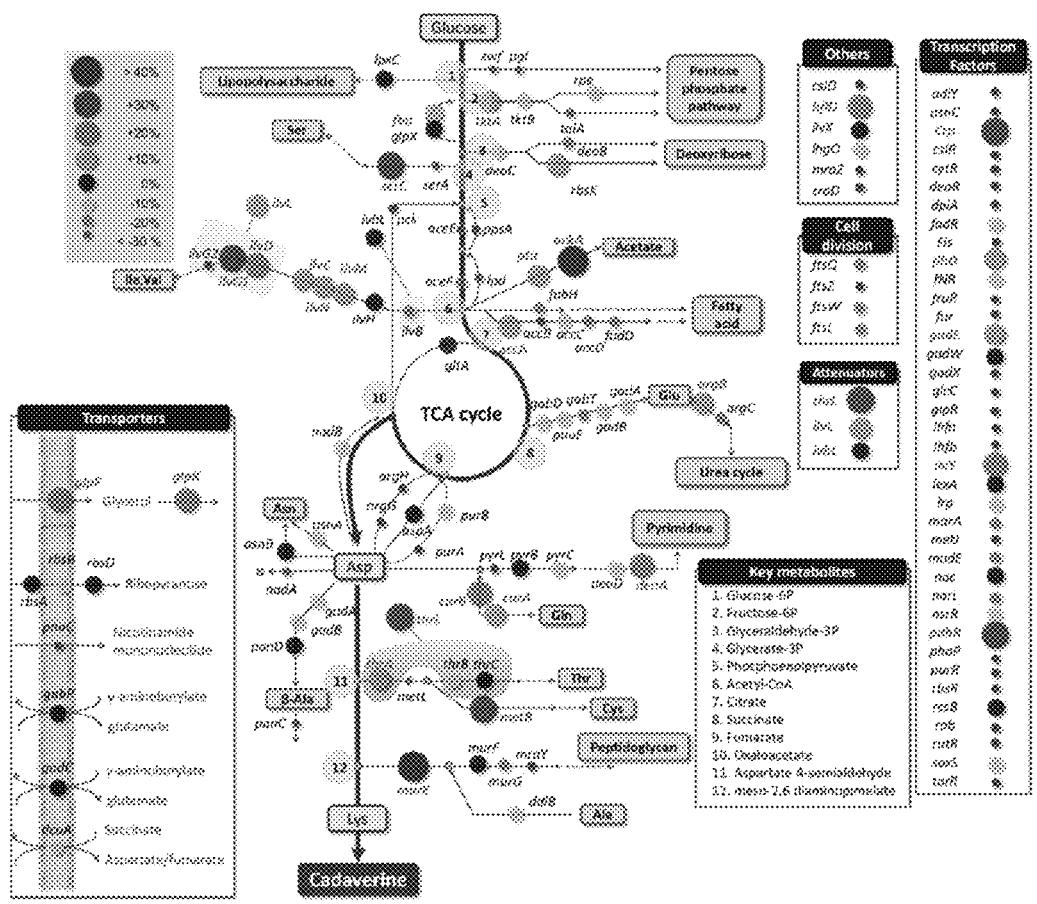
FIG. 27 shows the cadaverine biosynthesis pathway in *E. coli* and the concentration of cadaverine produced upon inhibition by synthetic sRNAs.

In another example of the present invention, the same experiment was performed on 130 candidate genes, and as a result, as shown in FIG. 27, it was found that the inhibition of expression of a total of 37 genes listed in Table 5 resulted in an increase in cadaverine production. The production of cadaverine in the basic strain was 1.4±0.05 g/L, and when it was taken as 100%, the strains in which the expression of each of murE and ack genes was inhibited showed increases in cadaverine production of 55% (2.15 g/L) for murE and 40% (1.96 g/L) for ack (FIG. 27).

Thus, in another further aspect, the present invention is directed to a recombinant microorganism having an enhanced ability to produce cadaverine, the recombinant microorganism being obtained by inactivating the function of at least one gene, selected from the group consisting of murE (UDP-N-acetylmuramoylalanyl-D-glutamate-2,6-diaminopimelate ligase), metB (cystathionine gamma-synthase), thrL (thr operon leader peptide), ackA (propionate kinase/acetate kinase activity), pdhR (pyruvate dehydrogenase complex regulator), ilvG_1 (acetolactate synthase II, large subunit, N-ter fragment (pseudogene)), carB (carbamoyl phosphate synthetase), serC (phosphohydroxythreonine aminotransferase/3-phosphoserine aminotransferase), ilvN (acetohydroxybutanoate synthase/acetolactate synthase), Crp (CRP transcriptional dual regulator), ilvD (dihydroxy acid dehydratase), ilvY (IlvY DNA-binding transcriptional dual regulator), glpK (glycerol kinase), glpF (glycerol MIP channel), pta (Phosphate acetyltransferase), tktA (transketolase I), hflD (lysogenization regulator), deoA (thymidine phosphorylase/uracil phosphorylase), gadE (GadE controls the transcription of genes involved in glutamate dependent system), rbsK (ribokinase), ilvL (ilvGEDA operon leader peptide), ilvC (acetohydroxy acid isomeroreductase), accA (acetyl-CoA carboxyltransferase, alpha-subunit), ilvM (acetohydroxybutanoate synthase/acetolactate synthase), argB (acetylglutamate kinase), thrA (aspartate kinase/homoserine dehydrogenase), carA (carbamoyl phosphate synthetase), fbp (fructose-1,6-bisphosphatase), rbsD (ribose pyranase), panD (Aspartate 1-decarboxylase), aspA (aspartate ammonia-lyase), rcsB (RcsB-BglJ DNA-binding transcriptional activator), ivbL (The ilvB operon leader peptide), lexA (LexA represses the transcription of several genes involved in the cellular response to DNA damage), rbsA (ribose ABC transporter), murF (D-alanyl-D-alanine-adding enzyme), and thrC (threonine synthase), in a host cell having the cadaverine biosynthesis pathway, and a method for producing the recombinant microorganism.

Preferably, the recombinant microorganism is obtained by inactivating the function of at least one gene selected from the group consisting of murE, metB, thrL, and ackA. Examples of a host cell having the cadaverine biosynthesis pathway include *E. coli, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus, Clostridium, Corynebacterium, Streptomyces, Bifidobacterium,* and *Cyclobacterium.*

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Examination of Performance of Synthetic sRNA 1-1: Construction of Synthetic sRNA and Construction of pWAS Plasmid for Regulation of Expression A basic plasmid as shown in FIG. 18 was constructed, in which an expression of a synthetic sRNA was being inhibited, but could be effectively expressed if required.

In the pWAS plasmid of FIG. 18, the synthetic sRNA can be constructed by inserting a target gene mRNA-binding region into a promoter ($P_R$) and a MicC Hfq binding region by site-directed mutagenesis.

The restriction enzymes used in this Example and the following Examples were purchased from New England Labs (USA), and PCR polymerase was purchased from Invitrogen (USA). Other reagents were indicated separately.

First, PCR was performed using a pKD46 plasmid (GenBank AY048746.1 (Datsenko et al, *PNAS,* 97(12): 6640-

6645, 2000)) as a template and primers of SEQ ID NOS: 2 and 3, and the araC-PBAD promoter was cloned into a pWA plasmid (FIG. 20, SEQ ID NO: 1) using SacI/EcoRI. Also, PCR was performed using primers of SEQ ID NOS: 4 and 5 from the phage lambda chromosome (Bioneer, Korea; GenBank NC_001416.1), and cI gene was obtained by cleaving with PacI/EcoRIand then ligated. In addition, a T1/TE sequence as a transcription termination sequence was additionally cloned into the plasmid after performing PCR. Herein, the T1/TE sequence was obtained by PCR using primers of SEQ ID NOS: 6 and 7 without template, and it was cleaved with EcoRI/XbaI and then ligated to the vector containing araC-pBAD-cI introduced therein, so that the termination of cI could be terminated. Using the above-constructed vector as a template, T1/TE was amplified by PCR using primers of SEQ ID NOS: 8 and 9, after which it was cleaved with XhoI/KpnI and ligated to the above-constructed vector so that the transcription of sRNA would be independently terminated. Site-directed mutagenesis was performed using the constructed vector as a template and primers of SEQ ID NOS: 10 and 11, thereby modifying the wild-type cI gene into the temperature-sensitive mutant gene cI (ts2).

Primer Sequences Used

[SEQ ID NO: 2]
5-AAGCTGGAGC TCAATACTAG TCGATTTATT ATGACAACTT
GACGGCTACA TC-3'

[SEQ ID NO: 3]
5'-GAATTCAATT AATTAATTAA AATTCCCAAA AAAACGGGTA
TGGAGAA-3'

[SEQ ID NO: 4]
5'-GGGAATTTTA ATTAAAAGGA GACCCGGGAT ATGAGCACAA
AAAAGAAACC ATTAACA-3'

[SEQ ID NO: 5]
5'-AATTATGAAT TCTTAGCCAA ACGTCTCTTC AGG-3'

[SEQ ID NO: 6]
5'-AATAT GAATTCCCAG GCATCAAATA AAACGAAAGG
CTCAGTCGAA AGACTGGGCC TTTCGTTTTA TCTGTTGTTT
GTCGGTGAAC GCTCTCTACT AGAGTC-3'

[SEQ ID NO: 7]
5'-AATAT TCTAGATATA AACGCAGAAA GGCCCACCCG
AAGGTGAGCC AGTGTGACTC TAGTAGAGAG CGTTCACCGA
CAAACAACAG ATAAAACGAA AG-3'

[SEQ ID NO: 8]
5'-TTTTTTCTCG AGCCAGGCAT CAAATAAAAC GAA-3'

[SEQ ID NO: 9]
5'-GAATTGGGTA CCTATAAACG CAGAAAGGCC CACC-3'

[SEQ ID NO: 10]
5'-gAAGTTAT CGCTAGTCAG TGGCC-3'

[SEQ ID NO: 11]
5'-CCCCACAACG GAACAACTCT-3'

Next, a sequence for use as a synthetic sRNA-based structure and a PR promoter were constructed by PCR in the following manner. For a MicC structure, PCR was performed using the *E. coli* W3110 chromosome (GenBank AP009048) as a template and primers of SEQ ID NOS: 12 and 13, and the PCR product was cloned using a TOPO cloning kit (Invitrogen), sequenced, and then ligated to the above-constructed vector using PstI/XhoI. For a SgrS structure, PCR was performed using the same template as above and primers of SEQ ID NOS: 14 and 15, and the PCR product was cloned using a TOPO cloning kit, sequenced, and then cloned into the above-constructed vector using PstI/XhoI. For a MicF structure, PCR was performed using primers of SEQ ID NOS: 16 and 17 without template, and the PCR product was cloned using a TOPO cloning kit, sequenced, and then cloned into the vector using PstI/XhoI. In this manner, three vectors having different fundamental structures could be constructed. Each of the sRNA structures is shown in FIG. 2. Either PCR for conforming cloning into this plasmid or sequencing was performed using primers of SEQ ID NOS: 18 and 19.

Primer Sequences Used

[SEQ ID NO: 12]
5'-CTGCAGGAAT TCTAACACCG TGCGTGTTGA CTATTTTACC
TCTGGCGGTG ATAATGGTTG CTTTCTGTTG GGCCATTGCA
TTGC-3'

[SEQ ID NO: 13]
5'-CTCGAGAAAA AAAGCCCGGA CGACTGTTC-3'

[SEQ ID NO: 14]
5'-CTGCAGGAAT TCTAACACCG TGCGTGTTGA
CTATTTTACC TCTGGCGGTG ATAATGGTTG CGATGAAGCA
AGGGGGTGC-3'

[SEQ ID NO: 15]
5'-CTCGAGAAAA AAAACCAGCA GGTATAATCT
GCTG-3'

[SEQ ID NO: 16]
5'-CTGCAGGAAT TCTAACACCG TGCGTGTTGA CTATTTTACC
TCTGGCGGTG ATAATGGTTG CTCATTTCTG AATG-3'

[SEQ ID NO: 17]
5'-TCGAGAAAAA AAACCGAATG CGAGGCATCC GGTTGAAATA
GGGGTAAACA GACATTCAGA AATGAGCAAC CATTATCAC-3'

[SEQ ID NO: 18]
5'-AGTGGGAACC TAGACACTAA-3'

[SEQ ID NO: 19]
5'-CTAGGTAAAC CCAGGAGG-3'

Figure 20:
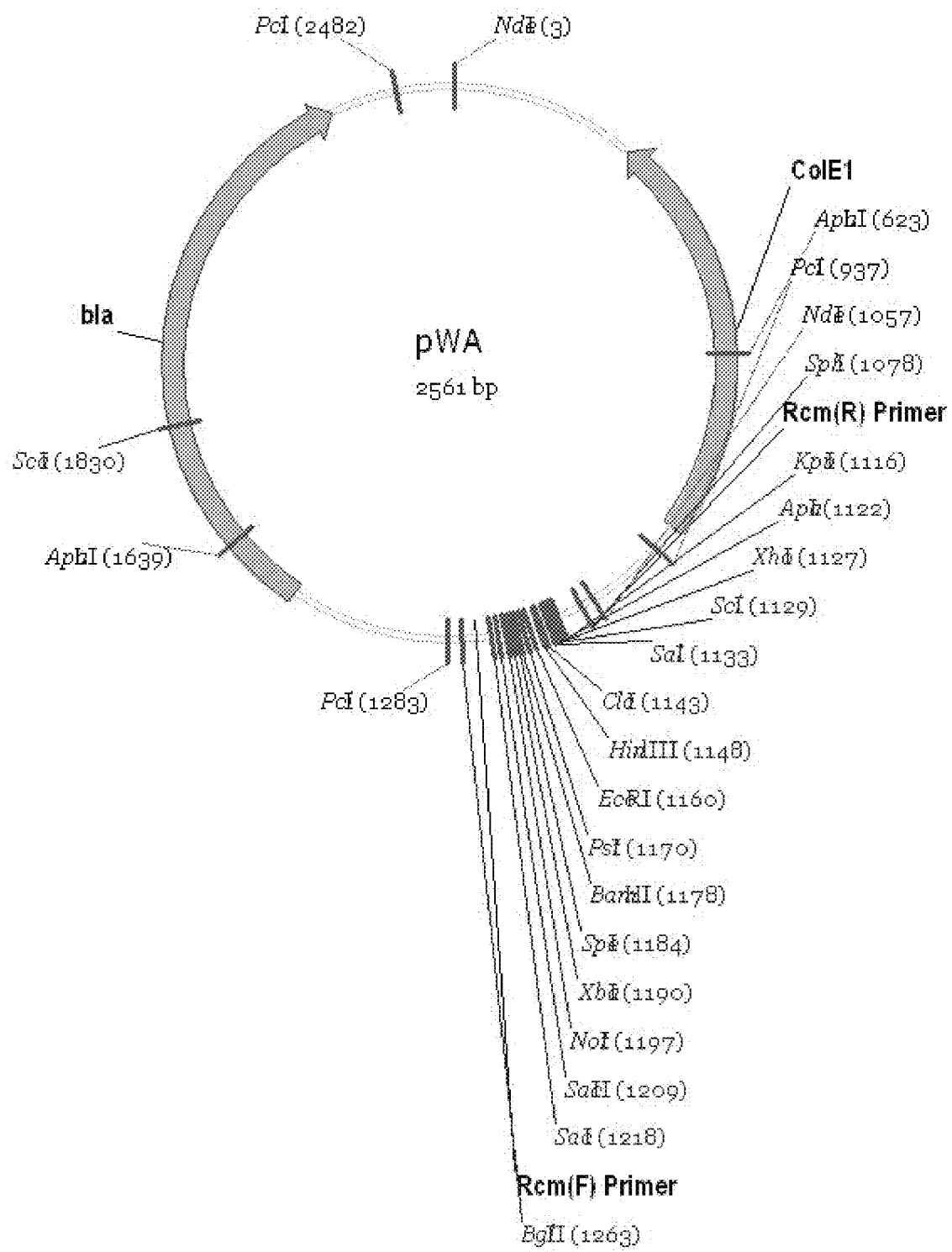
FIG. 20 is a schematic view of a pWA vector.

As a result, the pWAS plasmid as shown in FIG. 20 was constructed. The PR promoter is a phage lambda promoter, and cI(ts2) is a phage lambda gene functioning to suppress the PR promoter and is a temperature-sensitive mutant protein that normally operates at 25° C. and loses its function at 37° C. (Jana et al, Protein Engineering, 13(3): 225-233, 1999). When the plasmid is cultured in 1% arabinose-containing LB medium (1% tryptone, 1% NaCl, 0.5% yeast extract) at 25° C., cI(ts2) is sufficiently expressed and its function is maintained intact, and thus it suppresses the PR promoter so that the synthetic sRNA is not expressed. However, when the plasmid is cultured at 37° C. in the absence of arabinose, cI(ts2) is not sufficiently expressed and loses its function due to its instability at the temperature, and thus it fails to suppress the PR promoter so that the synthetic sRNA is expressed.

Figure 21:
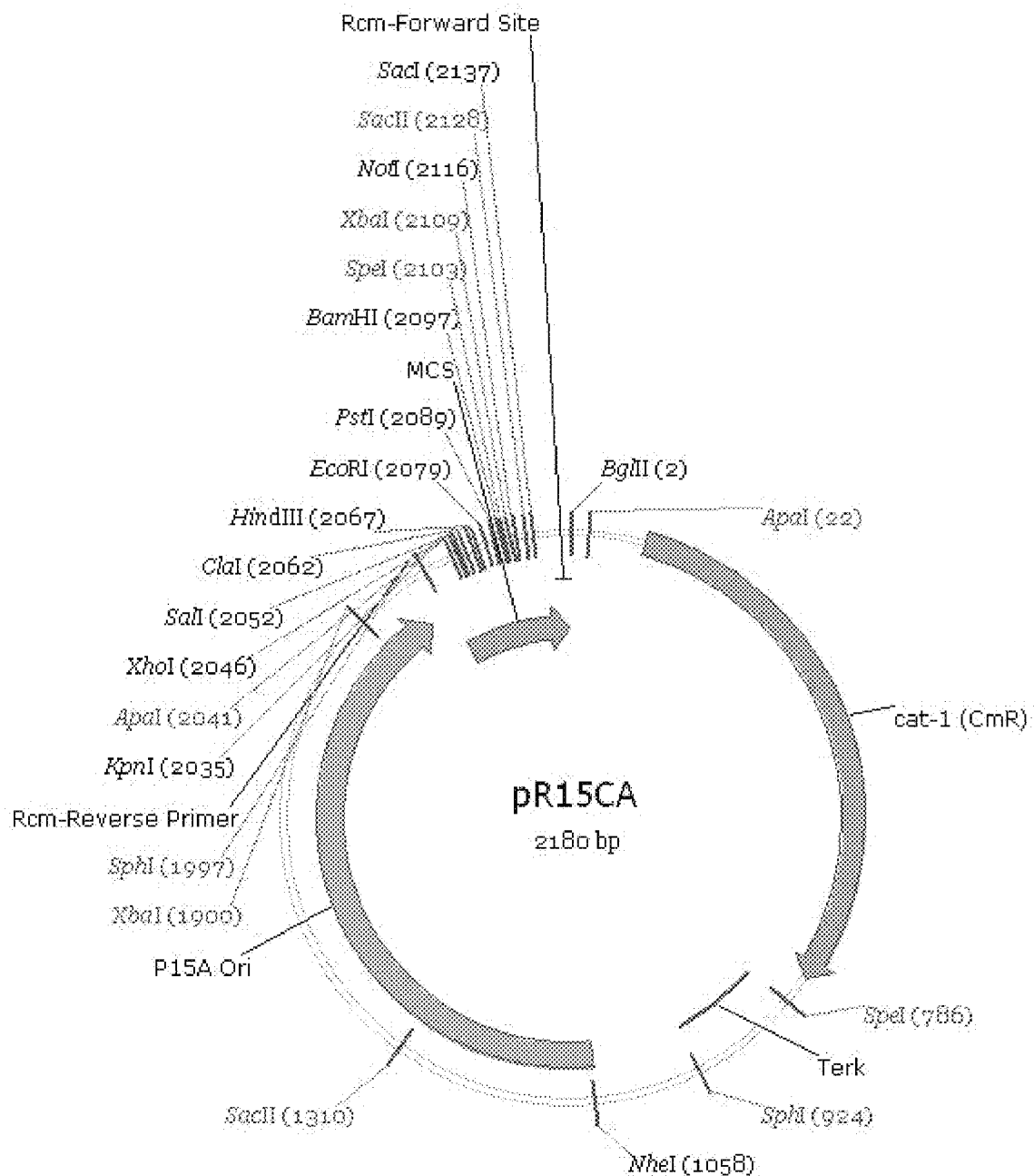
FIG. 21 is a schematic view of a pR15CA vector.
Figure 22:
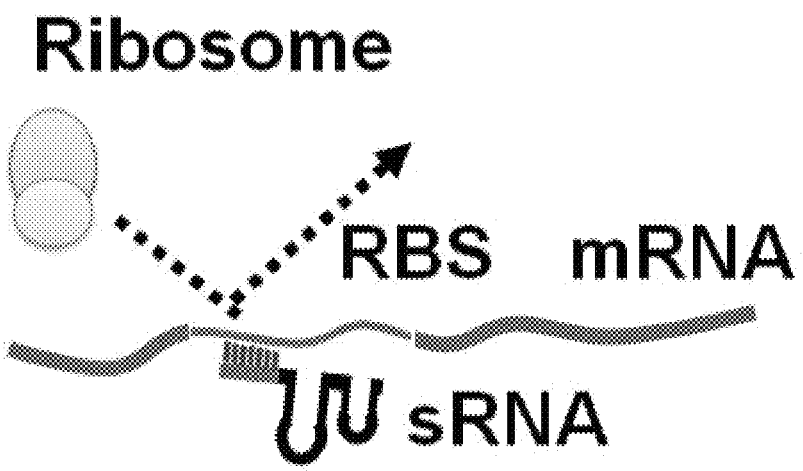
FIG. 22 shows the principle of operation of a synthetic sRNA.

1-2: Construction of Reporter Plasmid for Testing the Performance of Synthetic sRNA A reporter plasmid for examining the function of the synthetic sRNA was constructed. A basic plasmid for cloning a reporter was pR15CA. The structure of the basic plasmid is shown in FIG. 21, and the sequence thereof is set forth in SEQ ID NO: 20.

T1/TE that is the transcription termination sequence of the reporter gene was amplified by PCR using the pWAS plasmid (constructed in Example 1-2) as a template and primers of SEQ ID NOS: 21 and 22, and the PCR product was cleaved with XhoI/KpnI and then cloned into a pR15CA plasmid. lac promoter for expression of DsRed2 gene was amplified using pBluescript SK+ (Stratagene) as a template and primers of SEQ ID NOS: 23 and 24, and the PCR product was cloned into the plasmid using EcoRI/XhoI. Finally, DsRed2 gene was amplified by PCR using pDsRed2-N1 (Clontech) as a template and primers of SEQ ID NOS: 25 and 26, and the PCR product was cloned into the pR15CA vector using PacI/XhoI, thereby constructing a reporter plasmid.

Primer Sequences Used

[SEQ ID NO: 21]
5'-ATAATTCTCG AGCCAGGCAT CAAATAAAAC GAAAGGCT-3'

[SEQ ID NO: 22]
5'-AATTAGGTAC CTATAAACGC AGAAAGGCCC ACC-3'

[SEQ ID NO: 23]
5'-AATTA GAATTCGTGGATAACCGTATTACCGCCTTTG-3'

[SEQ ID NO: 24]
5'-AATTACTCGA GAATTATTTA ATTAATAAAG TTAATTTTTT TTTTTTGTGT GAAATTGTTA TCCGCTC-3'

[SEQ ID NO: 25]
5'-AATTATTAAT TAAAAGGAGG ACAAATATAT GGCGAGC-3'

[SEQ ID NO: 26]
5'-AATTACTCGA GTTACGCCAC CAGGGCATAG TTTTCATCAT TTGCCGCCAG GAACAGGTGG TGGCGGCCCT CGGT-3'

1-3: Construction of sRNAs for Selection of Synthetic sRNA-Based Structures and Examination of Performance Thereof In order to insert a sequence, which targets the ribosome-binding site (RBS) of DsRed2 mRNA, into each of the three pWAS plasmids constructed in Example 1-1 and containing the sRNA-based structures (MicC, SgrS, and MicF), respectively, PCR was performed using the following primers. The RBS of DsRed2 and the sequence that binds thereto are shown in FIG. 2.

First, site-directed mutagenesis was performed by PCR using the plasmid of Example 1-1 (containing the MicC-based structure in pWAS) and primers of SEQ ID NO: 27 and 28 to insert a DsRed2-targeting complementary binding sequence in the front of the MicC-based structure, thereby constructing a synthetic sRNA having a DsRed2-targeting MicC structure. The product of the PCR for site-directed mutagenesis was purified on DNA gel, treated with DpnI for 1 hour, and then treated with T4 polynucleotide kinase and T4 DNA ligase for 4 hours, followed by transformation into DH5-alpha. According to the same procedure as described above, site-directed mutagenesis was performed using the pWAS-SgrS-based structure-containing vector as a template and primers of SEQ ID NOS: 29 and 30, thereby constructing a synthetic sRNA having a SgrS-based structure. Also, site-directed mutagenesis was performed using the pWAS-MicF-based structure-containing vector as a template and primers of SEQ ID NOS: 31 and 32, thereby constructing a synthetic sRNA having a MicF-based structure. Each of the three different synthetic sRNAs constructed as described above was transformed into *E. coli* DH5-alpha (Invitrogen, USA) transformed with the reporter plasmid, and then the *E. coli* cells were cultured in an LB medium containing 35 µg/ml chloramphencol and 50 µg/ml ampicillin at 37° C. to stationary phase, and then the fluorescence was measured in a FACSCalibur flow cytometry system (Becton Dickinson).

Primer Sequences Used

[SEQ ID NO: 27]
5'-GCGAGCAGTGAGAACGTCATAAGTCAACTTTCAGAATTGCGGTC ATCCCA-3'

[SEQ ID NO: 28]
5'-CATATATTTGTCCTCCTTAAATCACCCGCCAGCAGATTATACC TG-3'

[SEQ ID NO: 29]
5'-GCGAGCAGTGAGAACGTCATGCAACCATTATCACCGCCAGAGGT AAAA-3'

[SEQ ID NO: 30]
5'-CATATATTTGTCCTCCTTTCATTTCTGAATGTCTGTTTACCCCT A-3'

[SEQ ID NO: 31]
5'-GCGAGCAGTGAGAACGTCATGCAACCATTATCACCGCCAGAGGTA AAA-3'

[SEQ ID NO: 32]
5'-CATATATTTGTCCTCCTTTCATTTCTGAATGTCTGTTTACCCC-3'

As a result, as can be seen in FIG. 3, the synthetic sRNA obtained by inserting the sequence targeting the RBS of DsRed2 mRNA into the Hfq binding site of SgrS inhibited the expression of DsRed2 by 85%, and the synthetic sRNA obtained by inserting the sequence targeting the RBS of DsRed2 mRNA into the Hfq binding site of MicC inhibited the expression of DsRed2 by 90%. In other words, it was shown that the selected three structures all assisted in the effective inhibition of expression, and particularly, the effect of the sRNA structure comprising the Hfq binding site of MicC was better.

Example 2

Screening of mRNA Position Effective for Function of Synthetic sRNA

In order to determine the position of binding to mRNA, effective for the stable function of synthetic sRNAs, synthetic rRNAs were constructed using the pWAS plasmid as a template so as to bind to various sites of DsRed2.

Regions, which are introduced into each of synthetic sRNAs and base-pair with DsRed2 mRNA, were amplified by PCR using the following primers in the same manner as described in Example 1-3 and were introduced into the pWAS plasmid comprising the Hfq binding site of MicC.

In FIG. 4, sequence A was obtained using primers of SEQ ID NOS: 27 and 28; sequence B1 was obtained using primers of SEQ ID NOS: 33 and 34; sequence B2 was obtained using primers of SEQ ID NOS: 35 and 36; C1 was obtained using primers of SEQ ID NOS: 37 and 38; C2 was obtained using primers of SEQ ID NOS: 39 and 40; D1 was obtained using primers of SEQ ID NOS: 41 and 42; D2 was obtained using primers of SEQ ID NOS: 43 and 44; E1 was obtained using primers of SEQ ID NOS: 45 and 46; E2 was obtained using primers of SEQ ID NOS: 47 and 48; F1 was obtained using primers of SEQ ID NOS: 49 and 50; F2 was obtained using primers of SEQ ID NOS: 51 and 52; G1 was obtained using primers of SEQ ID NOS: 53 and 54; and G2 was obtained using primers of SEQ ID NOS: 55 and 56.

Primer Sequences Used

[SEQ ID NO: 33]
5'-GACAAATATATGGCGAGCAGTGAGAA-3'

[SEQ ID NO: 34]
5'-TTTCTGTTGGGCCATTGCATTGC-3'

[SEQ ID NO: 35]
5'-CACCGAGCAACCATTATCACCGCCAGA-3'

```
                                                [SEQ ID NO: 36]
5'-ATGACGTTCTCACTGCTCGCCA-3'

[SEQ ID NO: 37]
5'-GCGAGCAGTGAGAACGTCAT-3'

[SEQ ID NO: 38]
5'-TTTCTGTTGGGCCATTGCATTGC-3'

[SEQ ID NO: 39]
5'-CACCGAGTTCATGCGCTTGCAACCATTATCACCGCCAGA-3'

[SEQ ID NO: 40]
5'-ATGACGTTCTCACTGCTCGCCA-3'

[SEQ ID NO: 41]
5'-TGTTCACCGGGCAACCATTATCACCGCCAGAGGTAAAA-3'

[SEQ ID NO: 42]
5'-GCTCCTCGCTTTCTGTTGGGCCATTGCATTGCCAC-3'

[SEQ ID NO: 43]
5'-CATCCTGGTGCAACCATTATCACCGCCAGAGGTAAAA-3'

[SEQ ID NO: 44]
5'-GGCACCACCCCGGTGAACAGCTCCTCGCTTTCT-3'

[SEQ ID NO: 45]
5'-GGGTGGTGCCGCAACCATTATCACCGCCAGAGGTAAAA-3'

[SEQ ID NO: 46]
5'-CGGTGAACATTTCTGTTGGGCCATTGCATTGCCAC-3'

[SEQ ID NO: 47]
5'-CGAGCTGGAGCAACCATTATCACCGCCAGAGGTAAAA-3'

[SEQ ID NO: 48]
5'-ACCAGGATGGGCACCACCCCGGTGAACATTTCT-3'

[SEQ ID NO: 49]
5'-CATCCTGGTCGCAACCATTATCACCGCCAGAGGTAAAA-3'

[SEQ ID NO: 50]
5'-GGCACCACCTTTCTGTTGGGCCATTGCATTGCCAC-3'

[SEQ ID NO: 51]
5'-GGCGACGTAGCAACCATTATCACCGCCAGAGGTAAAA-3'

[SEQ ID NO: 52]
5'-GTCCAGCTCGACCAGGATGGGCACCACCTTT-3'

[SEQ ID NO: 53]
5'-ACTACAAGAAGCGCAACCATTATCACCGCCAGA-3'

[SEQ ID NO: 54]
5'-CGGGGATGTCGGTTTCTGTTGGGCCATTGCATTGC-3'

[SEQ ID NO: 55]
5'-CAAGAAGCTGTCGCAACCATTATCACCGCCAGA-3'

[SEQ ID NO: 56]
5'-TAGTCGGGGATTTTCTGTTGGGCCATTGCATTGC-3'
```

Each of the constructed synthetic sRNAs was transformed into a DH5-alpha strain transformed with the reporter plasmid constructed in Example 1-2, and a decrease in fluorescence of DsRed2 in each of the strains was measured.

As a result, as can be seen in FIG. 5, when the sRNA was bound to part or all of the RBS of DsRed2 mRNA, the expression of DsRed2 mRNA was inhibited by 90-99%. When the sRNA was bound to regions other than the RBS, the inhibition of expression of the DsRed2 mRNA was irregular (47-90%). Such results suggest that, when the sRNA comprises a region that can bind complementarily to the RBS of mRNA of the target gene, it is more effective for inhibition of the mRNA expression of the target gene.

Example 3

Construction of sRNAs for Other Target mRNAs and Measurement of Cross-Reactivity In order to examine whether the sRNA according to the present invention can inhibit the expression of mRNA of genes other than DsRed2, a sequence complementary to the RBS of mRNA of each of the LuxR, AraC and KanR gene was inserted into the MicC structure by site-directed mutagenesis so as to bind to the RBS. The sequence complementary to the RBS of each of the target mRNAs is underlined and indicated by a red color in FIG. 6.

The synthetic sRNA Anti-LuxR was constructed by site-directed mutagenesis using the pWAS plasmid (containing the MicC-based structure) as a template and primers of SEQ ID NOS: 57 and 58, and Anti-AraC was constructed using primers of SEQ ID NOS: 59 and 60, and Anti-KanR was constructed using primers of SEQ ID NOS: 61 and 62. In order to examine the expression level of each of the genes, a fusion protein of each gene with DsRed2 was constructed. For this purpose, PCR was amplified using the reporter plasmid of Example 1-2 containing the DsRed-encoding sequence as a template and primers of SEQ ID NOS: 64 and 26, and the PCR product was cleaved with PacI/XhoI restriction enzymes and then introduced into the reporter plasmid of Example 1-2.

The LuxR gene was amplified by PCR using the *Vibrio fisheri* ES114 chromosome (GenBank CP000020.2, CP000021.2) as a template and primers of SEQ ID NOS: 65 and 66, and the PCR product was treated with PacI/ClaI and then cloned into a new reporter plasmid constructed in Example 1-2, thereby constructing a LuxR-DsRed2 fusion protein. AraC and KanR genes were amplified by PCR using a primer pair of SEQ ID NOS: 67 and 68 and a primer pair of SEQ ID NOS: 69 and 70, respectively, and then cloned in the same manner as described above.

Primer Sequences Used

```
                                                [SEQ ID NO: 57]
5'-TTAATTAAAATCTACTCTAGAGGTGCAGGGGCAGGCGCTGGTGCGG
GTGCCATGGCGAGCAGTGAGAACGTCAT-3'

[SEQ ID NO: 58]
5'-AATACTCCGCGGTATAAACGCAGAAAGGCCCACC-3'

[SEQ ID NO: 59]
5'-TCATTTTGATTGCTCCTTTTTCTGTTGGGCCATTGCATTGC-3'

[SEQ ID NO: 60]
5'-CTGAAGCGCAAAATGATCGCAACCATTATCACCGCCAGA-3'

[SEQ ID NO: 61]
5'-CCATCCGTTTTTCTCCTTTTTCTGTTGGGCCATTGCATTGC-3'

[SEQ ID NO: 62]
5'-GAACAAGATGGATTGCGCAACCATTATCACCGCCAGA-3'

[SEQ ID NO: 63]
5'-AATCATGTAAACGACTCCTTTTTCTGTTGGGCCATTGCATTGC-3'

[SEQ ID NO: 64]
5'-AATTATTAATTAAAATCTACATCGATGGTGCAGGGGCAGGCGCTGG
TGCGGGTGCCATGGCGAGCAGTGAGAACGTCAT-3'

[SEQ ID NO: 65]
5'-AATTATTAATTAAGGAGCAATCAAAATGAACATCAAGAACATCAAC
GCG-3'

[SEQ ID NO: 66]
5'-AATTAATCGATATTTTTAAGGTATGGACAATTAATGGCGC-3'
```

-continued

[SEQ ID NO: 67]
5'-AATTATTAATTAAAAGGAGAAAAACGGATGGCTG-3'

[SEQ ID NO: 68]
5'-AATTAATCGATTGACAACTTGACGGCTACATCATTCA-3'

[SEQ ID NO: 69]
5'-AATTATTAATTAAGGAGTCGTTTACATGATTGAACAAGATGGATTG
CACG-3'

[SEQ ID NO: 70]
5'-AATTAATCGATGAAGAACTCGTCAAGAAGGCGATA-3'

Next, as shown in FIG. 7A, each of the constructed plasmids containing the three synthetic sRNAs and the three target genes, respectively, was transformed into a DH5-alpha strain, and then the relative fluorescence of DsRed2 in the strain, and the results of the measurement are shown in FIG. 7B.

As a result, it could be seen that the synthetic sRNA constructed by the method of the present invention showed an expression inhibitory effect of 80-86% against the target gene. In addition, the expression level of the non-target genes was similar to that in the case in which no sRNA was contained.

Such results indicate that the synthetic sRNA according to the preparation method of the present invention can effectively inhibit only the expression of mRNA of the target gene. In addition, as shown in FIG. 8, when the energy of binding to the target mRNA is −53 kcal/mol or lower and when the energy of binding to other mRNAs −13 kcal/mol or higher, no cross-reactivity will occur.

Example 4

Production of Tyrosine-Producing Recombinant Microorganism Using Synthetic sRNA

In order to construct a recombinant microorganism for producing the aromatic compound tyrosine, an experiment for selecting a strain having the highest ability to produce tyrosine and a combination of genes inhibited in the strain was performed by: (1) constructing a plasmid that overexpresses enzymes involved in the pathway of biosynthesis of aromatic compounds, particularly tyrosine, to enhance the metabolic fluxes toward the compounds; (2) constructing synthetic sRNAs for the purpose of inhibiting the expression of genes encoding the enzymes and proteins that can go to pathways opposite to the tyrosine biosynthesis pathway, in order to direct intracellular metabolic fluxes toward the tyrosine biosynthesis pathway; and (3) transforming the plasmid into 14 different E. coli strains, and then additionally transforming various combinations of the synthetic sRNAs into the strains.

4-1: Construction of Basic Plasmid for Enhancing the Activity of the Pathway of Biosynthesis of Aromatic Compounds First, a plasmid that overexpresses enzymes required to enhance the activity of the pathway of biosynthesis of aromatic compounds was constructed.

Figure 9:
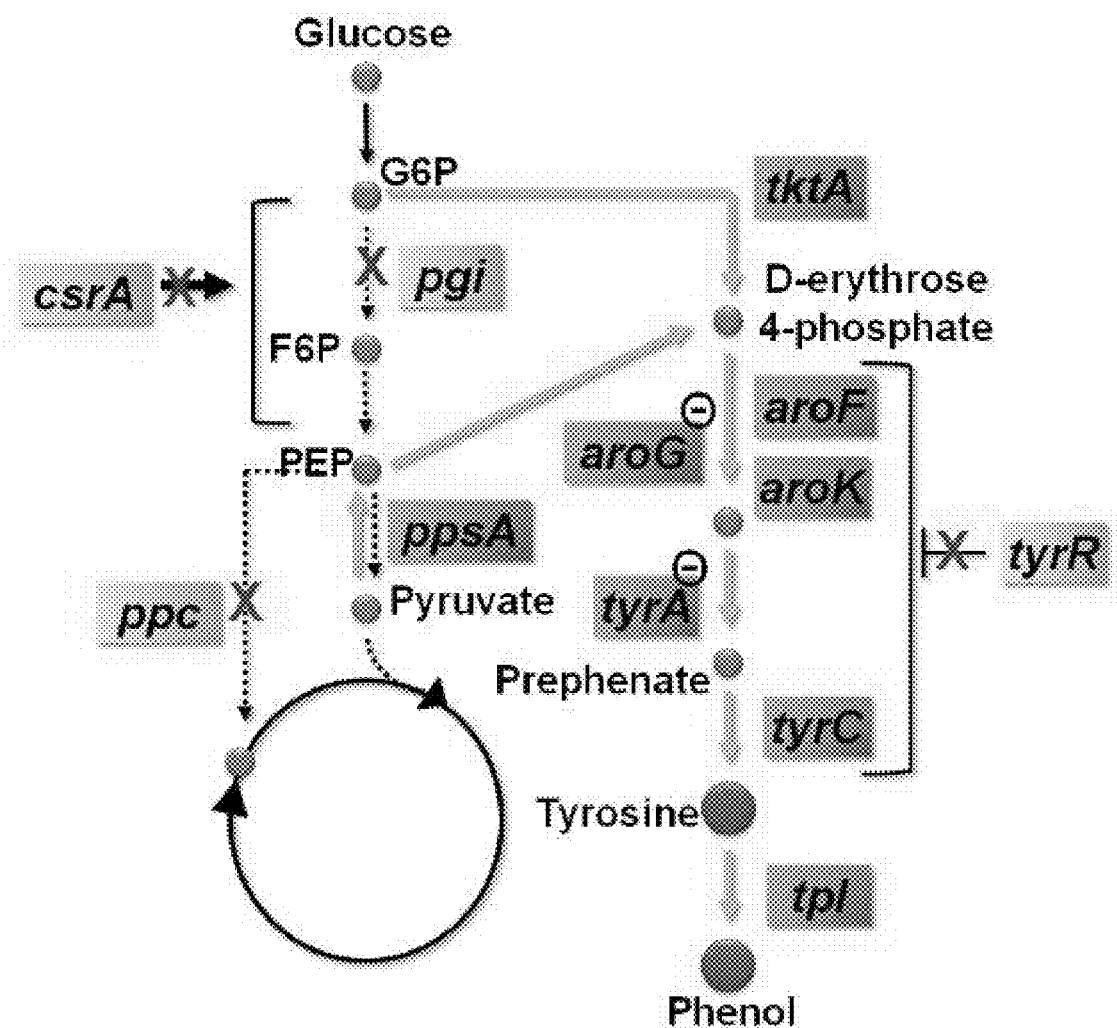
FIG. 9 shows the tyrosine biosynthesis pathway in a microorganism.

The target genes used in this Example were ppsA that encodes phenolpthiocerol synthesis type-I polyketide synthase A, tktA that encodes transketolase, aroG and aroF that encode 3-deoxy-7-phosphoheptulonate synthase, aroK that encodes shikimate kinase I, and tyrA that encodes chorismate mutase, and tyrC that encodes Zymomonas mobilis-derived prephenate dehydrogenase (FIG. 9).

First, as shown in FIG. 10, a pTyr-b plasmid containing no synthetic sRNA was constructed. Specifically, a pTac15k plasmid (Hiszczynska-Sawicka et al., Plasmid 38:174, 1997) was used as a basic plasmid, and aroF gene was amplified by PCR using the E. coli W3110 chromosome (GenBank AP009048) as a template and primers of SEQ ID NOS: 71 and 72, and then cloned into the pTac15k plasmid using EcoRI/SacI. Next, tktA gene was amplified by PCR using the E. coli W3110 chromosome as a template and primers of SEQ ID NOS: 73 and 74, and then cloned into the plasmid using XbaI/SphI. Next, ppsA gene was amplified by PCR using the E. coli W3110 chromosome as a template and primers of SEQ ID NOS: 75 and 76, and then cleaved with SacI/SpeI, after which the cleaved gene was ligated into the plasmid vector cleaved with SacI/XbaI. In this way, a pTyr-b plasmid containing no synthetic sRNA was constructed.

Primer Sequences Used

[SEQ ID NO: 71]
5'-AATTATGAATTCATGCAAAAAGACGCGCTGAATAAC-3'

[SEQ ID NO: 72]
5'-TAATTGAGCTCTTAAGCCACGCGAGCCGTCA-3'

[SEQ ID NO: 73]
5'-ATCATATCTAGAAGGAGGTTATTCATGTCCTCACGTAAAGA-3'

[SEQ ID NO: 74]
5'-TTCGTTGCATGCTTACAGCAGTTCTTTTG-3'

[SEQ ID NO: 75]
5'-AATTAAGAGCTCTTAATTAACGGTTAAATATGCAAAGATAAAT
GCG-3'

[SEQ ID NO: 76]
5'-AATTAAACTAGATTATTTCTTCAGTTCAGCCAGG-3'

Next, the remaining genes that are involved in tyrosine biosynthesis were cloned by constructing a pTyr-a plasmid (FIG. 10). These genes were to be expressed by a BBa_J23113 promoter registered in the MIT Registry (http://partsregistry.org). Specifically, the promoter of interest was constructed by PCR using primers of SEQ ID NOS: 77 and 78 without template. The constructed promoter was cloned using a TOPO cloning kit and sequenced to confirm error, after which it was cleaved with SacI/NotI and then ligated into the pWA plasmid of Example 1. The transcription termination sequence T1/TE was amplified by PCR using the pWAS plasmid of Example 1 as a template and primers of SEQ ID NOS: 79 and 80, and then ligated downstream of the promoter. In this way, a pWA-J23113-T1/TE plasmid was constructed, and then the remaining genes were cloned into this plasmid. Then, the region ranging from the promoter to T1/TE was amplified by PCR and cloned into a pWA plasmid, thereby constructing a pTyr-a plasmid as shown in FIG. 10.

Primer Sequences Used

[SEQ ID NO: 77]
5'-GAGCTCCTGATGGCTAGCTCAGTCCTAGGGATTATGCTAGCCATAT
CGAAAGGATAGTCTTGATAACCATAAGTTTAATTAAGCGGCCGC-3'

[SEQ ID NO: 78]
5'-GCGGCCGCTTAATTAAACTTATGGTTATCAAGACTATCCTTTCGAT
ATGGCTAGCATAATCCCTAGGACTGAGCTAGCCATCAGGAGCTC-3'

[SEQ ID NO: 79]
5'-ATAATTGAATTCCCAGGCATCAAATAAAACGAAAGGC-3'

[SEQ ID NO: 80]
5'- CGAATTGGGTACCTATAAACGCAGAAAGGCCCACCCG-3'

Specifically, tyrA gene was amplified by PCR using the E. coif W3110 chromosome as a template with primers of SEQ ID NOS: 81 and 82, and it was cleaved with PacI/EcoRI and cloned into the pWA-J23113-T1/TE plasmid, thereby constructing a gene consisting of promoter-coding sequence-transcription termination sequence. tyrA is sensitive to feedback inhibition by tyrosine, and for this reason, in order to remove the feedback inhibition, two amino acid residues of the tyrA were removed by site-directed mutagenesis with A354V/M531. Herein, A354V mutation was attempted using primers of SEQ ID NOS: 83 and 84, and the resulting plasmid was subjected to M531 mutation using primers of SEQ ID NOS: 85 and 86, thereby removing the feedback inhibition (Lutke-Eversloh et al, Applied Microbiology and Biotechnology, 75:103, 1999).

[SEQ ID NO: 81]
5'-AATCATTTAATTAAACGGCTCGCGTGGCTTAAG-3'

[SEQ ID NO: 82]
5'-AATTAAGAATTCTTACTGGCGATTGTCATTCGCC-3'

[SEQ ID NO: 83]
5'-TTTGGCCTCGCGTCGTGCA-3'

[SEQ ID NO: 84]
5'-ATAGATGCCTCGCGCTCCG-3'

[SEQ ID NO: 85]
5'-TGCAGCGTTTTCAGAGTGAAAGCC-3'

[SEQ ID NO: 86]
5'-CGTAATCGCCGAACCAGTGCTC-3'

In the same manner as described above, aroG, aroK and tyrC were cloned. Specifically, aroG was amplified by PCR using the E. coli W3110 chromosome as a template and primers of SEQ ID NOS: 87 and 88, and aroK was amplified by PCR using primers of SEQ ID NOS: 89 and 90, and tyrC was amplified by PCR using the Zymomonas mobilis chromosome (ZM6 strain, ATCC29191) as a template and primers of SEQ ID NOS: 91 and 92. The PCR products were cleaved with PacI/EcoRI and then cloned into pWA-J23113-T1/TE. Among these genes, aroG is also sensitive to feedback inhibition, and thus subjected to A146N amino acid mutation. This mutation was performed by site-directed mutagenesis using primers of SEQ ID NOS: 93 and 94, similar to the case of tyrA (Lutke-Eversloh et al, Applied Microbiology and Biotechnology, 75:103, 1999).

[SEQ ID NO: 87]
5'-TTAATTAAAGGAGAAAAAATGAATTATCAGAACGACGATTTAC-3'

[SEQ ID NO: 88]
5'-GAATTCTTACCCGCGACGCGCTTTT-3'

[SEQ ID NO: 89]
5'-AATTAATTAATTAAGACTCTCGCAATATCTTATG-3'

[SEQ ID NO: 90]
5'-AATTAAGAATTCTTAGTTGCTTTCCAGCATGTG-3'

[SEQ ID NO: 91]
5'-TTAATTAAGGAGAAAAAAATGACCGTCTTTAAGCATATTGCCA-3'

[SEQ ID NO: 92]
5'-GAATTCTTAAGGGTGAATATCGTGGTCTGTTTTT-3'

[SEQ ID NO: 93]
5'-AATATGATCACCCCACAATATCTCG-3'

[SEQ ID NO: 94]
5'-GAGAAACTCACCTGCCGCT-3'

The pWA-J23113-tyrA (A354V/M531) (or aroG (A146N), aroK, tyrC)-T1/TE constructed as described above was subjected to PCR with primers of SEQ ID NOS: 95 and 96 to amplify the total region ranging from the promoter to T1/TE, and the PCR product was cleaved with SpeI/SacI and cloned into pWA cleaved with XbaI/SacI. XbaI and SpeI have characteristics in that they can complementarily bind to each other, but disappear once did bind as the one sequence of cleaved region is different. Because the primer of SEQ ID NO: 96 includes XbaI and SacI, the PCR-amplified gene can be infinitely cloned using SpeI/SacI, and the vector can be infinitely cloned using XbaI/SacI.

[SEQ ID NO: 95]
5'-AATTAAACTA GTCTGATGGC TAGCTCAGT-3'

[SEQ ID NO: 96]
5'-ATTAATGAGC TCATAATTTC TAGATATAAA CGCAGAAAGG CC-3'

In this way, tyrA(A354/M531), aroG(A146N), tyrC and aroK were sequentially cloned into pWA.

4-2: Examination of Tyrosine Productivity of 14 Different E. coli Strains Using Plasmids The two plasmids constructed as described above were transformed into the following 14 different E. coli strains containing no synthetic sRNA: K-12 strains (C600 (ATCC 23738), DH5α (Invitrogen), ER2925 (New England Labs), JM110 (Agilent Technologies), MG1655 (Invitrogen), S17-1 (ATCC 47055), T1R(One shot(R) ccdB SurvivalTM2 T1R, Invitrogen), TG1 (ZymoResearch), TOP10 (Invitrogen), W3110 (ATCC 39936), XL1-Blue (Agilent Technologies)), B strain (BL21(DE3, Promega), W strain (ATCC 9637), and a hybrid of K-12 and B strains (HB101, Promega).

The resulting recombinant microorganisms were cultured in an LB medium containing 50/ml ampicillin and 50/ml kanamycin to the stationary phase, and then transferred at a volume ratio of 1/100 into a flask containing 50 ml of medium. Then, the microbial cells were cultured at 37° C. up to 48, and the maximum tyrosine concentration during the culture was measured.

TABLE 1

| Compound | Concentration |
| --- | --- |
| $(NH_4)_2HPO_4$ | 2 g/L |
| KH2PO4 | 6.75 g/L |
| Citric acid | 0.85 g/L |
| Yeast extract | 3 g/L |
| Succinic acid | 0.1 g/L |
| Glucose | 20 g/L |
| Trace element solution | 5 ml/L (Table 2) |

TABLE 2

| Compound | Concentration |
| --- | --- |
| $FeSO_4 \cdot 7H_2O$ | 10 g/L |
| $ZnSO_4 \cdot 7H_2O$ | 2.2 g/L |
| $MnSO_4 \cdot 7H_2O$ | 0.58 g/L |
| $CuSO_4 \cdot 5H_2O$ | 1 g/L |
| $(NH_4)_6Mo_7O_{24} \cdot 4H_2O$ | 0.1 g/L |
| $Na_2B_4O_7 \cdot 10H_2O$ | 0.02 |
| 35% HCl | 10 ml |

A sample was taken from the flask at 6-hour intervals, adjusted to a pH of 1 by adding HCl thereto, and then incubated at room temperature for 30 minutes. Next, the sample was centrifuged for 5 minutes, and the concentration of tyrosine in the supernatant was measured by HPLC (Agilent Technologies). The column used was Zorbax SB-Aq column (3×250 mm; Agilent Technologies).

"No sRNA" indicated in the first column of FIG. 11 indicates the production of tyrosine in the *E. coli* strains having only the two plasmids constructed as described above. The 14 different *E. coli* strains produced various concentrations (0-1.0 g/L) of tyrosine. This suggests that the different *E. coli* strains have different metabolic abilities and that, in order to maximize the production of metabolites, it is important to select a suitable strain in addition to discovering a suitable gene whose flux in metabolic networks is to be regulated. In this Experiment, the S17-1 strain showed the highest production of tyrosine.

4-3: Construction of Synthetic sRNA for Identification of Gene Contributing to Increase in Tyrosine Production and Construction of Final pTyr-a/pTyr-b Plasmid In the above Examples, it was shown that the activity of the basic tyrosine biosynthesis pathway is sufficient to produce tyrosine. In this Example, an experiment was performed to identify gene, which are to be silenced in order to further increase productivity, by synthetic sRNAs. Specifically, in order to silence the tyrR gene that inhibits the expression of enzymes involved in the tyrosine biosynthesis pathway and to direct more flux to the tyrosine biosynthesis pathway, csrA and pgi were silenced, and ppc encoding enzyme for converting to phosphoenolpyruvate and increasing the amount of phosphoenolpyruvate was silenced to increase the amount of phosphoenolpyruvate.

Anti-tyrR was constructed by site-directed mutagenesis using the above-constructed pWAS plasmid as a template and primers of SEQ ID NOS: 97 and 98. In the same manner, anti-ppc was constructed using primers of SEQ ID NOS: 99 and 100, and anti-csrA was constructed using primers of SEQ ID NOS: 101 and 102, and anti-pgi was constructed using primers of SEQ ID NOS: 103 and 104.

Primer Sequences Used

```
                                      [SEQ ID NO: 97]
5'-AGTCTTTTGTGCAACCATTATCACCGCC-3'

[SEQ ID NO: 98]
5'-TCCAGACGCATTTTCTGTTGGGCCATTGCATT-3'

[SEQ ID NO: 99]
5'-TATTCCGCATTG GCAACCATTATCACCGCC-3'

[SEQ ID NO: 100]
5'-TTGTTCGTTCATTTTCTGTTGGGCCATTGC-3'

[SEQ ID NO: 101]
5'-ACTCGTCGAGTT GCAACCATTATCACCGCC-3'

[SEQ ID NO: 102]
5'-CAGAATCAGCATTTTCTGTTGGGCCATTGC-3'

[SEQ ID NO: 103]
5'-AATCCAACGCAGGCAACCATTATCACCGCC-3'

[SEQ ID NO: 104]
5'-GATGTTTTTCATTTTCTGTTGGGCCATTGC-3'
```

The pBAD, cI(ts) system introduced into pWAS in order to increase the expression regulatory effect of the synthetic sRNA was introduced into pTyr-a containing no synthetic sRNA. Specifically, PCR was performed using pWAS as a template and primers of SEQ ID NOS: 105 and 96, and the PCR product was cleaved with SpeI/SacI and ligated with the constructed vector cleaved with XbaI/SacI.

Next, in the same manner as above, anti-csrA, anti-pgi or anti-ppc was amplified using primers of SEQ ID NOS: 104 and 94, the PCR product (sRNA) was cleaved with SpeI/SacI and ligated with the constructed vector cleaved with XbaI/SacI. In this way, three pTyr-a plasmids having different sRNAs were constructed (FIG. 10). However, the tpl gene shown in FIG. 10 is used for phenol production, and thus was not cloned in this stage. The tpl gene will be described in detail in the Example related to the production of phenol. anti-tyrR was cloned into pTyr-b. Specifically, anti-tyrR was amplified by PCR using primers of SEQ ID NOS: 106 and 107, and then cleaved with SpeI/NheI. Also, the constructed pTyr-b vector containing no sRNA was cleaved with NheI, and then ligated with the anti-tyrR, thereby constructing a pTyr-b vector containing the sRNA.

Primer Sequences Used

```
                                      [SEQ ID NO: 105]
5'-TAATTTACTA GTATGGCTGA AGCGCAAAAT GATCC-3'

[SEQ ID NO: 106]
5'-AATTAAACTA GTTAACACCG TGCGTGTTGA-3'

[SEQ ID NO: 107]
5'-AATTAAGCTA GCTATAAACG CAGAAAGGCCCA-3'
```

4-4: Experiment on the Production of Tyrosine in 14 Different Recombinant *E. coli* Strains with Synthetic sRNA A total of four combinations, including a combination of the constructed pTyr-b containing anti-tyrR and pTyr-b containing no sRNA, and a combination of the constructed pTyr-b containing anti-tyrR and pTyr-b containing each of the sRNAs, were transformed into 14 different *E. coli* strains. The strains were cultured in the same manner as the above-described flask culture method, and the highest tyrosine concentration within 48 hours after start of the culture was measured.

As a result, as shown in FIG. 11, the best combination was the case in which the tyrR and csrA genes in the S17-1 strain were silenced. This combination showed tyrosine in a concentration of 2.0 g/L in the flask.

Among the combinations, the combination of anti-tyrR+anti-ppc and the combination of anti-tyrR-anti-pgi showed a decrease in tyrosine production. Particularly, as can be seen in FIG. 12, the growth of the host cells introduced with anti-pgi was inhibited, and thus the overall production of tyrosine decreased.

4-5: Restoration of Cell Growth and Increase in Tyrosine Production by the Regulation of Expression Using Synthetic sRNA As described in Example 4-4, when the expression of pgi was inhibited, the growth of the cells was inhibited, resulting in a decrease in the overall production of tyrosine. This suggests that, when the growth of cells is somewhat restored even though the metabolic flux entering the tyrosine biosynthesis pathway is lost, the overall production of tyrosine can be increased. Based on this suggestion, the expression of pgi gene was regulated. This regulation was performed by deleting part of (one or two) nucleotides from the pgi binding sequence and anti-pgi sequence to reduce the binding energy. Specifically, using the pWAS cloned with anti-pgi as a template, anti-pgi-D1 comprising a deletion of one nucleotide was constructed by site-directed mutagenesis using primers of SEQ ID NOS: 108 and 104, and anti-pgi-D2 comprising a deletion of two nucleotides was constructed by site-directed mutagenesis using primers of SEQ ID NOS: 109 and 104 (FIG. 13).

Primer Sequences Used

```
                                        [SEQ ID NO: 108]
    5'-ATCCAACGCAGGCAACCATTATCACCGCC-3'

[SEQ ID NO: 109]
    5'-TCCAACGCAGGCAACCATTATCACCGCC-3'
```

Each of the constructed genes was cloned into the pTyr-a plasmid in the same manner as described in Example 4-3, and each of the plasmids was cloned into 14 different *E. coli* strains. Then, the production of tyrosine in each of the strains was examined.

As a result, as can be seen in FIG. 11, when one or more nucleotides of the binding sequence of the synthetic sRNA were deleted to reduce the binding energy, the production of tyrosine in all the recombinant *E. coli* strains was increased. Particularly, as can be seen in FIG. 11, when the growth rate of the TOP10 strain having the lowest ability to produce tyrosine was compared with that of the S17-1 strain having the highest ability to produce tyrosine, it can be seen that, as the binding energy of the sRNA decreased, the growth rate of the host microorganisms was gradually restored.

Through this Example, it can be seen that the synthetic sRNA according to the present invention can be used to inhibit the expression of the target gene and its ability to inhibit the expression of the target gene can be regulated, suggesting that the sRNA gene can be used to regulate the expression of various target genes.

4-6: Comparison of Inhibition of Expression of Target Gene by Synthetic sRNA Between Strains From the results of the above Examples, it can be seen that the production of tyrosine differs between the strains, suggesting that it is important to select the most suitable strain. In addition, it can be seen that the conventional gene deletion method is time-consuming, whereas the synthetic sRNA according to the present invention can be easily constructed and can be quickly applied to various strains, suggesting that the synthetic sRNA is very suitable for the measurement of metabolic capabilities of strains and the selection of the most suitable strain. However, although sRNAs are evolutionally highly conserved in known prokaryotic cells, and thus the possibility of difference in the target gene inhibitory effect of the synthetic sRNA between strains is low. In order to verify this fact, the following experiment was performed.

In this Example, genes were constructed in the same manner as described in Example 3. In Example 3, DsRed2 was fused with each of luxR, araC and kanR genes, but in this Example, DsRed2 was fused with each of pgi, csrA, tyrR and ppc genes, the degree of expression of each gene was measured by fluorescence. Herein, the comparison of gene expression was performed between the S17-1 strain having the highest tyrosine productivity and the TOP10 strain having the lowest tyrosine productivity. If there is no difference in gene expression between the S17-1 strain and the TOP10 strain, there will be no difference in gene expression between other strains.

For cloning of pgi, pgi was amplified by PCR using the S17-1 chromosome as a template and primers of SEQ ID NOS: 110 and 111, and the PCR product was cleaved with PacI/XhoI, and then cloned into the DsRed2 reporter plasmid of Example 3. In the same manner, tyrR was amplified by PCR using primers of SEQ ID NOS: 112 and 113, csrA was amplified by PCR using primers of SEQ ID NOS: 114 and 115, ppc was amplified by PCR using primers of SEQ ID NOS: 116 and 117, and the PCR products were cloned. When the inhibition of expression of the gene of interest in the S17-1 strain was to be measured, cloning in the S17-1 chromosome was performed, and when it was to be measured in the TOP10 strain, cloning in the TOP10 chromosome was performed.

Primer Sequences Used

```
                                        [SEQ ID NO: 110]
    5'-AATTATTAATTAAACAATTCTCAAAATCAGAAG
    AGTATTGCTA-3'

[SEQ ID NO: 111]
    5'-AATTACTCGAGCAGCATCTGATCGTCGAAGG-3'

[SEQ ID NO: 112]
    5'-AATTATTAATTAATAATTGTTCTTTTTTCAGGT
    GAAGGTTCCC-3'

[SEQ ID NO: 113]
    5'-AATTACTCGAGACCGCGTAAATCAATGCCTC TTA-3'

[SEQ ID NO: 114]
    5'-AATTATTAATTAACTCTTTTAATCTTTCAA
    GGAGCAAAGA-3'

[SEQ ID NO: 115]
    5'-AATTACTCGAGACGCTGGTAGATCTCTTCAC G-3'\

[SEQ ID NO: 116]
    5'-AATTATTAATTAAATAAGATGGGGTGTCTGGGGTAAT-3'

[SEQ ID NO: 117]
    5'-AATTACTCGAGATCATTGCCAGCGCGTGAAG-3'
```

As a result, as can be seen in FIG. 14, anti-tyrR showed inhibition rates of 85.6±9.4% and 80.0±9.1% in S17-1 and TOP10, respectively, and anti-csrA showed inhibition rates of 84.9±9.8% and 87.8±6.7%. The remaining sRNAs showed inhibition rates similar to those shown by these sRNAs. This suggests that the synthetic sRNAs show inhibition rates similar between strains and exhibit the same effect in various strains.

4-7: Fermentation of S17-1 Strain Transformed with pTyr-a(Anti-csrA)/pTyr-b(Anti-tyrR) Plasmid The finally selected S17-1 strain was transformed with each of pTyr-a(anti-csrA) and pTyr-b(anti-tyrR) plasmids, and the recombinant microorganisms were subjected to fed-batch fermentation.

Specifically, 200 ml of the recombinant microorganisms were cultured in an LB medium containing 1% arabinose, 25 μg/ml ampicillin and 25 μg/ml kanamycin at 37° C., and the culture was performed in a 2 L fermentor (Bioflo 3000, New Brunswick Scientific Co., Edison, N.J.). Herein, the initial OD was 0.5. Feeding solution was composed of 600 g/L glucose, 7.5 g/L $(NH_4)_2SO_4$, 2 g/L $KH_2PO_4$ and 5 g/L yeast extract, and whenever the pH of the medium in the fermentor changed by 0.01 from 6.8, the pH was adjusted by addition of 25%(v/v) $NH_4OH$. Also, the concentration of dissolved oxygen was maintained at a constant level of 40% by supplying 1 vvm (air volume/working volume/min), and the agitation speed was automatically controlled to an rpm of up to 1000.

The culture was performed for a total of 110 hours. The OD of the cells and the production of tyrosine are shown in FIG. 15. As can be seen in FIG. 15, tyrosine was produced at a concentration of up to 21.9 g/L.

4-8: Production of Phenol in Various *E. coli* Strains

An experiment on the conversion of produced tyrosine to phenol was performed. Specifically, for expression of the tpl gene that converts tyrosine to phenol, a placIQ promoter was synthesized using primers of SEQ ID NOS: 118 and 119 without template, and the synthesized promoter was cleaved with SacI/PacI and then cloned into pWA-J23113-T1/TE to replace the promoter. Also, tpl gene was amplified by PCR from the *Pasteurella multocida* chromosome (GenBank, 002663.1) using primers of SEQ ID NOS: 120 and 121, and then cloned into pWA-placIQ-T1/TE by using PacI/EcoRI. The gene constructed as described above was amplified by PCR using primers of SEQ ID NOS: 122 and 96, and cleaved with SpeI/SacI, and then ligated to the pTyr-a (anti-csrA) plasmid cleaved with XbaI/SacI, thereby constructing a pTyr-a (anti-csrA)-TPL plasmid.

[SEQ ID NO: 118]
5'-GAGCTCTTGGTGCAAAACCTTTCGCGGTATGGCATGATAGCGCCAA
GCACATATCGAAAGGATAGTCTTGATAACCATAAGTTTAATTAA-3'

[SEQ ID NO: 119]
5'-TTAATTAAACTTATGGTTATCAAGACTATCCTTTCGATATGTGCTT
GGCGCTATCATGCCATACCGCGAAAGGTTTTGCACCAGAGCTC-3'

[SEQ ID NO: 120]
5'-TTAATTAAAGGAGAAAGATTATGAGAAACTATCCTGCAGAACCTTA
TA-3'

[SEQ ID NO: 121]
5'-GAATTCTTAATGGTGATGATGGTGATGCGCTTACGCTTTCGGTTCA
AAACGCG-3'

[SEQ ID NO: 122]
5'-CATTAACTAGTTGGTGCAAAACCTTTCGCG-3'

The constructed plasmid together with the pTyr-b (anti-tyrR) plasmid was transformed into the 14 different *E. coli* strains tested in Example 4-2, and then flask culture of each recombinant strain was performed in the same manner as the above-described tyrosine culture method, and the highest phenol production during 48 hours of culture was measured.

Figure 16:
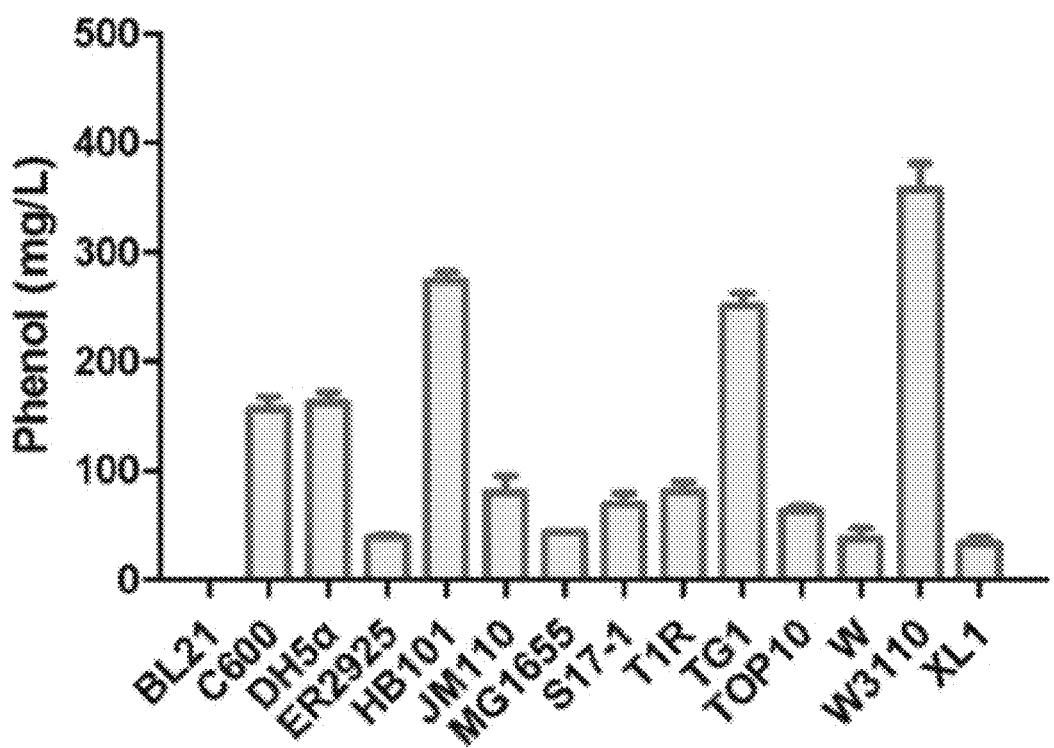
FIG. 16 is a graphic diagram showing the concentrations of phenol produced in various *E. coli* strains.

As a result, as can be seen in FIG. 16, the W3110 strain showed the highest phenol production (357.6 mg/L), and the S17-1 strain that showed the highest tyrosine productivity in the above Example showed a phenol production of 68.8 mg/L.

Example 5

Production of Cadaverine-Producing Recombinant Microorganism Using Synthetic sRNA In this Example, the metabolic flux of the lysine biosynthesis pathway was enhanced, and then selection of the gene to be silenced in order to further increase the production of cadaverine in a recombinant microorganism that converts lysine to cadaverine using lysine decarboxylase (CadA) was performed.

FIG. 16 shows pathways of biosynthesis of cadaverine from glucose. These biosynthesis pathways include consumption pathways for production of other metabolites. To increase the production of cadaverine, it is preferred to block networks that consume metabolites.

In this Example, 8 candidate genes capable of suppressing these networks were selected, and synthetic sRNAs capable of inhibiting the expression of these genes were constructed. The selected candidate genes were as follows: gltA (citrate synthase), thrA (aspartate kinase I), thrB (homoserine kinase), thrC (threonine synthase), thrL (throperonleaderpeptide), metB (cystathionine gamma-synthase), murE (UDP-N-acetylmuramoyl-L-alanyl-D-glutamate-L-lysine ligase), and murF (UDP-N-acetylmuramoylalanyl-D-glutamyl-2,6-diaminopimelate-D-alanyl-D-alaninligase).

Specifically, anti-glt (synthetic sRNA) was constructed by site-directed mutagenesis using pWAS (constructed in Example 1) as a template and primers of SEQ ID NOS: 123 and 124. In the same manner, anti-metB was constructed using primers of SEQ ID NOS: 125 and 126; anti-murE was constructed using primers of SEQ ID NOS: 127 and 128; anti-murF was constructed using primers of SEQ ID NOS: 129 and 130; anti-thrA was constructed using primers of SEQ ID NOS: 131 and 132; anti-thrB was constructed using primers of SEQ ID NOS: 133 and 134; anti-thrC was constructed using primers of SEQ ID NOS: 135 and 136; and anti-thrL was constructed using primers of SEQ ID NOS: 137 and 138.

Primer Sequences Used

[SEQ ID NO: 123]
5'-AAAGCAAAACTCGCAACCATTATCACCGCC-3'

[SEQ ID NO: 124]
5'-TGTATCAGCCATTTTCTGTTGGGCCATTGCATTG-3'

[SEQ ID NO: 125]
5'-ACAGGCCACCATGCAACCATTATCACCGCC-3'

[SEQ ID NO: 126]
5'-TTACGCGTCATTTTCTGTTGGGCCATTGCATTG-3'

[SEQ ID NO: 127]
5'-AATTTGCGCGACGCAACCATTATCACCGCC-3'

[SEQ ID NO: 128]
5'-ACGATCTGCCACTTTCTGTTGGGCCATTGCATTG-3'

[SEQ ID NO: 129]
5'-AACCCTTAGCCAGCAACCATTATCACCGCC-3'

[SEQ ID NO: 130]
5'-ACGCTAATCATTTTCTGTTGGGCCATTGCATTG-3'

[SEQ ID NO: 131]
5'-AAGTTCGGCGGTGCAACCATTATCACCGCC-3'

[SEQ ID NO: 132]
5'-CAACACTCGCATTTTCTGTTGGGCCATTGCATTG-3'

[SEQ ID NO: 133]
5'-TATGCCCCGGCTGCAACCATTATCACCGCC-3'

[SEQ ID NO: 134]
5'-AACTTTAACCATTTTCTGTTGGGCCATTGCATTG-3'

[SEQ ID NO: 135]
5'-AATCTGAAAGATGCAACCATTATCACCGCC-3'

[SEQ ID NO: 136]
5'-GTAGAGTTTCATTTTCTGTTGGGCCATTGCATTG-3'

[SEQ ID NO: 137]
5'-AGCACCACCATTGCAACCATTATCACCGCC-3'

[SEQ ID NO: 138]
5'-AATGCGTTTCATTTTCTGTTGGGCCATTGCATTG-3'

The genes constructed by site-directed mutagenesis using the primer sequences were transformed into DH5a cells (Invitrogen) in the following manner. Culture was performed using a plate medium containing LB-agar, 1% arabinose and 100 μg/ml ampicillin at 25° C. for 2 days, and the resulting colonies were cultured in liquid LB medium containing 1% agarose and 100 μg/ml ampicillin. Then, plasmids were purified from the cells and sequenced, and a correct plasmid was used in a subsequent experiment. This culture in the presence of 1% arabinose and at 25° C. effectively inhibits the expression of the synthetic sRNA, and thus is an essential process. In addition, if the chromosomal gene that is targeted by the synthetic sRNA has a very significant influence on the growth of host cells, the growth of the cells will be insufficient when the expression of the synthetic sRNA is not inhibited. This influence of the synthetic sRNA can cause difficulty in subsequent experiments, and thus is avoided. However, if the synthetic sRNA has no influence on the cell growth, culture may be performed in the absence of arabinose or at 37° C. When culture for the production of a desired metabolic product is performed, the synthetic sRNA should be sufficiently expressed, and thus in this case, culture was performed in the absence of arabinose and at 37° C.

Each of the synthetic sRNAs constructed as described above was transformed into the recombinant microorganism XQ56 (containing a p15CadA plasmid) that produces cadaverine with high efficiency. The XQ56 strain used in this Example was constructed by the method of Qian (Qian, Biotechnology and Bioengineering, 108(1):93-103, 2011). Briefly, in order to produce cadaverine, speE, speG, puuA and ygjG genes that are cadaverine-degrading enzymes were deleted from *E. coli*, and in order to increase the production of cadaverine precursor metabolites, iclR was also deleted. In addition, in order to remove feedback inhibition by lysine that is an immediate precursor of cadaverine, the chromosome was modified such that the promoters of dapA, dapB and lysA genes are constitutively expressed without being inhibited by lysine. Finally, in order to sufficiently produce cadaverine, the cadA gene that produces cadaverine from lysine was overexpressed in the form of a plasmid (p15CadA). In this way, the XQ56 strain used in the present invention was constructed.

After transformation, the resulting colonies were transferred to liquid LB medium (1% arabinose, 25 µg/ml ampicillin, and 25 µg/ml kanamycin) and cultured at 25° C. to the stationary phase. Then, the cells were transferred at a volume ratio of 1/100 into a flask containing 50 ml of medium (see Table 3 below) and were then cultured at 37° C. for 24 hours. Then, the supernatant of the medium was sampled, and the concentration of cadaverine in the sample was measured by HPLC analysis. Specifically, the sample was allowed to react with o-phthaldialdehyde, and then analyzed by reverse-phase HPLC (Qian, Biotechnology and Bioengineering, 108(1):93-103, 2011).

TABLE 3

| Compound | Concentration |
| --- | --- |
| (NH$_4$)$_2$HPO$_4$ | 2 g/L |
| KH$_2$PO$_4$ | 6.75 g/L |
| Citric acid | 0.85 g/L |
| MgSO$_4$•7H$_2$O | 0.7 g/L |
| (NH$_4$)$_2$SO$_4$ | 3 g/L |
| Glucose | 20 g/L |
| Trace element solution | 5 ml/L (Table 4) |

TABLE 4

| Compound | Concentration |
| --- | --- |
| (NH$_4$)$_2$HPO$_4$ | 2 g/L |
| KH$_2$PO$_4$ | 6.75 g/L |
| Citric acid | 0.85 g/L |
| MgSO$_4$•7H$_2$O | 0.7 g/L |
| (NH$_4$)$_2$SO$_4$ | 3 g/L |
| Glucose | 20 g/L |
| Trace element solution | 5 ml/L (Table 4) |

As a result, as can be seen in FIG. 19, the production of cadaverine in the basic strain (XQ56, containing a p15CadA plasmid) was 1.4±0.05 g/L, and when it was taken as 100%, the strains in which the expressions of each of murE, metB and thrL among the eight candidate genes were inhibited showed increases in cadaverine production of 55% (2.15 g/L) for murE, 24% (1.73 g/L) for metB and 34% (1.87 g/L) for thrL. Such experimental results suggest that the synthetic sRNAs according to the present invention can be used to regulate the mRNA expression of various target genes.

Example 6

Regulation of Inhibitory Efficiency of Synthetic sRNAs and Measurement of the Change in Cell Growth with Change in Number of Introduced Synthetic sRNAs 6-1: Regulation of Inhibitory Efficiency of Synthetic sRNAs of Example 3

In order to verify that the inhibitory efficiency of the synthetic sRNA can be controlled by regulating the energy of binding between the synthetic sRNA and the target mRNA, synthetic anti-DsRed2 sRNA and anti-LacZ sRNA with various binding energies were constructed using, as a template, a plasmid containing the MicC structure and the PR promoter for expression thereof in the pWAS plasmid.

In the case of anti-DsRed2 sRNA, binding site sequences were randomly produced as described below in order to produce a broad energy range, and in the case of anti-lacZ sRNA, each binding sequence corresponding to the energy range was designed as described below using the UNAFold program. When DsRed2 was used, various anti-DsRed2 sRNAs were produced by the above-described site-directed mutagenesis using primers of SEQ ID NOS: 169 and 170, and when LacZ was used, various anti-LacZ sRNAs were produced by site-directed mutagenesis using forward/reverse primers such as primers of SEQ ID NOS: 171/172, 173/174, . . . 195/196.

Primers for Anti-dsRed2 Variants

[SEQ ID NO: 169]
5'-NNNNNNNNNNNNNNNNNNGCAACCATTATCACCGCCA-3'

[SEQ ID NO: 170]
5'-NNNNNNNNNNNNNNNNNNTTTCTGTTGGGCCATTGCATTG-3'

(N is any nucleotide).
Primers for Anti-LacZ variants

[SEQ ID NO: 171]
5'-ATGATGCAACCATTATCACCGCCAGAGGTAAAA-3'

[SEQ ID NO: 172]
5'-GGTCAT TTTCTGTTGGGCCATTGCATTGCCAC-3'

[SEQ ID NO: 173]
5'-ATGATTGCAACCATTATCACCGCCAGAGGTAAAA-3'

[SEQ ID NO: 174]
5'-GGTCAT TTTCTGTTGGGCCATTGCATTGCCAC-3'

[SEQ ID NO: 175]
5'-TGATTAGCAACCATTATCACCGCCAGAGGTAAAA-3'

[SEQ ID NO: 176]
5'-TGGTCAT TTTCTGTTGGGCCATTGCATTGCCAC-3'

[SEQ ID NO: 177]
5'-TGATTACGCAACCATTATCACCGCCAGAGGTAAAA-3'

[SEQ ID NO: 178]
5'-TGGTCAT TTTCTGTTGGGCCATTGCATTGCCAC-3'

[SEQ ID NO: 179]
5'-GATTACGGCAACCATTATCACCGCCAGAGGTAAAA-3'

[SEQ ID NO: 180]
5'-ATGGTCAT TTTCTGTTGGGCCATTGCATTGCCAC-3'

[SEQ ID NO: 181]
5'-GATTACGGGCAACCATTATCACCGCCAGAGGTAAAA-3'

-continued

```
                                         [SEQ ID NO: 182]
5'-ATGGTCAT TTTCTGTTGGGCCATTGCATTGCCAC-3'

[SEQ ID NO: 183]
5'-ATTACGGAGCAACCATTATCACCGCCAGAGGTAAAA-3'

[SEQ ID NO: 184]
5'-CATGGTCATTTTCTGTTGGGCCATTGCATTGCCAC-3'

[SEQ ID NO: 185]
5'-TTACGGATTGCAACCATTATCACCGCCAGAGGTAAAA-3'

[SEQ ID NO: 186]
5'-TCATGGTCATTTTCTGTTGGGCCATTGCATTGCCAC-3'

[SEQ ID NO: 187]
5'-TTACGGATTCGCAACCATTATCACCGCCAGAGGTAAAA-3'

[SEQ ID NO: 188]
5'-TCATGGTCATTTTCTGTTGGGCCATTGCATTGCCAC-3'

[SEQ ID NO: 189]
5'-TACGGATTCAGCAACCATTATCACCGCCAGAGGTAAAA-3'

[SEQ ID NO: 190]
5'-ATCATGGTCATTTTCTGTTGGGCCATTGCATTGCCAC-3'

[SEQ ID NO: 191]
5'-TACGGATTCACGCAACCATTATCACCGCCAGAGGTAAAA-3'

[SEQ ID NO: 192]
5'-ATCATGGTCATTTTCTGTTGGGCCATTGCATTGCCAC-3'

[SEQ ID NO: 193]
5'-ACGGATTCACTGGCAACCATTATCACCGCCAGAGGTAAAA-3'

[SEQ ID NO: 194]
5'-AATCATGGTCATTTTCTGTTGGGCCATTGCATTGCCAC-3'

[SEQ ID NO: 195]
5'-GGATTCACTGGCCGGCAACCATTATCACCGCCAGAGGTAAAA-3'

[SEQ ID NO: 196]
5'-GTAATCATGGTCATTTTCTGTTGGGCCATTGCATTGCCAC-3'
```

Specifically, various sRNAs that binds to each mRNA with a binding energy ranging from 0 to −60 kcal/mol, and the degree of inhibition of expression of the target mRNA by each of the synthetic sRNAs was measured.

In the case of DsRed2, cells were cultured in LB medium to the exponential phase, and then 1 ml of the medium was centrifuged at 5,000 rpm to remove the medium component while allowing only cells to remain. 1 ml of PBS buffer was added to the remaining cells so that the cells were easily mixed, and then DsRed2 protein in the cells was excited at a wavelength of 563 nm, and fluorescence emitted therefrom was measured by FACS at 582 nm. The intensity of the emitted fluorescence was corrected by subtracting the intensity of fluorescence emitted from the cells cultured under DsRed2-free conditions. The highest value among the measured intensities was taken as 1, and other fluorescence intensities were normalized based on the value.

In the case of LacZ, cells were cultured in the same medium to the same phase as those used in the case of DsRed2, and then 800 μl of a permeabilization solution (60 mM $Na_2HPO_4$, mM $NaH_2PO_3$, 10 mM KCl, 1 mM $MgSO_4$, 3.56 ul/ml beta-mercaptoethanol) was added to 20 μl of the culture. 200 ul of a substrate solution (60 mM $Na_2HPO_4$, 40 mM $NaH_2PO_4$, 2 mg/ml o-nitrophenyl-beta-D-galatosize (ONPG)) was also added. Next, the cells were allowed to stand at 37° C. for a sufficient time so that a color development reaction occurred, and then 500 μl of a stop solution (1M $Na_2CO_3$) was added to stop the reaction, and the absorbance at 420 nm was measured. The highest value among the values of color development of LacZ measured from various sRNAs was taken as 1, and other values were normalized based on the value to determine the relative values.

As a result, as can be seen in FIG. 23 that show the results of the two experiments, when the binding energy ranged from about −10 kcal/mol to −40 kcal/mol, the expression of the target gene was linearly inhibited. This indicates that, when the synthetic sRNA according to the present invention is constructed so that it binds to the target mRNA with a binding energy between −10 kcal/mol and −40 kcal/mol, it can inhibit the expression of the target mRNA to the desired level.

6-2: Measurement of the Change in Cell Growth with Change in Number of Introduced Synthetic sRNAs of Example 3

When a synthetic sRNA is additionally introduced into a plasmid in order to regulate the expression of the target gene and are produced in cells, it can interfere with the growth of the cells by using the energy source of the cells. Thus, the effects of the additionally introduced synthetic sRNA on cell growth and intracellular protein expression were examined (FIG. 24a). Specifically, 0 to 4 synthetic sRNAs introduced into a plasmid having a ColE1 replication origin, and then a change in the expression level of DsRed2 gene in the plasmid was measured. A synthetic sRNA was introduced into the EcoRI and KpnI sites of a plasmid having a ColE1 replication origin, thereby constructing a plasmid (Rmo) containing one sRNA. Using the constructed plasmid as a template, PCR was performed with primers of SEQ ID NOS: 197 and 198, and the PCR product was cleaved with SacI and BglII and introduced into the Rmo plasmid, thereby constructing a plasmid (Rmo2) containing two sRNAs. Using the Rmo as a template, PCR was performed with primers of SEQ ID NOS: 199 and 200, and the PCR product was cleaved with SpeI/BamHI, and then introduced into the Rmo2 plasmid, thereby constructing a plasmid (Rmo3) containing three sRNAs. Using the Rmo as a template, PCR was performed with primers of SEQ ID NOS: 201 and 202, and the PCR product was cleaved with SphI and SalI, and then introduced into the Rmo3 plasmid, thereby constructing a plasmid (Rmo4) containing four sRNAs. The expression levels of DsRed2 from the plasmids containing 0-4 sRNAs were determined by measuring fluorescence intensity as described above.

```
                                         [SEQ ID NO: 197]
5'-AATTAA AGATCT TAACACCGTGCGTGTTGA-3'

[SEQ ID NO: 198]
5'-GAGCTC TATAAACGCAGAAAGGCCCA-3'

[SEQ ID NO: 199]
5'-ACTAGT TAACACCGTGCGTGTTGA-3'

[SEQ ID NO: 200]
5'-GGATCC TATAAACGCAGAAAGGCCCA-3'

[SEQ ID NO: 201]
5'-GCATGC TAACACCGTGCGTGTTGA-3'

[SEQ ID NO: 202]
5'-GTCGAC TATAAACGCAGAAAGGCCCA-3'
```

As a result, it can be seen that, even when up to three synthetic sRNAs are introduced, they do not influence the expression of DsRed2 (FIG. 24b). In addition, whether the introduction of 0-4 sRNAs has any influence on the growth rate of cells was measured. In this case, the optical density (600 nm) at the log growth phase of cells was measured and fitted into the following cell growth curve equation to calculate cell growth constant (k) per time:

$$y=y_0\exp(k \cdot t)$$

wherein $y_0$ is the initial O.D.600 value, and t is time. As a result, it could be seen that, when up to three synthetic sRNAs were introduced, the k value slightly decreased, but the decrease was not significant. This indicates that the introduction of up to three synthetic sRNAs into cells does not significantly influence the growth of the cells (FIG. 24c).

6-3: Regulation of Inhibitory Efficiency of Synthetic sRNAs of Example 4-5

Like the case of pgi of Example 4-5, the binding sequence of anti-csrA sRNA was modified to change the binding energy, so that the expression level of the csrA gene was diversified. Specifically, PCR was performed using a pWAS-anti-csrA plasmid as a template and the following primer pairs, thereby substituting the binding sequence.

```
                                     [SEQ ID NO: 203]
5'-TTCCTCGTCG GCAACCATTA TCACCGCC-3'

[SEQ ID NO: 204]
5'-GAATCAGCATTTTCTGTTGGGCCATTGC-3'

[SEQ ID NO: 205]
5'-GACTCGTCGA GGCAACCATT ATCACCGCC-3'

[SEQ ID NO: 206]
5'-AGAATCAGCATTTTCTGTTGGGCCATTGC-3'

[SEQ ID NO: 207]
5'-TAACTCGTCG GCAACCATTA TCACCGCC-3'

[SEQ ID NO: 208]
5'-GAATCAGCATTTTCTGTTGGGCCATTGC-3'

[SEQ ID NO: 209]
5'-TCGTCGAGTT GGTGGGCAAC CATTATCACC GCC-3'

[SEQ ID NO: 210]
5'-TCAGA ATCAGCATTTTCTGTTGGGCCATTGC-3'

[SEQ ID NO: 211]
5'-CCGTCGAGTT GGTGGGCAAC CATTATCACC GCC-3'

[SEQ ID NO: 212]
5'-TCAGA ATCAGCATTTTCTGTTGGGCCATTGC-3'

[SEQ ID NO: 213]
5'-AGTCGAGTTG GTGAGGCAAC CATTATCACC GCC-3'

[SEQ ID NO: 214]
5'-CGTCA GAATCAGCATTTTCTGTTGGGCCATTGC-3'

[SEQ ID NO: 215]
5'-GTCGAGTTGG TGAGGGCAAC CATTATCACC GCC-3'

[SEQ ID NO: 216]
5'-AGTCA GAATCAGCATTTTCTGTTGGGCCATTGC-3'

[SEQ ID NO: 217]
5'-TCGAGTTGGT GAGGGCAACC ATTATCACCG CC-3'

[SEQ ID NO: 218]
5'-CGGTCA GAATCAGCATTTTCTGTTGGGCCATTGC-3'
```

Various anti-csrAs constructed as described above were amplified by PCR using pWAS as a template and primers of SEQ ID NOS: 105 and 96, and the PCR products were cleaved with SpeI/SacI and ligated with a pTyr-a vector cleaved with XbaI/SacI. In this way, various anti-csrA sRNAs with a binding energy ranging from −30 kcal/mol to −50 kcal/mol were constructed. The synthetic sRNAs constructed in this way were introduced into the S17-1 E. coli strain showing the highest yield, and the production of tyrosine was measured in the same manner as described in Example 4-4.

Figure 25:
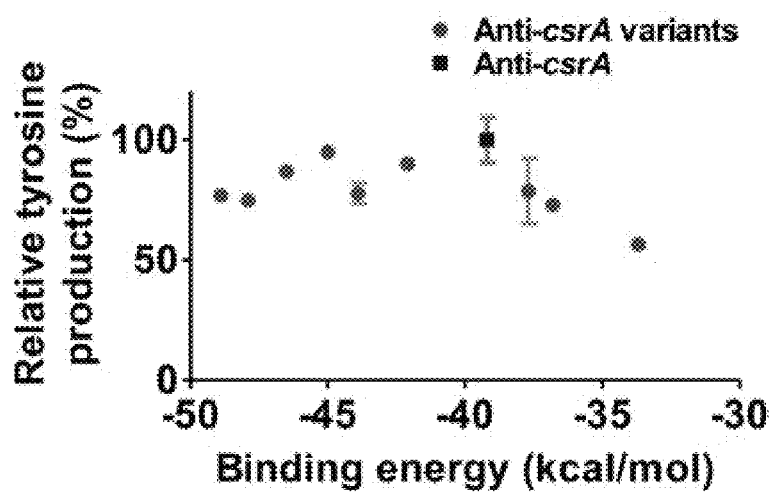
FIG. 25 shows the results of examining the production of tyrosine using Anti-csrA with various binding energies.

As a result, as can be seen in FIG. 25, the highest yield was shown at an energy value of −39.2 kcal/mol. This binding energy value is identical to that in the case of the above-constructed anti-csrA sRNAs.

This suggests that the synthetic sRNAs can be used to inhibit the expression of the target gene and that the inhibitory efficiency thereof can be regulated.

Example 7

Identification of additional genes for increasing tyrosine production

In this Example, in order to identify genes other than tyrR/csrA genes, which have positive effects on tyrosine production when being inhibited, 84 sRNAs were constructed, which can control genes that are involved in glycolysis and TCA networks and transcription regulators that regulate the expression thereof.

The genes are listed below.

accA (acetyl-CoA carboxyltransferase, alpha-subunit)
accB (biotinylated biotin-carboxyl carrier protein)
accC (acetyl-CoA carboxylase)
accD (acetyl-CoA carboxyltransferase, beta-subunit)
aceE (subunit of E1p component of pyruvate dehydrogenase complex)
aceF (pyruvate dehydrogenase)
ackA (propionate kinase/acetate kinase activity)
adiY (AdiY is a positive DNA-binding transcriptional regulator that controls the arginine) decarboxylase (adi) system)
argB (acetylglutamate kinase)
argC (N-acetylglutamylphosphate reductase)
argG (argininosuccinate synthase)
argH (argininosuccinate lyase)
asnC (transcriptional regulator that activates the expression of asnA, a gene involved in the synthesis of asparagine)
aspA (aspartate ammonia-lyase)
crp (CRP transcriptional dual regulator)
csiD (predicted protein. CsiD is the product of a gene induced by carbon starvation)
csiR (DNA-binding transcriptional repressor)
cytR (transcription factor required for transport and utilization of ribonucleosides and deoxyribonucleosides)
dcuA (The DcuA transporter is one of three transporters known to be responsible for the uptake of C4-dicarboxylates such as fumarate under anaerobic conditions)
deoB (phosphopentomutase)
deoC (deoxyribose-phosphate aldolase)
deoR (The transcriptional repressor DeoR, for "Deoxyribose Regulator," is involved in the negative expression of genes related to transport and catabolism of deoxyribonucleoside nucleotides)
fabH (KASIII, β-ketoacyl-ACP synthases)
fadD (fatty acyl-CoA synthetase)
fadR (FadR Fatty acid degradation Regulon, is a multifunctional dual regulator that exerts negative control over the fatty acid degradative regulon [Simons80, Simons80a] and acetate metabolism)
fbp (fructose-1,6-bisphosphatase)
fnr (FNR is the primary transcriptional regulator that mediates the transition from aerobic to anaerobic growth)
fruR (FruR is a dual transcriptional regulator that plays a pleiotropic role to modulate the direction of carbon flow through the different metabolic pathways of energy metabolism, but independently of the CRP regulator)

ftsL (essential cell division protein FtsL)
ftsQ (essential cell division protein FtsQ)
ftsW (essential cell division protein FtsW)
ftsZ (essential cell division protein FtsZ)
fur (Fur-Fe+2 DNA-binding transcriptional dual regulator)
gabD (succinate semialdehyde dehydrogenase, NADP+-dependent)
gabP (APC transporter)
gabT (4-aminobutyrate aminotransferase)
gadA (glutamate decarboxylase A subunit)
gadB (glutamate decarboxylase B subunit)
gadC (GABA APC transporter)
glcC (GntR family transcriptional regulator, glc operon transcriptional activator)
glpK (glycerol kinase)
glpR (sn-Glycerol-3-phosphate repressor)
glpX (fructose 1,6-bisphosphatase II)
gltA (citrate synthase)
hfld (lysogenization regulator)
ihfa (IHF, Integration host factor, is a global regulatory protein)
ihfb (IHF, Integration host factor, is a global regulatory protein)
ilvB (acetohydroxybutanoate synthase/acetolactate synthase)
ilvC (acetohydroxy acid isomeroreductase)
ilvD (dihydroxy acid dehydratase)
ilvG_1 (acetolactate synthase II, large subunit, N-ter fragment (pseudogene))
ilvG_2 (acetolactate synthase II, large subunit, C-ter fragment (pseudogene))
ilvH (acetolactate synthase/acetohydroxybutanoate synthase)
ilvL (ilvGEDA operon leader peptide)
ilvM (acetohydroxybutanoate synthase/acetolactate synthase)
ilvN (acetohydroxybutanoate synthase/acetolactate synthase)
ilvX (Predicted small protein)
lexA (LexA represses the transcription of several genes involved in the cellular response to DNA damage)
lpxC (UDP-3-O-acyl-N-acetylglucosamine deacetylase)
marA (MarA participates in controlling several genes involved in resistance to antibiotics, oxidative stress, organic solvents and heavy metals.)
metJ (MetJ transcriptional repressor)
modE (ModE is the principal regulator that controls the transcription of operons involved in the transport of molybdenum and synthesis of molybdoenzymes and molybdate-related functions)
nadB (L-aspartate oxidase)
narL (nitrate/nitrite response regulator
pck (phosphoenolpyruvate carboxykinase)
PdhR (PdhR, "pyruvate dehydrogenase complex regulator," regulates genes involved in the pyruvate dehydrogenase complex)
phoP (PhoP-Phosphorylated DNA-binding transcriptional dual regulator. Member of the two-component regulatory system phoQ/phoP involved in adaptation to low Mg2+ environments and the control of acid resistance genes)
pnuC (PnuC NMN transporter)
ppsA (phosphoenolpyruvate synthetase)
pta (Phosphate acetyltransferase)
purA (adenylosuccinate synthetase)
purB (adenylosuccinate lyase)
purR (PurR-Hypoxanthine DNA-binding transcriptional repressor. PurR dimer controls several genes involved in purine nucleotide biosynthesis and its own synthesis)
puuE (4-aminobutyrate aminotransferase)
rbsA (ribose ABC transporter)
rbsB (ribose ABC transporter)
rbsD (ribose pyranase)
rbsK (ribokinase)
rbsR (The transcription factor RbsR, for "Ribose Repressor," is negatively autoregulated and controls the transcription of the operon involved in ribose catabolism and transport)
rcsB (RcsB-BglJ DNA-binding transcriptional activator. RcsB protein for "Regulator capsule synthesis B," is a response regulator that belongs to the multicomponent RcsF/RcsC/RcsD/RcsA-RcsB phosphorelay system and is involved in the regulation of the synthesis of colanic acid capsule, cell division, periplasmic proteins, motility, and a small RNA)
rutR (RutR regulates genes directly or indirectly involved in the complex pathway of pyrimidine metabolism)
serA (alpha-ketoglutarate reductase/D-3-phosphoglycerate dehydrogenase)
serC (phosphohydroxythreonine aminotransferase/3-phosphoserine aminotransferase)
soxS (dual transcriptional activator and participates in the removal of superoxide and nitric oxide)
sroD (SroD small RNA)
zwf (glucose 6-phosphate-1-dehydrogenase)

In addition, primer sequences used to construct the genes are as follows:

```
anti-accA
                                        [SEQ ID NO: 219]
5'-TTCCTTGATTTTGCAACCATTATCACCGCC-3'
                                        [SEQ ID NO: 220]
5'-ATTCAGACTCATTTTCTGTTGGGCCATTGCATTG-3' anti-accB
                                        [SEQ ID NO: 221]
5'-AAGATTAAAAAAGCAACCATTATCACCGCC-3'
                                        [SEQ ID NO: 222]
5'-ACGAATATCCATTTTCTGTTGGGCCATTGCATTG-3' anti-accC
                                        [SEQ ID NO: 223]
5'-ATTGTTATTGCCGCAACCATTATCACCGCC-3'
                                        [SEQ ID NO: 224]
5'-TTTATCCAGCATTTTCTGTTGGGCCATTGCATTG-3' anti-accD
                                        [SEQ ID NO: 225]
5'-GAACGAATTAAAGCAACCATTATCACCGCC-3'
                                        [SEQ ID NO: 226]
5'-AATCCAGCTCATTTTCTGTTGGGCCATTGCATTG-3' anti-aceE
                                        [SEQ ID NO: 227]
5'-TTCCCAAATGACGCAACCATTATCACCGCC-3'
                                        [SEQ ID NO: 228]
5'-ACGTTCTGACATTTTCTGTTGGGCCATTGCATTG-3' anti-aceF
                                        [SEQ ID NO: 229]
5'-ATCAAAGTACCGGCAACCATTATCACCGCC-3'
                                        [SEQ ID NO: 230]
5'-TTCGATAGCCATTTTCTGTTGGGCCATTGCATTG-3' anti-ackA
                                        [SEQ ID NO: 231]
5'-GCAACGTTAGTCGCAACCATTATCACCGCC-3'
                                        [SEQ ID NO: 232]
5'-TCCCCGGAACATTCATTTTCTGTTGGGCCATTGCATTG-3' anti-adiY
```

```
                              [SEQ ID NO: 233]
5'-AGCGACCAACCTGCAACCATTATCACCGCC-3'
                              [SEQ ID NO: 234]
5'-GCAAATCCTCATTTTCTGTTGGGCCATTGCATTG-3' anti-argB
                              [SEQ ID NO: 235]
5'-ATTATCAAACTGGCAACCATTATCACCGCC-3'
                              [SEQ ID NO: 236]
5'-TAATGGATTCATTTTCTGTTGGGCCATTGCATTG-3' anti-argC
                              [SEQ ID NO: 237]
5'-CTGATTGTGGGTGCAACCATTATCACCGCC-3'
                              [SEQ ID NO: 238]
5'-CGTATTCAACATTTTCTGTTGGGCCATTGCATTG-3' anti-argG
                              [SEQ ID NO: 239]
5'-CTCAAGCATCTCGCAACCATTATCACCGCC-3'
                              [SEQ ID NO: 240]
5'-AATCGTCGTCATTTTCTGTTGGGCCATTGCATTG-3' anti-argH
                              [SEQ ID NO: 241]
5'-GGCGGGCGTTTTGCAACCATTATCACCGCC-3'
                              [SEQ ID NO: 242]
5'-CCAAAGTGCCATTTTCTGTTGGGCCATTGCATTG-3' anti-asnC
                              [SEQ ID NO: 243]
5'-CTGATCGACAATGCAACCATTATCACCGCC-3'
                              [SEQ ID NO: 244]
5'-ATAATTTTCCATTTTCTGTTGGGCCATTGCATTG-3' anti-aspA
                              [SEQ ID NO: 245]
5'-ATTCGTATCGAAGCAACCATTATCACCGCC-3'
                              [SEQ ID NO: 246]
5'-GTTGTTTGACATTTTCTGTTGGGCCATTGCATTG-3' anti-crp
                              [SEQ ID NO: 247]
5'-AAACCGCAAACAGCAACCATTATCACCGCC-3'
                              [SEQ ID NO: 248]
5'-GCCAAGCACCATTTTCTGTTGG GCCATTGCATTG-3' anti-csiD
                              [SEQ ID NO: 249]
5'-ACCGCCGTACAAGCAACCATTATCACCGCC-3'
                              [SEQ ID NO: 250]
5'-CAGTGCATTCATTTTCTGTTGGGCCATTGCATTG-3' anti-csiR
                              [SEQ ID NO: 251]
5'-TCTCTGGATGGCGCAACCATTATCACCGCC-3'
                              [SEQ ID NO: 252]
5'-CGTAATGGTCATTTTCTGTTGGGCCATTGCATTG-3' anti-cytR
                              [SEQ ID NO: 253]
5'-AAGCAGGAAACTGCAACCATTATCACCGCC-3'
                              [SEQ ID NO: 254]
5'-CTTCGCTTTCACTTTCTGTTGGGCCATTGCATTG-3' anti-dcuA
                              [SEQ ID NO: 255]
5'-GAACTCATCATAGCAACCATTATCACCGCC-3'
                              [SEQ ID NO: 256]
5'-TACAACTAGCATTTTCTGTTGGGCCATTGCATTG-3' anti-deoB
                              [SEQ ID NO: 257]
5'-TTTATTATGGTGGCAACCATTATCACCGCC-3'
                              [SEQ ID NO: 258]
5'-TGCACGTTTCATTTTCTGTTGG CCATTGCATTG-3' anti-deoC
                              [SEQ ID NO: 259]
5'-AAAGCAAGCAGCGCAACCATTATCACCGCC-3'
                              [SEQ ID NO: 260]
5'-CAGATCAGTCATTTTCTGTTGG GCCATTGCATTG-3' anti-deoR
                              [SEQ ID NO: 261]
5'-CGCGAAGAGCGTGCAACCATTATCACCGCC-3'
                              [SEQ ID NO: 262]
5'-ACGTGTTTCCATTTTCTGTTGGGCCATTGCATTG-3' anti-fabH
                              [SEQ ID NO: 263]
5'-TAATGGAGCTGTCATTTTCTGTTGGGCCATTGCATTG-3'
                              [SEQ ID NO: 264]
5'-ACCCTATTGATCGTTGCAACCATTATCACCGCCAGA-3' anti-fadD
                              [SEQ ID NO: 265]
5'-TGGCTTAACCGTGCAACCATTATCACCGCC-3'
                              [SEQ ID NO: 266]
5'-AACCTTCTTCAATTTCTGTTGGGCCATTGCATTG-3' anti-fadR
                              [SEQ ID NO: 267]
5'-GCGCAAAGCCCGGCAACCATTATCACCGCC-3'
                              [SEQ ID NO: 268]
5'-CTTAATGACCATTTTCTGTTGGGCCATTGCATTG-3' anti-fbp
                              [SEQ ID NO: 269]
5'-GGTGAATTTATTGCAACCATTATCACCGCC-3'
                              [SEQ ID NO: 270]
5'-TAACGTTTTCATTTTCTGTTGG GCCATTGCATTG-3' anti-fnr
                              [SEQ ID NO: 271]
5'-AAGCGAATTATAGCAACCATTATCACCGCC-3'
                              [SEQ ID NO: 272]
5'-TTCCGGGATCATTTTCTGTTGG GCCATTGCATTG-3' anti-fruR
                              [SEQ ID NO: 273]
5'-GAAATCGCTCGGGCAACCATTATCACCGCC-3'
                              [SEQ ID NO: 274]
5'-ATCCAGTTTCACTTTCTGTTGG GCCATTGCATTG-3' anti-ftsL
                              [SEQ ID NO: 275]
5'-GTGACAGAAGCTGCAACCATTATCACCGCC-3'
                              [SEQ ID NO: 276]
5'-TCTGCTGATCATTTTCTGTTGGGCCATTGCATTG-3' anti-ftsQ
                              [SEQ ID NO: 277]
5'-GCTCTGAACACGGCAACCATTATCACCGCC-3'
                              [SEQ ID NO: 278]
5'-AGCCTGCGACATTTTCTGTTGGGCCATTGCATTG-3' anti-ftsW
                              [SEQ ID NO: 279]
5'-CTCCCTCGCCTGGCAACCATTATCACCGCC-3'
                              [SEQ ID NO: 280]
5'-AGATAAACGCATTTTCTGTTGGGCCATTGCATTG-3' anti-ftsZ
                              [SEQ ID NO: 281]
5'-ATGGAACTTACCGCAACCATTATCACCGCC-3'
                              [SEQ ID NO: 282]
5'-TGGTTCAAACATTTTCTGTTGGGCCATTGCATTG-3' anti-fur
                              [SEQ ID NO: 283]
5'-AATACCGCCCTAGCAACCATTATCACCGCC-3'
                              [SEQ ID NO: 284]
5'-GTTATCAGTCATTTTCTGTTGG GCCATTGCATTG-3' anti-gabD
                              [SEQ ID NO: 285]
5'-GACAGTAACTTAGCAACCATTATCACCGCC-3'
```

-continued anti-gabP

[SEQ ID NO: 287]
5'-TCGCAACCACATGCAACCATTATCACCGCC-3'
[SEQ ID NO: 288]
5'-TGATTGCCCCATTTTCTGTTGGGCCATTGCATTG-3' anti-gabT

[SEQ ID NO: 289]
5'-AAAGAGTTAATGGCAACCATTATCACCGCC-3'
[SEQ ID NO: 290]
5'-ATTGCTGTTCATTTTCTGTTGGGCCATTGCATTG-3' anti-gadA

[SEQ ID NO: 291]
5'-CTGTTAACGGATGCAACCATTATCACCGCC-3'
[SEQ ID NO: 292]
5'-CTTCTGGTCCATTTTCTGTTGGGCCATTGCATTG-3' anti-gadB

[SEQ ID NO: 293]
5'-CAAGTAACGGATGCAACCATTATCACCGCC-3'
[SEQ ID NO: 294]
5'-CTTCTTATCCATTTTCTGTTGGGCCATTGCATTG-3' anti-gadC

[SEQ ID NO: 295]
5'-GTACAGACAGGTGCAACCATTATCACCGCC-3'
[SEQ ID NO: 296]
5'-TGATGTAGCCATTTTCTGTTGGGCCATTGCATTG-3' anti-glcC

[SEQ ID NO: 297]
5'-ACGTTCATCTTTCATTTTCTGTTGGGCCATTGCATTG-3'
[SEQ ID NO: 298]
5'-CGCCCTATTTGCGAAGCAACCATTATCACCGCCAGA-3' anti-glpK

[SEQ ID NO: 299]
5'-AAATATATCGTTGCAACCATTATCACCGCC-3'
[SEQ ID NO: 300]
5'-TTTTTCAGTCATTTTCTGTTGG GCCATTGCATTG-3' anti-glpR

[SEQ ID NO: 301]
5'-CAACGTCACAACGCAACCATTATCACCGCC-3'
[SEQ ID NO: 302]
5'-TGTTTGTTTCATTTTCTGTTGG GCCATTGCATTG-3' anti-glpX

[SEQ ID NO: 303]
5'-CTTGCCATCGAAGCAACCATTATCACCGCC-3'
[SEQ ID NO: 304]
5'-TTCTCGTCTCATTTTCTGTTGG GCCATTGCATTG-3' anti-gltA

[SEQ ID NO: 305]
5'-AAAGCAAAACTCGCAACCATTATCACCGCC-3'
[SEQ ID NO: 306]
5'-TGTATCAGCCATTTTCTGTTGGGCCATTGCATTG-3' anti-hfld

[SEQ ID NO: 307]
5'-TACTATGACATCGCAACCATTATCACCGCC-3'
[SEQ ID NO: 308]
5'-ATTCTTTGCCACTTTCTGTTGGGCCATTGCATTG-3' anti-ihfa

[SEQ ID NO: 309]
5'-TTTTGTAAGCGCCATTTTCTGTTGGGCCATTGCATTG-3'
[SEQ ID NO: 310]
5'-GCTGAAATGTCAGAAGCAACCATTATCACCGCCAGA-3' anti-ihfb

[SEQ ID NO: 311]
5'-TTCTGACTTGGTCATTTTCTGTTGGGCCATTGCATTG-3'

[SEQ ID NO: 312]
5'-TTGATAGAAAGACTTGCAACCATTATCACCGCCAGA-3' anti-ilvB

[SEQ ID NO: 313]
5'-GGCACAACATCGGCAACCATTATCACCGCC-3'
[SEQ ID NO: 314]
5'-CGAACTTGCCATTTTCTGTTGGGCCATTGCATTG-3' anti-ilvC

[SEQ ID NO: 315]
5'-TTCAATACACTGGCAACCATTATCACCGCC-3'
[SEQ ID NO: 316]
5'-GTAGTTAGCCATTTTCTGTTGGGCCATTGCATTG-3' anti-ilvD

[SEQ ID NO: 317]
5'-CGTTCCGCCACCGCAACCATTATCACCGCC-3'
[SEQ ID NO: 318]
5'-GTACTTAGGCATTTTCTGTTGGGCCATTGCATTG-3' anti-ilvG_1

[SEQ ID NO: 319]
5'-CACAGTGGGTGGCAACCATTATCACCGCC-3'
[SEQ ID NO: 320]
5'-CGCCATTCATTTTCTGTTGGGCCATTGCATTG-3' anti-ilvG_2

[SEQ ID NO: 321]
5'-AACAACTGTCGGGCAACCATTATCACCGCC-3'
[SEQ ID NO: 322]
5'-TTAACAACAATTTCTGTTGGGCCATTGCATTG-3' anti-ilvH

[SEQ ID NO: 323]
5'-TTATCAGTCTTAGCAACCATTATCACCGCC-3'
[SEQ ID NO: 324]
5'-TATCCGGCGCATTTTCTGTTGGGCCATTGCATTG-3' anti-ilvL

[SEQ ID NO: 325]
5'-CTACGAGTGATTGCAACCATTATCACCGCC-3'
[SEQ ID NO: 326]
5'-AAGGGCTGTCATTTTCTGTTGGGCCATTGCATTG-3' anti-ilvM

[SEQ ID NO: 327]
5'-CAGGTCAATGTAGCAACCATTATCACCGCC-3'
[SEQ ID NO: 328]
5'-ATGTTGCATCATTTTCTGTTGGGCCATTGCATTG-3' anti-ilvN

[SEQ ID NO: 329]
5'-ACTCATGACAACGCAACCATTATCACCGCC-3'
[SEQ ID NO: 330]
5'-TGTGTTTTGCATTTTCTGTTGGGCCATTGCATTG-3' anti-ilvX

[SEQ ID NO: 331]
5'-ACAAAATTCTGTGCAACCATTATCACCGCC-3'
[SEQ ID NO: 332]
5'-GCTGTTATTCATTTTCTGTTGGGCCATTGCATTG-3' anti-lexA

[SEQ ID NO: 333]
5'-ACGGCCAGGCAAGCAACCATTATCACCGCC-3'
[SEQ ID NO: 334]
5'-TAACGCTTTCATTTTCTGTTGGGCCATTGCATTG-3' anti-lpxC

[SEQ ID NO: 335]
5'-AGGACACTTAAAGCAACCATTATCACCGCC-3'
[SEQ ID NO: 336]
5'-TTGTTTGATCATTTTCTGTTGGGCCATTGCATTG-3' anti-marA

[SEQ ID NO: 337]
5'-GCAACGTTAGTCGCAACCATTATCACCGCC-3'

[SEQ ID NO: 286]
5'-GTTAAGTTTCATTTTCTGTTGGGCCATTGCATTG-3'

-continued

[SEQ ID NO: 338]
5'-TCCCCGGAACATTTTCTGTTGGGCCATTGCATTG-3' anti-metJ

[SEQ ID NO: 339]
5'-AGCGGCGAATATGCAACCATTATCACCGCC-3'
[SEQ ID NO: 340]
5'-CCATTCAGCCATTTTCTGTTGGGCCATTGCATTG-3' anti-modE

[SEQ ID NO: 341]
5'-ATCCTTCTCACCGCAACCATTATCACCGCC-3'
[SEQ ID NO: 342]
5'-TTCGGCCTGCATTTTCTGTTGGGCCATTGCATTG-3' anti-nadB

[SEQ ID NO: 343]
5'-CCTGAACATTCAGCAACCATTATCACCGCC-3'
[SEQ ID NO: 344]
5'-GAGAGTATTCATTTTCTGTTGGGCCATTGCATTG-3' anti-nagC

[SEQ ID NO: 345]
5'-CCGCCTGGTGTCATTTTCTGTTGGGCCATTGCATTG-3'
[SEQ ID NO: 346]
5'-ACAAGCTCAGATAGGGCAACCATTATCACCGCCAGA-3' anti-narL

[SEQ ID NO: 347]
5'-GAACCGGCTACTGCAACCATTATCACCGCC-3'
[SEQ ID NO: 348]
5'-CTGATTACTCATTTTCTGTTGGGCCATTGCATTG-3' anti-pck

[SEQ ID NO: 349]
5'-AATGGTTTGACCGCAACCATTATCACCGCC-3'
[SEQ ID NO: 350]
5'-GTTAACGCGCATTTTCTGTTGGGCCATTGCATTG-3' anti-PdhR

[SEQ ID NO: 351]
5'-AAAATCCGCCAAGCAACCATTATCACCGCC-3'
[SEQ ID NO: 352]
5'-GCTGTAGGCCATTTTCTGTTGGGCCATTGCATTG-3' anti-phoP

[SEQ ID NO: 353]
5'-GTTGTTGAAGACGCAACCATTATCACCGCC-3'
[SEQ ID NO: 354]
5'-CAGTACGCGCATTTTCTGTTGGGCCATTGCATTG-3' anti-pnuC

[SEQ ID NO: 355]
5'-AGTGTGCAGAATGCAACCATTATCACCGCC-3'
[SEQ ID NO: 356]
5'-AAAAAAATCCATTTTCTGTTGGGCCATTGCATTG-3' anti-ppsA

[SEQ ID NO: 357]
5'-GGCTCGTCACCGGCAACCATTATCACCGCC-3'
[SEQ ID NO: 358]
5'-ATTGTTGGACATTTTCTGTTGG GCCATTGCATTG-3' anti-purA

[SEQ ID NO: 359]
5'-GTCGTCGTACTGGCAACCATTATCACCGCC-3'
[SEQ ID NO: 360]
5'-GTTGTTACCCATTTTCTGTTGGGCCATTGCATTG-3' anti-purB

[SEQ ID NO: 361]
5'-TCACTGACCGCCGCAACCATTATCACCGCC-3'
[SEQ ID NO: 362]
5'-GGATAATTCCATTTTCTGTTGGGCCATTGCATTG-3' anti-purR

[SEQ ID NO: 363]
5'-AAAGATGTAGCGGCAACCATTATCACCGCC-3'

[SEQ ID NO: 364]
5'-TATTGTTGCCATTTTCTGTTGGGCCATTGCATTG-3' anti-puuE

[SEQ ID NO: 365]
5'-GAATTCCATCAGGCAACCATTATCACCGCC-3'
[SEQ ID NO: 366]
5'-ATTGTTGCTCATTTTCTGTTGGGCCATTGCATTG-3' anti-rbsA

[SEQ ID NO: 367]
5'-CTTCAGCTTAAAGCAACCATTATCACCGCC-3'
[SEQ ID NO: 368]
5'-TAATGCTTCCATTTTCTGTTGG CCATTGCATTG-3' anti-rbsB

[SEQ ID NO: 369]
5'-AAACTGGCTACCGCAACCATTATCACCGCC-3'
[SEQ ID NO: 370]
5'-TTTCATGTTCATTTTCTGTTGG CCATTGCATTG-3' anti-rbsD

[SEQ ID NO: 371]
5'-ACCGTTCTTAATGCAACCATTATCACCGCC-3'
[SEQ ID NO: 372]
5'-GCCTTTTTTCATTTTCTGTTGG CCATTGCATTG-3' anti-rbsK

[SEQ ID NO: 373]
5'-GGCAGCCTCGTTGCAACCATTATCACCGCC-3'
[SEQ ID NO: 374]
5'-TGCGTTTTGCATTTTCTGTTGG CCATTGCATTG-3' anti-rbsR

[SEQ ID NO: 375]
5'-AAAGATGTTGCCGCAACCATTATCACCGCC-3'
[SEQ ID NO: 376]
5'-CATTGTAGCCAATTTCTGTTGG CCATTGCATTG-3' anti-rcsB

[SEQ ID NO: 377]
5'-AACGTAATTATTGCAACCATTATCACCGCC-3'
[SEQ ID NO: 378]
5'-CATATTGTTCATTTTCTGTTGGGCCATTGCATTG-3' anti-rutR

[SEQ ID NO: 379]
5'-GCAGTGAAAACAGCAACCATTATCACCGCC-3'
[SEQ ID NO: 380]
5'-GCCTTGCGTCATTTTCTGTTGGGCCATTGCATTG-3' anti-serA

[SEQ ID NO: 381]
5'-TCGCTGGAGAAAGCAACCATTATCACCGCC-3'
[SEQ ID NO: 382]
5'-TACCTTTGCCATTTTCTGTTGGGCCATTGCATTG-3' anti-serC

[SEQ ID NO: 383]
5'-TTCAATTTTAGTGCAACCATTATCACCGCC-3'
[SEQ ID NO: 384]
5'-GATTTGAGCCATTTTCTGTTGGGCCATTGCATTG-3' anti-soxS

[SEQ ID NO: 385]
5'-AAAATTATTCAGGCAACCATTATCACCGCC-3'
[SEQ ID NO: 386]
5'-CTGATGGGACATTTTCTGTTGG CCATTGCATTG-3' anti-sroD

[SEQ ID NO: 387]
5'-GCGCGCGGCAAAGCAACCATTATCACCGCC-3'
[SEQ ID NO: 388]
5'-TTCGTCACGTAATTTCTGTTGGGCCATTGCATTG-3' anti-zwf

[SEQ ID NO: 389]
5'-CAAACAGCCCAGGCAACCATTATCACCGCC-3'
[SEQ ID NO: 390]
5'-CGTTACCGCCATTTTCTGTTGG CCATTGCATTG-3'

Specifically, the binding sequence of genes was substituted by site-directed mutagenesis using a pWAS anti-csrA plasmid as a template and the above-described primers. The genes constructed by site-directed mutagenesis were transformed into DH5a cells (Invitrogen) in the following manner. Culture was performed using a plate medium containing LB-agar, 1% arabinose and 100 µg/ml ampicillin at 25° C. for 2 days, and the resulting colonies were cultured in liquid LB medium containing 1% agarose and 100 µg/ml ampicillin. Then, plasmids were purified from the cells and sequenced, and a correct plasmid was used in a subsequent experiment. This culture in the presence of 1% arabinose and at 25° C. effectively inhibits the expression of the synthetic sRNA, and thus is an essential process. In addition, if the chromosomal gene that is targeted by the synthetic sRNA has a very significant influence on the growth of host cells, the growth of the cells will be insufficient when the expression of the synthetic sRNA is not inhibited. This influence of the synthetic sRNA can cause difficulty in subsequent experiments, and thus is avoided. However, if the synthetic sRNA has no influence on the cell growth, culture may be performed in the absence of arabinose or at 37° C. When culture for the production of a desired metabolic product is performed, the synthetic sRNA should be sufficiently expressed, and thus in this case, culture was performed in the absence of arabinose and at 37° C.

The plasmid constructed as described above was subjected to PCR using primers of SEQ ID NOS: 105 and 96, and the PCR product was cleaved with SpeI/SacI and ligated with a pTyr-a vector cleaved with XbaI/SacI, thereby additionally introducing sRNA.

Figure 26:
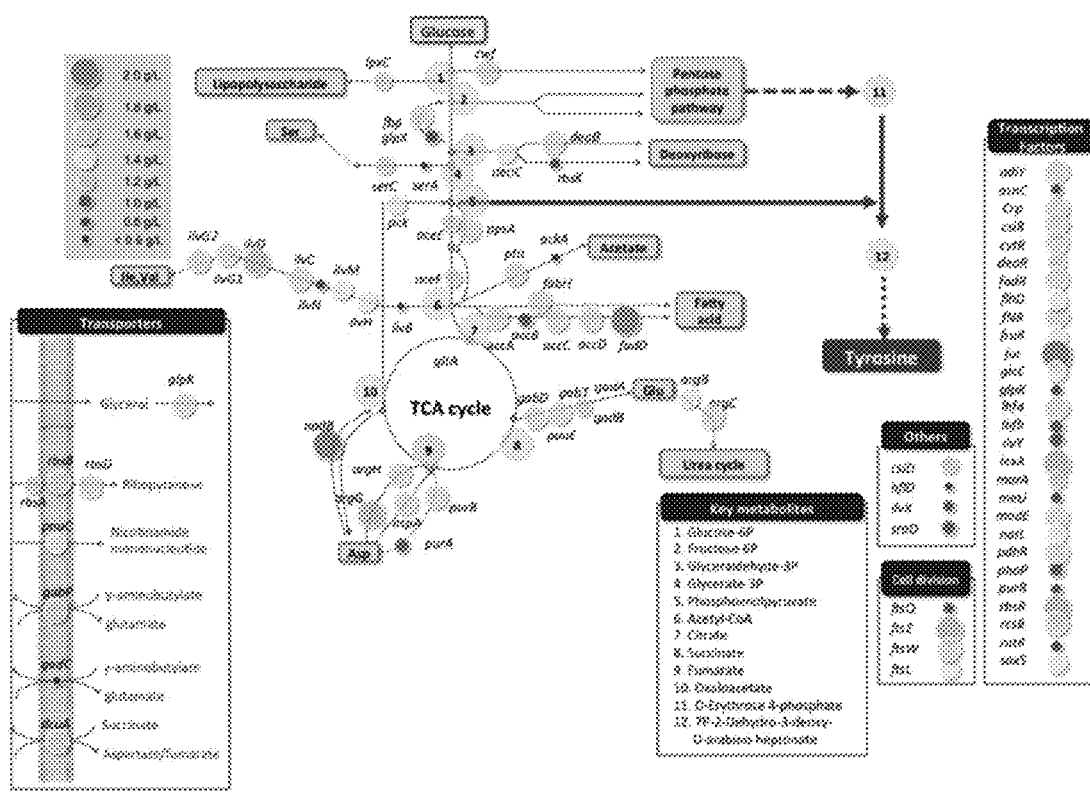
FIG. 26 shows the results of measuring the production of tyrosine after introducing synthetic sRNAs that inhibit genes involved in the key metabolic pathways of cells.

As a result, as can be seen in FIG. 26, the production of tyrosine varied depending on the kind of target gene, a gene showing productivity higher than the tyrR/csrA gene combination was not found. Thus, it could be seen that the tyrR/csrA gene combination was the optimum target for tyrosine production in the S17-1 strain. It is obvious that this high-throughput gene screening can be used in the production of not only tyrosine, but also various metabolic products.

Example 8

Production of Cadaverine-Producing Recombinant Microorganism Using Synthetic sRNA and Optimization of Cadaverine Production by Stepwise Regulation of Expression of murE Gene 8-1: Production of Cadaverine-Producing Recombinant Microorganism Using Synthetic sRNA In addition to Example 5, the metabolic flux of the lysine biosynthesis pathway was enhanced, and then selection of a gene to be silenced to further increase cadaverine production in a recombinant microorganism that converts lysine to cadaverine using lysine decarboxylase (CadA) was performed. FIG. 27 shows the pathways of biosynthesis of cadaverine from glucose, and these biosynthesis pathways include consumption pathways for production of other metabolites. In this Example, in order to increase cadaverine production, 130 candidate genes capable of networks that naturally consume metabolites were selected, and synthetic sRNAs capable of inhibiting the expression of the candidate genes were constructed. The 130 candidate genes include the 84 candidate genes of Example 7 and could be constructed by the primers used in Example 7. Meanwhile, the additional 46 candidate genes and the primers used for construction thereof are as follows.

asnA (asparagine synthetase A)
asnB (asparagine synthetase B)
carA (carbamoyl phosphate synthetase)
carB (carbamoyl phosphate synthetase)
ddlB (D-alanine-D-alanine ligase B)
deoA (thymidine phosphorylase/uracil phosphorylase)
deoD (purine nucleoside phosphorylase deoD-type)
dpiA (dual transcriptional regulator involved in anaerobic citrate catabolism)
fis (Fis, "factor for inversion stimulation", is a small DNA-binding and bending protein whose main role appears to be the organization and maintenance of nucleoid structure)
gadE (GadE controls the transcription of genes involved in glutamate dependent system)
gadW (GadW controls the transcription of genes involved in glutamate dependent system)
gadX (GadX controls the transcription of genes involved in glutamate dependent system)
glpF (GlpF glycerol MIP channel)
ilvY (IlvY DNA-binding transcriptional dual regulator)
ivbL (The ilvB operon leader peptide (IvbL))
lhgO (L-2-hydroxyglutarate oxidase)
lpd (Lipoamide dehydrogenase)
lrp (Lrp is a dual transcriptional regulator for at least 10% of the genes in *Escherichia coli*. These genes are involved in amino acid biosynthesis and catabolism, nutrient) transport, pili synthesis, and other cellular functions, including 1-carbon metabolism)
metB (O-succinylhomoserine lyase/O-succinylhomoserine(thiol)-lyase)
metL (aspartate kinase/homoserine dehydrogenase)
mraY (phospho-N-acetylmuramoyl-pentapeptide transferase)
mraZ (Unknown function)
murF (UDP-N-acetylmuramoylalanyl-D-glutamate 2,6-diaminopimelate ligase)
murF (D-alanyl-D-alanine-adding enzyme)
murG (N-acetylglucosaminyl transferase)
nac (Nacregulates, without a coeffector, genes involved in nitrogen metabolism under nitrogen-limiting conditions)
nadA (quinolinate synthase)
nsrR (NsrR, the "nitrite-sensitive repressor" regulates genes involved in cell protection against nitric oxide (NO))
panC (pantothenate synthetase)
panD (Aspartate 1-decarboxylase)
pgl (6-phosphogluconolactonase)
pyrB (aspartate carbamoyltransferase, PyrB subunit)
pyrC (dihydroorotase)
pyrL (aspartate carbamoyltransferase, PyrI subunit)
rob (Rob is a transcriptional dual regulator. Its N-terminal domain shares 49% identity with MarA and SoxS. These proteins activate a common set of about 50 target genes, the marA/soxS/rob regulon, involved in antibiotic resistance, superoxide resistance, and tolerance to organic solvents and heavy metals.)
rpe (ribulose phosphate 3-epimerase)
talA (transaldolase A)
thrA (aspartate kinase/homoserine dehydrogenase)
thrB (homoserine kinase)
thrC (threonine synthase)
thrL (thr operon leader peptide)
tktA (transketolase I)
tktB (transketolase II)
torR (two-component system, OmpR family, torCAD operon response regulator TorR)

Primer sequences used for construction sRNA

```
anti-asnA
                                    [SEQ ID NO: 391]
5'-TACATTGCCAAAGCAACCATTATCACCGCC-3'
                                    [SEQ ID NO: 392]
5'-AGCGGTTTTCATTTTCTGTTGGGCCATTGCATTG-3' anti-asnB
```

```
                                    [SEQ ID NO: 393]
5'-TTTGGCGTATTCGCAACCATTATCACCGCC-3'
                                    [SEQ ID NO: 394]
5'-AATTGAACACATTTTCTGTTGGGCCATTGCATTG-3' anti-carA
                                    [SEQ ID NO: 395]
5'-GCGCTATTGGTTGCAACCATTATCACCGCC-3'
                                    [SEQ ID NO: 396]
5'-TGACTTAATCAATTTCTGTTGGGCCATTGCATTG-3' anti-carB
                                    [SEQ ID NO: 397]
5'-ACAGATATAAAAGCAACCATTATCACCGCC-3'
                                    [SEQ ID NO: 398]
5'-ACGTTTTGGCATTTTCTGTTGGGCCATTGCATTG-3' anti-ddlB
                                    [SEQ ID NO: 399]
5'-ATCGCGGTCCTGCAACCATTATCACCGCC-3'
                                    [SEQ ID NO: 400]
5'-TTTATCAGTCATTTTCTGTTGGGCCATTGCATTG-3' anti-deoA
                                    [SEQ ID NO: 401]
5'-CAAGAAATTATTGCAACCATTATCACCGCC-3'
                                    [SEQ ID NO: 402]
5'-TGCGAGAAACAATTTCTGTTGG GCCATTGCATTG-3' anti-deoD
                                    [SEQ ID NO: 403]
5'-CACATTAATGCAGCAACCATTATCACCGCC-3'
                                    [SEQ ID NO: 404]
5'-TGGGGTAGCCATTTTCTGTTGG GCCATTGCATTG-3' anti-dpiA
                                    [SEQ ID NO: 405]
5'-TAATGGAGCTGTCATTTTCTGTTGGGCCATTGCATTG-3'
                                    [SEQ ID NO: 406]
5'-ACCCTATTGATCGTTGCAACCATTATCACCGCCAGA-3' anti-fis
                                    [SEQ ID NO: 407]
5'-CGCGTAAATTCTGCAACCATTATCACCGCC-3'
                                    [SEQ ID NO: 408]
5'-TTGTTCGAACATTTTCTGTTGGGCCATTGCATTG-3' anti-gadE
                                    [SEQ ID NO: 409]
5'-ATGACGAAAGATGCAACCATTATCACCGCC-3'
                                    [SEQ ID NO: 410]
5'-GAGAAAAATCATTTTCTGTTGGGCCATTGCATTG-3' anti-gadW
                                    [SEQ ID NO: 411]
5'-TGCTCGGTGATCGCAACCATTATCACCGCC-3'
                                    [SEQ ID NO: 412]
5'-GACATGAGTCATTTTCTGTTGGGCCATTGCATTG-3' anti-gadX
                                    [SEQ ID NO: 413]
5'-CATGGGAATTGTGCAACCATTATCACCGCC-3'
                                    [SEQ ID NO: 414]
5'-TAGTGATTGCATTTTCTGTTGGGCCATTGCATTG-3' anti-glpF
                                    [SEQ ID NO: 415]
5'-TCAACCTTGAAAGCAACCATTATCACCGCC-3'
                                    [SEQ ID NO: 416]
5'-TGTTTGACTCATTTTCTGTTGG GCCATTGCATTG-3' anti-ilvY
                                    [SEQ ID NO: 417]
5'-GATCTGAAAACCGCAACCATTATCACCGCC-3'
                                    [SEQ ID NO: 418]
5'-GCGTAAATCCACTTTCTGTTGGGCCATTGCATTG-3' anti-ivbL
                                    [SEQ ID NO: 419]
5'-ATGCTCAACGCAGCAACCATTATCACCGCC-3'
                                    [SEQ ID NO: 420]
5'-GGAAGTAGTCATTTTCTGTTGGGCCATTGCATTG-3' anti-lhgO
                                    [SEQ ID NO: 421]
5'-GTGATTATTGGCGCAACCATTATCACCGCC-3'
                                    [SEQ ID NO: 422]
5'-AAAATCATACATTTTCTGTTGGGCCATTGCATTG-3' anti-lpd
                                    [SEQ ID NO: 423]
5'-ATCAAAACTCAGGCAACCATTATCACCGCC-3'
                                    [SEQ ID NO: 424]
5'-TTCAGTACTCATTTTCTGTTGGGCCATTGCATTG-3' anti-lrp
                                    [SEQ ID NO: 425]
5'-AAGAAGCGCCCTGCAACCATTATCACCGCC-3'
                                    [SEQ ID NO: 426]
5'-GCTATCTACCATTTTCTGTTGGGCCATTGCATTG-3' anti-metB
                                    [SEQ ID NO: 427]
5'-ACAGGCCACCATGCAACCATTATCACCGCC-3'
                                    [SEQ ID NO: 428]
5'-TTACGCGTCATTTTCTGTTGGGCCATTGCATTG-3' anti-metL
                                    [SEQ ID NO: 429]
5'-GCGCAGGCAGGGGCAACCATTATCACCGCC-3'
                                    [SEQ ID NO: 430]
5'-AATCACACTCATTTTCTGTTGGGCCATTGCATTG-3' anti-mraY
                                    [SEQ ID NO: 431]
5'-CTGGCCGAACATGCAACCATTATCACCGCC-3'
                                    [SEQ ID NO: 432]
5'-CCAAACTAACATTTTCTGTTGGGCCATTGCATTG-3' anti-mraZ
                                    [SEQ ID NO: 433]
5'-GCAACGTTAGTCGCAACCATTATCACCGCC-3'
                                    [SEQ ID NO: 434]
5'-TCCCCGGAACATTTTCTGTTGGGCCATTGCATTG-3' anti-murE
                                    [SEQ ID NO: 435]
5'-AATTTGCGCGACGCAACCATTATCACCGCC-3'
                                    [SEQ ID NO: 436]
5'-ACGATCTGCCACTTTCTGTTGGGCCATTGCATTG-3' anti-murF
                                    [SEQ ID NO: 437]
5'-AACCCTTAGCCAGCAACCATTATCACCGCC-3'
                                    [SEQ ID NO: 438]
5'-ACGCTAATCATTTTCTGTTGGGCCATTGCATTG-3' anti-murG
                                    [SEQ ID NO: 439]
5'-GGAAAGCGATTAGCAACCATTATCACCGCC-3'
                                    [SEQ ID NO: 440]
5'-TTGACCACTCATTTTCTGTTGGGCCATTGCATTG-3' anti-nac
                                    [SEQ ID NO: 441]
5'-CGCCTGAAATACGCAACCATTATCACCGCC-3'
                                    [SEQ ID NO: 442]
5'-TCTGAAGTTCATTTTCTGTTGGGCCATTGCATTG-3' anti-nadA
                                    [SEQ ID NO: 443]
5'-TTTGATCCAGACGCAACCATTATCACCGCC-3'
                                    [SEQ ID NO: 444]
5'-CATTACGCTCATTTTCTGTTGGGCCATTGCATTG-3' anti-nsrR
                                    [SEQ ID NO: 445]
5'-ACTCGTTAACTGCACTTTCTGTTGGGCCATTGCATTG-3'
```

```
                                          [SEQ ID NO: 446]
5'-TTCACTGATTACGGAGCAACCATTATCACCGCCAGA-3' anti-panC
                                          [SEQ ID NO: 447]
5'-GAAACCCTGCCGGCAACCATTATCACCGCC-3'
                                          [SEQ ID NO: 448]
5'-GATAATTAACACTTTCTGTTGGGCCATTGCATTG-3' anti-panD
                                          [SEQ ID NO: 449]
5'-ATGCTGCAGGGCGCAACCATTATCACCGCC-3'
                                          [SEQ ID NO: 450]
5'-CGTGCGAATCATTTTCTGTTGGGCCATTGCATTG-3' anti-pgl
                                          [SEQ ID NO: 451]
5'-GTTTATATCGCCGCAACCATTATCACCGCC-3'
                                          [SEQ ID NO: 452]
5'-TGTTTGCTTCATTTTCTGTTGG GCCATTGCATTG-3' anti-pyrB
                                          [SEQ ID NO: 453]
5'-CTATATCAGAAAGCAACCATTATCACCGCC-3'
                                          [SEQ ID NO: 454]
5'-CGGATTAGCCATTTTCTGTTGGGCCATTGCATTG-3' anti-pyrC
                                          [SEQ ID NO: 455]
5'-TCCCAGGTATTAGCAACCATTATCACCGCC-3'
                                          [SEQ ID NO: 456]
5'-TGGTGCAGTCATTTTCTGTTGGGCCATTGCATTG-3' anti-pyrI
                                          [SEQ ID NO: 457]
5'-AATAAATTGCAGGCAACCATTATCACCGCC-3'
                                          [SEQ ID NO: 458]
5'-ATCGTGTGTCATTTTCTGTTGGGCCATTGCATTG-3' anti-rob
                                          [SEQ ID NO: 459]
5'-GGCATTATTCGCGCAACCATTATCACCGCC-3'
                                          [SEQ ID NO: 460]
5'-GGCCTGATCCATTTTCTGTTGG GCCATTGCATTG-3' anti-rpe
                                          [SEQ ID NO: 461]
5'-TTGATTGCCCCCGCAACCATTATCACCGCC-3'
                                          [SEQ ID NO: 462]
5'-ATACTGTTTCATTTTCTGTTGG GCCATTGCATTG-3' anti-talA
                                          [SEQ ID NO: 463]
5'-GACGGCATCAAAGCAACCATTATCACCGCC-3'
                                          [SEQ ID NO: 464]
5'-TAACTCGTTCATTTTCTGTTGG GCCATTGCATTG-3' anti-talB
                                          [SEQ ID NO: 465]
5'-TTGACCTCCCTTGCAACCATTATCACCGCC-3'
                                          [SEQ ID NO: 466]
5'-TTTGTCCGTCATTTTCTGTTGG GCCATTGCATTG-3' anti-thrA
                                          [SEQ ID NO: 467]
5'-AAGTTCGGCGGTGCAACCATTATCACCGCC-3'
                                          [SEQ ID NO: 468]
5'-CAACACTCGCATTTTCTGTTGGGCCATTGCATTG-3' anti-thrC
                                          [SEQ ID NO: 469]
5'-AATCTGAAAGATGCAACCATTATCACCGCC-3'
                                          [SEQ ID NO: 470]
5'-GTAGAGTTTCATTTTCTGTTGGGCCATTGCATTG-3' anti-thrL
                                          [SEQ ID NO: 471]
5'-AGCACCACCATTGCAACCATTATCACCGCC-3'
                                          [SEQ ID NO: 472]
5'-AATGCGTTTCATTTTCTGTTGGGCCATTGCATTG-3' anti-tktA
                                          [SEQ ID NO: 473]
5'-AAAGAGCTTGCCGCAACCATTATCACCGCC-3'
                                          [SEQ ID NO: 474]
5'-ACGTGAGGACATTTTCTGTTGG GCCATTGCATTG-3' anti-tktB
                                          [SEQ ID NO: 475]
5'-GACCTTGCCAATGCAACCATTATCACCGCC-3'
                                          [SEQ ID NO: 476]
5'-TTTTCGGGACATTTTCTGTTGG GCCATTGCATTG-3' anti-torR
                                          [SEQ ID NO: 477]
5'-ATTGTTATTGTTGCAACCATTATCACCGCC-3'
                                          [SEQ ID NO: 478]
5'-GTGATGTGGCATTTTCTGTTGGGCCATTGCATTG-3'
```

The construction of each synthetic sRNA, the transformation of the synthetic sRNA into the XQ56 (containing a p15CadA plasmid), and the measurement of cadaverine concentration were performed in the same manner as described in Example 5.

As a result, when the production of cadaverine in the basic strain was taken as 100% in the same manner as Example 5, the inhibition of the murE gene showed the highest cadaverine production (55%, 2.15 g/L), and the inhibition of ack showed a cadaverine production of 1.96 g/L (40%). The overall results are shown in FIGS. 27, and 37 target genes that increase cadaverine production are shown in Table 5 below.

TABLE 5

37 target genes that increase cadaverine production

| Gene | Relative cadaverine increase (%)* | SD | Essential gene** | Description |
|---|---|---|---|---|
| murE | 154.495 | 11.50508 | Y | UDP-N-acetylmuramoylalanyl-D-glutamate 2,6-diaminopimelate ligase |
| ackA | 140.2173513 | 63.90312836 | Y | propionate kinase/acetate kinase activity |
| thrL | 133.9679 | 2.929674 |  | thr operon leader peptide |
| PdhR | 131.3433 | 3.18948 |  | PdhR, "pyruvate dehydrogenase complex regulator," regulates genes involved in the pyruvate dehydrogenase complex |
| ilvG_1 | 127.484472 | 7.246746515 |  | acetolactate synthase II, large subunit, N-ter fragment [pseudogene] |
| metB | 123.5249 | 9.932535 |  | O-succinylhomoserine lyase/O-succinylhomoserine(thiol)-lyase |
| carB | 121.7908903 | 5.78275732 |  | carbamoyl phosphate synthetase |
| serC | 120.2898551 | 5.85595678 |  | phosphohydroxythreonine aminotransferase/ 3-phosphoserine aminotransferase |

TABLE 5-continued 37 target genes that increase cadaverine production

| Gene | Relative cadaverine increase (%)* | SD | Essential gene** | Description |
|---|---|---|---|---|
| ilvN | 118.73706 | 5.123962183 | | acetohydroxybutanoate synthase/acetolactate synthase |
| crp | 117.5501085 | 23.49702658 | | CRP transcriptional dual regulator |
| ilvD | 117.494824 | 18.0070671 | | dihydroxy acid dehydratase |
| ilvY | 117.0807453 | 12.59030708 | | ilvY DNA-binding transcriptional dual regulator |
| glpK | 116.5113872 | 0.365997299 | | glycerol kinase |
| glpF | 116.1490683 | 19.08185954 | | GlpF glycerol MIP channel |
| pta | 113.92 | 4.9 | | Phosphate acetyltransferase |
| tktA | 113.5093166 | 15.73786385 | Y | transketolase I |
| hfld | 113.3540373 | 4.099169746 | | lysogenisation regulator |
| deoA | 113.0952381 | 6.358352958 | | thymidine phosphorylase/uracil phosphorylase |
| gadE | 112.6811594 | 18.51946332 | | GadE controls the transcription of genes involved in glutamate dependent system |
| rbsK | 110.5072464 | 2.708380011 | | ribokinase |
| ilvL | 110.4554865 | 2.488781632 | | ilvGEDA operon leader peptide |
| ilvC | 110.1449275 | 6.0023557 | | acetohydroxy acid isomeroreductase |
| accA | 109.7826067 | 13.54190005 | Y | acetyl-CoA carboxyltransferase, alpha-subunit |
| ilvM | 108.3850532 | 11.85831248 | | acetohydroxybutanoate synthase/acetolactate synthase |
| argB | 108.1780538 | 8.659972988 | | acetylglutamate kinase |
| thrA | 106.1544 | 11.37465 | | aspartate kinase/homoserine dehydrogenase |
| carA | 105.9006211 | 5.123962183 | | carbamoyl phosphate synthetase |
| fbp | 105.8488613 | 8.293975689 | | fructose-1,6-bisphosphatase |
| rbsD | 105.6935818 | 8.051940573 | | ribose pyranase |
| parD | 105.5383023 | 0.951592977 | | Aspartate 1-decarboxylase |
| aspA | 104.1407867 | 5.123962183 | | aspartate ammonia-lyase |
| rcsB | 102.8985507 | 6.734350297 | | RcsB-BglJ DNA-binding transcriptional activator. RcsB protein for "Regulator capsule synthesis B," is a response regulator that belongs to the multicomponent RcsF/RcsC/RcsD/RcsA-RcsB phosphorelay system and is involved in the regulation of the synthesis of colanic acid capsule, cell division, periplasmic proteins, motility, and a small RNA. |
| lvbL | 102.0186335 | 5.343560562 | | The ilvB operon leader peptide (lvbL) |
| lexA | 101.8115942 | 0.658795138 | Y | LexA represses the transcription of several genes involved in the cellular response to DNA damage |
| rbsA | 101.77 | 4.83 | | ribose ABC transporter |
| murF | 101.1368 | 5.956948 | Y | D-alanyl-D-alanine-adding enzyme |
| thrC | 100.2564 | 8.703182 | | threonine synthase |

*Cadaverine production (1.4 g/L) in a genetically engineered E. coli strain reported in the literature [Qian, Z.-G. et al. Biotechnol Bioeng 108: 93-103, 2011] was taken as 100%.
**Essential gene: gene essential for cell survival. See the data of http://tubic.tju.edu.cn/deg/ for information thereon.

8-2: Optimization of Cadaverine Production by Stepwise Regulation of Expression of murE Gene Like the case of anti-csrA mentioned in Example 6, in this Example, the binding energy of anti-murE was diversified so that the expression of the murE gene was regulated stepwise, and whether the regulation of expression of the murE gene has any influence on the final production of cadaverine was examined.

According to the synthetic sRNA preparation method described in the above Example, various anti-murEs (synthetic sRNAs) were constructed by site-directed mutagenesis using the following primer pairs, and the constructed anti-murE pWAS plasmids (FIG. 18) were transformed into the XQ56 strain containing the p15CadA plasmid.

[SEQ ID NO: 479]
5'-GATCGTGCAACCATTATCACCGCC-3'

[SEQ ID NO: 480]
5'-TGCCACTTTCTGTTGGGCCATTGCATTG-3'

[SEQ ID NO: 481]
5'-GTCGTAAGCAACCATTATCACCGCC-3'

[SEQ ID NO: 482]
5'-CTGCCACTTTCTGTTGGGCCATTGCATTG-3'

[SEQ ID NO: 483]
5'-TCGTAATTGCAACCATTATCACCGCC-3'

[SEQ ID NO: 484]
5'-TCTGCCACTTTCTGTTGGGCCATTGCATTG-3'

[SEQ ID NO: 485]
5'-TAATTTGCGCGGCAACCATTATCACCGCC-3'

[SEQ ID NO: 486]
5'-CGATCTGCCACTTTCTGTTGGGCCATTGCATTG-3'

[SEQ ID NO: 487]
5'-ATTTGCGCGACCTGCAACCATTATCACCGCC-3'

[SEQ ID NO: 488]
5'-TACGATCTGCCACTTTCTGTTGGGCCATTGCATTG-3'

[SEQ ID NO: 489]
5'-TTTGCGCGACCTTCGCAACCATTATCACCGCC-3'

[SEQ ID NO: 490]
5'-TTACGATCTGCCACTTTCTGTTGGGCCATTGCATTG-3'

[SEQ ID NO: 491]
5'-TTGCGCGACCTTCTTGCAACCATTATCACCGCC-3'

[SEQ ID NO: 492]
5'-ATTACGATCTGCCACTTTCTGTTGGGCCATTGCATTG-3'

Figure 28:
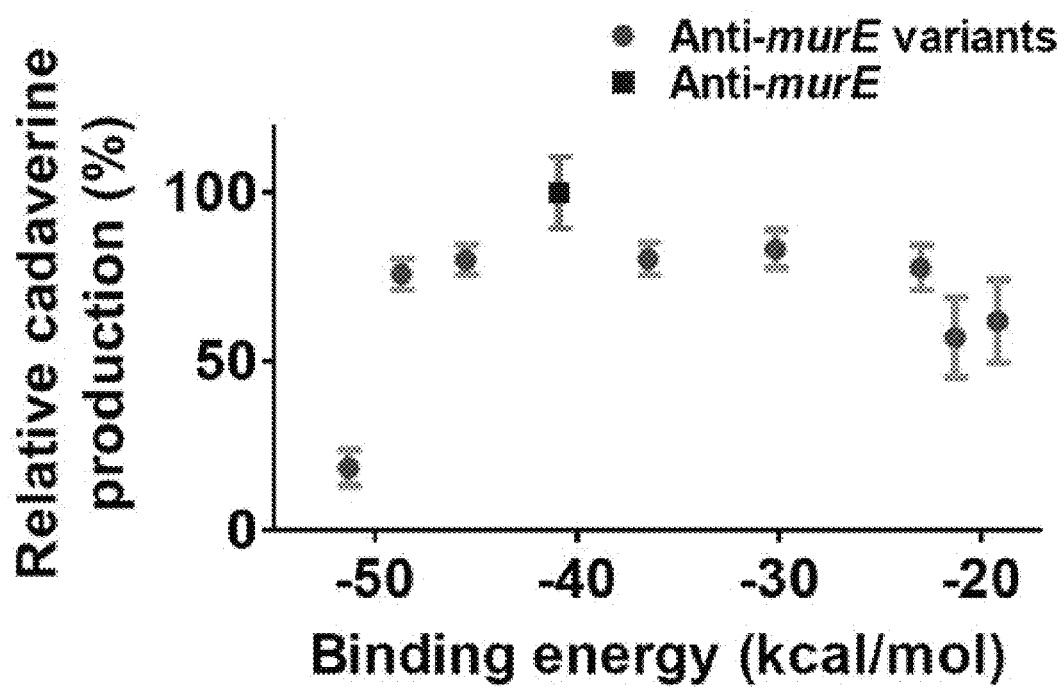
FIG. 28 shows the results of measuring the effects of Anti-murE synthetic sRNAs having various binding energies on the production of cadaverine.

As a result, as can be seen in FIG. 28, the binding energy ranged from −20 kcal/mol to −50 kcal/mol. Like the case of anti-csrA, the constructed basic anti-murE (blue square, FIG. 28) showed the highest cadaverine production, and at binding energy values higher or lower than that of basic anti-murE, the cadaverine production decreased.

In this Example, in order to examine whether the amount of murE protein is actually changed by anti-murE having different binding energy, the XQ56 strain transformed with the p15CadA/pWAS-anti-murE plasmid was cultured, followed by 2D-PAGE analysis. In this Example, the removal of anti-murE alone, and anti-murEs having binding energy values of −19.2, −36.5, −40.9 and −48.7 kcal/mol, were used. Specifically, cells were collected from each flask-cultivated sample and suspended in a resuspension buffer (10 mM Tris-HCl (pH 8.0), 1.5 mM $MgCl_2$, 10 mM KCl, 0.5 mM dithiothreitol, and 0.1% w/v sodium dodecyl sulfate (SDS)). The suspension was mixed with lysis buffer (7 M urea, 2 M thiourea, 40 mM Tris, 65 mM dithiothreitol, and 4% w/v 3-[(3-cholamidopropyl)dimethylammonio]-1-propanesulfonate (CHAPS)), and then centrifuged at 13000×g and 4° C. for 10 minutes, and the supernatant was collected. The protein concentration in the supernatant was measured by the Bradford method (Bradford M M, Anal Biochem 72, 248254, 1976), and 150 ug of the protein was mixed with 340 ul of rehydration buffer (7 M urea, 2 M thiourea, 20 mM dithiothreitol, 2% w/vCHAPS, 0.8% w/v immobilized pH gradient (IPG) buffer (Amersham Biosciences, Uppsala, Sweden), and 1% v/v cocktail protease inhibitor), and then loaded onto immobiline dry strip (IPG) gels (18 cm, pH 3-10 NL; Amersham Biosciences). The IPG strip loaded with the sample was rehydrated in the Protean IEF Cell for 12 hours, focused at 20° C. and 250 V for 3 hours, and then maintained at 6000V until it reached 65 kV h. The strip was equilibrated in a solution (containing 6 M urea, 0.375 M Tris-HCl (pH 8.8), 20% w/v glycerol, 2% w/v SDS, 130 mM dithiothreitol, and 0.002% w/v bromophenol blue) at room temperature for 15 minutes, and equilibrated again in a solution (having the same composition as mentioned above, except containing 135 mM iodoacetamide in place of DTT) at room temperature for 15 minutes. Then, the strip was transferred onto 12% w/v SDS-polyacrylamide gel. The protein spot was examined with the PlusOnes Silver Staining Kit (Amersham Biosciences) and quantitatively analyzed with Coomassie brilliant blue dye.

For quantification of the MurE protein, the amount of the MurE protein relative to the expression level of the housekeeping protein EF-Tu was measured, and the measured values were compared.

As a result, as can be seen in FIG. 29, as the binding energy of anti-murE (synthetic sRNA) used increased, the amount of MurE protein decreased. Thus, it can be seen that the amount of the target protein can be effectively diversified by suitably designing the binding energy of the synthetic sRNA.

Figure 30:
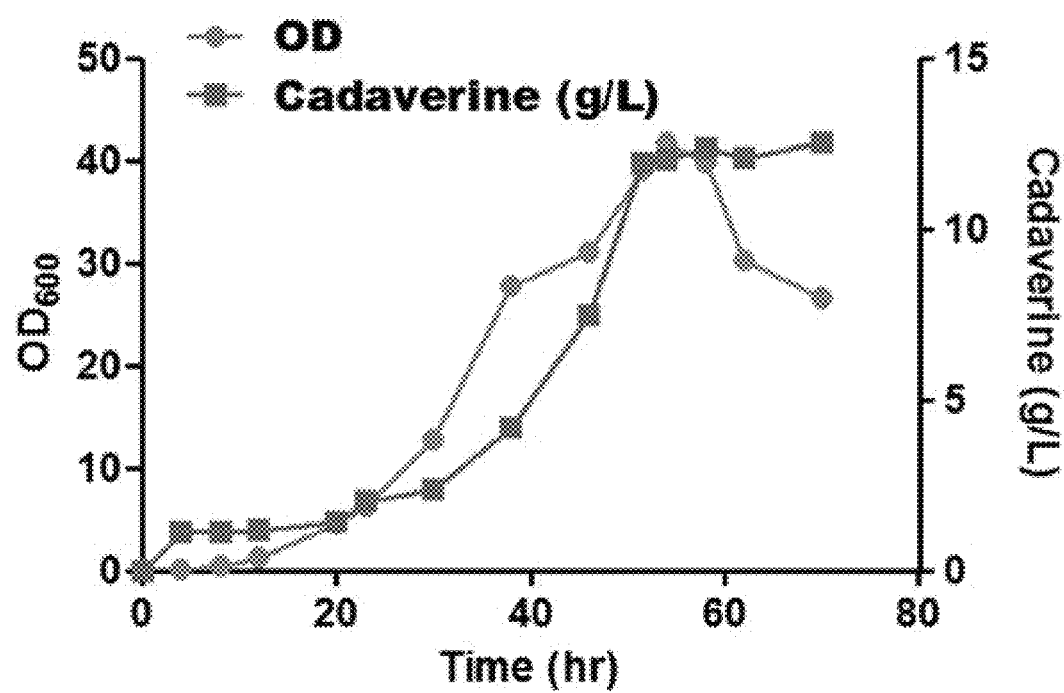
FIG. 30 shows the results of fermentation of a final strain containing Anti-murE.

The XQ56 with the finally selected anti-murE was fermented under the same conditions as those reported in the literature (Qian et al, *Biotechnol. Bioeng.* 108, 93-103 (2011)). As a result, as shown in FIG. 30, a total of 12.6 g/L of cadaverine could be obtained, and this production was about 31% higher than the previously reported production (9.6 g/L) reported in the literature. In the fermentation experiment, single colonies were cultured an R/2 medium containing 10 g/L glucose, 10 g/L arabinose and 3 g/L $(NH_4)SO_4$ at 25° C., and then subjected to fed-batch fermentation in a 6.6 L jar having 2 L of the same medium components (excluding arabinose) as described above. The pH was maintained at a constant pH of 6.8 with 10M KOH, and feeding solution contained 577 g/L glucose, 7 g/L $MgSO_4$ $7H_2O$, and 115 g/L $(NH4)_2SO_4$. The R/2 medium contained 2 g/L $(NH_4)_2HPO_4$, 6.75 g/L $KH_2PO_4$, 0.85 g/L citric acid, 0.7 g/L $MgSO_4$ $7H_2O$, and 5 ml/L of trace metal solution (Table 2).

INDUSTRIAL APPLICABILITY

As described above, the present invention provides a synthetic sRNA that can effectively inhibit the expression of the target gene without modifying the sequence of the target gene, unlike a gene deletion method, and a method for preparing the synthetic sRNA. The synthetic sRNA according to the present invention has an advantage in that the degree of inhibition of the target gene can be controlled by regulating the ability of the synthetic sRNA to bind to the mRNA of the target gene. The use of the synthetic sRNA that regulates the expression of the target gene makes it possible to effectively construct a recombinant microorganism without using a conventional gene deletion method and to reduce the expression of the target gene, and thus the synthetic sRNA is useful for the production of recombinant microorganisms. Also, the synthetic sRNA can be quickly applied to various strains, and thus is very suitable for the measurement of metabolic capabilities of strains and the selection of the most suitable strain. In addition, recombinant microorganisms, which are obtained by metabolic flux manipulation using the synthetic sRNA and produce tyrosine or cadaverine with high efficiency, are useful in the drug and industrial fields. In other words, the use of the sRNA according to the present invention can make it easy to select target genes whose expression is to be inhibited for the highly efficient production of metabolites. Accordingly, the synthetic sRNA can be used to construct recombinant strains for efficient production of various metabolites and to establish efficient methods for production of various metabolites, and thus is highly useful.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An sRNA for inhibiting gene expression in prokaryotes, the sRNA comprising:
   (i) a Hfq binding site derived from the sRNA of any one of MicC, SgrS and MicF; and
   (ii) a region that base-pairs with the target gene mRNA, wherein the Hfq binding site of (i) is derived from MicC, the target gene mRNA of (ii) is not OmpC, the Hfq binding site of (i) is derived from SgrS, the target gene mRNA of (ii) is not PtsG and the Hfq binding site (i) is derived from MicF, the target gene mRNA of (ii) is not OmpC, OmpF, OmpA or lpp;
   wherein the region that base-pairs with the target gene mRNA is constructed so that the energy of binding to the target gene mRNA is in the range from −10 kcal/mol to −40 kcal/mol; and
   wherein the region that base-pairs with the target gene mRNA base-pairs with all or part of the ribosome binding site of the target gene mRNA except for the Shine-Dalgarno sequence of the target gene mRNA.

2. The sRNA of claim 1, wherein a site that does not bind to the mRNA of the target gene is formed by deleting or substituting one or more nucleotides in the region that base-pairs with the target gene mRNA.

3. The sRNA of claim 1, wherein a site that does not bind to the mRNA of the target is formed by inserting or deleting one or more nucleotides in the region that base-pairs with the target gene mRNA.

4. The sRNA of claim 1, wherein the region that base-pairs with the target gene mRNA is constructed so that the energy of binding to the target gene mRNA is in the range from −20 kcal/mol to −40 kcal/mol.

5. The sRNA of claim 1, wherein the sRNA comprises an Hfq binding site derived from the sRNA of MicC.

6. The sRNA of claim 1, wherein the prokaryotes are selected from the group consisting of *E. coli, Rhizobium, Bifidobacterium, Rhodococcus, Candida, Erwinia, Enterobacter, Pasteurella, Mannheimia, Actinobacillus, Aggregatibacter, Xanthomonas, Vibrio, Pseudomonas, Azotobacter, Acinetobacter, Ralstonia, Agrobacterium, Rhizobium, Rhodobacter, Zymomonas, Bacillus, Staphylococcus, Lactococcus, Streptococcus, Lactobacillus, Clostridium, Corynebacterium, Streptomyces, Bifidobacterium,* and *Cyclobacterium.*

7. The sRNA of claim 1, wherein target gene mRNA is an mRNA of a gene selected from the group consisting of DsRed2, LuxR, AraC, KanR (kanamycin resistance gene), tyrR (tyrosine regulator), ppc (phosphoenolpyruvate carboxylase), csrA (carbon storage regulator), pgi (glucose-6-phosphate isomerase), glt (citrate synthase), accA (acetyl-CoA carboxyltransferase, alpha-subunit), accB (biotinylated biotin-carboxyl carrier protein), accC (acetyl-CoA carboxylase), accD (acetyl-CoA carboxyltransferase, beta-subunit), aceE (subunit of E1p component of pyruvate dehydrogenase complex), aceF (pyruvate dehydrogenase), ackA (propionate kinase/acetate kinase activity), adiY (AdiY is a positive DNA-binding transcriptional regulator that controls the arginine) decarboxylase (adi) system), argB (acetylglutamate kinase), argC (N-acetylglutamylphosphate reductase), argG (argininosuccinate synthase), argH (argininosuccinate lyase), asnC (transcriptional regulator that activates the expression of asnA, a gene involved in the synthesis of asparagine), aspA (aspartate ammonia-lyase), crp (CRP transcriptional dual regulator), csiD (CsiD product of a gene induced by carbon starvation), csiR (DNA-binding transcriptional repressor), cytR (transcription factor required for transport and utilization of ribonucleosides and deoxyribonucleosides), dcuA (DcuA, one of three transporters known to be responsible for the uptake of C4-dicarboxylates such as fumarate under anaerobic conditions), deoB (phosphopentomutase), deoC (deoxyribose-phosphate aldolase), deoR ("Deoxyribose Regulator," involved in the negative expression of genes related to transport and catabolism of deoxyribonucleoside nucleotides), fabH (KASIII, -ketoacyl-ACP synthases), fadD (fatty acyl-CoA synthetase), fadR (FadR Fatty acid degradation Regulon, is a multifunctional dual regulator that exerts negative control over the fatty acid degradative regulon [Simons80, Simons80a] and acetate metabolism), fbp (fructose-1,6-bisphosphatase), fnr (FNR is the primary transcriptional regulator that mediates the transition from aerobic to anaerobic growth), fruR (FruR is a dual transcriptional regulator that plays a pleiotropic role to modulate the direction of carbon flow through the different metabolic pathways of energy metabolism, but independently of the CRP regulator), ftsL (essential cell division protein FtsL), ftsQ (essential cell division protein FtsQ), ftsW (essential cell division protein FtsW), ftsZ (essential cell division protein FtsZ), fur (Fur-Fe+2 DNA-binding transcriptional dual regulator), gabD (succinate semialdehyde dehydrogenase, NADP+-dependent), gabP (APC transporter), gabT (4-aminobutyrate aminotransferase), gadA (glutamate decarboxylase A subunit), gadB (glutamate decarboxylase B subunit), gadC (GABA APC transporter), glcC (GntR family transcriptional regulator, glc operon transcriptional activator), glpK (glycerol kinase), glpR (sn-Glycerol-3-phosphate repressor), glpX (fructose 1,6-bisphosphatase II), gltA (citrate synthase), hfld (lysogenization regulator), ihfa (IHF, Integration host factor, is a global regulatory protein), ihfb (IHF, Integration host factor, is a global regulatory protein), ilvB (acetohydroxybutanoate synthase/acetolactate synthase), ilvC (acetohydroxy acid isomeroreductase), ilvD (dihydroxy acid dehydratase), ilvG_1 (acetolactate synthase II, large subunit, N-ter fragment (pseudogene)), ilvG_2 (acetolactate synthase II, large subunit, C-ter fragment (pseudogene)), ilvH (acetolactate synthase/acetohydroxybutanoate synthase), ilvL (ilvGEDA operon leader peptide), ilvM (acetohydroxybutanoate synthase/acetolactate synthase), ilvN (acetohydroxybutanoate synthase/acetolactate synthase), ilvX (Predicted small protein), lexA (LexA represses the transcription of several genes involved in the cellular response to DNA damage), lpxC (UDP-3-O-acyl-N-acetylglucosamine deacetylase), marA (MarA participates in controlling several genes involved in resistance to antibiotics, oxidative stress, organic solvents and heavy metals), metJ (MetJ transcriptional repressor), modE (ModE is the principal regulator that controls the transcription of operons involved in the transport of molybdenum and synthesis of molybdoenzymes and molybdate-related functions), nadB (L-aspartate oxidase), narL (nitrate/nitrite response regulator), pck (phosphoenolpyruvate carboxykinase), PdhR (PdhR, "pyruvate dehydrogenase complex regulator," regulates genes involved in the pyruvate dehydrogenase complex), phoP (PhoP-Phosphorylated DNA-binding transcriptional dual regulator Member of the two-component regulatory system phoQ/phoP involved in adaptation to low Mg2+ environments and the control of acid resistance genes), pnuC (PnuC NMN transporter), ppsA (phosphoenolpyruvate synthetase), pta (Phosphate acetyltransferase), purA (adenylosuccinate synthetase), purB (adenylosuccinate lyase), purR (PurR-Hypoxanthine DNA-binding transcriptional repressor PurR dimer controls several genes involved in purine nucleotide biosynthesis and its own synthesis), puuE (4-aminobutyrate aminotransferase), rbsA (ribose ABC transporter), rbsB (ribose ABC transporter), rbsD (ribose pyranase), rbsK (ribokinase), rbsR (The transcription factor RbsR, for "Ribose Repressor," is negatively autoregulated and controls the transcription of the operon involved in ribose catabolism and transport), rcsB (RcsB-BglJ DNA-binding transcriptional activator RcsB protein for "Regulator capsule synthesis B," is a response regulator that belongs to the multicomponent RcsF/RcsC/RcsD/RcsA-RcsB phosphorelay system and is involved in the regulation of the synthesis of colanic acid capsule, cell division, periplasmic proteins, motility, and a small RNA), rutR (RutR regulates genes directly or indirectly involved in the complex pathway of pyrimidine metabolism), serA (alpha-ketoglutarate reductase/D-3-phosphoglycerate dehydrogenase), serC (phosphohydroxythreonine aminotransferase/3-phosphoserine aminotransferase), soxS (dual transcriptional activator and participates in the removal of superoxide and nitric oxide), sroD (SroD small RNA), zwf (glucose 6-phosphate-1-dehydrogenase), asnA (asparagine synthetase A), asnB (asparagine synthetase B), carA (carbamoyl phosphate synthetase), carB (carbamoyl phosphate synthetase), ddlB (D-alanine-D-alanine ligase B), deoA (thymidine phosphorylase/uracil phosphorylase), deoD (purine nucleoside phosphorylase deoD-type), dpiA (dual transcriptional regulator involved in anaerobic citrate catabolism), fis (Fis, "factor for inversion stimulation", is a small DNA-binding and bending protein whose main role appears to be the organization and maintenance of nucleoid structure), gadE (GadE controls the transcription of genes involved in glutamate dependent system), gadW (GadW controls the transcription of genes involved in glutamate dependent system), gadX (GadX controls the transcription of genes involved in glutamate dependent system), glpF (GlpF glycerol MIP channel), ilvY (IlvY DNA-binding transcriptional dual regulator), ivbL (The ilvB operon leader peptide (IvbL)), lhgO (L-2-hydroxyglutarate oxidase), lpd (Lipoamide dehydrogenase), lrp (Lrp is a dual transcriptional regulator for at least 10% of the genes in *Escherichia coli*, These genes are involved in amino acid biosynthesis and catabolism, nutrient) transport, pili synthesis, and other cellular functions, including 1-carbon metabolism), metB (O-succinylhomoserine lyase/O-succinylhomoserine(thiol)-lyase), metL (aspartate kinase/homoserine dehydrogenase), mraY (phospho-N-acetylmuramoyl-pentapeptide transferase), mraZ (Unknown function), murE (UDP-N-acetylmuramoylalanyl-D-glutamate 2,6-diaminopimelate ligase), murF (D-alanyl-D-alanine-adding enzyme), murG (N-acetylglucosaminyl transferase), nac (Nacregulates, without a coeffector, genes involved in nitrogen metabolism under nitrogen-limiting conditions), nadA (quinolinate synthase), nsrR (NsrR, the "nitrite-sensitive repressor" regulates genes involved in cell protection against nitric oxide (NO)), panC (pantothenate synthetase), panD (Aspartate 1-decarboxylase), pgl (6-phosphogluconolactonase), pyrB (aspartate carbamoyltransferase, PyrB subunit), pyrC (dihydroorotase), pyrL (aspartate carbamoyltransferase, PyrI subunit), rob (Rob is a transcriptional dual regulator whose N-terminal domain shares 49% identity with MarA and SoxS, which activate a common set of about 50 target genes, the marA/soxS/rob regulon, involved in antibiotic resistance, superoxide resistance, and tolerance to organic solvents and heavy metals), rpe (ribulose phosphate 3-epimerase), talA (transaldolase A), thrA (aspartate kinase/homoserine dehydrogenase), thrB (homoserine kinase), thrC (threonine synthase), thrL (thr operon leader peptide), tktA (transketolase I), tktB (transketolase II), and torR (two-component system, OmpR family, torCAD operon response regulator TorR).

8. An isolated nucleic acid encoding the sRNA of claim 1.

9. An expression vector comprising an isolated nucleic acid encoding the sRNA of claim 1.

10. A recombinant microorganism having the sRNA of claim 1 introduced therein.

11. A recombinant microorganism transformed with the expression vector of claim 9.

* * * * *